US011118196B2

(12) United States Patent
Rezania et al.

(10) Patent No.: US 11,118,196 B2
(45) Date of Patent: *Sep. 14, 2021

(54) UNIVERSAL DONOR CELLS

(71) Applicant: CRISPR THERAPEUTICS AG, Zug (CH)

(72) Inventors: Alireza Rezania, Cambridge, MA (US); Rebeca Ramos-Zayas, Cambridge, MA (US)

(73) Assignee: CRISPR THERAPEUTICS AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/013,208

(22) Filed: Sep. 4, 2020

(65) Prior Publication Data

US 2021/0071201 A1 Mar. 11, 2021

Related U.S. Application Data

(60) Provisional application No. 62/896,473, filed on Sep. 5, 2019, provisional application No. 62/979,771, filed on Feb. 21, 2020.

(51) Int. Cl.
| | |
|---|---|
| *C12N 15/90* | (2006.01) |
| *C07K 14/705* | (2006.01) |
| *C07K 14/74* | (2006.01) |
| *C12N 5/0735* | (2010.01) |
| *C12N 5/074* | (2010.01) |
| *C12N 5/10* | (2006.01) |

(52) U.S. Cl.
CPC ...... *C12N 15/907* (2013.01); *C07K 14/70532* (2013.01); *C07K 14/70539* (2013.01); *C12N 5/0606* (2013.01); *C12N 5/0696* (2013.01); *C12N 5/10* (2013.01); *C07K 2319/02* (2013.01); *C07K 2319/03* (2013.01); *C07K 2319/09* (2013.01); *C12N 2310/20* (2017.05); *C12N 2800/80* (2013.01)

(58) Field of Classification Search
CPC .. C12N 15/907; C12N 5/0606; C12N 5/0696; C12N 5/10; C12N 2310/20; C12N 2800/80; C07K 14/70532; C07K 14/70539; C07K 2319/02; C07K 2319/03; C07K 2319/09
USPC ............. 435/325, 320.1, 463; 424/93.1
See application file for complete search history.

(56) References Cited

U.S. PATENT DOCUMENTS

| | | | |
|---|---|---|---|
| 5,034,506 A | 7/1991 | Summerton et al. | |
| 7,432,104 B2 | 10/2008 | Mitalipova et al. | |
| 7,510,876 B2 | 3/2009 | D'Amour et al. | |
| 7,541,185 B2 | 6/2009 | D'Amour et al. | |
| 7,695,963 B2 | 4/2010 | Agulnick et al. | |
| 7,695,965 B2 | 4/2010 | Martinson et al. | |
| 7,964,402 B2 | 6/2011 | Terskikh et al. | |
| 7,985,585 B2 | 7/2011 | D'Amour et al. | |
| 8,008,075 B2 | 8/2011 | Green et al. | |
| 8,129,182 B2 | 3/2012 | D'Amour et al. | |
| 8,153,429 B2 | 4/2012 | Robins et al. | |
| 8,187,878 B2 | 5/2012 | Dalton et al. | |
| 8,211,699 B2 | 7/2012 | Robins et al. | |
| 8,278,106 B2 | 10/2012 | Martinson et al. | |
| 8,334,138 B2 | 12/2012 | Robins et al. | |
| 8,338,170 B2 | 12/2012 | Kelly et al. | |
| 8,586,357 B2 | 11/2013 | D'Amour et al. | |
| 8,633,024 B2 | 1/2014 | D'Amour et al. | |
| 8,685,726 B2 | 4/2014 | Schulz et al. | |
| 8,859,286 B2 | 10/2014 | Agulnick | |
| 8,895,300 B2 | 11/2014 | Schulz | |
| 8,906,616 B2 | 12/2014 | Zhang et al. | |
| 8,999,944 B2 | 4/2015 | Berk | |
| 9,109,245 B2 | 8/2015 | Agulnick et al. | |
| 9,365,830 B2 | 6/2016 | Schulz et al. | |
| 10,030,229 B2 | 7/2018 | Peterson et al. | |
| 10,391,156 B2 | 8/2019 | Bhoumik et al. | |
| 10,724,052 B2 | 7/2020 | Rezania et al. | |
| 10,865,424 B2 | 12/2020 | Rezania et al. | |
| 2005/0266554 A1 | 12/2005 | D'Amour et al. | |

(Continued)

FOREIGN PATENT DOCUMENTS

| | | |
|---|---|---|
| WO | 92/04033 A1 | 3/1992 |
| WO | 01/83692 A2 | 11/2001 |

(Continued)

OTHER PUBLICATIONS

Kotini et al. (2016) Mol. Ther.-Nucleic Acids, vol. 5, e394; doi:10.1038/mtna.2016.99, pp. 1-8.*
GenEmbl Accession No. AY254342, submitted 2003.*
Goeckel et al. (2019) Fungal Biol Biotechnol, vol. 6(2), doi:org/10.1186/s40694-019-0065-x, p. 1-11.*
Gornalusse et al. (2017) Nat. Biotech., doi:10.1038/npt.3860, pp. 1-11.*
Pellenz et al. (2019) Human Gene Therapy, vol. 30(7), 814-828.*
Verma et al. (2017) Mol. Biol., vol. 1513, 119-140, doi:10.1007/978-1-4939-6539-7_9, pp. 1-23.*

(Continued)

*Primary Examiner* — Anne Marie S Wehbe
(74) *Attorney, Agent, or Firm* — Polsinelli PC; Tara A. Nealey; Shirley Bissen

(57) ABSTRACT

Genetically modified cells that are compatible with multiple subjects, e.g., universal donor cells, and methods of generating said genetic modified cells are provided herein. The universal donor cells comprise at least one genetic modification within or near at least one gene that encodes a survival factor, wherein the genetic modification comprises an insertion of a polynucleotide encoding a tolerogenic factor. The universal donor cells may further comprise at least one genetic modification within or near a gene that encodes one or more MHC-I or MHC-II human leukocyte antigens or a component or a transcriptional regulator of a MHC-I or MHC-II complex, wherein said genetic modification comprises an insertion of a polynucleotide encoding a second tolerogenic factor.

25 Claims, 42 Drawing Sheets

Specification includes a Sequence Listing.

(56) References Cited

U.S. PATENT DOCUMENTS

| | | | |
|---|---|---|---|
| 2006/0222633 | A1 | 10/2006 | Shlomchik et al. |
| 2007/0122905 | A1 | 5/2007 | D'Amour et al. |
| 2009/0170198 | A1 | 7/2009 | Rezania |
| 2009/0269845 | A1 | 10/2009 | Rezania |
| 2010/0015100 | A1 | 1/2010 | Xu |
| 2010/0112692 | A1 | 5/2010 | Rezania |
| 2010/0112693 | A1 | 5/2010 | Rezania et al. |
| 2010/0233755 | A1 | 9/2010 | D'Amour et al. |
| 2010/0272695 | A1 | 10/2010 | Agulnick et al. |
| 2011/0014702 | A1 | 1/2011 | Xu |
| 2011/0014703 | A1 | 1/2011 | Xu et al. |
| 2011/0151560 | A1 | 6/2011 | Xu |
| 2011/0151561 | A1 | 6/2011 | Davis et al. |
| 2012/0052575 | A1 | 3/2012 | Rezania |
| 2012/0052576 | A1 | 3/2012 | Rezania |
| 2013/0189777 | A1 | 7/2013 | Rezania |
| 2013/0330823 | A1 | 12/2013 | Rezania |
| 2014/0068797 | A1 | 3/2014 | Doudna et al. |
| 2014/0134195 | A1 | 5/2014 | Russell |
| 2014/0162359 | A1 | 6/2014 | Rezania |
| 2014/0186305 | A1 | 7/2014 | Rezania |
| 2014/0186953 | A1 | 7/2014 | Rezania |
| 2014/0242693 | A1 | 8/2014 | Fryer et al. |
| 2014/0295552 | A1 | 10/2014 | Fryer et al. |
| 2015/0218522 | A1 | 8/2015 | Peterson et al. |
| 2015/0329828 | A1 | 11/2015 | Rezania |
| 2016/0215268 | A1 | 7/2016 | Fryer et al. |
| 2017/0029778 | A1 | 2/2017 | Peterson et al. |
| 2018/0100158 | A1 | 4/2018 | Del'Guidice et al. |
| 2019/0015487 | A1 | 1/2019 | Bhoumik et al. |
| 2019/0223416 | A1 | 7/2019 | Lesko |
| 2019/0309259 | A1* | 10/2019 | Meissner ............ C12N 5/0696 |
| 2020/0080107 | A1 | 3/2020 | Rezania |
| 2020/0347403 | A1 | 11/2020 | Rezania et al. |
| 2021/0069256 | A1 | 3/2021 | Rezania et al. |
| 2021/0070835 | A1 | 3/2021 | Rezania et al. |
| 2021/0070836 | A1 | 3/2021 | Rezania et al. |
| 2021/0070837 | A1 | 3/2021 | Rezania et al. |

FOREIGN PATENT DOCUMENTS

| | | | |
|---|---|---|---|
| WO | 2009/155669 | A1 | 12/2009 |
| WO | 2013/090648 | A1 | 6/2013 |
| WO | 2013/159879 | A1 | 10/2013 |
| WO | 2013/192005 | A2 | 12/2013 |
| WO | 2014/200180 | A1 | 12/2014 |
| WO | 2015/065524 | A2 | 5/2015 |
| WO | 2016/183041 | A2 | 11/2016 |
| WO | 2017/079673 | A1 | 5/2017 |
| WO | 2018/035387 | A1 | 2/2018 |
| WO | 2018/089011 | A1 | 5/2018 |
| WO | 2018/132783 | A1 | 7/2018 |
| WO | 2019/076486 | A1 | 4/2019 |
| WO | 2020/049535 | A1 | 3/2020 |

OTHER PUBLICATIONS

Geneseq Accession No. BBQ97661, submitted 2015.*
Geneseq Accession No. BDA07999, submitted 2016.*
Belfort et al., "Homing Endonucleases: From Genetic Anomalies to Programmable Genomic Clippers," Methods in Molecular Biology, 2014, pp. 1-27, vol. 1123.
Bix et al., "Rejection of class I MHC-deficient haemopoietic cells by irradiated MHC-matched mice," Nature, 1991, pp. 329-331, vol. 349.
Boch et al., "Breaking the Code of DNA Binding Specificity of TAL-Type III Effectors," Science, 2009, pp. 1509-1512, vol. 326.
Boissel et al., "megaTALs: a rare-cleaving nuclease architecture for therapeutic genome engineering," Nucleic Acids Research, 2014, pp. 2591-2601, vol. 42, No. 4.
Boissel et al., "Assembly and Characterization of megaTALs for Hyperspecific Genome Engineering Applications,", Chromosomal Mutagenesis, Methods in Molecular Biology, Second Edition, Chapter 9, 2015, pp. 171-196, vol. 1239.
Braasch et al., "Novel Antisense and Peptide Nucleic Acid Strategies for Controlling Gene Expression," Biochemistry, 2002, pp. 4503-4510, vol. 41, No. 14.
Ceccaldi et al., "Homologous recombination-deficient tumors are hyper-dependent on POLQ-mediated repair," Nature, 2015, pp. 258-262, vol. 518, and Supplementary Material.
Cermak et al., "Efficient design and assembly of custom TALEN and other TAL effector-based constructs for DNA targeting," Nucleic Acids Research, 2011, e82, pp. 1-11, vol. 39, No. 12.
Cermak et al., "Efficient Design and Assembly of Custom TALENs Using the Golden Gate Platform," Chromosomal Mutagenesis, Methods in Molecular Biology, Second Edition, Chapter 7, 2015, pp. 133-159, vol. 1239.
Cho et al., "Familiar ends with alternative endings," Nature, 2015, pp. 174-176, vol. 518.
Cox et al., "Therapeutic Genome Editing: Prospects and Challenges," Nature Medicine, 2015, pp. 121-131, vol. 21, No. 2.
Deltcheva et al., "CRISPR RNA maturation by trans-encoded small RNA and host factor RNase III," Nature, 2011, pp. 602-607, vol. 471.
Dreier et al., "Insights into the Molecular Recognition of the 5'-GNN-3' Family of DNA Sequences by Zinc Finger Domains," Journal of Molecular Biology, 2000, pp. 489-502, vol. 303.
Dreier et al., "Development of Zinc Finger Domains for Recognition of the 5'-ANN-3' Family of DNA Sequences and Their Use in the Construction of Artificial Transcription Factors," The Journal of Biological Chemistry, 2001, pp. 29466-29478, vol. 276, No. 31.
Dreier et al., "Development of Zinc Finger Domains for Recognition of the 5'-CNN-3' Family DNA Sequences and Their Use in the Construction of Artificial Transcription Factors," The Journal of Biological Chemistry, 2005, pp. 35588-35597, vol. 280, No. 42.
Duan et al., "Differentiation and Characterization of Metabolically Functioning Hepatocytes from Human Embryonic Stem Cells," Stem Cells, 2010, pp. 674-686, vol. 28.
Fleischhauer et al. "Bone Marrow-Allograft Rejection by T Lymphocytes Recognizing a Single Amino Acid Difference in HLA-B44," The New England Journal of Medicine, 1990, pp. 1818-1822, vol. 323, No. 26.
Fonfara et al., "Phylogeny of Cas9 determines functional exchangeability of dual-RNA and Cas9 among orthologous type II CRISPR-Cas systems," Nucleic Acids Research, 2014, pp. 2577-2590, vol. 42, No. 4.
Gebeyehu et al., "Novel biotinylated nucleotide—analogs for labeling and colorimetric detection of DNA," Nucleic Acids Research, 1987, pp. 4513-4534, vol. 15, No. 11.
Gornalusse et al., "HLA-E-expressing pluripotent stem cells escape allogeneic responses and lysis by NK cells," Nature Biotechnology, 2017, pp. 765-773, vol. 35.
Grau et al., "TALENoffer: genome-wide TALEN off-target prediction," Bioinformatics, 2013, pp. 2931-2932, vol. 29, No. 22.
Gross et al., "Pertussis Toxin Promoter Sequences Involved in Modulation," Journal of Bacteriology, 1989, pp. 4026-4030, vol. 171, No. 7.
Guilinger et al., "Fusion of catalytically inactive Cas9 to FokI nuclease improves the specificity of genome modification," Nature Biotechnology, 2014, pp. 577-582, vol. 32, No. 6.
Guilinger et al., "Broad Specificity Profiling of TALENs Results in Engineered Nucleases With Improved DNA Cleavage Specificity," Nature Methods, 2014, pp. 429-435, vol. 11, No. 4.
Hafez et al., "Homing endonucleases: DNA scissors on a mission," Genome, 2012, pp. 553-569, vol. 55.
Heasman, "Morpholino Oligos: Making Sense of Antisense?," Developmental Biology, 2002, pp. 209-214, vol. 243.
Hong et al., "Rhesus iPSC Safe Harbor Gene-Editing Platform for Stable Expression of Transgenes in Differentiated Cells of All Germ Layers," Molecular Therapy, 2017, pp. 44-53, vol. 25, No. 1.
Jinek et al., "A Programmable Dual-RNA-Guided DNA Endonuclease in Adaptive Bacterial Immunity," Science, 2012, pp. 816-821, vol. 337.

(56) References Cited

OTHER PUBLICATIONS

Kent et al., "Mechanism of Microhomology-Mediated End-Joining Promoted by Human DNA Polymerase Theta," Nature Structural and Molecular Biology, 2015, pp. 230-237, vol. 22, No. 3.
Kleinstiver et al., "The I-TevI Nuclease and Linker Domains Contribute to the Specificity of Monomeric TALENs," Genes/Genomes/Genetics, 2014, pp. 1155-1165, vol. 4.
Lacerra et al., "Restoration of hemoglobin A synthesis in erythroid cells from peripheral blood of thalassemic patients," PNAS, 2000, pp. 9591-9596, vol. 97, No. 17.
Li et al., "Modularly assembled designer TAL effector nucleases for targeted gene knockout and gene replacement in eukaryotes," Nucleic Acids Research, 2011, pp. 6315-6325, vol. 39, No. 14.
Liu et al., "Validated Zinc Finger Protein Designs for All 16 GNN DNA Triplet Targets," The Journal of Biological Chemistry, 2002, pp. 3850-3856, vol. 277, No. 6.
Lu et al., "Generating Hypoimmunogenic Human Embryonic Stem Cells by the Disruption of Beta 2-Microglobulin," Stem Cell Rev and Rep, 2013, pp. 806-813, vol. 9.
Ma et al., "Highly Efficient Differentiation of Functional Hepatocytes From Human Induced Pluripotent Stem Cells," Stem Cells Translational Medicine, 2013, pp. 409-419, vol. 2.
Mak et al., "The crystal structure of TAL effector PthXo1 bound to its DNA target," Science, 2012, pp. 716-719, vol. 335.
Mateos-Gomez et al., "Mammalian Polymerase Theta Promotes Alternative-NHEJ and Suppresses Recombination," Nature, 2015, pp. 254-257, vol. 518.
Moscou et al., "A Simple Cipher Governs DNA Recognition by TAL Effectors," Science, 2009, p. 1501, vol. 326.
Nasevicius et al. "Effective targeted gene 'knockdown' in zebrafish," Nature Genetics, 2000, pp. 216-220, vol. 26.
Peer et al., "Special delivery: targeted therapy with small RNAs," Gene Therapy, 2011, pp. 1127-1133, vol. 18.
Rezania et al., "Reversal of diabetes with insulin-producing cells derived in vitro from human pluripotent stem cells," Nature Biotechnology, 2014, pp. 1121-1133, vol. 32, No. 11.
Rubinstein, "HLA Matching for Bone Marrow Transplantation—How Much Is Enough?," The New England Journal of Medicine, 2001, pp. 1842-1844, vol. 345, No. 25.
Sadelain et al., "Safe harbours for the integration of new DNA in the human genome," Nature Reviews/Cancer, 2012, pp. 51-58, vol. 12.
Sapranauskas et al., "The *Streptococcus thermophilus* CRISPR/Cas system provides immunity in *Escherichia coli*," Nucleic Acids Research, 2011, pp. 9275-9282, vol. 39, No. 21.
Sawitza et al., Bile acids induce hepatic differentiation of mesenchymal stem cells, Scientific Reports, 2015, pp. 1-15, vol. 5.
Schulz et al., "A Scalable System for Production of Functional Pancreatic Progenitors from Human Embryonic Stem Cells," PLoS One, 2012, e37004, pp. 1-17, vol. 7, No. 5.
Segal et al., "Toward controlling gene expression at will: Selection and design of zinc finger domains recognizing each of the 5'-GNN-3' DNA target sequences," PNAS, 1999, pp. 2758-2763, vol. 96.
Steentoft et al., "Precision genome editing: A small revolution for glycobiology," Glycobiology, 2014, pp. 663-680, vol. 24, No. 8.
Thielen et al., "Identification of an Anti-diabetic, Orally Available Small Molecule that Regulates TXNIP Expression and Glucagon Action," Cell Metabolism, 2020, pp. 1-13, vol. 32.
Tsai et al., "Dimeric CRISPR RNA-guided FokI nucleases for highly specific genome editing," Nature Biotechnology, 2014, pp. 569-576, vol. 32, No. 6.
Wang et al., "Cyclohexene Nucleic Acids (CeNA): Serum Stable Oligonucleotides that Activate RNase H and Increase Duplex Stability with Complementary RNA," Journal of the American Chemical Society, 2000, pp. 8595-8602, vol. 122, No. 36.
Wang et al., "Rapid and Efficient Assembly of Transcription Activator-Like Effector Genes by USER Cloning," Journal of Genetics and Genomics, 2014, pp. 339-347, vol. 41.
Weber et al., "A Modular Cloning System for Standardized Assembly of Multigene Constructs," PLoS ONE, 2011, e16765, pp. 1-11, vol. 6, No. 2.
Wolfs et al., "MegaTevs: single-chain dual nucleases for efficient gene disruption," Nucleic Acids Research, 2014, pp. 8816-8829, vol. 42, No. 13.
Wondafrash et al., "Thioredoxin-Interacting Protein as a Novel Potential Therapeutic Target in Diabetes Mellitus and Its Underlying Complications," Diabetes, Metabolic Syndrome and Obesity: Targets and Therapy, 2020, pp. 43-51, vol. 13.
Zarcone et al., "Human Leukemia-derived Cell Lines and Clones as Models for Mechanistic Analysis of Natural Killer Cell-mediated Cytotoxicity," Cancer Research, 1987, pp. 2674-2682, vol. 47.
Agulnick et al., "Insulin-Producing Endocrine Cells Differentiated In Vitro From Human Embryonic Stem Cells Function in Macroencapsulation Devices In Vivo," Stem Cells Translational Medicine, 2015, pp. 1214-1222, vol. 4.
Andrade et al., "Evidence for premature aging due to oxidative stress in iPSCs from Cockayne syndrome," Human Molecular Genetics, 2012, pp. 3825-3834, vol. 21, No. 17.
Aquino-Lopez et al., "Interferon Gamma Induces Changes in Natural Killer (NK) Cell Ligand Expression and Alters NK Cell-Mediated Lysis of Pediatric Cancer Cell Lines," Frontiers in Immunology, 2017, pp. 1-12, vol. 8, No. 391.
Bauche et al., 2014, Geneseq Accession No. BBQ97661, Computer printout, pp. 5-7.
Bonini et al., "HSV-TK Gene Transfer into Donor Lymphocytes for Control of Allogeneic Graft-Versus-Leukemia," Science, 1997, pp. 1719-1724, vol. 276.
Bordignon et al., "Transfer of the HSV-tk Gene into Donor Peripheral Blood Lymphocytes for In Vivo Modulation of Donor Anti-Tumor Immunity after Allogeneic Bone Marrow Transplantation," Human Gene Therapy, 1995, pp. 813-819, vol. 6.
Chutkow et al., "Deletion of the α-Arrestin Protein Txnip in Mice Promotes Adiposity and Adipogenesis While Preserving Insulin Sensitivity," Diabetes, 2010, pp. 1424-1434, vol. 59.
Cowan et al., 2016, N_Geneseq_201922, Accession No. BDA08012, computer printout, pp. 6-7 (Cowan 2016a).
Cowan et al., 2016, Geneseq Accession No. BDA07999, Computer printout, pp. 5-7 (Cowan 2016b).
D'Amour et al., "Production of pancreatic hormone-expressing endocrine cells from human embryonic stem cells," Nature Biotechnology, 2006, pp. 1392-1401, vol. 24, No. 11.
DeKelver et al., "Functional genomics, proteomics, and regulatory DNA analysis in isogenic settings using zinc finger nuclease-driven transgenesis into a safe harbor locus in the human genome," Genome Research, 2010, pp. 1133-1142, vol. 20.
Del Campo et al., "Immune escape of cancer cells with beta2-microglobulin loss over the course of metastatic melanoma," International Journal of Cancer, 2014, pp. 102-113, vol. 134.
Denu et al., *Effects of Oxidative Stress on Mesenchymal Stem Cell Biology, Oxidative Medicine and Cellular Longevity, 2016, pp. 1-9, vol. 2016, No. 1.
Devi et al., "TXNIP regulates mitophagy in retinal Muller cells under high-glucose conditions: implications for diabetic retinopathy," Cell Death and Disease, 2017, e2777, pp. 1-12, vol. 8.
Devi et al., "TXNIP regulates mitophagy in retinal Muller cells under high-glucose conditions: implications for diabetic retinopathy," Cell Death and Disease, 2017, Supplementary Data, pp. 1-15.
Han et al., "Generation of hypoimmunogenic human pluripotent stem cells," PNAS, 2019, pp. 10441-10446, vol. 116, No. 21.
Joosten et al, "Characteristics of HLA-E Restricted T-Cell Responses and Their Role in Infectious Diseases," Journal of Immunology Research, 2016, Article ID 2695396, pp. 1-11.
Karabekian et al., "HLA Class I Depleted hESC as a Source of Hypoimmunogenic Cells for Tissue Engineering Applications," Tissue Engineering: Part A, 2015, pp. 2559-2571, vol. 21.
Katsu-Jimenez, et al., "Absence of TXNIP in Humans Leads to Lactic Acidosis and Low Serum Methionine Linked to Deficient Respiration on Pyruvate," Diabetes, 2019, pp. 709-723, vol. 68.
Knoepfler, "Deconstructing Stem Cell Tumorigenicity: A Roadmap to Safe Regenerative Medicine," Stem Cells, 2009, pp. 1050-1056, vol. 27.
Liu et al., "The Immunogenicity and Immune Tolerance of Pluripotent Stem Cell Derivatives," Frontiers in Immunology, 2017, pp. 1-6, vol. 8, No. 645.

(56) References Cited

OTHER PUBLICATIONS

Liu et al., "All mixed up: defining roles for β-cell subtypes in mature islets," Genes & Development, 2017, pp. 228-240, vol. 31.

Nabavi et al., "Anti-inflammatory effects of Melatonin: a mechanistic review," Critical Reviews in Food Science and Nutrition, 2018, pp. 1-63.

Nagaraj et al., "Identification of thioredoxin-interacting protein (TXNIP) as a downstream target for IGF1 action," PNAS, 2018, pp. 1045-1050, vol. 115, No. 5.

Pagliuca et al., "Generation of Functional Human Pancreatic β Cells In Vitro," Cell, 2014, pp. 428-439, vol. 159.

Parham, "MHC Class I Molecules and KIRS in Human History, Health and Survival," Nature Reviews/Immunology, 2005, pp. 201-214, vol. 5.

Pegram et al., "Activating and inhibitory receptors of natural killer cells," Immunology and Cell Biology, 2011, pp. 216-224, vol. 89.

Rezania et al., "Production of Functional Glucagon-Secreting α-Cells From Human Embryonic Stem Cells," Diabetes, 2011, pp. 239-247, vol. 60.

Rezania et al., "Maturation of Human Embryonic Stem Cell-Derived Pancreatic Progenitors Into Functional Islets Capable of Treating Pre-existing Diabetes in Mice," Diabetes, 2012, pp. 2016-2029, vol. 61.

Rezania et al., "Enrichment of Human Embryonic Stem Cell-Derived NKX6.1—Expressing Pancreatic Progenitor Cells Accelerates the Maturation of Insulin-Secreting Cells In Vivo," Stem Cells, 2013, pp. 2432-2442, vol. 31.

Russ et al., "Controlled induction of human pancreatic progenitors produces functional beta-like cells in vitro," The EMBO Journal, 2014, pp. 1759-1772, vol. 34, No. 13.

Scholpp et al., "Morpholino-Induced Knockdown of Zebrafish Engrailed Gens eng2 and eng3 Reveals Redundant and Unique Functions in Midbrain-Hindbrain Boundary Development," Genesis, 2001, pp. 129-133, vol. 30.

Schuldiner et al., "Selective Ablation of Human Embryonic Stem Cells Expressing a "Suicide " Gene," Stem Cells, 2003, pp. 257-265, vol. 21.

Sluch et al., "CRISPR-editing of hESCs allows for production of immune evasive cells capable of differentiation to pancreatic progenitors for future type 1 diabetes therapy", Sep. 1, 2019, Abstract. Retrieved from the Internet: URL:https://27funs395cqh24ygs021so4j-wpengine.netdna-ssl.com/wp-content/uploads/2019/09/ViaCyte-CRISPR-EASD-Abstract-September-2019.pdf [retrieved Nov. 8, 2019].

Sluch et al., "CRISPR-editing of hESCs allows for production of immune evasive cells capable of differentiation to pancreatic progenitors for future type 1 diabetes therapy", Sep. 17, 2019, 6 pgs. Retrieved from the Internet:URL: http://ir.crisprtx.com/static-files/af584c8b-5264-4bdd-a409-fec52e06d365.

Takahashi et al., "Induction of Pluripotent Stem Cells from Mouse Embryonic and Adult Fibroblast Cultures by Defined Factors," Cell, 2006, pp. 663-676, vol. 126.

Wang et al., "Tumor cell-intrinsic PD-1 receptor is a tumor suppressor and mediates resistance to PD-1 blockade therapy," PNAS, 2020, pp. 6640-6650, vol. 117, No. 12.

Wang et al., "Targeted Disruption of the β2-Microglobulin Gene Minimizes the Immunogenicity of Human Embryonic Stem Cells," Stem Cells Translational Medicine, 2015, pp. 1234-1245, vol. 4.

Zhang et al., "Efficient preparation of a TXNIP knockout mouse model by transcription activator-like effector nucleases (TALEN)," Chinese Journal of Comparative Medicine, 2015, pp. 9-13, vol. 25, No. 6 (with English abstract).

International Search Report and Written Opinion from International Application No. PCT/IB2020/058279, dated Nov. 20, 2020; 10 pgs.

International Search Report and Written Opinion from International Application No. PCT/IB2020/058281, dated Dec. 11, 2020; 32 pgs.

Office Action from related U.S. Appl. No. 17/013,154, dated Jan. 13, 2021; 26 pgs.

Office Action from related U.S. Appl. No. 17/013,143, dated Jan. 28, 2021; 10 pgs.

Office Action from related U.S. Appl. No. 17/013,135, dated Feb. 12, 2021; 18 pgs.

Office Action from related U.S. Appl. No. 17/013,162, dated Feb. 16, 2021; 11 pgs.

* cited by examiner wt PECs                Seed clone

SEQUENCE LISTING

```
<160> NUMBER OF SEQ ID NOS: 57

<210> SEQ ID NO 1
<211> LENGTH: 20
<212> TYPE: DNA
<213> ORGANISM: Homo sapiens

<400> SEQUENCE: 1
gctactctct ctttctggcc                                               20

<210> SEQ ID NO 2
<211> LENGTH: 20
<212> TYPE: DNA
<213> ORGANISM: Homo sapiens

<400> SEQUENCE: 2
ggccgagatg tctcgctccg                                               20

<210> SEQ ID NO 3
<211> LENGTH: 20
<212> TYPE: DNA
<213> ORGANISM: Homo sapiens

<400> SEQUENCE: 3
cgcgagcaca gctaaggcca                                               20

<210> SEQ ID NO 4
<211> LENGTH: 20
<212> TYPE: DNA
<213> ORGANISM: Artificial Sequence
<220> FEATURE:
<223> OTHER INFORMATION: Synthesized

<400> SEQUENCE: 4
```

```
cagacagcaa actcacccag                                                  20

<210> SEQ ID NO 5
<211> LENGTH: 20
<212> TYPE: DNA
<213> ORGANISM: Artificial Sequence
<220> FEATURE:
<223> OTHER INFORMATION: Synthesized

<400> SEQUENCE: 5
aaactttgtc ccgaccctcc                                                  20

<210> SEQ ID NO 6
<211> LENGTH: 130
<212> TYPE: DNA
<213> ORGANISM: Artificial Sequence
<220> FEATURE:
<223> OTHER INFORMATION: Synthesized

<400> SEQUENCE: 6
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120 agggggttcct                                                           130

<210> SEQ ID NO 7
<211> LENGTH: 800
<212> TYPE: DNA
<213> ORGANISM: Homo sapiens

<400> SEQUENCE: 7
gttctagggt ggaaactaag agaatgatgt acctagaggg cgctggaagc tctaaagccc      60
tagcagttac tgcttttact attagtggtc gttttttctt ccccccgcc ccccgacaaa      120 tcaacagaac aaagaaaatt acctaaacag caaggacata gggaggaact tcttggcaca     180
gaactttcca acacttttt cctgaaggga tacaagaagc aagaaaggta ctctttcact      240
aggaccttct ctgagctgtc ctcaggatgc ttttgggact attttttctta cccagagaat    300 ggagaaaccc tgcagggaat tcccaagctg tagttataaa cagaagttct ccttctgcta    360
ggtagcattc aaagatctta atcttctggg tttccgtttt ctcgaatgaa aaatgcaggt    420
ccgagcagtt aactggctgg ggcaccatta gcaagtcact tagcatctct ggggccagtc    480
tgcaaagcga gggggcagcc ttaatgtgcc tccagcctga agtcctagaa tgagcgcccg    540
gtgtcccaag ctggggcgcg caccccagat cggaggcgc cgatgtacag acagcaaact     600
cacccagtct agtgcatgcc ttcttaaaca tcacgagact ctaagaaaag gaaactgaaa    660
acgggaaagt ccctctctct aacctggcac tgcgtcgctg gcttgagac aggtgacggt     720 ccctgcgggc cttgtcctga ttggctgggc acgcgtttaa tataagtgga ggcgtcgcgc    780
tggcgggcat tcctgaagct                                                800

<210> SEQ ID NO 8
<211> LENGTH: 380
<212> TYPE: DNA
<213> ORGANISM: Cytomegalovirus

<400> SEQUENCE: 8
gacattgatt attgactagt tattaatagt aatcaattac gggtcatta gttcatagcc      60 catatatgga gttccgcgtt acataactta cggtaaatgg cccgcctggc tgaccgccca    120
acgacccccg cccattgacg tcaataatga cgtatgttcc catagtaacg ccaatagggg    180
```

```
ctttccattg acgtcaatgg gtggactatt tacggtaaac tgcccacttg gcagtacatc      240
aagtgtatca tatgccaagt acgcccccta ttgacgtcaa tgacggtaaa tggcccgcct      300
ggcattatgc ccagtacatg accttatggg actttcctac ttggcagtac atctacgtat      360
tagtcatcgc tattaccatg                                                  380
```

```
<210> SEQ ID NO 9
<211> LENGTH: 276
<212> TYPE: DNA
<213> ORGANISM: Gallus gallus

<400> SEQUENCE: 9
```

```
tcgaggtgag ccccacgttc tgcttcactc tccccatctc ccccccctcc ccaccccaa       60 ttttgtattt atttattttt taattatttt gtgcagcgat ggggggcggg ggggggggg      120 cgcgcgccag gcggggcggg gcggggcgag gggcggggcg gggcgaggcg gagaggtgcg     180
gcggcagcca atcagagcgg cgcgctccga aagtttcctt ttatggcgag gcggcggcgg     240
cggcggccct ataaaaagcg aagcgcgcgg cgggcg                                276
```

```
<210> SEQ ID NO 10
<211> LENGTH: 1009
<212> TYPE: DNA
<213> ORGANISM: Artificial Sequence
<220> FEATURE:
<223> OTHER INFORMATION: Synthesized

<400> SEQUENCE: 10
```

```
ggagtcgctg cgttgccttc gccccgtgcc ccgctccgcg ccgcctcgcg ccgcccgccc      60
cggctctgac tgaccgcgtt actcccacag gtgagcgggc gggacggccc ttctcctccg     120
ggctgtaatt agcgcttggt ttaatgacgg ctcgtttctt ttctgtggct gcgtgaaagc     180
cttaaagggc tccgggaggg ccctttgtgc ggggggagc ggctcggggg gtgcgtgcgt      240
gtgtgtgtgc gtggggagcg ccgcgtgcgg cccgcgctgc ccggcggctg tgagcgctgc     300
gggcgcggcg cggggctttg tgcgctccgc gtgtgcgcga gggagcgcg gccggggcg       360 gtgccccgcg gtgcggggg gctgcgaggg gaacaaaggc tgcgtgcggg gtgtgtgcgt     420
gggggggtga gcaggggtg tgggcgcgg ggtcgggctg taacccccc ctgcaccccc       480 ctcccccgagt tgctgagcac ggcccggctt cgggtgcggg gctccgtgcg gggcgtggcg     540
cggggctcgc cgtgccgggc gggggtggc ggcaggtggg ggtgccgggc ggggcgggc      600 cgcctcgggc cggggagggc tcgggggagg ggcgcggcgg ccccggagcg ccggcggctg     660
tcgaggcgcg gcgagccgca gccattgcct tttatggtaa tcgtgcgaga gggcgcaggg     720
acttcctttg tcccaaatct ggcggagccg aaatctggga ggcgccgccg cacccctct      780 agcgggcgcg ggcgaagcgg tgcggcgccg gcaggaagga aatgggcggg gagggccttc     840
gtgcgtcgcc gcgccgccgt ccccttctcc atctccagcc tcggggctgc cgcagggga      900 cggctgcctt cggggggac ggggcagggc ggggttcggc ttctggcgtg tgaccggcgg     960
ctctagagcc tctgctaacc atgttcatgc cttcttcttt ttcctacag                 1009
```

```
<210> SEQ ID NO 11
<211> LENGTH: 873
<212> TYPE: DNA
<213> ORGANISM: Homo sapiens

<400> SEQUENCE: 11
```

-continued

| | |
|---|---|
| atgaggatat tgctgtctt tatattcatg acctactggc atttgctgaa cgcatttact | 60 |
| gtcacggttc ccaaggacct atatgtggta gagtatggta gcaatatgac aattgaatgc | 120 |
| aaattcccag tagaaaaaca attagacctg gctgcactaa ttgtctattg ggaaatggag | 180 |
| gataagaaca ttattcaatt tgtgcatgga gaggaagacc tgaaggttca gcatagtagc | 240 |
| tacagacaga gggcccggct gttgaaggac cagctctccc tgggaaatgc tgcacttcag | 300 |
| atcacagatg tgaaattgca ggatgcaggg gtgtaccgct gcatgatcag ctatggtggt | 360 |
| gccgactaca agcgaattac tgtgaaagtc aatgccccat acaacaaaat caaccaaaga | 420 |
| attttggttg tggatccagt cacctctgaa catgaactga catgtcaggc tgagggctac | 480 |
| cccaaggccg aagtcatctg acaagcagt gaccatcaag tcctgagtgg taagaccacc | 540 |
| accaccaatt ccaagagaga ggagaaactt ttcaatgtga ccagcacact gagaatcaac | 600 |
| acaacaacta atgagatttt ctactgcact tttaggagat tagatcctga ggaaaaccat | 660 |
| acagctgaat tggtcatccc agaactacct ctggcacatc ctccaaatga aaggactcac | 720 |
| ttggtaattc tgggagccat cttattatgc cttggtgtag cactgacatt catcttccgt | 780 |
| ttaagaaaag ggagaatgat ggatgtgaaa aaatgtggca tccaagatac aaactcaaag | 840 |
| aagcaaagtg atacacattt ggaggagacg taa | 873 |

<210> SEQ ID NO 12
<211> LENGTH: 225
<212> TYPE: DNA
<213> ORGANISM: Bos taurus

<400> SEQUENCE: 12

| | |
|---|---|
| ctgtgccttc tagttgccag ccatctgttg tttgccccctc cccgtgcct tccttgaccc | 60 |
| tggaaggtgc cactcccact gtccttttcct aataaaatga ggaaattgca tcgcattgtc | 120 |
| tgagtaggtg tcattctatt ctgggggggtg gggtggggca ggacagcaag ggggaggatt | 180 |
| gggaagacaa tagcaggcat gctggggatg cggtgggctc tatgg | 225 |

<210> SEQ ID NO 13
<211> LENGTH: 800
<212> TYPE: DNA
<213> ORGANISM: Homo sapiens

<400> SEQUENCE: 13

| | |
|---|---|
| ccagcgtgag tctctcctac cctcccgctc tggtccttcc tctcccgctc tgcaccctct | 60 |
| gtggccctcg ctgtgctctc tcgctccgtg acttcccttc tccaagttct ccttggtggc | 120 |
| ccgccgtggg gctagtccag ggctggatct cggggaagcg gcggggtggc ctgggagtgg | 180 |
| ggaaggggt gcgcacccgg gacgcgcgct acttgcccct ttcggcgggg agcagggag | 240 |
| acctttggcc tacggcgacg ggagggtcgg gacaaagttt agggcgtcga taagcgtcag | 300 |
| agcgccgagg ttggggggagg gtttctcttc cgctctttcg cggggcctct ggctccccca | 360 |
| gcgcagctgg agtgggggac gggtaggctc gtcccaaagg cgcggcgctg aggtttgtga | 420 |
| acgcgtggag gggcgcttgg ggtctggggg aggcgtcgcc cgggtaagcc tgtctgctgc | 480 |
| ggctctgctt cccttagact ggagagctgt ggacttcgtc taggcgcccg ctaagttcgc | 540 |
| atgtcctagc acctctgggt ctatgtgggg ccacaccgtg gggaggaaac agcacgcgac | 600 |
| gtttgtagaa tgcttggctg tgatacaaag cggtttcgaa taattaactt atttgttccc | 660 |
| atcacatgtc acttttaaaa aattataaga actacccgtt attgacatct ttctgtgtgc | 720 |
| caaggacttt atgtgctttg cgtcatttaa ttttgaaaac agttatcttc cgccatagat | 780 | aactactatg gttatcttct                                                800

<210> SEQ ID NO 14
<211> LENGTH: 141
<212> TYPE: DNA
<213> ORGANISM: Artificial Sequence
<220> FEATURE:
<223> OTHER INFORMATION: Synthesized

<400> SEQUENCE: 14
aggaacccct agtgatggag ttggccactc cctctctgcg cgctcgctcg ctcactgagg    60
ccgggcgacc aaaggtcgcc cgacgcccgg gctttgcccg ggcggcctca gtgagcgagc   120
gagcgcgcag ctgcctgcag g                                            141

<210> SEQ ID NO 15
<211> LENGTH: 20
<212> TYPE: DNA
<213> ORGANISM: Homo sapiens

<400> SEQUENCE: 15
gaagcgtgtc ttcatagcgc                                                20

<210> SEQ ID NO 16
<211> LENGTH: 20
<212> TYPE: DNA
<213> ORGANISM: Homo sapiens

<400> SEQUENCE: 16
ttactcgtgt caaagccgtt                                                20

<210> SEQ ID NO 17
<211> LENGTH: 20
<212> TYPE: DNA
<213> ORGANISM: Homo sapiens

<400> SEQUENCE: 17
tgtcaaagcc gttaggatcc                                                20

<210> SEQ ID NO 18
<211> LENGTH: 20
<212> TYPE: DNA
<213> ORGANISM: Homo sapiens

<400> SEQUENCE: 18
gccgttagga tcctggcttg                                                20

<210> SEQ ID NO 19
<211> LENGTH: 20
<212> TYPE: DNA
<213> ORGANISM: Homo sapiens

<400> SEQUENCE: 19
gcggagtggc taaagtgctt                                                20

<210> SEQ ID NO 20
<211> LENGTH: 20
<212> TYPE: DNA
<213> ORGANISM: Homo sapiens

<400> SEQUENCE: 20
tccgcaagcc aggatcctaa                                                20

```
<210> SEQ ID NO 21
<211> LENGTH: 20
<212> TYPE: DNA
<213> ORGANISM: Homo sapiens

<400> SEQUENCE: 21
gttcggcttt gagcttcctc                                              20

<210> SEQ ID NO 22
<211> LENGTH: 20
<212> TYPE: DNA
<213> ORGANISM: Homo sapiens

<400> SEQUENCE: 22
gagatggtga tcatgagacc                                              20

<210> SEQ ID NO 23
<211> LENGTH: 20
<212> TYPE: DNA
<213> ORGANISM: Homo sapiens

<400> SEQUENCE: 23
ttgtactcat atttgtttcc                                              20

<210> SEQ ID NO 24
<211> LENGTH: 20
<212> TYPE: DNA
<213> ORGANISM: Homo sapiens

<400> SEQUENCE: 24
aacaaatatg agtacaagtt                                              20

<210> SEQ ID NO 25
<211> LENGTH: 800
<212> TYPE: DNA
<213> ORGANISM: Homo sapiens

<400> SEQUENCE: 25
accgctctca gaccagaaac gtccacaccc gccctccgat ggcctgtcgc cctggctagg    60
ttttagggtc agtgggatcc tccttccact ggacccggga gaagacgctc aacagccccc   120
tccttcccct ccttcctctc cttcctctcc ttccccctc cctgcgccgc tccagagcgc    180
aacaaccatt ttcccagcca ggagcacacc gtgtccacgc gccacagcga tctcactgat   240
tggtcgggct cctggtaaac aaggaccggg cagccaatgg gagggatgtg cacgagggca   300
gcacgagcct ccgggccagc gctcgcgtgg ctcttctggc ccgggctact atatagagac   360
gtttccgcct cctgcttgaa actaacccct cttttttctcc aaaggagtgc ttgtggagat   420
cggatctttt ctccagcaat tgggggaaag aaggcttttt ctctgaatta gcttagtgta   480
accagcggcg tatatttttt aggcgccttt tcgaaaacct agtagttaat attcatttgt   540
ttaaatctta ttttattttt aagctcaaac tgcttaagaa taccttaatt ccttaaagtg   600
aaataatttt ttgcaaaggg gtttcctcga tttggagctt ttttttttctt ccaccgtcat   660 ttctaactct taaaccaac tcagttccat catggtgatg ttcaagaaga tcaagtcttt   720
tgaggtggtc tttaacgacc ctgaaaaggt gtacggcagt ggcgagaagg tggctggccg    780
ggtgatagtg gaggtgtgtg                                              800

<210> SEQ ID NO 26
<211> LENGTH: 60
```

```
<212> TYPE: DNA
<213> ORGANISM: Homo sapiens

<400> SEQUENCE: 26
atgtctcgct ccgtggcctt agctgtgctc gcgctactct ctctttctgg cctggaggct      60

<210> SEQ ID NO 27
<211> LENGTH: 27
<212> TYPE: DNA
<213> ORGANISM: Homo sapiens

<400> SEQUENCE: 27
gtcatggcgc cccgaaccct cttcctg                                          27

<210> SEQ ID NO 28
<211> LENGTH: 45
<212> TYPE: DNA
<213> ORGANISM: Artificial Sequence
<220> FEATURE:
<223> OTHER INFORMATION: Synthesized

<400> SEQUENCE: 28
ggtggaggcg gttcaggcgg aggtggctct ggcggtggcg gatcg                      45

<210> SEQ ID NO 29
<211> LENGTH: 297
<212> TYPE: DNA
<213> ORGANISM: Homo sapiens

<400> SEQUENCE: 29
atccagcgta ctccaaagat tcaggtttac tcacgtcatc cagcagagaa tggaaagtca      60
aatttcctga attgctatgt gtctgggttt catccatccg acattgaagt tgacttactg     120
aagaatggag agagaattga aaaagtggag cattcagact tgtctttcag caaggactgg     180
tctttctatc tcttgtacta cactgaattc acccccactg aaaaagatga gtatgcctgc     240
cgtgtgaacc atgtgacttt gtcacagccc aagatagtta agtgggatcg agacatg       297

<210> SEQ ID NO 30
<211> LENGTH: 60
<212> TYPE: DNA
<213> ORGANISM: Artificial Sequence
<220> FEATURE:
<223> OTHER INFORMATION: Synthesized

<400> SEQUENCE: 30
ggtggtggtg gttctggtgg tggtggttct ggcggcggcg gctccggtgg tggtggatcc      60

<210> SEQ ID NO 31
<211> LENGTH: 1011
<212> TYPE: DNA
<213> ORGANISM: Homo sapiens

<400> SEQUENCE: 31
ggctcccact ccttgaagta tttccacact tccgtgtccc ggcccggccg cggggagccc      60
cgcttcatct ctgtgggcta cgtggacgac acccagttcg tgcgcttcga caacgacgcc     120
gcgagtccga ggatggtgcc gcgggcgccg tggatggagc aggagggtc agagtattgg     180 gaccgggaga cacggagcgc caggacacc gcacagattt tccgagtgaa tctgcggacg     240
ctgcgcggct actacaatca gagcgaggcc gggtctcaca ccctgcagtg gatgcatggc     300
tgcgagctgg ggcccgacgg gcgcttcctc cgcgggtatg aacagttcgc ctacgacggc     360
```

| | |
|---|---|
| aaggattatc tcaccctgaa tgaggacctg cgctcctgga ccgcggtgga cacggcggct | 420 |
| cagatctccg agcaaaagtc aaatgatgcc tctgaggcgg agcaccagag agcctacctg | 480 |
| gaagacacat gcgtggagtg gctccacaaa tacctggaga aggggaagga gacgctgctt | 540 |
| cacctggagc ccccaaagac acacgtgact caccacccca tctctgacca tgaggccacc | 600 |
| ctgaggtgct gggccctggg cttctaccct gcggagatca cactgacctg gcagcaggat | 660 |
| ggggagggcc atacccagga cacggagctc gtggagacca ggcctgcagg ggatggaacc | 720 |
| ttccagaagt gggcagctgt ggtggtgcct tctggagagg agcagagata cacgtgccat | 780 |
| gtgcagcatg aggggctacc cgagcccgtc accctgagat ggaagccggc ttcccagccc | 840 |
| accatcccca tcgtgggcat cattgctggc ctggttctcc ttggatctgt ggtctctgga | 900 |
| gctgtggttg ctgctgtgat atggaggaag aagagctcag gtggaaaagg agggagctac | 960 |
| tctaaggctg agtggagcga cagtgcccag gggtctgagt ctcacagctt g | 1011 |

<210> SEQ ID NO 32
<211> LENGTH: 800
<212> TYPE: DNA
<213> ORGANISM: Homo sapiens

<400> SEQUENCE: 32

| | |
|---|---|
| cagggatccc agcagtgcaa acagacttcg gagtacctgc gctatgaaga cacgcttctt | 60 |
| ctggaagacc agccaacagg taagcggccc aattcattgt tggagggtga agctgatta | 120 |
| gagaagagaa ttgaatacac aaaacctgta cgaaatgttt taagttgctc agtttgagtg | 180 |
| gtttgaatta cgtgttgttg cttcctttt tctgttttaa tttgcagaca ttctcctccc | 240 |
| cccccaaaaa aagggtgat ttgtacaatt ttttatggtg ctgtgtccta aggggatcc | 300 |
| tgaggggcgt tgcctcgggt agttaaagtc ttatgtgtgc ataagttgct tattctttgt | 360 |
| ctacttccta tttgagatgt tagtagagaa ctgtcctggg tgaatctttc agtattgcag | 420 |
| ggcttggcaa cttgctgccc gacaaaatac atcagaattt ctctttaaga acaatatggg | 480 |
| atggattaaa aaatatatat atgggatgaa attggggggta cttcaatacc ttgcatgcca | 540 |
| cccaagcatt ccttatcaca cagatgcatt ttaagtgtaa cagcaagcct aatggctact | 600 |
| cgattttctt tcccttcagg tgagaatgag atggtgatca tgagacctgg aaacaaatat | 660 |
| gagtacaagt tcggctttga gcttcctcag gggtaaatat cagctaaatg catctttgaa | 720 |
| cttttctgtc taaaatatct tgccctcctt tgatcactta ctgttcttgg agagcgtttt | 780 |
| aaaattttca ttttcttgac | 800 |

<210> SEQ ID NO 33
<211> LENGTH: 7133
<212> TYPE: DNA
<213> ORGANISM: Artificial Sequence
<220> FEATURE:
<223> OTHER INFORMATION: Synthesized

<400> SEQUENCE: 33

| | |
|---|---|
| cctgcaggca gctgcgcgct cgctcgctca ctgaggccgc ccgggcgtcg ggcgaccttt | 60 |
| ggtcgcccgg cctcagtgag cgagcgagcg cgcagagagg gagtggccaa ctccatcact | 120 |
| aggggttcct gcggccgcac gcgtgttcta gggtggaaac taagagaatg atgtacctag | 180 |
| agggcgctgg aagctctaaa gccctagcag ttactgcttt tactattagt ggtcgttttt | 240 |
| ttctcccccc cgcccccga caaatcaaca gaacaaagaa aattacctaa acagcaagga | 300 |
| catagggagg aacttcttgg cacagaactt tccaaacact ttttcctgaa gggatacaag | 360 |

```
aagcaagaaa ggtactcttt cactaggacc ttctctgagc tgtcctcagg atgcttttgg    420
gactattttt cttacccaga gaatggagaa accctgcagg gaattcccaa gctgtagtta    480
taaacagaag ttctccttct gctaggtagc attcaaagat cttaatcttc tgggtttccg    540
ttttctcgaa tgaaaaatgc aggtccgagc agttaactgg ctggggcacc attagcaagt    600
cacttagcat ctctggggcc agtctgcaaa gcgaggggc agccttaatg tgcctccagc    660
ctgaagtcct agaatgagcg cccggtgtcc caagctgggg cgcgcacccc agatcggagg    720
gcgccgatgt acagacagca aactcaccca gtctagtgca tgccttctta aacatcacga    780
gactctaaga aaaggaaact gaaaacggga agtccctct ctctaacctg gcactgcgtc     840
gctggcttgg agacaggtga cggtccctgc gggccttgtc ctgattggct gggcacgcgt    900
ttaatataag tggaggcgtc gcgctggcgg gcattcctga agctaagctt gtggacgata    960
tcgaattcgc acgacattga ttattgacta gttattaata gtaatcaatt acgggtcat   1020 tagttcatag cccatatatg gagttccgcg ttacataact tacggtaaat ggcccgcctg   1080
gctgaccgcc caacgacccc cgcccattga cgtcaataat gacgtatgtt cccatagtaa   1140
cgccaatagg gactttccat tgacgtcaat gggtggacta tttacggtaa actgcccact   1200
tggcagtaca tcaagtgtat catatgccaa gtacgccccc tattgacgtc aatgacggta   1260
aatggcccgc ctggcattat gcccagtaca tgaccttatg gactttcct acttggcagt    1320 acatctacgt attagtcatc gctattacca tgggtcgagg tgagccccac gttctgcttc    1380
actctcccca tctccccccc ctccccaccc ccaattttgt atttatttat tttttaatta   1440
ttttgtgcag cgatggggc ggggggggggg ggggcgcgcg ccaggcgggg cggggcgggg    1500
cgaggggcgg ggcggggcga ggcggagagg tgcggcggca gccaatcaga gcggcgcgct   1560
ccgaaagttt cctttatgg cgaggcggcg gcggcggcgg ccctataaaa agcgaagcgc    1620
gcggcgggcg ggagtcgctg cgttgccttc gccccgtgcc ccgctccgcg ccgcctcgcg   1680
ccgcccgccc cggctctgac tgaccgcgtt actcccacag gtgagcgggc gggacggccc   1740
ttctcctccg gctgtaatt agcgcttggt ttaatgacgg ctcgtttctt ttctgtggct    1800
gcgtgaaagc cttaaagggc tccggagggg ccctttgtgc ggggggagc ggctcggggg    1860 gtgcgtgcgt gtgtgtgtgc gtggggagcg ccgcgtgcgg cccgcgctgc ccggcggctg   1920
tgagcgctgc gggcgcggcg cggggctttg tgcgctccgc gtgtgcgcga ggggagcgcg   1980
gccgggggcg gtgccccgcg gtgcgggggg gctgcgaggg gaacaaaggc tgcgtgcggg   2040
gtgtgtgcgt gggggggtga gcaggggggtg tgggcgcggc ggtcgggctg taacccccc    2100 ctgcaccccc ctccccgagt tgctgagcac ggcccggctt cgggtgcggg gctccgtgcg   2160
gggcgtggcg cggggctcgc cgtgccggc gggggtggc ggcaggtggg ggtgccgggc     2220 ggggcgggc cgcctcgggc cggggagggc tcggggagg ggcgcggcgg ccccggagcg     2280
ccggcggctg tcgaggcgcg gcgagccgca gccattgcct tttatggtaa tcgtgcgaga   2340
gggcgcaggg acttcctttg tcccaaatct ggcggagccg aaatctggga ggcgccgccg   2400
caccccctct agcgggcgcg ggcgaagcgg tgcggcgccg gcaggaagga aatgggcggg   2460
gagggccttc gtgcgtcgcc gcgccgccgt ccccttctcc atctccagcc tcggggctgc   2520
cgcaggggga cggctgcctt cgggggggac ggggcagggc ggggttcggc ttctggcgtg   2580
tgaccggcgg ctctagagcc tctgctaacc atgttcatgc cttcttcttt ttcctacagg   2640
ggggatccgt ttatctgcag aattcgccct tgacgtcgcc accatgagga tatttgctgt   2700
```

```
ctttatattc atgacctact ggcatttgct gaacgcattt actgtcacgg ttcccaagga    2760
cctatatgtg gtagagtatg gtagcaatat gacaattgaa tgcaaattcc cagtagaaaa    2820
acaattagac ctggctgcac taattgtcta ttgggaaatg gaggataaga acattattca    2880
atttgtgcat ggagaggaag acctgaaggt tcagcatagt agctacagac agagggcccg    2940
gctgttgaag gaccagctct ccctgggaaa tgctgcactt cagatcacag atgtgaaatt    3000
gcaggatgca ggggtgtacc gctgcatgat cagctatggt ggtgccgact acaagcgaat    3060
tactgtgaaa gtcaatgccc catacaacaa aatcaaccaa agaattttgg ttgtggatcc    3120
agtcacctct gaacatgaac tgacatgtca ggctgagggc taccccaagg ccgaagtcat    3180
ctggacaagc agtgaccatc aagtcctgag tggtaagacc accaccacca attccaagag    3240
agaggagaaa cttttcaatg tgaccagcac actgagaatc aacacaacaa ctaatgagat    3300
tttctactgc acttttagga gattagatcc tgaggaaaac catacagctg aattggtcat    3360
cccagaacta cctctggcac atcctccaaa tgaaaggact cacttggtaa ttctgggagc    3420
catcttatta tgccttggtg tagcactgac attcatcttc cgtttaagaa aagggagaat    3480
gatggatgtg aaaaaatgtg gcatccaaga tacaaactca agaagcaaa gtgatacaca     3540
tttgaggag acgtaaccgc tgatcagcct cgactgtgcc ttctagttgc cagccatctg     3600
ttgtttgccc ctcccccgtg ccttccttga ccctggaagg tgccactccc actgtccttt    3660
cctaataaaa tgaggaaatt gcatcgcatt gtctgagtag gtgtcattct attctggggg    3720
gtgggggtgg gcaggacagc aaggggagg attgggaaga caatagcagg catgctgggg    3780
atgcggtggg ctctatgggt cgacccagcg tgagtctctc ctaccctccc gctctggtcc    3840
ttcctctccc gctctgcacc ctctgtggcc ctcgctgtgc tctctcgctc cgtgacttcc    3900
cttctccaag ttctccttgg tggcccgccg tggggctagt ccaggctgg atctcgggga    3960
agcggcgggg tggcctggga gtggggaagg gggtgcgcac ccgggacgcg cgctacttgc    4020
cccttcggc ggggagcagg ggagacccttt ggcctacggc gacggagggg tcgggacaaa    4080
gtttagggcg tcgataagcg tcagagcgcc gaggttgggg gagggtttct cttccgctct    4140
ttcgcggggc ctctggctcc cccagcgcag ctggagtggg ggacgggtag gctcgtccca    4200
aaggcgcggc gctgaggttt gtgaacgcgt ggaggggcgc ttggggtctg ggggaggcgt    4260
cgccccgggta agcctgtctg ctgcggctct gcttccctta gactgagag ctgtggactt    4320
cgtctaggcg cccgctaagt tcgcatgtcc tagcacctct gggtctatgt ggggccacac    4380
cgtggggagg aaacagcacg cgacgttttgt agaatgcttg gctgtgatac aaagcggttt    4440
cgaataatta acttatttgt tcccatcaca tgtcactttt aaaaaattat aagaactacc    4500
cgttattgac atctttctgt gtgccaagga ctttatgtgc tttgcgtcat ttaattttga    4560
aaacagttat cttccgccat agataactac tatggttatc ttctggtaac cacgtgcgga    4620
ccgaggctgc agcgtcgtcc tccctaggaa cccctagtga tggagttggc cactccctct    4680
ctgcgcgctc gctcgctcac tgaggccggg cgaccaaagg tcgcccgacg cccgggcttt    4740
gcccgggcgg cctcagtgag cgagcgagcg cgcagctgcc tgcaggggcg cctgatgcgg    4800
tattttctcc ttacgcatct gtgcggtatt tcacaccgca tacgtcaaag caaccatagt    4860
acgcgccctg tagcggcgca ttaagcgcgg cgggtgtggt ggttacgcgc agcgtgaccg    4920
ctacacttgc cagcgcccta gcgcccgctc ctttcgcttt cttcccttcc tttctcgcca    4980
cgttcgccgg ctttccccgt caagctctaa atcgggggct ccctttaggg ttccgattta    5040
gtgctttacg gcacctcgac cccaaaaaac ttgatttggg tgatggttca cgtagtgggc    5100
```

```
catcgccctg atagacggtt tttcgcccctt tgacgttgga gtccacgttc tttaatagtg    5160
gactcttgtt ccaaactgga acaacactca accctatctc gggctattct tttgatttat    5220
aagggatttt gccgatttcg gcctattggt taaaaatga gctgatttaa caaaaattta    5280
acgcgaattt taacaaaata ttaacgttta caattttatg gtgcactctc agtacaatct    5340
gctctgatgc cgcatagtta agccagcccc gacacccgcc aacacccgct gacgcgccct    5400
gacgggcttg tctgctcccg gcatccgctt acagacaagc tgtgaccgtc tccgggagct    5460
gcatgtgtca gaggttttca ccgtcatcac cgaaacgcgc gagacgaaag gcctcgtga    5520
tacgcctatt tttataggtt aatgtcatga acaataaaac tgtctgctta cataaacagt    5580
aatacaaggg gtgttatgag ccatattcaa cgggaaacgt cgaggccgcg attaaattcc    5640
aacatggatg ctgatttata tgggtataaa tgggctcgcg ataatgtcgg gcaatcaggt    5700
gcgacaatct atcgcttgta tgggaagccc gatgcgccag agttgtttct gaaacatggc    5760
aaaggtagcg ttgccaatga tgttacagat gagatggtca gactaaactg gctgacggaa    5820
tttatgcctc ttccgaccat caagcatttt atccgtactc ctgatgatgc atggttactc    5880
accactgcga tccccggaaa aacagcattc caggtattag aagaatatcc tgattcaggt    5940
gaaaatattg ttgatgcgct ggcagtgttc ctgcgccggt tgcattcgat tcctgtttgt    6000
aattgtcctt ttaacagcga tcgcgtattt cgtctcgctc aggcgcaatc acgaatgaat    6060
aacggtttgg ttgatgcgag tgattttgat gacgagcgta atggctggcc tgttgaacaa    6120
gtctggaaag aaatgcataa acttttgcca ttctcaccgg attcagtcgt cactcatggt    6180
gatttctcac ttgataacct tattttgac gaggggaaat taataggttg tattgatgtt    6240
ggacgagtcg gaatcgcaga ccgataccag gatcttgcca tcctatggaa ctgcctcggt    6300
gagttttctc cttcattaca gaaacggctt tttcaaaaat atggtattga taatcctgat    6360
atgaataaat tgcagtttca tttgatgctc gatgagtttt tctaatctca tgaccaaaat    6420
cccttaacgt gagttttcgt tccactgagc gtcagacccc gtagaaaaga tcaaaggatc    6480
ttcttgagat cctttttttc tgcgcgtaat ctgctgcttg caaacaaaaa aaccaccgct    6540
accagcggtg gtttgtttgc cggatcaaga gctaccaact cttttttccga aggtaactgg    6600
cttcagcaga gcgcagatac caaatactgt ccttctagtg tagccgtagt taggccacca    6660
cttcaagaac tctgtagcac cgcctacata cctcgctctg ctaatcctgt taccagtggc    6720
tgctgccagt ggcgataagt cgtgtcttac cgggttggac tcaagacgat agttaccgga    6780
taaggcgcag cggtcgggct gaacgggggg ttcgtgcaca cagcccagct tggagcgaac    6840
gacctacacc gaactgagat acctacagcg tgagctatga gaaagcgcca cgcttcccga    6900
agggagaaag gcggacaggt atccggtaag cggcagggtc ggaacaggag agcgcacgag    6960
ggagcttcca gggggaaacg cctggtatct ttatagtcct gtcgggtttc gccacctctg    7020
acttgagcgt cgatttttgt gatgctcgtc aggggggcgg agcctatgga aaaacgccag    7080
caacgcggcc ttttacggt tcctggcctt ttgctggcct tttgctcaca tgt           7133
```

<210> SEQ ID NO 34
<211> LENGTH: 7763
<212> TYPE: DNA
<213> ORGANISM: Artificial Sequence
<220> FEATURE:
<223> OTHER INFORMATION: Synthesized

<400> SEQUENCE: 34

```
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggccgcac gcgtaccgct ctcagaccag aaacgtccac acccgccctc     180
cgatggcctg tcgccctggc taggttttag ggtcagtggg atcctccttc cactggaccc     240
gggagaagac gctcaacagc cccctccttc ccctccttcc tctccttcct ctccttcccc     300
cctccctgcg ccgctccaga gcgcaacaac cattttccca gccaggagca caccgtgtcc     360
acgcgccaca gcgatctcac tgattggtcg ggctcctggt aaacaaggac cgggcagcca     420
atgggaggga tgtgcacgag ggcagcacga gcctccgggc cagcgctcgc gtggctcttc     480
tggcccgggc tactatatag agacgtttcc gcctcctgct tgaaactaac ccctctttt      540 ctccaaagga gtgcttgtgg agatcggatc ttttctccag caattggggg aaagaaggct     600
ttttctctga attagcttag tgtaaccagc ggcgtatatt ttttaggcgc cttttcgaaa     660
acctagtagt taatattcat ttgtttaaat cttattttat ttttaagctc aaactgctta     720
agaatacctt aattccttaa agtgaaataa ttttttgcaa aggggtttcc tcgatttgga     780 gcttttttt tcttccaccg tcatttctaa ctcttaaaac caactcagtt ccatcatggt     840
gatgttcaag aagatcaagt cttttgaggt ggtcttaac gaccctgaaa aggtgtacgg     900
cagtggcgag aaggtggctg gccgggtgat agtggaggtg tgtgaagctt gtggacgata     960
tcgaattcgc acgacattga ttattgacta gttattaata gtaatcaatt acggggtcat    1020
tagttcatag cccatatatg gagttccgcg ttacataact tacggtaaat ggcccgcctg    1080
gctgaccgcc caacgacccc cgcccattga cgtcaataat gacgtatgtt cccatagtaa    1140
cgccaatagg gactttccat tgacgtcaat gggtggacta tttacggtaa actgcccact    1200
tggcagtaca tcaagtgtat catatgccaa gtacgccccc tattgacgtc aatgacggta    1260
aatggcccgc ctggcattat gcccagtaca tgaccttatg gactttcct acttggcagt    1320 acatctacgt attagtcatc gctattacca tgggtcgagg tgagccccac gttctgcttc    1380
actctcccca tctcccccc ctccccaccc ccaattttgt atttatttat ttttaatta    1440 ttttgtgcag cgatggggc ggggggggg ggggcgcgcg ccaggcgggg cggggcgggg    1500
cgaggggcgg ggcggggcga ggcggagagg tgcggcggca gccaatcaga gcggcgcgct    1560
ccgaaagttt cctttatgg cgaggcgcg cggcggcgg ccctataaaa agcgaagcgc    1620
gcggcgggcg ggagtcgctg cgttgccttc gccccgtgcc ccgctccgcg ccgcctcgcg    1680
ccgcccgccc cggctctgac tgaccgcgtt actcccacag gtgagcgggc gggacggccc    1740
ttctcctccg ggctgtaatt agcgcttggt ttaatgacgg ctcgtttctt ttctgtggct    1800
gcgtgaaagc cttaaagggc tccgggaggg ccctttgtgc ggggggggagc ggctcggggg    1860 gtgcgtgcgt gtgtgtgtgc gtggggagcg ccgcgtgcgg cccgcgctgc ccggcggctg    1920
tgagcgctgc gggcgcggcg cggggctttg tgcgctccgc gtgtgcgcga ggggagcgcg    1980 gccggggggcg gtgcccgcg gtgcgggggg gctgcgaggg gaacaaaggc tgcgtgcggg    2040
gtgtgtgcgt ggggggtga gcaggggtg tgggcgcggc ggtcgggctg taaccccccc    2100
ctgcaccccc ctccccgagt tgctgagcac ggcccggctt cggtgcggg gctccgtgcg    2160 gggcgtggcg cggggctcgc cgtgccgggc gggggtggc ggcaggtggg ggtgccgggc    2220
ggggcggggc cgcctcgggc cggggagggc tcggggagg ggcgcggcgg ccccggagcg    2280
ccggcggctg tcgaggcgcg gcgagccgca gccattgcct tttatggtaa tcgtgcgaga    2340
gggcgcaggg acttcctttg tcccaaatct ggcggagccg aaatctggga ggcgccgccg    2400
```

-continued

```
caccccctct agcgggcgcg ggcgaagcgg tgcggcgccg gcaggaagga aatgggcggg    2460
gagggccttc gtgcgtcgcc gcgccgccgt ccccttctcc atctccagcc tcggggctgc    2520
cgcaggggga cggctgcctt cggggggggac ggggcagggc ggggttcggc ttctggcgtg    2580
tgaccggcgg ctctagagcc tctgctaacc atgttcatgc cttcttcttt ttcctacagg    2640
ggggatccgt ttatctgcag aattcgccct tgacgtcgcc accatgtctc gctccgtggc    2700
cttagctgtg ctcgcgctac tctctctttc tggcctggag gctgtcatgg cgcccgaac    2760 cctcttcctg ggtggaggcg gttcaggcgg aggtggctct ggcggtggcg gatcgatcca    2820
gcgtactcca aagattcagg tttactcacg tcatccagca gagaatggaa agtcaaattt    2880
cctgaattgc tatgtgtctg ggtttcatcc atccgacatt gaagttgact tactgaagaa    2940
tggagagaga attgaaaaag tggagcattc agacttgtct ttcagcaagg actggtcttt    3000
ctatctcttg tactacactg aattcacccc cactgaaaaa gatgagtatg cctgccgtgt    3060
gaaccatgtg actttgtcac agcccaagat agttaagtgg gatcgagaca tgggtggtgg    3120
tggttctggt ggtggtggtt ctggcggcgg cggctccggt ggtggtggat ccggctccca    3180
ctccttgaag tatttccaca cttccgtgtc ccggcccggc cgcggggagc cccgcttcat    3240
ctctgtgggc tacgtggacg acacccagtt cgtgcgcttc gacaacgacg ccgcgagtcc    3300
gaggatggtg ccgcgggcgc cgtggatgga gcaggagggg tcagagtatt gggaccggga    3360
gacacggagc gccagggaca ccgcacagat tttccgagtg aatctgcgga cgctgcgcgg    3420
ctactacaat cagagcgagg ccgggtctca cacccctgcag tggatgcatg gctgcgagct    3480
ggggcccgac gggcgcttcc tccgcgggta tgaacagttc gcctacgacg gcaaggatta    3540 tctcacccctg aatgaggacc tgcgctcctg gaccgcggtg gacacggcgg ctcagatctc    3600
cgagcaaaag tcaaatgatg cctctgaggc ggagcaccag agagcctacc tggaagacac    3660
atgcgtggag tggctccaca aatacctgga gaaggggaag gagacgctgc ttcacctgga    3720 gccccccaaag acacacgtga ctcaccaccc catctctgac catgaggcca ccctgaggtg    3780
ctgggccctg gcttctacc ctgcggagat cacactgacc tggcagcagg atggggaggg    3840
ccatacccag gacacggagc tcgtggagac caggcctgca ggggatggaa ccttccagaa    3900
gtgggcagct gtggtggtgc cttctggaga ggagcagaga tacacgtgcc atgtgcagca    3960 tgagggcta cccgagcccg tcaccctgag atggaagccg gcttcccagc ccaccatccc    4020
catcgtgggc atcattgctg gcctggttct ccttggatct gtggtctctg agctgtggt    4080 tgctgctgtg atatggagga agaagagctc aggtggaaaa ggaggggagct actctaaggc    4140 tgagtggagc gacagtgccc aggggtctga gtctcacagc ttgtaaccgc tgatcagcct    4200
cgactgtgcc ttctagttgc cagccatctg ttgtttgccc ctccccgtg ccttccttga    4260 ccctggaagg tgccactccc actgtccttt cctaataaaa tgaggaaatt gcatcgcatt    4320
gtctgagtag tgtcattct attctggggg gtggggtggg gcaggacagc aagggggagg    4380
attgggaaga caatagcagg catgctgggg atgcggtggg ctctatgggt cgaccaggga    4440
tcccagcagt gcaaacagac ttcggagtac ctgcgctatg aagacacgct tcttctggaa    4500
gaccagccaa caggtaagcg gcccaattca ttgttggagg gtgaaagctg attagagaag    4560
agaattgaat acacaaaacc tgtacgaaat gttttaagtt gctcagtttg agtggtttga    4620
attacgtgtt gttgcttcct tttttctgtt ttaatttgca gacattctcc tcccccccca    4680
aaaaaaaggg tgatttgtac aattttttat ggtgctgtgt cctaaagggg atcctgaggg    4740
```

```
gcgttgcctc gggtagttaa agtcttatgt gtgcataagt tgcttattct ttgtctactt    4800
cctatttgag atgttagtag agaactgtcc tgggtgaatc tttcagtatt gcagggcttg    4860
gcaacttgct gcccgacaaa atacatcaga atttctcttt aagaacaata tgggatggat    4920
taaaaaatat atatatggga tgaaattggg ggtacttcaa taccttgcat gccacccaag    4980
cattccttat cacacagatg cattttaagt gtaacagcaa gcctaatggc tactcgattt    5040
tctttccctt caggtgagaa tgagatggtg atcatgagac ctggaaacaa atatgagtac    5100
aagttcggct ttgagcttcc tcaggggtaa atatcagcta aatgcatctt tgaacttttc    5160
tgtctaaaat atcttgccct cctttgatca cttactgttc ttggagagcg ttttaaaatt    5220
ttcattttct tgacggtaac cacgtgcgga ccgaggctgc agcgtcgtcc tccctaggaa    5280
cccctagtga tggagttggc cactccctct ctgcgcgctc gctcgctcac tgaggccggg    5340
cgaccaaagg tcgcccgacg cccgggcttt gcccgggcgg cctcagtgag cgagcgagcg    5400
cgcagctgcc tgcaggggcg cctgatgcgg tattttctcc ttacgcatct gtgcggtatt    5460
tcacaccgca tacgtcaaag caaccatagt acgcgccctg tagcggcgca ttaagcgcgg    5520
cgggtgtggt ggttacgcgc agcgtgaccg ctacacttgc cagcgcccta gcgcccgctc    5580
cttttcgctt tcttcccttc ctttctcgcca cgttcgccgg ctttccccgt caagctctaa    5640
atcgggggct ccctttaggg ttccgattta gtgctttacg gcacctcgac cccaaaaaac    5700
ttgatttggg tgatggttca cgtagtgggc catcgccctg atagacggtt tttcgccctt    5760
tgacgttgga gtccacgttc tttaatagtg gactcttgtt ccaaactgga caacactca    5820
accctatctc gggctattct tttgatttat aagggatttt gccgatttcg gcctattggt    5880
taaaaaatga gctgatttaa caaaaattta acgcgaattt taacaaaata ttaacgttta    5940
caattttatg gtgcactctc agtacaatct gctctgatgc cgcatagtta agccagcccc    6000
gacacccgcc aacacccgct gacgcgccct gacgggcttg tctgctcccg gcatccgctt    6060
acagacaagc tgtgaccgtc tccgggagct gcatgtgtca gaggttttca ccgtcatcac    6120
cgaaacgcgc gagacgaaag ggcctcgtga tacgcctatt tttataggtt aatgtcatga    6180
acaataaaac tgtctgctta cataaacagt aatacaaggg gtgttatgag ccatattcaa    6240
cgggaaacgt cgaggccgcg attaaattcc aacatggatg ctgatttata tgggtataaa    6300
tgggctcgcg ataatgtcgg gcaatcaggt gcgacaatct atcgcttgta tgggaagccc    6360
gatgcgccag agttgtttct gaaacatggc aaaggtagcg ttgccaatga tgttacagat    6420
gagatggtca gactaaactg gctgacggaa tttatgcctc ttccgaccat caagcatttt    6480
atccgtactc ctgatgatgc atggttactc accactgcga tccccggaaa aacagcattc    6540
caggtattag aagaatatcc tgattcaggt gaaaatattg ttgatgcgct ggcagtgttc    6600
ctgcgccggt tgcattcgat tcctgtttgt aattgtcctt ttaacagcga tcgcgtattt    6660
cgtctcgctc aggcgcaatc acgaatgaat aacggtttgg ttgatgcgag tgattttgat    6720
gacgagcgta atggctggcc tgttgaacaa gtctggaaag aaatgcataa acttttgcca    6780
ttctcaccgg attcagtcgt cactcatggt gatttctcac ttgataacct tattttgac    6840
gaggggaaat taataggttg tattgatgtt ggacgagtcg gaatcgcaga ccgataccag    6900
gatcttgcca tcctatggaa ctgcctcggt gagttttctc cttcattaca gaaacggctt    6960
tttcaaaaat atggtattga taatcctgat atgaataaat tgcagtttca tttgatgctc    7020
gatgagtttt tctaatctca tgaccaaaat cccttaacgt gagttttcgt tccactgagc    7080
gtcagacccc gtagaaaaga tcaaaggatc ttcttgagat cctttttttc tgcgcgtaat    7140
```

```
ctgctgcttg caaacaaaaa aaccaccgct accagcggtg gtttgtttgc cggatcaaga    7200
gctaccaact cttttttccga aggtaactgg cttcagcaga gcgcagatac caaatactgt    7260
ccttctagtg tagccgtagt taggccacca cttcaagaac tctgtagcac cgcctacata    7320
cctcgctctg ctaatcctgt taccagtggc tgctgccagt ggcgataagt cgtgtcttac    7380
cgggttggac tcaagacgat agttaccgga taaggcgcag cggtcgggct gaacgggggg    7440
ttcgtgcaca cagcccagct tggagcgaac gacctacacc gaactgagat acctacagcg    7500
tgagctatga gaaagcgcca cgcttcccga agggagaaag gcggacaggt atccggtaag    7560
cggcagggtc ggaacaggag agcgcacgag ggagcttcca gggggaaacg cctggtatct    7620
ttatagtcct gtcgggtttc gccacctctg acttgagcgt cgattttttgt gatgctcgtc    7680 agggggggcgg agcctatgga aaaacgccag caacgcggcc ttttttacggt tcctggcctt    7740 ttgctggcct tttgctcaca tgt                                            7763

<210> SEQ ID NO 35
<211> LENGTH: 20
<212> TYPE: DNA
<213> ORGANISM: Homo sapiens

<400> SEQUENCE: 35
tataagtgga ggcgtcgcgc                                                  20

<210> SEQ ID NO 36
<211> LENGTH: 20
<212> TYPE: DNA
<213> ORGANISM: Homo sapiens

<400> SEQUENCE: 36
gagtagcgcg agcacagcta                                                  20

<210> SEQ ID NO 37
<211> LENGTH: 20
<212> TYPE: DNA
<213> ORGANISM: Homo sapiens

<400> SEQUENCE: 37
actggacgcg tcgcgctggc                                                  20

<210> SEQ ID NO 38
<211> LENGTH: 20
<212> TYPE: DNA
<213> ORGANISM: Homo sapiens

<400> SEQUENCE: 38
aagtggaggc gtcgcgctgg                                                  20

<210> SEQ ID NO 39
<211> LENGTH: 20
<212> TYPE: DNA
<213> ORGANISM: Homo sapiens

<400> SEQUENCE: 39
ggccacggag cgagacatct                                                  20

<210> SEQ ID NO 40
<211> LENGTH: 20
<212> TYPE: DNA
<213> ORGANISM: Homo sapiens
```

```
<400> SEQUENCE: 40
gcccgaatgc tgtcagcttc                                              20

<210> SEQ ID NO 41
<211> LENGTH: 20
<212> TYPE: DNA
<213> ORGANISM: Homo sapiens

<400> SEQUENCE: 41
ctcgcgctac tctctctttc                                              20

<210> SEQ ID NO 42
<211> LENGTH: 20
<212> TYPE: DNA
<213> ORGANISM: Homo sapiens

<400> SEQUENCE: 42
tcctgaagct gacagcattc                                              20

<210> SEQ ID NO 43
<211> LENGTH: 20
<212> TYPE: DNA
<213> ORGANISM: Homo sapiens

<400> SEQUENCE: 43
ttcctgaagc tgacagcatt                                              20

<210> SEQ ID NO 44
<211> LENGTH: 20
<212> TYPE: DNA
<213> ORGANISM: Homo sapiens

<400> SEQUENCE: 44
actctctctt tctggcctgg                                              20

<210> SEQ ID NO 45
<211> LENGTH: 23
<212> TYPE: DNA
<213> ORGANISM: Homo sapiens

<400> SEQUENCE: 45
gaagcgtgtc ttcatagcgc agg                                          23

<210> SEQ ID NO 46
<211> LENGTH: 23
<212> TYPE: DNA
<213> ORGANISM: Homo sapiens

<400> SEQUENCE: 46
ttactcgtgt caaagccgtt agg                                          23

<210> SEQ ID NO 47
<211> LENGTH: 23
<212> TYPE: DNA
<213> ORGANISM: Homo sapiens

<400> SEQUENCE: 47
tgtcaaagcc gttaggatcc tgg                                          23

<210> SEQ ID NO 48
<211> LENGTH: 23
<212> TYPE: DNA
<213> ORGANISM: Homo sapiens
```

```
<400> SEQUENCE: 48
gccgttagga tcctggcttg cgg                                          23

<210> SEQ ID NO 49
<211> LENGTH: 23
<212> TYPE: DNA
<213> ORGANISM: Homo sapiens

<400> SEQUENCE: 49
gcggagtggc taaagtgctt tgg                                          23

<210> SEQ ID NO 50
<211> LENGTH: 23
<212> TYPE: DNA
<213> ORGANISM: Homo sapiens

<400> SEQUENCE: 50
tccgcaagcc aggatcctaa cgg                                          23

<210> SEQ ID NO 51
<211> LENGTH: 23
<212> TYPE: DNA
<213> ORGANISM: Homo sapiens

<400> SEQUENCE: 51
gttcggcttt gagcttcctc agg                                          23

<210> SEQ ID NO 52
<211> LENGTH: 23
<212> TYPE: DNA
<213> ORGANISM: Homo sapiens

<400> SEQUENCE: 52
gagatggtga tcatgagacc tgg                                          23

<210> SEQ ID NO 53
<211> LENGTH: 23
<212> TYPE: DNA
<213> ORGANISM: Homo sapiens

<400> SEQUENCE: 53
ttgtactcat atttgtttcc agg                                          23

<210> SEQ ID NO 54
<211> LENGTH: 23
<212> TYPE: DNA
<213> ORGANISM: Homo sapiens

<400> SEQUENCE: 54
aacaaatatg agtacaagtt cgg                                          23

<210> SEQ ID NO 55
<211> LENGTH: 1500
<212> TYPE: DNA
<213> ORGANISM: Artificial Sequence
<220> FEATURE:
<223> OTHER INFORMATION: Synthesized

<400> SEQUENCE: 55
atgtctcgct ccgtggcctt agctgtgctc gcgctactct ctctttctgg cctggaggct    60
gtcatggcgc cccgaaccct cttcctgggt ggaggcggtt caggcggagg tggctctggc   120
```

```
ggtggcggat cgatccagcg tactccaaag attcaggttt actcacgtca tccagcagag    180
aatggaaagt caaatttcct gaattgctat gtgtctgggt ttcatcgatc cgacattgaa    240
gttgacttac tgaagaatgg agagagaatt gaaaaagtgg agcattcaga cttgtctttc    300
agcaaggact ggtctttcta tctcttgtac tacactgaat tcaccccccac tgaaaaagat   360 gagtatgcct gccgtgtgaa ccatgtgact ttgtcacagc caagatagt taagtgggat    420 cgagacatgg gtggtggtgg ttctggtggt ggtggttctg gcggcggcgg ctccggtggt   480
ggtggatccg gctcccactc cttgaagtat ttccacactt ccgtgtcccg gcccggccgc   540
ggggagcccc gcttcatctc tgtgggctac gtggacgaca cccagttcgt gcgcttcgac   600
aacgacgccg cgagtccgag gatggtgccg cgggcgccgt ggatggagca ggagggggtca  660 gagtattggg accggagac acggagcgcc agggacaccg cacagatttt ccgagtgaat   720
ctgcggacgc tgcgcggcta ctacaatcag agcgaggccg ggtctcacac cctgcagtgg   780
atgcatggct gcgagctggg gcccgacggg cgcttcctcc gcgggtatga acagttcgcc   840
tacgacggca aggattatct cacccctgaat gaggacctgc gctcctggac cgcggtggac   900
acggcggctc agatctccga gcaaaagtca aatgatgcct ctgaggcgga gcaccagaga   960
gcctacctgg aagacacatg cgtggagtgg ctccacaaat acctggagaa ggggaaggag   1020
acgctgcttc acctggagcc cccaaagaca cacgtgactc accacccca tctctgaccat  1080 gaggccaccc tgaggtgctg ggcctggc ttctaccctg cggagatcac actgacctgg   1140
cagcaggatg ggagggcca tacccaggac acggagctcg tggagaccag gcctgcaggg   1200 gatgaacct tccagaagtg ggcagctgtg gtggtgcctt ctggagagga gcagagatac   1260
acgtgccatg tgcagcatga ggggctaccc gagcccgtca ccctgagatg aagccggct   1320 tcccagccca ccatccccat cgtgggcatc attgctggcc tggttctcct tggatctgtg   1380
gtctctggag ctgtggttgc tgctgtgata tggaggaaga agagctcagg tggaaaagga   1440
gggagctact ctaaggctga gtggagcgac agtgcccagg ggtctgagtc tcacagcttg   1500
```

<210> SEQ ID NO 56
<211> LENGTH: 7460
<212> TYPE: DNA
<213> ORGANISM: Artificial Sequence
<220> FEATURE:
<223> OTHER INFORMATION: Synthesized

<400> SEQUENCE: 56

```
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggccgcac gcgtaccgct ctcagaccag aaacgtccac accgcccctc    180
cgatggcctg tcgccctggc taggttttag ggtcagtggg atcctccttc cactggaccc    240
gggagaagac gctcaacagc cccctccttc ccctccttcc tctccttcct ctccttcccc    300
cctccctgcg ccgctccaga gcgcaacaac cattttccca gccaggagca caccgtgtcc    360
acgcgccaca gcgatctcac tgattggtcg ggctcctggt aaacaaggac cgggcagcca    420
atgggaggga tgtgcacgag ggcagcacga gcctccgggc cagcgctcgc gtggctcttc    480
tggcccgggc tactatatag agacgtttcc gcctcctgct tgaaactaac ccctcttttt    540
ctccaaagga gtgcttgtgg agatcggatc ttttctccag caattggggg aaagaaggct    600
ttttctctga attagcttag tgtaaccagc ggcgtatatt ttttaggcgc ttttcgaaa     660 acctagtagt taatattcat ttgtttaaat cttattttat ttttaagctc aaactgctta    720
```

```
agaatacctt aattccttaa agtgaaataa ttttttgcaa aggggtttcc tcgatttgga    780
gcttttttt  tcttccaccg tcatttctaa ctcttaaaac caactcagtt ccatcatggt    840
gatgttcaag aagatcaagt cttttgaggt ggtctttaac gaccctgaaa aggtgtacgg    900
cagtggcgag aaggtggctg ccgggtgat  agtggaggtg tgtgaagctt gtggacgata    960
tcgaattcgc acgacattga ttattgacta gttattaata gtaatcaatt acggggtcat   1020
tagttcatag cccatatatg gagttccgcg ttacataact tacggtaaat ggcccgcctg   1080
gctgaccgcc caacgacccc cgcccattga cgtcaataat gacgtatgtt cccatagtaa   1140
cgccaatagg gactttccat tgacgtcaat gggtggacta tttacggtaa actgcccact   1200
tggcagtaca tcaagtgtat catatgccaa gtacgccccc tattgacgtc aatgacggta   1260
aatggcccgc ctggcattat gcccagtaca tgaccttatg gactttcct  acttggcagt   1320
acatctacgt attagtcatc gctattacca tgggtcgagg tgagccccac gttctgcttc   1380
actctcccca tctccccccc ctccccaccc ccaattttgt atttatttat tttttaatta   1440
ttttgtgcag cgatggggc  ggggggggg  ggggcgcgcg ccaggcgggg cggggcgggg   1500
cgagggcgg  ggcggggcga ggcggagagg tgcggcggca gccaatcaga gcggcgcgct   1560
ccgaaagttt cctttatgg  cgaggcggcg gcggcggcgg ccctataaaa agcgaagcgc   1620
gcggcgggcg ggagtcgctg cgttgccttc gccccgtgcc ccgctccgcg ccgcctcgcg   1680
ccgcccgccc cggctctgac tgaccgcgtt actcccacag gtgagcgggc gggacggccc   1740
ttctcctccg ggctgtaatt agcgcttggt ttaatgacgg ctcgtttctt ttctgtggct   1800
gcgtgaaagc cttaaagggc tccggagggc ccctttgtgc ggggggagc  ggctcggggg   1860
gtgcgtgcgt gtgtgtgtgc gtggggacg  ccgcgtgcgg cccgcgctgc ccggcggctg   1920
tgagcgctgc gggcgcggcg cggggctttg tgcgctccgc gtgtgcgcga ggggagcgcg   1980
gccggggcg  gtgccccgcg gtgcggggg  gctgcgaggg gaacaaaggc tgcgtgcggg   2040
gtgtgtgcgt gggggggtga gcaggggtg  tgggcgcggc ggtcgggctg taacccccc   2100
ctgcacccc  ctccccgagt tgctgagcac ggcccggctt cgggtgcggg gctccgtgcg   2160
gggcgtggcg cggggctcgc cgtgccgggc ggggggtggc ggcaggtggg ggtgccgggc   2220
ggggcgggc  cgcctcgggc cggggagggc tcggggagg  ggcgcggcgg ccccggagcg   2280
ccggcggctc tagagcctct gctaaccatg ttcatgcctt cttctttttc ctacagggg   2340
gatccgttta tctgcagaat tcgcccttga cgtcgccacc atgtctcgct ccgtggcctt   2400
agctgtgctc cgcgctactct ctcttctctgg cctggaggct gtcatggcgc cccgaaccct   2460
cttcctgggt ggaggcggtt caggcggagg tggctctggc ggtggcggat cgatccagcg   2520
tactccaaag attcaggttt actcacgtca tccagcagag aatggaaagt caaatttcct   2580
gaattgctat gtgtctgggt ttcatccatc cgacattgaa gttgacttac tgaagaatgg   2640
agagagaatt gaaaagtgg  agcattcaga cttgtctttc agcaaggact ggtcttttcta   2700
tctcttgtac tacactgaat tcaccccccac tgaaaaagat gagtatgcct gccgtgtgaa   2760
ccatgtgact ttgtcacagc ccaagatagt taagtgggat cgagacatgg gtggtggtgg   2820
ttctggtggt ggtggttctg gcggcggcgg ctccggtggt ggtggatccg ctcccactc   2880
cttgaagtat ttccacactt ccgtgtcccg gccggccgc  ggggagcccc gcttcatctc   2940
tgtgggctac gtgacgcaca cccagttcgt gcgcttcgac aacgacgccg cgagtccgag   3000
gatggtgccg cgggcgccgt ggatggagca ggaggggtca gagtattggg accgggagac   3060
```

```
acggagcgcc agggacaccg cacagatttt ccgagtgaat ctgcggacgc tgcgcggcta    3120
ctacaatcag agcgaggccg ggtctcacac cctgcagtgg atgcatggct gcagctggg     3180 gcccgacggg cgcttcctcc gcgggtatga acagttcgcc tacgacggca aggattatct    3240
caccctgaat gaggacctgc gctcctggac cgcggtggac acggcggctc agatctccga    3300
gcaaaagtca aatgatgcct ctgaggcgga gcaccagaga gcctacctgg aagacacatg    3360
cgtggagtgg ctccacaaat acctggagaa ggggaaggag acgctgcttc acctggagcc    3420
cccaaagaca cacgtgactc accacccat ctctgaccat gaggccaccc tgaggtgctg     3480
ggccctgggc ttctaccctg cggagatcac actgacctgg cagcaggatg ggagggcca    3540 tacccaggac acggagctcg tggagaccag gcctgcaggg gatggaacct tccagaagtg    3600
ggcagctgtg gtggtgcctt ctggagagga gcagagatac acgtgccatg tgcagcatga    3660
ggggctaccc gagcccgtca ccctgagatg gaagccggct tcccagccca ccatccccat    3720
cgtgggcatc attgctggcc tggttctcct tggatctgtg gtctctggag ctgtggttgc    3780
tgctgtgata tggaggaaga gagctcagg tggaaaagga gggagctact ctaaggctga    3840
gtggagcgac agtgcccagg ggtctgagtc tcacagcttg taaccgctga tcagcctcga    3900
ctgtgccttc tagttgccag ccatctgttg tttgcccctc cccgtgcct tccttgaccc     3960 tggaaggtgc cactcccact gtcctttcct aataaaatga ggaaattgca tcgcattgtc    4020
tgagtaggtg tcattctatt ctgggggtg gggtggggca ggacagcaag ggggaggatt    4080
gggaagacaa tagcaggcat gctggggatg cggtgggctc tatgggtcga ccagggatcc    4140
cagcagtgca aacagacttc ggagtacctg cgctatgaag acacgcttct tctggaagac    4200
cagccaacag gtaagcggcc caattcattg ttggagggtg aaagctgatt agagaagaga    4260
attgaataca caaaacctgt acgaaatgtt ttaagttgct cagtttgagt ggtttgaatt    4320
acgtgttgtt gcttcctttt ttctgtttta atttgcagac attctcctcc cccccaaaa     4380 aaaagggtga tttgtacaat tttttatggt gctgtgtcct aaaggggatc ctgaggggcg    4440
ttgcctcggg tagttaaagt cttatgtgtg cataagttgc ttattctttg tctacttcct    4500
atttgagatg ttagtagaga actgtcctgg gtgaatcttt cagtattgca gggcttggca    4560
acttgctgcc cgacaaaata catcagaatt tctctttaag aacaatatgg gatggattaa    4620
aaaatatata tatgggatga aattgggggt acttcaatac cttgcatgcc acccaagcat    4680
tccttatcac acagatgcat tttaagtgta acagcaagcc taatggctac tcgattttct    4740
ttcccttcag gtgagaatga gatggtgatc atgagacctg gaaacaaata tgagtacaag    4800
ttcggctttg agcttcctca ggggtaaata tcagctaaat gcatctttga acttttctgt    4860 ctaaatatc ttgccctcct ttgatcactt actgttcttg gagagcgttt taaaattttc     4920
attttcttga cggtaaccac gtgcggaccg aggctgcagc gtcgtcctcc ctaggaaccc    4980
ctagtgatgg agttggccac tccctctctg cgcgctcgct cgctcactga ggccgggcga    5040
ccaaaggtcg cccgacgccc gggctttgcc cgggcggcct cagtgagcga gcgagcgcgc    5100
agctgcctgc aggggcgcct gatgcggtat tttctcctta cgcatctgtg cggtatttca    5160
caccgcatac gtcaaagcaa ccatagtacg cgccctgtag cggcgcatta gcgcggcgg    5220 gtgtggtggt tacgcgcagc gtgaccgcta cacttgccag cgccctagcg cccgctcctt    5280
tcgctttctt cccttccttt ctcgccacgt tcgccggctt tccccgtcaa gctctaaatc    5340
gggggctccc tttagggttc cgatttagtg ctttacggca cctcgacccc aaaaaacttg    5400
atttgggtga tggttcacgt agtgggccat cgccctgata gacggttttt cgccctttga    5460
```

```
cgttggagtc cacgttcttt aatagtggac tcttgttcca aactggaaca acactcaacc    5520
ctatctcggg ctattctttt gatttataag ggattttgcc gatttcggcc tattggttaa    5580
aaaatgagct gatttaacaa aaatttaacg cgaattttaa caaaatatta acgtttacaa    5640
ttttatggtg cactctcagt acaatctgct ctgatgccgc atagttaagc cagccccgac    5700
acccgccaac acccgctgac gcgccctgac gggcttgtct gctcccggca tccgcttaca    5760
gacaagctgt gaccgtctcc gggagctgca tgtgtcagag gttttcaccg tcatcaccga    5820
aacgcgcgag acgaaagggc ctcgtgatac gcctattttt ataggttaat gtcatgaaca    5880
ataaaactgt ctgcttacat aaacagtaat acaaggggtg ttatgagcca tattcaacgg    5940
gaaacgtcga ggccgcgatt aaattccaac atggatgctg atttatatgg gtataaatgg    6000
gctcgcgata atgtcgggca atcaggtgcg acaatctatc gcttgtatgg gaagcccgat    6060
gcgccagagt tgtttctgaa acatggcaaa ggtagcgttg ccaatgatgt tacagatgag    6120
atggtcagac taaactggct gacggaattt atgcctcttc cgaccatcaa gcattttatc    6180
cgtactcctg atgatgcatg gttactcacc actgcgatcc ccggaaaaac agcattccag    6240
gtattagaag aatatcctga ttcaggtgaa aatattgttg atgcgctggc agtgttcctg    6300
cgccggttgc attcgattcc tgtttgtaat tgtcctttta acagcgatcg cgtatttcgt    6360
ctcgctcagg cgcaatcacg aatgaataac ggtttggttg atgcgagtga ttttgatgac    6420
gagcgtaatg gctggcctgt tgaacaagtc tggaaagaaa tgcataaact tttgccattc    6480
tcaccggatt cagtcgtcac tcatggtgat ttctcacttg ataaccttat ttttgacgag    6540
gggaaattaa taggttgtat tgatgttgga cgagtcggaa tcgcagaccg ataccaggat    6600
cttgccatcc tatggaactg cctcggtgag ttttctcctt cattacagaa acggcttttt    6660
caaaaatatg gtattgataa tcctgatatg aataaattgc agtttcattt gatgctcgat    6720
gagtttttct aatctcatga ccaaaatccc ttaacgtgag ttttcgttcc actgagcgtc    6780
agaccccgta gaaaagatca aaggatcttc ttgagatcct ttttttctgc gcgtaatctg    6840
ctgcttgcaa acaaaaaaac caccgctacc agcggtggtt tgtttgccgg atcaagagct    6900
accaactctt tttccgaagg taactggctt cagcagagcg cagataccaa atactgtcct    6960
tctagtgtag ccgtagttag gccaccactt caagaactct gtagcaccgc ctacatacct    7020
cgctctgcta atcctgttac cagtggctgc tgccagtggc gataagtcgt gtcttaccgg    7080
gttggactca agacgatagt taccggataa ggcgcagcgg tcgggctgaa cggggggttc    7140
gtgcacacag cccagcttgg agcgaacgac ctacaccgaa ctgagatacc tacagcgtga    7200
gctatgagaa agcgccacgc ttcccgaagg gagaaaggcg gacaggtatc cggtaagcgg    7260
cagggtcgga acaggagagc gcacgaggga gcttccaggg ggaaacgcct ggtatcttta    7320
tagtcctgtc gggtttcgcc acctctgact tgagcgtcga ttttgtgat gctcgtcagg    7380 ggggcggagc ctatgaaaaa acgccagcaa cgcggccttt ttacggttcc tggccttttg    7440
ctggcctttt gctcacatgt                                                7460
```

<210> SEQ ID NO 57
<211> LENGTH: 706
<212> TYPE: DNA
<213> ORGANISM: Artificial Sequence
<220> FEATURE:
<223> OTHER INFORMATION: Synthesized

<400> SEQUENCE: 57

```
ggagtcgctg cgttgccttc gccccgtgcc ccgctccgcg ccgcctcgcg ccgcccgccc      60
cggctctgac tgaccgcgtt actcccacag gtgagcgggc gggacggccc ttctcctccg     120
ggctgtaatt agcgcttggt ttaatgacgg ctcgtttctt ttctgtggct gcgtgaaagc     180
cttaaagggc tccggagg cccttttgtgc ggggggage ggctcggggg gtgcgtgcgt      240
gtgtgtgtgc gtggggagcg ccgcgtgcgg cccgcgctgc ccggcggctg tgagcgctgc     300
gggcgcggcg cggggctttg tgcgctccgc gtgtgcgcga ggggagcgcg gccggggcg      360 gtgccccgcg gtgcggggg gctgcgaggg gaacaaaggc tgcgtgcggg gtgtgtgcgt      420
gggggggtga gcagggggtg tgggcgcggc ggtcgggctg tacccccccc ctgcaccccc     480
ctccccgagt tgctgagcac ggcccggctt cgggtgcggg gctccgtgcg gggcgtggcg     540
cggggctcgc cgtgccggc ggggggtggc ggcaggtggg ggtgccggc ggggcgggc       600 cgcctcgggc cggggagggc tcgggggagg ggcgcggcgg ccccggagcg ccggcggctc     660
tagagcctct gctaaccatg ttcatgcctt cttctttttc ctacag                    706
```

UNIVERSAL DONOR CELLS

CROSS-REFERENCE TO RELATED APPLICATIONS

This application claims the benefit of U.S. Provisional Application No. 62/896,473, filed Sep. 5, 2019, and U.S. Provisional Application No. 62/979,771, filed Feb. 21, 2020, the disclosure of each is hereby incorporated by reference in its entirety.

INCORPORATION BY REFERENCE OF SEQUENCE LISTING

This application contains a Sequence Listing that has been submitted in ASCII format via EFS-Web and is hereby incorporated by reference in its entirety. The ASCII copy, created on Sep. 2, 2020, is named CT124-US3-100867-667136-Sequence-Listing_ST25.txt, and is about 53,000 bytes in size.

FIELD OF THE INVENTION

The invention relates to the field of gene editing and, in some embodiments, to genetic modifications for the purposes of generating cells that are compatible with multiple subjects, e.g., universal donor cells.

BACKGROUND

Various approaches have been proposed to overcome allogeneic rejection of transplanted or engrafted cells including HLA-matching, blocking pathways that trigger T-cell activation with antibodies, use of a cocktail of immune suppressive drugs, and autologous cell therapy. Another strategy to dampen graft rejection involves minimization of allogenic differences between transplanted or engrafted cells and the recipient. The cell surface-expressed human leukocyte antigens (HLAs), molecules encoded by genes located in the human major histocompatibility complex on chromosome 6, are the major mediators of immune rejection. Mismatch of a single HLA gene between the donor and subject can cause a robust immune response (Fleischhauer K. et al. "Bone marrow-allograft rejection by T lymphocytes recognizing a single amino acid difference in HLA-B44," N Engl J Med., 1990, 323:1818-1822). HLA genes are divided into MHC class I (MHC-I) and MHC class II (MHC-II). MHC-I genes (HLA-A, HLA-B, and HLA-C) are expressed in almost all tissue cell types, presenting "non-self" antigen-processed peptides to CD8+ T cells, thereby promoting their activation to cytolytic CD8+ T cells. Transplanted or engrafted cells expressing "non-self" MHC-I molecules will cause a robust cellular immune response directed at these cells and ultimately resulting in their demise by activated cytolytic CD8+ T cells. MHC-I proteins are intimately associated with beta-2-microglobulin (B2M) in the endoplasmic reticulum, which is essential for forming functional MHC-I molecules on the cell surface.

In contrast to the wide cellular expression of MHC-I genes, expression of MHC-II genes is restricted to antigen-presenting cells such as dendritic cells, macrophages, and B cells. HLA antigen genes are the most polymorphic genes observed in the human genome (Rubinstein P., "HLA matching for bone marrow transplantation—how much is enough?" N Engl J Med., 2001, 345:1842-1844). The generation of a "universal donor" cell that is compatible with any HLA genotype provides an alternative strategy that could resolve the immune rejection and associated economical costs of current methodologies for immune evasion.

To generate such a line of universal donor cell(s), one previous approach has been to functionally disrupt the expression of MHC-I and MHC-II class genes. This could be achieved through genetic disruption, e.g., of both genetic alleles encoding the MHC-I light chain, B2M. The resulting B2M-null cell line and its derivatives would be expected to exhibit greatly reduced surface MHC-I and thus, reduced immunogenicity to allogeneic CD8+ T cells. The transcription activator-like effector nuclease (TALEN) targeting approach has been used to generate B2M-deficient hESC lines by deletion of a few nucleotides in exon 2 of the B2M gene (Lu, P. et al., "Generating hypoimmunogenic human embryonic stem cells by the disruption of beta 2-microglobulin," Stem Cell Rev. 2013, 9:806-813). Although the B2M-targeted hESC lines appeared to be surface HLA-I deficient, they were found to still contain mRNAs specific for B2M and MHC-I. The B2M and MHC-I mRNAs were expressed at levels equivalent to those of untargeted hESCs (both constitutive and IFN-g induced). Thus, concern exists that these TALEN B2M-targeted hESC lines might express residual cell surface MHC-I that would be sufficient to cause immune rejection, such as has been observed with B2M2/2 mouse cells that also express B2M mRNA (Gross, R. and Rappuoli, R. "Pertussis toxin promoter sequences involved in modulation," Proc Natl Acad Sci, 1993, 90:3913-3917). Although the TALEN B2M targeted hESC lines were not examined for off-target cleavage events, the occurrence of nonspecific cleavage when using TALENs remains a significant issue that would impose a major safety concern on their clinical use (Grau, J. et al. "TALENoffer: genome-wide TALEN off-target prediction," Bioinformatics, 2013, 29:2931-2932; Guilinger J. P. et al. "Broad specificity profiling of TALENs results in engineered nucleases with improved DNA-cleavage specificity," Nat Methods 2014, 11:429-435). Further, another report generated IPS cells that escaped allogeneic recognition by knocking out a first B2M allele and knocking in a HLA-E gene at a second B2M allele, which resulted in surface expression of HLA-E dimers or trimers in the absence of surface expression of HLA-A, HLA-B, or HLA-C (Gornalusse, G. G. et al., "HLA-E-expressing pluripotent stem cells escape allogeneic responses and lysis by NK cells," Nature Biotechnology, 2017, 35, 765-773).

A potential limitation of some of the above strategies are that MHC class I-negative cells are susceptible to lysis by natural killer (NK) cells as HLA molecules serve as major ligand inhibitors to natural killer (NK) cells. Host NK cells have been shown to eliminate transplanted or engrafted B2M-/- donor cells, and a similar phenomenon occurs in vitro with MHC class-I-negative human leukemic lines (Bix, M. et al., "Rejection of class I MHC-deficient haemopoietic cells by irradiated MHC-matched mice," Nature, 1991, 349, 329-331; Zarcone, D. et al., "Human leukemia-derived cell lines and clones as models for mechanistic analysis of natural killer cell-mediated cytotoxicity," Cancer Res. 1987, 47, 2674-2682). Thus, there exists a need to improve upon previous methods to generate universal donor cells that can evade the immune response as well as a need to generate cells that can survive post-engraftment. As described herein, cell survival post-engraftment may be mediated by a host of other pathways independent of allogeneic rejection e.g., hypoxia, reactive oxygen species, nutrient deprivation, and oxidative stress. Also as described herein, genetic introduction of survival factors (genes and/or proteins) may help cells to survive post-engraftment. As described herein, a

SUMMARY

In some aspects, the present disclosure encompasses a method for generating a universal donor cell. The method comprises delivering to a cell (a) a site-directed nuclease targeting a site within or near a gene that encodes a survival factor, and (b) a nucleic acid comprising a nucleotide sequence encoding a tolerogenic factor that is flanked by (i) a nucleotide sequence homologous with a region located left of the target site of (a) and (ii) a nucleotide sequence homologous with a region located right of the target site of (a), wherein the site-directed nuclease cleaves the target site of (a) and the nucleic acid of (b) is inserted at a site that partially overlaps, completely overlaps, or is contained within, the site of (a), thereby generating a universal donor cell, wherein the universal donor cell has increased cell survival compared to a cell in which the nucleic acid of (b) has not been inserted.

In some embodiments, the survival factor is TXNIP, ZNF143, FOXO1, JNK, or MANF, and the tolerogenic factor is PD-L1, HLA-E, HLA-G, CTLA-4, or CD47. In specific embodiments, the survival factor is TXNIP and the tolerogenic factor is HLA-E. In embodiments in which the site-directed nuclease is a CRISPR system comprising a CRISPR nuclease and a guide RNA (gRNA), the CRISPR nuclease is a Type II Cas9 nuclease or a Type V Cfp1 nuclease, and the CRISPR nuclease is linked to at least one nuclear localization signal. In some embodiments, the gRNA targets a polynucleotide sequence chosen from SEQ ID NOS: 15-24 or 45-54, and (i) consists essentially of a nucleotide sequence of SEQ ID NO: 25 and (ii) consists essentially of a nucleotide sequence of SEQ ID NO: 32.

In some embodiments, the method further comprises delivering to the cell (c) a site-directed nuclease targeting a site within or near a gene that encodes one or more of a MHC-I or MHC-II human leukocyte antigens or a component or a transcriptional regulator of a MHC-I or MHC-II complex, and (d) a nucleic acid comprising a nucleotide sequence encoding a tolerogenic factor that is flanked by (iii) a nucleotide sequence homologous with a region located left of the target site of (c) and a (iv) nucleotide sequence homologous with a region located right of the target site of (c), wherein the tolerogenic factor of (d) differs from the tolerogenic factor (b), wherein the site-directed nuclease cleaves the target site of (c) and the nucleic acid of (d) is inserted at a site that partially overlaps, completely overlaps, or is contained within, the site of (c), wherein the universal donor cell has increased immune evasion and/or cell survival compared to a cell in which the nucleic acid of (d) has not been inserted.

In some embodiments, the gene that encodes the one or more MHC-I or MHC-II human leukocyte antigens or the component or the transcriptional regulator of the MHC-I or MHC-II complex is a MHC-I gene chosen from HLA-A, HLA-B, or HLA-C, a MHC-II gene chosen from HLA-DP, HLA-DM, HLA-DOA, HLA-DOB, HLA-DQ, or HLA-DR, or a gene chosen from B2M, NLRC5, CIITA, RFX5, RFXAP, or RFXANK, and the tolerogenic factor is PD-L1, HLA-E, HLA-G, CTLA-4, or CD47. In specific embodiments, the gene that encodes the one or more MHC-I or MHC-II human leukocyte antigens or the component or the transcriptional regulator of the MHC-I or MHC-II complex is B2M, and the tolerogenic factor is PD-L1. In embodiments in which the site-directed nuclease is a CRISPR system comprising a CRISPR nuclease and a gRNA, the CRISPR nuclease is a Type II Cas9 nuclease or a Type V Cfp1 nuclease, and the CRISPR nuclease is linked to at least one nuclear localization signal. In some embodiments, the gRNA targets a polynucleotide sequence chosen from SEQ ID NOS: 1-3 or 35-44, and (iii) consists essentially of a nucleotide sequence of SEQ ID NO: 7, and (iv) consists essentially of a nucleotide sequence of SEQ ID NO: 13.

In some embodiments, the nucleotide sequence encoding a tolerogenic factor of (b) and (d) is operably linked to an exogenous promoter. The exogenous promoter can be chosen from a constitutive, inducible, temporal-, tissue-, or cell type-specific promoter. In some embodiments, the exogenous promoter is a CMV, EF1α, PGK, CAG, or UBC promoter. In specific embodiments, the exogenous promoter is a CAG promoter.

The present disclosure also encompasses the universal donor cells generated by the methods disclosed herein. In some embodiments, the cell is a mammalian cell. In some embodiments, the cell is a human cell. In some embodiments, the cell is a stem cell. In some embodiments, the cell is a pluripotent stem cell (PSC), an embryonic stem cell (ESC), an adult stem cell (ASC), an induced pluripotent stem cell (iPSC), or a hematopoietic stem and progenitor cell (HSPC) (also called a hematopoietic stem cell (HSC)). In some embodiments, the cell is a differentiated cell. In some embodiments, the cell is a somatic cell.

In general, the universal donor cells disclosed herein are capable of being differentiated into lineage-restricted progenitor cells or fully differentiated somatic cells. In some embodiments, the lineage-restricted progenitor cells are pancreatic endoderm progenitors, pancreatic endocrine progenitors, mesenchymal progenitor cells, muscle progenitor cells, blast cells, hematopoietic progenitor cells, or neural progenitor cells, and the fully differentiated somatic cells are endocrine secretory cells such as pancreatic beta cells, epithelial cells, endodermal cells, macrophages, hepatocytes, adipocytes, kidney cells, blood cells, or immune system cells. In some embodiments, the fully differentiated somatic cells are cardiomyocytes.

A further aspect of the present disclosure provides a method for treating a subject in need thereof, wherein the method comprises obtaining or having obtained the universal donor cells as disclosed herein following differentiation into lineage-restricted progenitor cells or fully differentiated somatic cells, and administering the lineage-restricted progenitor cells or fully differentiated somatic cells to the subject. Also provided is a method of obtaining cells for administration to a subject in need thereof, the method comprising obtaining or having obtained the universal donor cells as disclosed herein, and maintaining the universal donor cells for a time and under conditions sufficient for the cells to differentiate into lineage-restricted progenitor cells or fully differentiated somatic cells. In some embodiments, the subject is a human who has, is suspected of having, or is at risk for a disease. In some embodiments, the disease is a genetically inheritable disease.

Still another aspect of the present disclosure encompasses a gRNA targeting a polynucleotide sequence chosen from SEQ ID NO: 15-24 or 45-54.

While the disclosure is susceptible to various modifications and alternative forms, specific embodiments thereof are shown by way of example in the drawings and will herein be described in detail. It should be understood, however, that the drawings and detailed description presented herein are not intended to limit the disclosure to the particular embodiments disclosed, but on the contrary, the intention is to cover all modifications, equivalents, and alternatives falling within the spirit and scope of the present disclosure as defined by the appended claims.

Other features and advantages of this disclosure will become apparent in the following detailed description of embodiments of this invention, taken with reference to the accompanying drawings.

BRIEF DESCRIPTION OF THE DRAWINGS

FIG. 11A shows B2M expression in wild type cells. FIG. 11B shows B2M expression in B2M KO cells. FIG. 11C shows B2M expression in PD-L1 KI/B2M KO cells. FIG. 11D shows PD-L1 expression in wild type cells. FIG. 11E shows PD-L1 expression in B2M KO cells. FIG. 11F shows PD-L1 expression in PD-L1 KI/B2M KO cells.

FIG. 12A shows MHC class I expression in wild type cells. FIG. 12B shows MHC class I expression in B2M KO cells. FIG. 12C shows MHC class I expression in PD-L1 KI/B2M KO cells. FIG. 12D shows MHC class II PD-L1 expression in wild type cells. FIG. 12E shows MHC class II expression in B2M KO cells. FIG. 12F shows MHC class II expression in PD-L1 KI/B2M KO cells.

FIG. 19B summarizes T-cell activation in the various cells. One-way ANOVA (α=0.05 with Dunnett's multiple comparisons test) with "CFSE-T alone" set as control. *, p<0.05; , p<0.01; *, p<0.001; ****, p<0.0001. n.s.=not significant.

FIG. 23A shows the selected gene expression over a differentiation time course of cells differentiated from an exemplary B2M KO/PD-L1 KI and TXNIP KO/HLA-E KI clone. FIGS. 23B-23F show gene expression of INS (FIG. 23B), NKX6.1 (FIG. 23C), GCG (FIG. 23D), SST (FIG. 23E), and GCK (FIG. 23F) in wild-type cells ("S6-Cyt49 WT"), non-cutting guide control ("S6-NCG #1") cells, and various B2M KO/PD-L1 KI and TXNIP KO/HLA-E KI clones ("S6-V1B-H9," "S6-V1B-3B11," "S6-V1B-1G7," and "S6-V1B-3C2") that were differentiated to Stage 6 with undifferentiated B2M KO/PD-L1 KI and TXNIP KO/HLA-E KI clone ("ES-V1B-H9") and wild-type islets ("Islets") as controls.

FIG. 27A shows the morphology, FIG. 27B shows selected gene expression over a differentiation time course, and FIG. 27C shows the percentage of CHGA$^-$/NKX6.1$^+$/PDX1$^+$ expressing cells in the differentiated population.

DETAILED DESCRIPTION

I. Definitions

Figure 1:
FIG. 1 shows TIDE analysis of B2M gRNA cutting in CyT49 cells. B2M-1, B2M-2, and B2M-3 gRNAs were tested.

Deletion: As used herein, the term "deletion", which may be used interchangeably with the terms "genetic deletion" or "knock-out", generally refers to a genetic modification wherein a site or region of genomic DNA is removed by any molecular biology method, e.g., methods described herein, e.g., by delivering to a site of genomic DNA an endonuclease and at least one gRNA. Any number of nucleotides can be deleted. In some embodiments, a deletion involves the removal of at least one, at least two, at least three, at least four, at least five, at least ten, at least fifteen, at least twenty, or at least 25 nucleotides. In some embodiments, a deletion involves the removal of 10-50, 25-75, 50-100, 50-200, or more than 100 nucleotides. In some embodiments, a deletion involves the removal of an entire target gene, e.g., a B2M gene. In some embodiments, a deletion involves the removal of part of a target gene, e.g., all or part of a promoter and/or coding sequence of a B2M gene. In some embodiments, a deletion involves the removal of a transcriptional regulator, e.g., a promoter region, of a target gene. In some embodiments, a deletion involves the removal of all or part of a coding region such that the product normally expressed by the coding region is no longer expressed, is expressed as a truncated form, or expressed at a reduced level. In some embodiments, a deletion leads to a decrease in expression of a gene relative to an unmodified cell.

Endonuclease: As used herein, the term "endonuclease" generally refers to an enzyme that cleaves phosphodiester bonds within a polynucleotide. In some embodiments, an endonuclease specifically cleaves phosphodiester bonds within a DNA polynucleotide. In some embodiments, an endonuclease is a zinc finger nuclease (ZFN), transcription activator like effector nuclease (TALEN), homing endonuclease (HE), meganuclease, MegaTAL, or a CRISPR-associated endonuclease. In some embodiments, an endonuclease is a RNA-guided endonuclease. In certain aspects, the RNA-guided endonuclease is a CRISPR nuclease, e.g., a Type II CRISPR Cas9 endonuclease or a Type V CRISPR Cpf1 endonuclease. In some embodiments, an endonuclease is a Cas1, Cas1B, Cas2, Cas3, Cas4, Cas5, Cash, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease, or a homolog thereof, a recombination of the naturally occurring molecule thereof, a codon-optimized version thereof, or a modified version thereof, or combinations thereof. In some embodiments, an endonuclease may introduce one or more single-stranded breaks (SSBs) and/or one or more double-stranded breaks (DSBs).

Genetic modification: As used herein, the term "genetic modification" generally refers to a site of genomic DNA that has been genetically edited or manipulated using any molecular biological method, e.g., methods described herein, e.g., by delivering to a site of genomic DNA an endonuclease and at least one gRNA. Example genetic modifications include insertions, deletions, duplications, inversions, and translocations, and combinations thereof. In some embodiments, a genetic modification is a deletion. In some embodiments, a genetic modification is an insertion. In other embodiments, a genetic modification is an insertion-deletion mutation (or indel), such that the reading frame of the target gene is shifted leading to an altered gene product or no gene product.

Guide RNA (gRNA): As used herein, the term "guide RNA" or "gRNA" generally refers to short ribonucleic acid that can interact with, e.g., bind to, to an endonuclease and bind, or hybridize to a target genomic site or region. In some embodiments, a gRNA is a single-molecule guide RNA (sgRNA). In some embodiments, a gRNA may comprise a spacer extension region. In some embodiments, a gRNA may comprise a tracrRNA extension region. In some embodiments, a gRNA is single-stranded. In some embodiments, a gRNA comprises naturally occurring nucleotides. In some embodiments, a gRNA is a chemically modified gRNA. In some embodiments, a chemically modified gRNA is a gRNA that comprises at least one nucleotide with a chemical modification, e.g., a 2'-O-methyl sugar modification. In some embodiments, a chemically modified gRNA comprises a modified nucleic acid backbone. In some embodiments, a chemically modified gRNA comprises a 2'-O-methyl-phosphorothioate residue. In some embodiments, a gRNA may be pre-complexed with a DNA endonuclease.

Insertion: As used herein, the term "insertion" which may be used interchangeably with the terms "genetic insertion" or "knock-in", generally refers to a genetic modification wherein a polynucleotide is introduced or added into a site or region of genomic DNA by any molecular biological method, e.g., methods described herein, e.g., by delivering to a site of genomic DNA an endonuclease and at least one gRNA. In some embodiments, an insertion may occur within or near a site of genomic DNA that has been the site of a prior genetic modification, e.g., a deletion or insertion-deletion mutation. In some embodiments, an insertion occurs at a site of genomic DNA that partially overlaps, completely overlaps, or is contained within a site of a prior genetic modification, e.g., a deletion or insertion-deletion mutation. In some embodiments, an insertion occurs at a safe harbor locus. In some embodiments, an insertion involves the introduction of a polynucleotide that encodes a protein of interest. In some embodiments, an insertion involves the introduction of a polynucleotide that encodes a tolerogenic factor. In some embodiments, an insertion involves the introduction of a polynucleotide that encodes a survival factor. In some embodiments, an insertion involves the introduction of an exogenous promoter, e.g., a constitutive promoter, e.g., a CAG promoter. In some embodiments, an insertion involves the introduction of a polynucleotide that encodes a noncoding gene. In general, a polynucleotide to be inserted is flanked by sequences (e.g., homology arms) having substantial sequence homology with genomic DNA at or near the site of insertion.

Major histocompatibility complex class I (MHC-I): As used herein, the terms "Major histocompatibility complex class I" or "MHC-I" generally refer to a class of biomolecules that are found on the cell surface of all nucleated cells in vertebrates, including mammals, e.g., humans; and function to display peptides of non-self or foreign antigens, e.g., proteins, from within the cell (i.e. cytosolic) to cytotoxic T cells, e.g., CD8+ T cells, in order to stimulate an immune response. In some embodiments, a MHC-I biomolecule is a MHC-I gene or a MHC-I protein. Complexation of MHC-I proteins with beta-2 microglobulin (B2M) protein is required for the cell surface expression of all MHC-I proteins. In some embodiments, decreasing the expression of a MHC-I human leukocyte antigen (HLA) relative to an unmodified cell involves a decrease (or reduction) in the expression of a MHC-I gene. In some embodiments, decreasing the expression of a MHC-I human leukocyte antigen (HLA) relative to an unmodified cell involves a decrease (or reduction) in the cell surface expression of a MHC-I protein. In some embodiments, a MHC-I biomolecule is HLA-A (NCBI Gene ID No: 3105), HLA-B (NCBI Gene ID No: 3106), HLA-C (NCBI Gene ID No: 3107), or B2M (NCBI Gene ID No: 567).

Major histocompatibility complex class II (MHC-II): As used herein, the term "Major histocompatibility complex class II" or "MHC-II" generally refer to a class of biomolecules that are typically found on the cell surface of antigen-presenting cells in vertebrates, including mammals, e.g., humans; and function to display peptides of non-self or foreign antigens, e.g., proteins, from outside of the cell (extracellular) to cytotoxic T cells, e.g., CD8+ T cells, in order to stimulate an immune response. In some embodiments, an antigen-presenting cell is a dendritic cell, macrophage, or a B cell. In some embodiments, a MHC-II biomolecule is a MHC-II gene or a MHC-II protein. In some embodiments, decreasing the expression of a MHC-II human leukocyte antigen (HLA) relative to an unmodified cell involves a decrease (or reduction) in the expression of a MHC-II gene. In some embodiments, decreasing the expression of a MHC-II human leukocyte antigen (HLA) relative to an unmodified cell involves a decrease (or reduction) in the cell surface expression of a MHC-II protein. In some embodiments, a MHC-II biomolecule is HLA-DPA (NCBI Gene ID No: 3113), HLA-DPB (NCBI Gene ID No: 3115), HLA-DMA (NCBI Gene ID No: 3108), HLA-DMB (NCBI Gene ID No: 3109), HLA-DOA (NCBI Gene ID No: 3111), HLA-DOB (NCBI Gene ID No: 3112), HLA-DQA (NCBI Gene ID No: 3117), HLA-DQB (NCBI Gene ID No: 3119), HLA-DRA (NCBI Gene ID No: 3122), or HLA-DRB (NCBI Gene ID No: 3123).

Polynucleotide: As used herein, the term "polynucleotide", which may be used interchangeably with the term "nucleic acid" generally refers to a biomolecule that comprises two or more nucleotides. In some embodiments, a polynucleotide comprises at least two, at least five at least ten, at least twenty, at least 30, at least 40, at least 50, at least 100, at least 200, at least 250, at least 500, or any number of nucleotides. For example, the polynucleotides may include at least 500 nucleotides, at least about 600 nucleotides, at least about 700 nucleotides, at least about 800 nucleotides, at least about 900 nucleotides, at least about 1000 nucleotides, at least about 2000 nucleotides, at least about 3000 nucleotides, at least about 4000 nucleotides, at least about 4500 nucleotides, or at least about 5000 nucleotides. A polynucleotide may be a DNA or RNA molecule or a hybrid DNA/RNA molecule. A polynucleotide may be single-stranded or double-stranded. In some embodiments, a polynucleotide is a site or region of genomic DNA. In some embodiments, a polynucleotide is an endogenous gene that is comprised within the genome of an unmodified cell or universal donor cell. In some embodiments, a polynucleotide is an exogenous polynucleotide that is not integrated into genomic DNA. In some embodiments, a polynucleotide is an exogenous polynucleotide that is integrated into genomic DNA. In some embodiments, a polynucleotide is a plasmid or an adeno-associated viral vector. In some embodiments, a polynucleotide is a circular or linear molecule.

Safe harbor locus: As used herein, the term "safe harbor locus" generally refers to any location, site, or region of genomic DNA that may be able to accommodate a genetic insertion into said location, site, or region without adverse effects on a cell. In some embodiments, a safe harbor locus is an intragenic or extragenic region. In some embodiments, a safe harbor locus is a region of genomic DNA that is typically transcriptionally silent. In some embodiments, a safe harbor locus is a AAVS1 (PPP1 R12C), ALB, Angptl3, ApoC3, ASGR2, CCR5, FIX (F9), G6PC, Gys2, HGD, Lp(a), Pcsk9, Serpina1, TF, or TTR locus. In some embodiments, a safe harbor locus is described in Sadelain, M. et al., "Safe harbours for the integration of new DNA in the human genome," Nature Reviews Cancer, 2012, Vol 12, pages 51-58.

Safety switch: As used herein, the term "safety switch" generally refers to a biomolecule that leads a cell to undergo apoptosis. In some embodiments, a safety switch is a protein or gene. In some embodiments, a safety switch is a suicide gene. In some embodiments, a safety switch, e.g., herpes simplex virus thymidine kinase (HSV-tk), leads a cell to undergo apoptosis by metabolizing a prodrug, e.g., ganciclovir. In some embodiments, the overexpressed presence of a safety switch on its own leads a cell to undergo apoptosis. In some embodiments, a safety switch is a p53-based molecule, HSV-tk, or inducible caspase-9.

Subject: As used herein, the term "subject" refers to a mammal. In some embodiments, a subject is non-human primate or rodent. In some embodiments, a subject is a human. In some embodiments, a subject has, is suspected of having, or is at risk for, a disease or disorder. In some embodiments, a subject has one or more symptoms of a disease or disorder.

Survival factor: As used herein, the term "survival factor" generally refers to a protein (e.g., expressed by a polynucleotide as described herein) that, when increased or decreased in a cell, enables the cell, e.g., a universal donor cell, to survive after transplantation or engraftment into a host subject at higher survival rates relative to an unmodified cell. In some embodiments, a survival factor is a human survival factor. In some embodiments, a survival factor is a member of a critical pathway involved in cell survival. In some embodiments, a critical pathway involved in cell survival has implications on hypoxia, reactive oxygen species, nutrient deprivation, and/or oxidative stress. In some embodiments, the genetic modification, e.g., deletion or insertion, of at least one survival factor enables a universal donor cell to survive fora longer time period, e.g., at least 1.05, at least 1.1, at least 1.25, at least 1.5, at least 2, at least 3, at least 4, at least 5, at least 10, at least 20, or at least 50 times longer time period, than an unmodified cell following engraftment. In some embodiments, a survival factor is ZNF143 (NCBI Gene ID No: 7702), TXNIP (NCBI Gene ID No: 10628), FOXO1 (NCBI Gene ID No: 2308), JNK (NCBI Gene ID No: 5599), or MANF (NCBI Gene ID No: 7873). In some embodiments, a survival factor is inserted into a cell, e.g., a universal donor cell. In some embodiments, a survival factor is deleted from a cell, e.g., a universal donor cell. In some embodiments, an insertion of a polynucleotide that encodes MANF enables a cell, e.g., a universal donor cell, to survive after transplantation or engraftment into a host subject at higher survival rates relative to an unmodified cell. In some embodiments, a deletion or insertion-deletion mutation within or near a ZNF143, TXNIP, FOXO1, or JNK gene enables a cell, e.g., a universal donor cell, to survive after transplantation or engraftment into a host subject at higher survival rates relative to an unmodified cell.

Tolerogenic factor: As used herein, the term "tolerogenic factor" generally refers to a protein (e.g., expressed by a polynucleotide as described herein) that, when increased or decreased in a cell, enables the cell, e.g., a universal donor cell, to inhibit or evade immune rejection after transplantation or engraftment into a host subject at higher rates relative to an unmodified cell. In some embodiments, a tolerogenic factor is a human tolerogenic factor. In some embodiments, the genetic modification of at least one tolerogenic factor (e.g., the insertion or deletion of at least one tolerogenic factor) enables a cell, e.g., a universal donor cell. to inhibit or evade immune rejection with rates at least 1.05, at least 1.1, at least 1.25, at least 1.5, at least 2, at least 3, at least 4, at least 5, at least 10, at least 20, or at least 50 times higher than an unmodified cell following engraftment. In some embodiments, a tolerogenic factor is HLA-E (NCBI Gene ID No: 3133), HLA-G (NCBI Gene ID No: 3135), CTLA-4 (NCBI Gene ID No: 1493), CD47 (NCBI Gene ID No: 961), or PD-L1 (NCBI Gene ID No: 29126). In some embodiments, a tolerogenic factor is inserted into a cell, e.g., a universal donor cell. In some embodiments, a tolerogenic factor is deleted from a cell, e.g., a universal donor cell. In some embodiments, an insertion of a polynucleotide that encodes HLA-E, HLA-G, CTLA-4, CD47, and/or PD-L1 enables a cell, e.g., a universal donor cell, to inhibit or evade immune rejection after transplantation or engraftment into a host subject.

Transcriptional regulator of MHC-I or MHC-II: As used herein, the term "transcriptional regulator of MHC-I or MHC-II" generally refers to a biomolecule that modulates, e.g., increases or decreases, the expression of a MHC-I and/or MHC-II human leukocyte antigen. In some embodiments, a biomolecule is a polynucleotide, e.g., a gene, or a protein. In some embodiments, a transcriptional regulator of MHC-I or MHC-II will increase or decrease the cell surface expression of at least one MHC-I or MHC-II protein. In some embodiments, a transcriptional regulator of MHC-I or MHC-II will increase or decrease the expression of at least one MHC-I or MHC-II gene. In some embodiments, the transcriptional regulator is CIITA (NCBI Gene ID No: 4261) or NLRC5 (NCBI Gene ID No: 84166). In some embodiments, deletion or reduction of expression of CIITA or NLRC5 decreases expression of at least one MHC-I or MHC-II gene.

Universal donor cell: As used herein, the term "universal donor cell" generally refers to a genetically modified cell that is less susceptible to allogeneic rejection during a cellular transplant and/or demonstrates increased survival after transplantation, relative to an unmodified cell. In some embodiments, a genetically modified cell as described herein is a universal donor cell. In some embodiments, the universal donor cell has increased immune evasion and/or cell survival compared to an unmodified cell. In some embodiments, the universal donor cell has increased cell survival compared to an unmodified cell. In some embodiments, a universal donor cell may be a stem cell. In some embodiments, a universal donor cell may be an embryonic stem cell (ESC), an adult stem cell (ASC), an induced pluripotent stem cell (iPSC), or a hematopoietic stem or progenitor cell (HSPC) (also called a hematopoietic stem cell (HSC)). In some embodiments, a universal donor cell may be a differentiated cell. In some embodiments, a universal donor cell may be a somatic cell (e.g., immune system cells). In some embodiments, a universal donor cell is administered to a subject. In some embodiments, a universal donor cell is administered to a subject who has, is suspected of having, or is at risk for a disease. In some embodiments, the universal donor cell is capable of being differentiated into lineage-restricted progenitor cells or fully differentiated somatic cells. In some embodiments, the lineage-restricted progenitor cells are pancreatic endoderm progenitors, pancreatic endocrine progenitors, mesenchymal progenitor cells, muscle progenitor cells, blast cells, hematopoietic progenitor cells, or neural progenitor cells. In some embodiments, the fully differentiated somatic cells are endocrine secretory cells such as pancreatic beta cells, epithelial cells, endodermal cells, macrophages, hepatocytes, adipocytes, kidney cells, blood cells, or immune system cells. In some embodiments, the fully differentiated somatic cells are cardiomyocytes.

Unmodified cell: As used herein, the term "unmodified cell" refers to a cell that has not been subjected to a genetic modification involving a polynucleotide or gene that encodes a MHC-I, MHC-I, transcriptional regulator of MHC-I or MHC-II, survival factor, and/or tolerogenic factor. In some embodiments, an unmodified cell may be a stem cell. In some embodiments, an unmodified cell may be an embryonic stem cell (ESC), an adult stem cell (ASC), an induced pluripotent stem cell (iPSC), or a hematopoietic stem or progenitor cell (HSPC) (also called a hematopoietic stem cell (HSC)). In some embodiments, an unmodified cell may be a differentiated cell. In some embodiments, an unmodified cell may be selected from somatic cells (e.g., immune system cells, e.g., a T cell, e.g., a CD8+ T cell). If a universal donor cell is compared "relative to an unmodified cell", the universal donor cell and the unmodified cell are the same cell type or share a common parent cell line, e.g., a universal donor iPSC is compared relative to an unmodified iPSC.

Within or near a gene: As used herein, the term "within or near a gene" refers to a site or region of genomic DNA that is an intronic or extronic component of a said gene or is located proximal to a said gene. In some embodiments, a site of genomic DNA is within a gene if it comprises at least a portion of an intron or exon of said gene. In some embodiments, a site of genomic DNA located near a gene may be at the 5' or 3' end of said gene (e.g., the 5' or 3' end of the coding region of said gene). In some embodiments, a site of genomic DNA located near a gene may be a promoter region or repressor region that modulates the expression of said gene. In some embodiments, a site of genomic DNA located near a gene may be on the same chromosome as said gene. In some embodiments, a site or region of genomic DNA is near a gene if it is within 50 Kb, 40 Kb, 30 Kb, 20 Kb, 10 Kb, 5 Kb, 1 Kb, or closer to the 5' or 3' end of said gene (e.g., the 5' or 3' end of the coding region of said gene).

II. Genome Editing Methods

Genome editing generally refers to the process of modifying the nucleotide sequence of a genome, preferably in a precise or pre-determined manner. In some embodiments, genome editing methods as described herein, e.g., the CRISPR-endonuclease system, may be used to genetically modify a cell as described herein, e.g., to create a universal donor cell. In some embodiments, genome editing methods as described herein, e.g., the CRISPR-endonuclease system, may be used to genetically modify a cell as described herein, e.g., to introduce at least one genetic modification within or near at least one gene that decreases the expression of one or more MHC-I and/or MHC-II human leukocyte antigens or other components of the MHC-I or MHC-II complex relative to an unmodified cell; to introduce at least one genetic modification that increases the expression of at least one polynucleotide that encodes a tolerogenic factor relative to an unmodified cell; and/or to introduce at least one genetic modification that increases or decreases the expression of at least one gene that encodes a survival factor relative to an unmodified cell.

Examples of methods of genome editing described herein include methods of using site-directed nucleases to cut deoxyribonucleic acid (DNA) at precise target locations in the genome, thereby creating single-strand or double-strand DNA breaks at particular locations within the genome. Such breaks can be and regularly are repaired by natural, endogenous cellular processes, such as homology-directed repair (HDR) and non-homologous end joining (NHEJ), as described in Cox et al., "Therapeutic genome editing: prospects and challenges,", Nature Medicine, 2015, 21(2), 121-31. These two main DNA repair processes consist of a family of alternative pathways. NHEJ directly joins the DNA ends resulting from a double-strand break, sometimes with the loss or addition of nucleotide sequence, which may disrupt or enhance gene expression. HDR utilizes a homologous sequence, or donor sequence, as a template for inserting a defined DNA sequence at the break point. The homologous sequence can be in the endogenous genome, such as a sister chromatid. Alternatively, the donor sequence can be an exogenous polynucleotide, such as a plasmid, a single-strand oligonucleotide, a double-stranded oligonucleotide, a duplex oligonucleotide or a virus, that has regions (e.g., left and right homology arms) of high homology with the nuclease-cleaved locus, but which can also contain additional sequence or sequence changes including deletions that can be incorporated into the cleaved target locus. A third repair mechanism can be microhomology-mediated end joining (MMEJ), also referred to as "Alternative NHEJ," in which the genetic outcome is similar to NHEJ in that small deletions and insertions can occur at the cleavage site. MMEJ can make use of homologous sequences of a few base pairs flanking the DNA break site to drive a more favored DNA end joining repair outcome, and recent reports have further elucidated the molecular mechanism of this process; see, e.g., Cho and Greenberg, Nature, 2015, 518, 174-76; Kent et al., Nature Structural and Molecular Biology, 2015, 22(3):230-7; Mateos-Gomez et al., Nature, 2015, 518, 254-57; Ceccaldi et al., Nature, 2015, 528, 258-62. In some instances, it may be possible to predict likely repair outcomes based on analysis of potential microhomologies at the site of the DNA break.

Each of these genome editing mechanisms can be used to create desired genetic modifications. A step in the genome editing process can be to create one or two DNA breaks, the latter as double-strand breaks or as two single-stranded breaks, in the target locus as near the site of intended mutation. This can be achieved via the use of endonucleases, as described and illustrated herein.

CRISPR Endonuclease System

The CRISPR-endonuclease system is a naturally occurring defense mechanism in prokaryotes that has been repurposed as a RNA-guided DNA-targeting platform used for gene editing. CRISPR systems include Types I, II, III, IV, V, and VI systems. In some aspects, the CRISPR system is a Type II CRISPR/Cas9 system. In other aspects, the CRISPR system is a Type V CRISPR/Cprf system. CRISPR systems rely on a DNA endonuclease, e.g., Cas9, and two noncoding RNAs—crisprRNA (crRNA) and trans-activating RNA (tracrRNA)—to target the cleavage of DNA.

The crRNA drives sequence recognition and specificity of the CRISPR-endonuclease complex through Watson-Crick base pairing, typically with a ~20 nucleotide (nt) sequence in the target DNA. Changing the sequence of the 5' 20 nt in the crRNA allows targeting of the CRISPR-endonuclease complex to specific loci. The CRISPR-endonuclease complex only binds DNA sequences that contain a sequence match to the first 20 nt of the single-guide RNA (sgRNA) if the target sequence is followed by a specific short DNA motif (with the sequence NGG) referred to as a protospacer adjacent motif (PAM).

TracrRNA hybridizes with the 3' end of crRNA to form an RNA-duplex structure that is bound by the endonuclease to form the catalytically active CRISPR-endonuclease complex, which can then cleave the target DNA.

Once the CRISPR-endonuclease complex is bound to DNA at a target site, two independent nuclease domains within the endonuclease each cleave one of the DNA strands three bases upstream of the PAM site, leaving a double-strand break (DSB) where both strands of the DNA terminate in a base pair (a blunt end).

In some embodiments, the endonuclease is a Cas9 (CRISPR associated protein 9). In some embodiments, the Cas9 endonuclease is from *Streptococcus pyogenes*, although other Cas9 homologs may be used, e.g., *S. aureus* Cas9, *N. meningitidis* Cas9, *S. thermophilus* CRISPR1 Cas9, *S. thermophilus* CRISPR 3 Cas9, or *T. denticola* Cas9. In other instance s, the CRISPR endonuclease is Cpf1, e.g., *L. bacterium* ND2006 Cpf1 or *Acidaminococcus* sp. BV3L6 Cpf1. In some embodiments, the endonuclease is Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease. In some embodiments, wild-type variants may be used. In some embodiments, modified versions (e.g., a homolog thereof, a recombination of the naturally occurring molecule thereof, codon-optimized thereof, or modified versions thereof) of the preceding endonucleases may be used.

The CRISPR nuclease can be linked to at least one nuclear localization signal (NLS). The at least one NLS can be located at or within 50 amino acids of the amino-terminus of the CRISPR nuclease and/or at least one NLS can be located at or within 50 amino acids of the carboxy-terminus of the CRISPR nuclease.

Exemplary CRISPR/Cas polypeptides include the Cas9 polypeptides as published in Fonfara et al., "Phylogeny of Cas9 determines functional exchangeability of dual-RNA and Cas9 among orthologous type II CRISPR-Cas systems," Nucleic Acids Research, 2014, 42: 2577-2590. The CRISPR/Cas gene naming system has undergone extensive rewriting since the Cas genes were discovered. Fonfara et al. also provides PAM sequences for the Cas9 polypeptides from various species.

Zinc Finger Nucleases

Zinc finger nucleases (ZFNs) are modular proteins comprised of an engineered zinc finger DNA binding domain linked to the catalytic domain of the type II endonuclease FokI. Because FokI functions only as a dimer, a pair of ZFNs must be engineered to bind to cognate target "half-site" sequences on opposite DNA strands and with precise spacing between them to enable the catalytically active FokI dimer to form. Upon dimerization of the FokI domain, which itself has no sequence specificity per se, a DNA double-strand break is generated between the ZFN half-sites as the initiating step in genome editing.

The DNA binding domain of each ZFN is typically comprised of 3-6 zinc fingers of the abundant Cys2-His2 architecture, with each finger primarily recognizing a triplet of nucleotides on one strand of the target DNA sequence, although cross-strand interaction with a fourth nucleotide also can be important. Alteration of the amino acids of a finger in positions that make key contacts with the DNA alters the sequence specificity of a given finger. Thus, a four-finger zinc finger protein will selectively recognize a 12 bp target sequence, where the target sequence is a composite of the triplet preferences contributed by each finger, although triplet preference can be influenced to varying degrees by neighboring fingers. An important aspect of ZFNs is that they can be readily re-targeted to almost any genomic address simply by modifying individual fingers. In most applications of ZFNs, proteins of 4-6 fingers are used, recognizing 12-18 bp respectively. Hence, a pair of ZFNs will typically recognize a combined target sequence of 24-36 bp, not including the typical 5-7 bp spacer between half-sites. The binding sites can be separated further with larger spacers, including 15-17 bp. A target sequence of this length is likely to be unique in the human genome, assuming repetitive sequences or gene homologs are excluded during the design process. Nevertheless, the ZFN protein-DNA interactions are not absolute in their specificity so off-target binding and cleavage events do occur, either as a heterodimer between the two ZFNs, or as a homodimer of one or the other of the ZFNs. The latter possibility has been effectively eliminated by engineering the dimerization interface of the FokI domain to create "plus" and "minus" variants, also known as obligate heterodimer variants, which can only dimerize with each other, and not with themselves. Forcing the obligate heterodimer prevents formation of the homodimer. This has greatly enhanced specificity of ZFNs, as well as any other nuclease that adopts these FokI variants.

A variety of ZFN-based systems have been described in the art, modifications thereof are regularly reported, and numerous references describe rules and parameters that are used to guide the design of ZFNs; see, e.g., Segal et al., Proc Natl Acad Sci, 1999 96(6):2758-63; Dreier B et al., J Mol Biol., 2000, 303(4):489-502; Liu Q et al., J Biol Chem., 2002, 277(6):3850-6; Dreier et al., J Biol Chem., 2005, 280(42):35588-97; and Dreier et al., J Biol Chem. 2001, 276(31):29466-78.

Transcription Activator-Like Effector Nucleases (TALENs)

TALENs represent another format of modular nucleases whereby, as with ZFNs, an engineered DNA binding domain is linked to the FokI nuclease domain, and a pair of TALENs operate in tandem to achieve targeted DNA cleavage. The major difference from ZFNs is the nature of the DNA binding domain and the associated target DNA sequence recognition properties. The TALEN DNA binding domain derives from TALE proteins, which were originally described in the plant bacterial pathogen *Xanthomonas* sp. TALEs are comprised of tandem arrays of 33-35 amino acid repeats, with each repeat recognizing a single base pair in the target DNA sequence that is typically up to 20 bp in length, giving a total target sequence length of up to 40 bp. Nucleotide specificity of each repeat is determined by the repeat variable diresidue (RVD), which includes just two amino acids at positions 12 and 13. The bases guanine, adenine, cytosine and thymine are predominantly recognized by the four RVDs: Asn-Asn, Asn-Ile, His-Asp and Asn-Gly, respectively. This constitutes a much simpler recognition code than for zinc fingers, and thus represents an advantage over the latter for nuclease design. Nevertheless, as with ZFNs, the protein-DNA interactions of TALENs are not absolute in their specificity, and TALENs have also benefitted from the use of obligate heterodimer variants of the FokI domain to reduce off-target activity.

Additional variants of the FokI domain have been created that are deactivated in their catalytic function. If one half of either a TALEN or a ZFN pair contains an inactive FokI domain, then only single-strand DNA cleavage (nicking) will occur at the target site, rather than a DSB. The outcome is comparable to the use of CRISPR/Cas9 or CRISPR/Cpf1 "nickase" mutants in which one of the Cas9 cleavage domains has been deactivated. DNA nicks can be used to drive genome editing by HDR, but at lower efficiency than with a DSB. The main benefit is that off-target nicks are quickly and accurately repaired, unlike the DSB, which is prone to NHEJ-mediated mis-repair.

A variety of TALEN-based systems have been described in the art, and modifications thereof are regularly reported; see, e.g., Boch, Science, 2009 326(5959):1509-12; Mak et al., Science, 2012, 335(6069):716-9; and Moscou et al., Science, 2009, 326(5959):1501. The use of TALENs based on the "Golden Gate" platform, or cloning scheme, has been described by multiple groups; see, e.g., Cermak et al., Nucleic Acids Res., 2011, 39(12):e82; Li et al., Nucleic Acids Res., 2011, 39(14):6315-25; Weber et al., PLoS One., 2011, 6(2):e16765; Wang et al., J Genet Genomics, 2014, 41(6):339-47.; and Cermak T et al., Methods Mol Biol., 2015 1239:133-59.

Homing Endonucleases

Homing endonucleases (HEs) are sequence-specific endonucleases that have long recognition sequences (14-44 base pairs) and cleave DNA with high specificity—often at sites unique in the genome. There are at least six known families of HEs as classified by their structure, including GIY-YIG, His-Cis box, H-N-H, PD-(D/E)xK, and Vsr-like that are derived from a broad range of hosts, including eukarya, protists, bacteria, archaea, cyanobacteria and phage. As with ZFNs and TALENs, HEs can be used to create a DSB at a target locus as the initial step in genome editing. In addition, some natural and engineered HEs cut only a single strand of DNA, thereby functioning as site-specific nickases. The large target sequence of HEs and the specificity that they offer have made them attractive candidates to create site-specific DSBs.

A variety of HE-based systems have been described in the art, and modifications thereof are regularly reported; see, e.g., the reviews by Steentoft et al., Glycobiology, 2014, 24(8):663-80; Belfort and Bonocora, Methods Mol Biol., 2014, 1123:1-26; and Hafez and Hausner, Genome, 2012, 55(8):553-69.

MegaTAL/Tev-mTALEN/MegaTev

As further examples of hybrid nucleases, the MegaTAL platform and Tev-mTALEN platform use a fusion of TALE DNA binding domains and catalytically active HEs, taking advantage of both the tunable DNA binding and specificity of the TALE, as well as the cleavage sequence specificity of the HE; see, e.g., Boissel et al., Nucleic Acids Res., 2014, 42: 2591-2601; Kleinstiver et al., G3, 2014, 4:1155-65; and Boissel and Scharenberg, Methods Mol. Biol., 2015, 1239: 171-96.

In a further variation, the MegaTev architecture is the fusion of a meganuclease (Mega) with the nuclease domain derived from the GIY-YIG homing endonuclease I-TevI (Tev). The two active sites are positioned ~30 bp apart on a DNA substrate and generate two DSBs with non-compatible cohesive ends; see, e.g., Wolfs et al., Nucleic Acids Res., 2014, 42, 8816-29. It is anticipated that other combinations of existing nuclease-based approaches will evolve and be useful in achieving the targeted genome modifications described herein.

dCas9-FokI or dCpf1-FokI and Other Nucleases

Combining the structural and functional properties of the nuclease platforms described above offers a further approach to genome editing that can potentially overcome some of the inherent deficiencies. As an example, the CRISPR genome editing system typically uses a single Cas9 endonuclease to create a DSB. The specificity of targeting is driven by a 20 or 24 nucleotide sequence in the guide RNA that undergoes Watson-Crick base-pairing with the target DNA (plus an additional 2 bases in the adjacent NAG or NGG PAM sequence in the case of Cas9 from *S. pyogenes*). Such a sequence is long enough to be unique in the human genome, however, the specificity of the RNA/DNA interaction is not absolute, with significant promiscuity sometimes tolerated, particularly in the 5' half of the target sequence, effectively reducing the number of bases that drive specificity. One solution to this has been to completely deactivate the Cas9 or Cpf1 catalytic function—retaining only the RNA-guided DNA binding function—and instead fusing a FokI domain to the deactivated Cas9; see, e.g., Tsai et al., Nature Biotech, 2014, 32: 569-76; and Guilinger et al., Nature Biotech., 2014, 32: 577-82. Because FokI must dimerize to become catalytically active, two guide RNAs are required to tether two FokI fusions in close proximity to form the dimer and cleave DNA. This essentially doubles the number of bases in the combined target sites, thereby increasing the stringency of targeting by CRISPR-based systems.

As further example, fusion of the TALE DNA binding domain to a catalytically active HE, such as I-TevI, takes advantage of both the tunable DNA binding and specificity of the TALE, as well as the cleavage sequence specificity of I-TevI, with the expectation that off-target cleavage can be further reduced.

RNA-Guided Endonucleases

The RNA-guided endonuclease systems as used herein can comprise an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100% amino acid sequence identity to a wild-type exemplary endonuclease, e.g., Cas9 from *S. pyogenes*, US2014/0068797 Sequence ID No. 8 or Sapranauskas et al., *Nucleic Acids Res,* 39(21): 9275-9282 (2011). The endonuclease can comprise at least 70, 75, 80, 85, 90, 95, 97, 99, or 100% identity to a wild-type endonuclease (e.g., Cas9 from *S. pyogenes*, supra) over 10 contiguous amino acids. The endonuclease can comprise at most: 70, 75, 80, 85, 90, 95, 97, 99, or 100% identity to a wild-type endonuclease (e.g., Cas9 from *S. pyogenes*, supra) over 10 contiguous amino acids. The endonuclease can comprise at least: 70, 75, 80, 85, 90, 95, 97, 99, or 100% identity to a wild-type endonuclease (e.g., Cas9 from *S. pyogenes*, supra) over 10 contiguous amino acids in a HNH nuclease domain of the endonuclease. The endonuclease can comprise at most: 70, 75, 80, 85, 90, 95, 97, 99, or 100% identity to a wild-type endonuclease (e.g., Cas9 from *S. pyogenes*, supra) over 10 contiguous amino acids in a HNH nuclease domain of the endonuclease. The endonuclease can comprise at least: 70, 75, 80, 85, 90, 95, 97, 99, or 100% identity to a wild-type endonuclease (e.g., Cas9 from *S. pyogenes*, supra) over 10 contiguous amino acids in a RuvC nuclease domain of the endonuclease. The endonuclease can comprise at most: 70, 75, 80, 85, 90, 95, 97, 99, or 100% identity to a wild-type endonuclease (e.g., Cas9 from *S. pyogenes*, supra) over 10 contiguous amino acids in a RuvC nuclease domain of the endonuclease.

The endonuclease can comprise a modified form of a wild-type exemplary endonuclease. The modified form of the wild-type exemplary endonuclease can comprise a mutation that reduces the nucleic acid-cleaving activity of the endonuclease. The modified form of the wild-type exemplary endonuclease can have less than 90%, less than 80%, less than 70%, less than 60%, less than 50%, less than 40%, less than 30%, less than 20%, less than 10%, less than 5%, or less than 1% of the nucleic acid-cleaving activity of the wild-type exemplary endonuclease (e.g., Cas9 from *S. pyogenes*, supra). The modified form of the endonuclease can have no substantial nucleic acid-cleaving activity. When an endonuclease is a modified form that has no substantial nucleic acid-cleaving activity, it is referred to herein as "enzymatically inactive."

Mutations contemplated can include substitutions, additions, and deletions, or any combination thereof. The mutation converts the mutated amino acid to alanine. The mutation converts the mutated amino acid to another amino acid (e.g., glycine, serine, threonine, cysteine, valine, leucine, isoleucine, methionine, proline, phenylalanine, tyrosine, tryptophan, aspartic acid, glutamic acid, asparagine, glutamine, histidine, lysine, or arginine). The mutation converts the mutated amino acid to a non-natural amino acid (e.g., selenomethionine). The mutation converts the mutated amino acid to amino acid mimics (e.g., phosphomimics). The mutation can be a conservative mutation. For example, the mutation converts the mutated amino acid to amino acids that resemble the size, shape, charge, polarity, conformation, and/or rotamers of the mutated amino acids (e.g., cysteine/serine mutation, lysine/asparagine mutation, histidine/phenylalanine mutation). The mutation can cause a shift in reading frame and/or the creation of a premature stop codon. Mutations can cause changes to regulatory regions of genes or loci that affect expression of one or more genes.

Guide RNAs

The present disclosure provides a guide RNAs (gRNAs) that can direct the activities of an associated endonuclease to a specific target site within a polynucleotide. A guide RNA can comprise at least a spacer sequence that hybridizes to a target nucleic acid sequence of interest, and a CRISPR repeat sequence. In CRISPR Type II systems, the gRNA also comprises a second RNA called the tracrRNA sequence. In the CRISPR Type II guide RNA (gRNA), the CRISPR repeat sequence and tracrRNA sequence hybridize to each other to form a duplex. In CRISPR Type V systems, the gRNA comprises a crRNA that forms a duplex. In some embodiments, a gRNA can bind an endonuclease, such that the gRNA and endonuclease form a complex. The gRNA can provide target specificity to the complex by virtue of its association with the endonuclease. The genome-targeting nucleic acid thus can direct the activity of the endonuclease.

Exemplary guide RNAs include a spacer sequences that comprises 15-200 nucleotides wherein the gRNA targets a genome location based on the GRCh38 human genome assembly. As is understood by the person of ordinary skill in the art, each gRNA can be designed to include a spacer sequence complementary to its genomic target site or region. See Jinek et al., Science, 2012, 337, 816-821 and Deltcheva et al., Nature, 2011, 471, 602-607.

The gRNA can be a double-molecule guide RNA. The gRNA can be a single-molecule guide RNA.

A double-molecule guide RNA can comprise two strands of RNA. The first strand comprises in the 5' to 3' direction, an optional spacer extension sequence, a spacer sequence and a minimum CRISPR repeat sequence. The second strand can comprise a minimum tracrRNA sequence (complementary to the minimum CRISPR repeat sequence), a 3' tracrRNA sequence and an optional tracrRNA extension sequence.

A single-molecule guide RNA (sgRNA) can comprise, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension can comprise elements that contribute additional functionality (e.g., stability) to the guide RNA. The single-molecule guide linker can link the minimum CRISPR repeat and the minimum tracrRNA sequence to form a hairpin structure. The optional tracrRNA extension can comprise one or more hairpins.

In some embodiments, a sgRNA comprises a 20 nucleotide spacer sequence at the 5' end of the sgRNA sequence. In some embodiments, a sgRNA comprises a less than a 20 nucleotide spacer sequence at the 5' end of the sgRNA sequence. In some embodiments, a sgRNA comprises a more than 20 nucleotide spacer sequence at the 5' end of the sgRNA sequence. In some embodiments, a sgRNA comprises a variable length spacer sequence with 17-30 nucleotides at the 5' end of the sgRNA sequence. In some embodiments, a sgRNA comprises a spacer extension sequence with a length of more than 1, 5, 10, 15, 20, 25, 30, 35, 40, 45, 50, 60, 70, 80, 90, 100, 120, 140, 160, 180, or 200 nucleotides. In some embodiments, a sgRNA comprises a spacer extension sequence with a length of less than 3, 5, 10, 15, 20, 25, 30, 35, 40, 45, 50, 60, 70, 80, 90, or 100 nucleotides.

In some embodiments, a sgRNA comprises a spacer extension sequence that comprises another moiety (e.g., a stability control sequence, an endoribonuclease binding sequence, or a ribozyme). The moiety can decrease or increase the stability of a nucleic acid targeting nucleic acid. The moiety can be a transcriptional terminator segment (i.e., a transcription termination sequence). The moiety can function in a eukaryotic cell. The moiety can function in a prokaryotic cell. The moiety can function in both eukaryotic and prokaryotic cells. Non-limiting examples of suitable moieties include: a 5' cap (e.g., a 7-methylguanylate cap (m7 G)), a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like).

In some embodiments, a sgRNA comprises a spacer sequence that hybridizes to a sequence in a target polynucleotide. The spacer of a gRNA can interact with a target polynucleotide in a sequence-specific manner via hybridization (i.e., base pairing). The nucleotide sequence of the spacer can vary depending on the sequence of the target nucleic acid of interest.

In a CRISPR-endonuclease system, a spacer sequence can be designed to hybridize to a target polynucleotide that is located 5' of a PAM of the endonuclease used in the system. The spacer may perfectly match the target sequence or may have mismatches. Each endonuclease, e.g., Cas9 nuclease, has a particular PAM sequence that it recognizes in a target DNA. For example, S. pyogenes Cas9 recognizes a PAM that comprises the sequence 5'-NRG-3', where R comprises either A or G, where N is any nucleotide and N is immediately 3' of the target nucleic acid sequence targeted by the spacer sequence.

A target polynucleotide sequence can comprise 20 nucleotides. The target polynucleotide can comprise less than 20 nucleotides. The target polynucleotide can comprise more than 20 nucleotides. The target polynucleotide can comprise at least: 5, 10, 15, 16, 17, 18, 19, 20, 21, 22, 23, 24, 25, 30 or more nucleotides. The target polynucleotide can comprise at most: 5, 10, 15, 16, 17, 18, 19, 20, 21, 22, 23, 24, 25, 30 or more nucleotides. The target polynucleotide sequence can comprise 20 bases immediately 5' of the first nucleotide of the PAM.

A spacer sequence that hybridizes to a target polynucleotide can have a length of at least about 6 nucleotides (nt). The spacer sequence can be at least about 6 nt, at least about 10 nt, at least about 15 nt, at least about 18 nt, at least about 19 nt, at least about 20 nt, at least about 25 nt, at least about 30 nt, at least about 35 nt or at least about 40 nt, from about 6 nt to about 80 nt, from about 6 nt to about 50 nt, from about 6 nt to about 45 nt, from about 6 nt to about 40 nt, from about 6 nt to about 35 nt, from about 6 nt to about 30 nt, from about 6 nt to about 25 nt, from about 6 nt to about 20 nt, from about 6 nt to about 19 nt, from about 10 nt to about 50 nt, from about 10 nt to about 45 nt, from about 10 nt to about 40 nt, from about 10 nt to about 35 nt, from about 10 nt to about 30 nt, from about 10 nt to about 25 nt, from about 10 nt to about 20 nt, from about 10 nt to about 19 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some examples, the spacer sequence can comprise 20 nucleotides. In some examples, the spacer can comprise 19 nucleotides. In some examples, the spacer can comprise 18 nucleotides. In some examples, the spacer can comprise 22 nucleotides.

In some examples, the percent complementarity between the spacer sequence and the target nucleic acid is at least about 30%, at least about 40%, at least about 50%, at least about 60%, at least about 65%, at least about 70%, at least about 75%, at least about 80%, at least about 85%, at least about 90%, at least about 95%, at least about 97%, at least about 98%, at least about 99%, or 100%. In some examples, the percent complementarity between the spacer sequence and the target nucleic acid is at most about 30%, at most about 40%, at most about 50%, at most about 60%, at most about 65%, at most about 70%, at most about 75%, at most about 80%, at most about 85%, at most about 90%, at most about 95%, at most about 97%, at most about 98%, at most about 99%, or 100%. In some examples, the percent complementarity between the spacer sequence and the target nucleic acid is 100% over the six contiguous 5'-most nucleotides of the target sequence of the complementary strand of the target nucleic acid. The percent complementarity between the spacer sequence and the target nucleic acid can be at least 60% over about 20 contiguous nucleotides. The length of the spacer sequence and the target nucleic acid can differ by 1 to 6 nucleotides, which may be thought of as a bulge or bulges.

A tracrRNA sequence can comprise nucleotides that hybridize to a minimum CRISPR repeat sequence in a cell. A minimum tracrRNA sequence and a minimum CRISPR repeat sequence may form a duplex, i.e. a base-paired double-stranded structure. Together, the minimum tracrRNA sequence and the minimum CRISPR repeat can bind to an RNA-guided endonuclease. At least a part of the minimum tracrRNA sequence can hybridize to the minimum CRISPR repeat sequence. The minimum tracrRNA sequence can be at least about 30%, about 40%, about 50%, about 60%, about 65%, about 70%, about 75%, about 80%, about 85%, about 90%, about 95%, or 100% complementary to the minimum CRISPR repeat sequence.

The minimum tracrRNA sequence can have a length from about 7 nucleotides to about 100 nucleotides. For example, the minimum tracrRNA sequence can be from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt or from about 15 nt to about 25 nt long. The minimum tracrRNA sequence can be approximately 9 nucleotides in length. The minimum tracrRNA sequence can be approximately 12 nucleotides. The minimum tracrRNA can consist of tracrRNA nt 23-48 described in Jinek et al., supra.

The minimum tracrRNA sequence can be at least about 60% identical to a reference minimum tracrRNA (e.g., wild type, tracrRNA from *S. pyogenes*) sequence over a stretch of at least 6, 7, or 8 contiguous nucleotides. For example, the minimum tracrRNA sequence can be at least about 65% identical, about 70% identical, about 75% identical, about 80% identical, about 85% identical, about 90% identical, about 95% identical, about 98% identical, about 99% identical or 100% identical to a reference minimum tracrRNA sequence over a stretch of at least 6, 7, or 8 contiguous nucleotides.

The duplex between the minimum CRISPR RNA and the minimum tracrRNA can comprise a double helix. The duplex between the minimum CRISPR RNA and the minimum tracrRNA can comprise at least about 1, 2, 3, 4, 5, 6, 7, 8, 9, or 10 or more nucleotides. The duplex between the minimum CRISPR RNA and the minimum tracrRNA can comprise at most about 1, 2, 3, 4, 5, 6, 7, 8, 9, or 10 or more nucleotides.

The duplex can comprise a mismatch (i.e., the two strands of the duplex are not 100% complementary). The duplex can comprise at least about 1, 2, 3, 4, or 5 or mismatches. The duplex can comprise at most about 1, 2, 3, 4, or 5 or mismatches. The duplex can comprise no more than 2 mismatches.

In some embodiments, a tracrRNA may be a 3' tracrRNA. In some embodiments, a 3' tracrRNA sequence can comprise a sequence with at least about 30%, about 40%, about 50%, about 60%, about 65%, about 70%, about 75%, about 80%, about 85%, about 90%, about 95%, or 100% sequence identity to a reference tracrRNA sequence (e.g., a tracrRNA from *S. pyogenes*).

In some embodiments, a gRNA may comprise a tracrRNA extension sequence. A tracrRNA extension sequence can have a length from about 1 nucleotide to about 400 nucleotides. The tracrRNA extension sequence can have a length of more than 1, 5, 10, 15, 20, 25, 30, 35, 40, 45, 50, 60, 70, 80, 90, 100, 120, 140, 160, 180, or 200 nucleotides. The tracrRNA extension sequence can have a length from about 20 to about 5000 or more nucleotides. The tracrRNA extension sequence can have a length of less than 5, 10, 15, 20, 25, 30, 35, 40, 45, 50, 60, 70, 80, 90, or 100 nucleotides. The tracrRNA extension sequence can comprise less than 10 nucleotides in length. The tracrRNA extension sequence can be 10-30 nucleotides in length. The tracrRNA extension sequence can be 30-70 nucleotides in length.

The tracrRNA extension sequence can comprise a functional moiety (e.g., a stability control sequence, ribozyme, endoribonuclease binding sequence). The functional moiety can comprise a transcriptional terminator segment (i.e., a transcription termination sequence). The functional moiety can have a total length from about 10 nucleotides (nt) to about 100 nucleotides, from about 10 nt to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt, from about 15 nt to about 80 nt, from about 15 nt to about 50 nt, from about 15 nt to about 40 nt, from about 15 nt to about 30 nt, or from about 15 nt to about 25 nt.

In some embodiments, a sgRNA may comprise a linker sequence with a length from about 3 nucleotides to about 100 nucleotides. In Jinek et al., supra, for example, a simple 4 nucleotide "tetraloop" (-GAAA-) was used (Jinek et al., Science, 2012, 337(6096):816-821). An illustrative linker has a length from about 3 nucleotides (nt) to about 90 nt, from about 3 nt to about 80 nt, from about 3 nt to about 70 nt, from about 3 nt to about 60 nt, from about 3 nt to about 50 nt, from about 3 nt to about 40 nt, from about 3 nt to about 30 nt, from about 3 nt to about 20 nt, from about 3 nt to about 10 nt. For example, the linker can have a length from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. The linker of a single-molecule guide nucleic acid can be between 4 and 40 nucleotides. The linker can be at least about 100, 500, 1000, 1500, 2000, 2500, 3000, 3500, 4000, 4500, 5000, 5500, 6000, 6500, or 7000 or more nucleotides. The linker can be at most about 100, 500, 1000, 1500, 2000, 2500, 3000, 3500, 4000, 4500, 5000, 5500, 6000, 6500, or 7000 or more nucleotides.

Linkers can comprise any of a variety of sequences, although in some examples the linker will not comprise sequences that have extensive regions of homology with other portions of the guide RNA, which might cause intramolecular binding that could interfere with other functional regions of the guide. In Jinek et al., supra, a simple 4 nucleotide sequence -GAAA- was used (Jinek et al., Science, 2012, 337(6096):816-821), but numerous other sequences, including longer sequences can likewise be used.

The linker sequence can comprise a functional moiety. For example, the linker sequence can comprise one or more features, including an aptamer, a ribozyme, a protein-interacting hairpin, a protein binding site, a CRISPR array, an intron, or an exon. The linker sequence can comprise at least about 1, 2, 3, 4, or 5 or more functional moieties. In some examples, the linker sequence can comprise at most about 1, 2, 3, 4, or 5 or more functional moieties.

In some embodiments, a sgRNA does not comprise a uracil, e.g., at the 3'end of the sgRNA sequence. In some embodiments, a sgRNA does comprise one or more uracils, e.g., at the 3'end of the sgRNA sequence. In some embodiments, a sgRNA comprises 1, 2, 3, 4, 5, 6, 7, 8, 9, or 10 uracils (U) at the 3' end of the sgRNA sequence.

A sgRNA may be chemically modified. In some embodiments, a chemically modified gRNA is a gRNA that comprises at least one nucleotide with a chemical modification, e.g., a 2'-O-methyl sugar modification. In some embodiments, a chemically modified gRNA comprises a modified nucleic acid backbone. In some embodiments, a chemically modified gRNA comprises a 2'-O-methyl-phosphorothioate residue. In some embodiments, chemical modifications enhance stability, reduce the likelihood or degree of innate immune response, and/or enhance other attributes, as described in the art.

In some embodiments, a modified gRNA may comprise a modified backbones, for example, phosphorothioates, phosphotriesters, morpholinos, methyl phosphonates, short chain alkyl or cycloalkyl intersugar linkages or short chain heteroatomic or heterocyclic intersugar linkages.

Morpholino-based compounds are described in Braasch and David Corey, Biochemistry, 2002, 41(14): 4503-4510; Genesis, 2001, Volume 30, Issue 3; Heasman, Dev. Biol., 2002, 243: 209-214; Nasevicius et al., Nat. Genet., 2000, 26:216-220; Lacerra et al., Proc. Natl. Acad. Sci., 2000, 97: 9591-9596.; and U.S. Pat. No. 5,034,506, issued Jul. 23, 1991.

Cyclohexenyl nucleic acid oligonucleotide mimetics are described in Wang et al., J. Am. Chem. Soc., 2000, 122: 8595-8602.

In some embodiments, a modified gRNA may comprise one or more substituted sugar moieties, e.g., one of the following at the 2' position: OH, SH, $SCH_3$, F, OCN, $OCH_3$, $OCH_3$ $O(CH_2)n$ $CH_3$, $O(CH_2)n$ $NH_2$, or $O(CH_2)n$ $CH_3$, where n is from 1 to about 10; C1 to C10 lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2$ $CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; 2'-O-(2-methoxyethyl); 2'-methoxy (2'-O—$CH_3$); 2'-propoxy (2'-$OCH_2$ $CH_2CH_3$); and 2'-fluoro (2'-F). Similar modifications may also be made at other positions on the gRNA, particularly the 3' position of the sugar on the 3' terminal nucleotide and the 5' position of 5' terminal nucleotide. In some examples, both a sugar and an internucleoside linkage, i.e., the backbone, of the nucleotide units can be replaced with novel groups.

Guide RNAs can also include, additionally or alternatively, nucleobase (often referred to in the art simply as "base") modifications or substitutions. As used herein, "unmodified" or "natural" nucleobases include adenine (A), guanine (G), thymine (T), cytosine (C), and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine, and 2,6-diaminopurine. Kornberg, A., DNA Replication, W. H. Freeman & Co., San Francisco, pp 75-77, 1980; Gebeyehu et al., Nucl. Acids Res. 1997, 15:4513. A "universal" base known in the art, e.g., inosine, can also be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are aspects of base substitutions.

Modified nucleobases can comprise other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine, and 3-deazaguanine and 3-deazaadenine.

Complexes of a Genome-Targeting Nucleic Acid and a Endonuclease

A gRNA interacts with an endonuclease (e.g., a RNA-guided nuclease such as Cas9), thereby forming a complex. The gRNA guides the endonuclease to a target polynucleotide.

The endonuclease and gRNA can each be administered separately to a cell or a subject. In some embodiments, the endonuclease can be pre-complexed with one or more guide RNAs, or one or more crRNA together with a tracrRNA. The pre-complexed material can then be administered to a cell or a subject. Such pre-complexed material is known as a ribonucleoprotein particle (RNP). The endonuclease in the RNP can be, for example, a Cas9 endonuclease or a Cpf1 endonuclease. The endonuclease can be flanked at the N-terminus, the C-terminus, or both the N-terminus and C-terminus by one or more nuclear localization signals (NLSs). For example, a Cas9 endonuclease can be flanked by two NLSs, one NLS located at the N-terminus and the second NLS located at the C-terminus. The NLS can be any NLS known in the art, such as a SV40 NLS. The molar ratio of genome-targeting nucleic acid to endonuclease in the RNP can range from about 1:1 to about 10:1. For example, the molar ratio of sgRNA to Cas9 endonuclease in the RNP can be 3:1.

Nucleic Acids Encoding System Components

The present disclosure provides a nucleic acid comprising a nucleotide sequence encoding a genome-targeting nucleic acid of the disclosure, an endonuclease of the disclosure, and/or any nucleic acid or proteinaceous molecule necessary to carry out the aspects of the methods of the disclosure. The encoding nucleic acids can be RNA, DNA, or a combination thereof.

The nucleic acid encoding a genome-targeting nucleic acid of the disclosure, an endonuclease of the disclosure, and/or any nucleic acid or proteinaceous molecule necessary to carry out the aspects of the methods of the disclosure can comprise a vector (e.g., a recombinant expression vector).

The term "vector" refers to a nucleic acid molecule capable of transporting another nucleic acid to which it has been linked. One type of vector is a "plasmid", which refers to a circular double-stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

In some examples, vectors can be capable of directing the expression of nucleic acids to which they are operatively linked. Such vectors are referred to herein as "recombinant expression vectors", or more simply "expression vectors", which serve equivalent functions.

The term "operably linked" means that the nucleotide sequence of interest is linked to regulatory sequence(s) in a manner that allows for expression of the nucleotide sequence. The term "regulatory sequence" is intended to include, for example, promoters, enhancers and other expression control elements (e.g., polyadenylation signals). Such regulatory sequences are well known in the art and are described, for example, in Goeddel; Gene Expression Technology: Methods in Enzymology, 1990, 185, Academic Press, San Diego, Calif. Regulatory sequences include those that direct constitutive expression of a nucleotide sequence in many types of host cells, and those that direct expression of the nucleotide sequence only in certain host cells (e.g., tissue-specific regulatory sequences). It will be appreciated by those skilled in the art that the design of the expression vector can depend on such factors as the choice of the target cell, the level of expression desired, and the like.

Expression vectors contemplated include, but are not limited to, viral vectors based on vaccinia virus, poliovirus, adenovirus, adeno-associated virus, SV40, herpes simplex virus, human immunodeficiency virus, retrovirus (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus) and other recombinant vectors. Other vectors contemplated for eukaryotic target cells include, but are not limited to, the vectors pXT1, pSG5, pSVK3, pBPV, pMSG, and pSVLSV40 (Pharmacia). Other vectors can be used so long as they are compatible with the host cell.

In some examples, a vector can comprise one or more transcription and/or translation control elements. Depending on the host/vector system utilized, any of a number of suitable transcription and translation control elements, including constitutive and inducible promoters, transcription enhancer elements, transcription terminators, etc. can be used in the expression vector. The vector can be a self-inactivating vector that either inactivates the viral sequences or the components of the CRISPR machinery or other elements.

Non-limiting examples of suitable eukaryotic promoters (i.e., promoters functional in a eukaryotic cell) include those from cytomegalovirus (CMV) immediate early, herpes simplex virus (HSV) thymidine kinase, early and late SV40, long terminal repeats (LTRs) from retrovirus, human elongation factor-1α promoter (EF1α), chicken beta-actin promoter (CBA), ubiquitin C promoter (UBC), a hybrid construct comprising the cytomegalovirus enhancer fused to the chicken beta-actin promoter (CAG), a hybrid construct comprising the cytomegalovirus enhancer fused to the promoter, the first exon, and the first intron of chicken beta-actin gene (CAG or CAGGS), murine stem cell virus promoter (MSCV), phosphoglycerate kinase-1 locus promoter (PGK), and mouse metallothionein-I promoter.

A promoter can be an inducible promoter (e.g., a heat shock promoter, tetracycline-regulated promoter, steroid-regulated promoter, metal-regulated promoter, estrogen receptor-regulated promoter, etc.). The promoter can be a constitutive promoter (e.g., CMV promoter, UBC promoter, CAG promoter). In some cases, the promoter can be a spatially restricted and/or temporally restricted promoter (e.g., a tissue specific promoter, a cell type specific promoter, etc.).

Introduction of the complexes, polypeptides, and nucleic acids of the disclosure into cells can occur by viral or bacteriophage infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

III. STRATEGIES TO EVADE IMMUNE RESPONSE AND INCREASE SURVIVAL

Described herein are strategies to enable genetically modified cells, i.e., universal donor cells, to increase their survival or viability and/or evade immune response following engraftment into a subject. In some embodiments, these strategies enable universal donor cells to survive and/or evade immune response at higher success rates than an unmodified cell. In some embodiments, genetically modified cells comprise the introduction of at least one genetic modification within or near at least one gene that encodes a survival factor, wherein the genetic modification comprises an insertion of a polynucleotide encoding a tolerogenic factor. The universal donor cells may further comprise at least one genetic modification within or near a gene that encodes one or more MHC-I or MHC-II human leukocyte antigens or a component or a transcriptional regulator of a MHC-I or MHC-II complex, wherein said genetic modification comprises an insertion of a polynucleotide encoding a second tolerogenic factor.

In some embodiments, genetically modified cells comprise the introduction of at least one genetic modification within or near at least one gene that decreases the expression of one or more MHC-I and MHC-II human leukocyte antigens relative to an unmodified cell; at least one genetic modification that increases the expression of at least one polynucleotide that encodes a tolerogenic factor relative to an unmodified cell; and at least one genetic modification that alters the expression of at least one gene that encodes a survival factor relative to an unmodified cell. In other embodiments, genetically modified cells comprise at least one deletion or insertion-deletion mutation within or near at least one gene that alters the expression of one or more MHC-I and MHC-II human leukocyte antigens relative to an unmodified cell; and at least one insertion of a polynucleotide that encodes at least one tolerogenic factor at a site that partially overlaps, completely overlaps, or is contained within, the site of a deletion of a gene that alters the expression of one or more MHC-I and MHC-II HLAs. In yet other embodiments, genetically modified cells comprise at least one genetic modification that alters the expression of at least one gene that encodes a survival factor relative to an unmodified cell.

The genes that encode the major histocompatibility complex (MHC) are located on human Chr. 6p21. The resultant proteins coded by the MHC genes are a series of surface proteins that are essential in donor compatibility during cellular transplantation. MHC genes are divided into MHC class I (MHC-I) and MHC class II (MHC-II). MHC-I genes (HLA-A, HLA-B, and HLA-C) are expressed in almost all tissue cell types, presenting "non-self" antigen-processed peptides to CD8+ T cells, thereby promoting their activation to cytolytic CD8+ T cells. Transplanted or engrafted cells expressing "non-self" MHC-I molecules will cause a robust cellular immune response directed at these cells and ultimately resulting in their demise by activated cytolytic CD8+ T cells. MHC-I proteins are intimately associated with beta-2-microglobulin (B2M) in the endoplasmic reticulum, which is essential for forming functional MHC-I molecules on the cell surface. In addition, there are three non-classical MHC-Ib molecules (HLA-E, HLA-F, and HLA-G), which have immune regulatory functions. MHC-II biomolecule include HLA-DP, HLA-DM, HLA-DOA, HLA-DOB, HLA-DQ, and HLA-DR. Due to their primary function in the immune response, MHC-I and MHC-II biomolecules contribute to immune rejection following cellular engraftment of non-host cells, e.g., cellular engraftment for purposes of regenerative medicine.

MHC-I cell surface molecules are composed of MHC-encoded heavy chains (HLA-A, HLA-B, or HLA-C) and the invariant subunit beta-2-microglobulin (B2M). Thus, a reduction in the concentration of B2M within a cell allows for an effective method of reducing the cell surface expression of MHC-I cell surface molecules.

In some embodiments, a cell comprises a genomic modification of one or more MHC-I or MHC-II genes. In some embodiments, a cell comprises a genomic modification of one or more polynucleotide sequences that regulates the expression of MHC-I and/or MHC-II. In some embodiments, a genetic modification of the disclosure is performed using any gene editing method including but not limited to those methods described herein.

In some embodiments, decreasing the expression of one or more MHC-I and MHC-II human leukocyte antigens relative to an unmodified cell is accomplished by targeting, e.g., for genetic deletion and/or insertion of at least one base pair, in a MHC-I and/or MHC-II gene directly. In some embodiments, decreasing the expression of one or more MHC-I and MHC-II human leukocyte antigens relative to an unmodified cell is accomplished by targeting, e.g., for genetic deletion, a CIITA gene. In some embodiments, decreasing the expression of one or more MHC-I and MHC-II human leukocyte antigens relative to an unmodified cell is accomplished by targeting, e.g., for genetic deletion, at least one transcriptional regulator of MHC-I or MHC-II. In some embodiments, a transcriptional regulator of MHC-I or MHC-II is a NLRC5, or CIITA gene. In some embodiments, a transcriptional regulator of MHC-I or MHC-II is a RFX5, RFXAP, RFXANK, NFY-A, NFY-B, NFY-C, IRF-1, and/or TAP1 gene.

In some embodiments, the genome of a cell has been modified to delete the entirety or a portion of a HLA-A, HLA-B, and/or HLA-C gene. In some embodiments, the genome of a cell has been modified to delete the entirety or a portion of a promoter region of a HLA-A, HLA-B, and/or HLA-C gene. In some embodiments, the genome of a cell has been modified to delete the entirety or a portion of a gene that encodes a transcriptional regulator of MHC-I or MHC-II. In some embodiments, the genome of a cell has been modified to delete the entirety or a portion of a promoter region of a gene that encodes a transcriptional regulator of MHC-I or MHC-II.

In some embodiments, the genome of a cell has been modified to decrease the expression of beta-2-microglobulin (B2M). B2M is a non-polymorphic gene that encodes a common protein subunit required for surface expression of all polymorphic MHC class I heavy chains. HLA-I proteins are intimately associated with B2M in the endoplasmic reticulum, which is essential for forming functional, cell-surface expressed HLA-I molecules. In some embodiments, the gRNA targets a site within the B2M gene comprising a 5'-GCTACTCTCTCTTTCTGGCC-3' sequence (SEQ ID NO: 1). In some embodiments, the gRNA targets a site within the B2M gene comprising a 5'-GGCCGA-GATGTCTCGCTCCG-3' sequence (SEQ ID NO: 2). In some embodiments, the gRNA targets a site within the B2M gene comprising a 5'-CGCGAGCACAGCTAAGGCCA-3' sequence (SEQ ID NO: 3). In alternate embodiments, the gRNA targets a site within the B2M gene comprising any of the following sequences: 5'-TATAAGTGGAGGCG-TCGCGC-3' (SEQ ID NO: 35), 5'-GAGTAGCG-CGAGCACAGCTA-3' (SEQ ID NO: 36), 5'-ACTGGACGCGTCGCGCTGGC-3' (SEQ ID NO: 37), 5'-AAGTGGAGGCGTCGCGCTGG-3' (SEQ ID NO: 38), 5-GGCCACGGAGCGAGACATCT-3' (SEQ ID NO: 39), 5'-GCCCGAATGCTGTCAGCTTC-3' (SEQ ID NO: 40). 5'-CTCGCGCTACTCTCTCTTTC-3' (SEQ ID NO: 41), 5'-TCCTGAAGCTGACAGCATTC-3' (SEQ ID NO: 42), 5'-TTCCTGAAGCTGACAGCATT-3' (SEQ ID NO: 43), or 5'-ACTCTCTCTTTCTGGCCTGG-3' (SEQ ID NO: 44). In some embodiments, the gRNA comprises a polynucleotide sequence of any one of SEQ ID NO: 1, SEQ ID NO: 2, SEQ ID NO: 3, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, or SEQ ID NO: 44. The gRNA/CRISPR nuclease complex targets and cleaves a target site in the B2M locus. Repair of a double-stranded break by NHEJ can result in a deletion of at least on nucleotide and/or an insertion of at least one nucleotide, thereby disrupting or eliminating expression of B2M. Alternatively, the B2M locus can be targeted by at least two CRISPR systems each comprising a different gRNA, such that cleavage at two sites in the B2M locus leads to a deletion of the sequence between the two cuts, thereby eliminating expression of B2M.

In some embodiments, the genome of a cell has been modified to decrease the expression of thioredoxin interacting protein (TXNIP). In some embodiments, the gRNA targets a site within the TXNIP gene comprising a 5'-GAAGCGTGTCTTCATAGCGC-3' sequence (SEQ ID NO: 15). In some embodiments, the gRNA targets a site within the TXNIP gene comprising a 5'-TTACTCGTGT-CAAAGCCGTT-3' sequence (SEQ ID NO: 16). In some embodiments, the gRNA targets a site within the TXNIP gene comprising a 5'-TGTCAAAGCCGTTAGGATCC-3' sequence (SEQ ID NO: 17). In some embodiments, the gRNA targets a site within the TXNIP gene comprising a 5'-GCCGTTAGGATCCTGGCTTG-3' sequence (SEQ ID NO: 18). In some embodiments, the gRNA targets a site within the TXNIP gene comprising a 5'-GCG-GAGTGGCTAAAGTGCTT-3' sequence (SEQ ID NO: 19). In some embodiments, the gRNA targets a site within the TXNIP gene comprising a 5'-TCCGCAAGCCAG-GATCCTAA-3' sequence (SEQ ID NO: 20). In some embodiments, the gRNA targets a site within the TXNIP gene comprising a 5'-GTTCGGCTTTGAGCTTCCTC-3' sequence (SEQ ID NO: 21). In some embodiments, the gRNA targets site within the TXNIP gene comprising a 5'-GAGATGGTGATCATGAGACC-3' sequence (SEQ ID NO: 22). In some embodiments, the gRNA targets a site within the TXNIP gene comprising a 5'-TTGTACTCATAT-TTGTTTCC-3' sequence (SEQ ID NO: 23). In some embodiments, the gRNA targets a site within the TXNIP gene comprising a 5'-AACAAATATGAGTACAAGTT-3' sequence (SEQ ID NO: 24). In some embodiments, the gRNA targets a site within the TXNIP gene comprising a 5'-GAAGCGTGTCTTCATAGCGCAGG-3' sequence (SEQ ID NO: 45). In some embodiments, the gRNA targets a site within the TXNIP gene comprising a 5'-TTACTCGTGT-CAAAGCCGTTAGG-3' sequence (SEQ ID NO: 46). In some embodiments, the gRNA targets a site within the TXNIP gene comprising a 5'-TGTCAAAGCCGTTAG-GATCCTGG-3' sequence (SEQ ID NO: 47). In some embodiments, the gRNA targets a site within the TXNIP gene comprising a 5'-GCCGTTAG-GATCCTGGCTTGCGG-3' sequence (SEQ ID NO: 48). In some embodiments, the gRNA targets a site within the TXNIP gene comprising a 5'-GCG-GAGTGGCTAAAGTGCTTTGG-3' sequence (SEQ ID NO: 49). In some embodiments, the gRNA targets a site within the TXNIP gene comprising a 5'-TCCGCAAGCCAGGATCCTAACGG-3' sequence (SEQ ID NO: 50). In some embodiments, the gRNA targets a site within the TXNIP gene comprising a 5'-GTTCGGCTTT-GAGCTTCCTCAGG-3' sequence (SEQ ID NO: 51). In some embodiments, the gRNA targets a site within the TXNIP gene comprising a 5'-GAGATGGTGATCATGA-GACCTGG-3' sequence (SEQ ID NO: 52). In some embodiments, the gRNA targets a site within the TXNIP gene comprising a 5'-TTGTACTCATATTTGTTTCCAGG-3' sequence (SEQ ID NO: 53). In some embodiments, the gRNA targets a site within the TXNIP gene comprising a 5'-AACAAATATGAGTACAAGTTCGG-3' sequence (SEQ ID NO: 54). In some embodiments, the gRNA targets a target site within the TXNIP gene that comprises a polynucleotide sequence of any one of SEQ ID NO: 15-24 or 45-54. In some embodiments, the gRNA targets a polynucleotide sequence of any one of SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24. The gRNA/CRISPR nuclease complex targets and cleaves a target site in the TXNIP gene locus. Repair of a double-stranded break by NHEJ can result in a deletion of at least on nucleotide and/or an insertion of at least one nucleotide, thereby disrupting or eliminating expression of TXNIP. Alternatively, insertion of a polynucleotide encoding an exogenous gene into the TXNIP gene locus can disrupt or eliminate expression of TXNIP.

In some embodiments, the genome of a cell has been modified to decrease the expression of Class II transactivator (CIITA). CIITA is a member of the LR or nucleotide binding domain (NBD) leucine-rich repeat (LRR) family of proteins and regulates the transcription of MHC-II by associating with the MHC enhanceosome. The expression of CIITA is induced in B cells and dendritic cells as a function of developmental stage and is inducible by IFN-γ in most cell types.

In some embodiments, the genome of a cell has been modified to decrease the expression of the NLR family, CARD domain containing 5 (NLRC5). NLRC5 is a critical regulator of MHC-I-mediated immune responses and, similar to CIITA, NLRC5 is highly inducible by IFN-γ and can translocate into the nucleus. NLRC5 activates the promoters of MHC-I genes and induces the transcription of MHC-I as well as related genes involved in MHC-I antigen presentation.

In some embodiments, tolerogenic factors can be inserted or reinserted into genetically modified cells to create immune-privileged universal donor cells. In some embodiments, the universal donor cells disclosed herein have been further modified to express one or more tolerogenic factors. Exemplary tolerogenic factors include, without limitation, one or more of HLA-C, HLA-E, HLA-F, HLA-G, PD-L1, CTLA-4-Ig, CD47, CI-inhibitor, and IL-35. In some embodiments, the genetic modification, e.g., insertion, of at least one polynucleotide encoding at least one tolerogenic factor enables a universal donor cell to inhibit or evade immune rejection with rates at least 1.05, at least 1.1, at least 1.25, at least 1.5, at least 2, at least 3, at least 4, at least 5, at least 10, at least 20, or at least 50 times higher than an unmodified cell following engraftment. In some embodiments, an insertion of a polynucleotide that encodes HLA-E, HLA-G, CTLA-4, CD47, and/or PD-L1 enables a universal donor cell to inhibit or evade immune rejection after transplantation or engraftment into a host subject.

The polynucleotide encoding the tolerogenic factor generally comprises left and right homology arms that flank the sequence encoding the tolerogenic factor. The homology arms have substantial sequence homology to genomic DNA at or near the targeted insertion site. For example, the left homology arm can be a nucleotide sequence homologous with a region located to the left or upstream of the target site or cut site, and the right homology arm can be a nucleotide sequence homologous with a region located to the right or downstream of the target site or cut site. The proximal end of each homology arm can be homologous to genomic DNA sequence abutting the cut site. Alternatively, the proximal end of each homology arm can be homologous to genomic DNA sequence located up to about 10, 20, 30, 40, 50, 60, or 70 nucleobases away from the cut site. As such, the polynucleotide encoding the tolerogenic factor can be inserted into the targeted gene locus within about 10, 20, 30, 40, 50, 60, or 70 base pairs of the cut site, and additional genomic DNA bordering the cut site (and having no homology to a homolog arm) can be deleted. The homology arms can range in length from about 50 nucleotides to several of thousands of nucleotides. In some embodiments, the homology arms can range in length from about 500 nucleotides to about 1000 nucleotides. The substantial sequence homology between the homology arms and the genomic DNA can be at least about 80%, at least about 85%, at least about 90%, at least about 95%, or at least about 99%.

In some embodiments, the homology arms are used with B2M guides (e.g., gRNAs comprising a nucleotide sequence of SEQ ID NO: 1-3, 35-44). In some embodiments, the homology arms are designed to be used with any B2M guide that would eliminate the start site of the B2M gene. In some embodiments, the B2M homology arms can comprise or consist essentially of a polynucleotide sequence of SEQ ID NO: 7 or 13, or a polynucleotide sequence having at least 85%, 90%, 95%, or 99% sequence identity with that of SEQ ID NO: 7 or 13. In some embodiments, the left B2M homology arm can comprise or consist essentially of SEQ ID NO: 7, or a polynucleotide sequence having at least 85%, 90%, 95%, or 99% sequence identity with that of SEQ ID NO: 7. In some embodiments, the right B2M homology arm can comprise or consist essentially of SEQ ID NO: 13, or a polynucleotide sequence having at least 85%, 90%, 95%, or 99% sequence identity with that of SEQ ID NO: 13.

In some embodiments, the homology arms are used with TXNIP guides (e.g., gRNAs comprising a nucleotide sequence of SEQ ID NO: 15-24). In some embodiments, the homology arms are designed to be used with any TXNIP guide that targets exon 1 of TXNIP (e.g., gRNAs comprising a nucleotide sequence of SEQ ID NO: 15-20). In some embodiments, the TXNIP homology arms can comprise or consist essentially of a polynucleotide sequence of SEQ ID NO: 25 or 32, or a polynucleotide sequence having at least 85%, 90%, 95%, or 99% sequence identity with that of SEQ ID NO: 25 or 32. In some embodiments, the left TXNIP homology arm can comprise or consist essentially of SEQ ID NO: 25, or a polynucleotide sequence having at least 85%, 90%, 95%, or 99% sequence identity with that of SEQ ID NO: 25. In some embodiments, the right TXNIP homology arm can comprise or consist essentially of SEQ ID NO: 32, or a polynucleotide sequence having at least 85%, 90%, 95%, or 99% sequence identity with that of SEQ ID NO: 32.

The at least one polynucleotide encoding at least one tolerogenic factor can be operably linked to an exogenous promoter. The exogenous promoter can be a constitutive, inducible, temporal-, tissue-, or cell type-specific promoter. In some embodiments, the exogenous promoter is a CMV, EF1α, PGK, CAG, or UBC promoter.

In some embodiments, the at least one polynucleotide encoding at least one tolerogenic factor is inserted into a safe harbor locus, e.g., the AAVS 1 locus. In some embodiments, the at least one polynucleotide encoding at least one tolerogenic factor is inserted into a site or region of genomic DNA that partially overlaps, completely overlaps, or is contained within (i.e., is within or near) a MHC-I gene, MHC-II gene, or a transcriptional regulator of MHC-I or MHC-II.

In some embodiments, a polynucleotide encoding PD-L1 is inserted at a site within or near a B2M gene locus. In some embodiments, a polynucleotide encoding PD-L1 is inserted at a site within or near a B2M gene locus concurrent with, or following a deletion of all or part of a B2M gene or promoter. The polynucleotide encoding PD-L1 is operably linked to an exogenous promoter. The exogenous promoter can be a CMV promoter. In some embodiments, the polynucleotide comprises a nucleotide sequence of SEQ ID NO: 11.

In some embodiments, a polynucleotide encoding HLA-E is inserted at a site within or near a B2M gene locus. In some embodiments, a polynucleotide encoding HLA-E is inserted at a site within or near a B2M gene locus concurrent with, or following a deletion of all or part of a B2M gene or promoter. The polynucleotide encoding HLA-E is operably linked to an exogenous promoter. The exogenous promoter can be a CMV promoter. In some embodiments, the polynucleotide comprises a nucleotide sequence of SEQ ID NO: 26, 27, 28, 29, 30, and/or 30. In some embodiments, the polynucleotide comprises a nucleotide sequence of SEQ ID NO: 55.

In some embodiments, a polynucleotide encoding HLA-G is inserted at a site within or near a HLA-A, HLA-B, or HLA-C gene locus. In some embodiments, a polynucleotide encoding HLA-G is inserted at a site within or near a HLA-A, HLA-B, or HLA-C gene locus concurrent with, or following a deletion of a HLA-A, HLA-B, or HLA-C gene or promoter.

In some embodiments, a polynucleotide encoding CD47 is inserted at a site within or near a CIITA gene locus. In some embodiments, a polynucleotide encoding CD47 is inserted at a site within or near a CIITA gene locus concurrent with, or following a deletion of a CIITA gene or promoter.

In some embodiments, a polynucleotide encoding HLA-G is inserted at a site within or near a HLA-A, HLA-B, or HLA-C gene locus concurrent with insertion of a polynucleotide encoding CD47 at a site within or near a CIITA gene locus.

In some embodiments, the at least one polynucleotide encoding at least one tolerogenic factor can be delivered to the cells as part of a vector. For example, the vector may be a plasmid vector. In various embodiments, the amount of plasmid vector delivered to the cells may range from about 0.5 μg to about 10 μg (per about $10^6$ cells). In some embodiments, the amount of plasmid may range from about 1 μg to about 8 μg, from about 2 μg to about 6 μg, or from about 3 μg to about 5 μg. In specific embodiments, the amount of plasmid delivered to the cells may be about 4 μg.

In some embodiments, a cell comprises increased or decreased expression of one or more survival factors. In some embodiments, a cell comprises an insertion of one or more polynucleotide sequences that encodes a survival factor. In some embodiments, a cell comprises a deletion of one of more survival factors. In some embodiments, a genetic modification of the disclosure is performed using any gene editing method including but not limited to those methods described herein. In some embodiments, a cell comprises increased or decreased expression of at least one survival factor relative to an unmodified cell. In some embodiments, a survival factor is a member or a critical pathway involved in cell survival, e.g., hypoxia, reactive oxygen species, nutrient deprivation, and/or oxidative stress. In some embodiments, the genetic modification of at least one survival factor enables a universal donor cell to survive for a longer time period, e.g., at least 1.05, at least 1.1, at least 1.25, at least 1.5, at least 2, at least 3, at least 4, at least 5, at least 10, at least 20, or at least 50 times longer time period, than an unmodified cell following engraftment. In some embodiments, a survival factor is ZNF143, TXNIP, FOXO1, JNK, or MANF.

In some embodiments, a cell comprises an insertion of a polynucleotide that encodes MANF enables a universal donor cell to survive after transplantation or engraftment into a host subject at higher survival rates relative to an unmodified cell. In some embodiments, a polynucleotide that encodes MANF is inserted into a safe harbor locus. In some embodiments, a polynucleotide that encodes MANF is inserted into a gene belonging to a MHC-I, MHC-II, or transcriptional regulator of MHC-I or MHC-II.

In some embodiments, the genome of a cell has been modified to delete the entirety or a portion of a ZNF143, TXNIP, FOXO1, and/or JNK gene. In some embodiments, the genome of a cell has been modified to delete the entirety or a portion of a promoter region of a ZNF143, TXNIP, FOXO1, and/or JNK gene.

In some embodiments, more than one survival factor is genetically modified within a cell.

In certain embodiments, cells having no MHC-II expression and moderate expression of MHC-I are genetically modified to have no surface expression of MHC-I or MHC-II. In another embodiment, cells with no surface expression of MHC-I/II are further edited to have expression of PD-L1, e.g., insertion of a polynucleotide encoding PD-L1. In yet another embodiment, cells with no surface expression of MHC-I/II are further edited to have expression of PD-L1, e.g., insertion of a polynucleotide encoding PD-L1, and are also genetically modified to increase or decrease the expression of at least one gene that encodes a survival factor relative to an unmodified cell.

In some embodiments, the cells further comprise increased or decreased expression, e.g., by a genetic modification, of one or more additional genes that are not necessarily implicated in either immune evasion or cell survival post-engraftment. In some embodiments, the cells further comprise increased expression of one or more safety switch proteins relative to an unmodified cell. In some embodiments, the cells comprise increased expression of one or more additional genes that encode a safety switch protein. In some embodiments, a safety switch is also a suicide gene. In some embodiments, a safety switch is herpes simplex virus-1 thymidine kinase (HSV-tk) or inducible caspase-9. In some embodiments, a polynucleotide that encodes at least one safety switch is inserted into a genome, e.g., into a safe harbor locus. In some other embodiments, the one or more additional genes that are genetically modified encode one or more of safety switch proteins; targeting modalities; receptors; signaling molecules; transcription factors; pharmaceutically active proteins or peptides; drug target candidates; and proteins promoting engraftment, trafficking, homing, viability, self-renewal, persistence, and/or survival thereof integrated with the construct.

One aspect of the present invention provides a method of generating genome-engineered universal donor cells, wherein a universal donor cell comprises at least one targeted genomic modification at one or more selected sites in genome, the method comprising genetically engineering a cell type as described herein by introducing into said cells one or more construct of to allow targeted modification at selected site; introducing into said cells one or more double strand breaks at the selected sites using one or more endonuclease capable of selected site recognition; and culturing the edited cells to allow endogenous DNA repair to generate targeted insertions or deletions at the selected sites; thereby obtaining genome-modified universal donor cells. The genome-modified universal donor cells can undergo successive rounds of genome modification such that multiple sites are targeted and modified. The genome-modified cells are cultured, characterized, selected, and expanded using techniques well known in the art. The universal donor cells generated by this method will comprise at least one functional targeted genomic modification, and wherein the genome-modified cells, if they are stem cells, are then capable of being differentiated into progenitor cells or fully-differentiated cells.

In some other embodiments, the genome-engineered universal donor cells comprise introduced or increased expression in at least one of HLA-E, HLA-G, CD47, or PD-L1. In some embodiments, the genome-engineered universal donor cells are HLA class I and/or class II deficient. In some embodiment, the genome-engineered universal donor cells comprise B2M null or low. In some embodiments, the genome-engineered universal donor cells comprise integrated or non-integrated exogenous polynucleotide encoding one or more of HLA-E, HLA-G, and PD-L1 proteins. In some embodiments, said introduced expression is an increased expression from either non-expressed or lowly expressed genes comprised in said cells. In some embodiments, the non-integrated exogenous polynucleotides are introduced using Sendai virus, AAV, episomal, or plasmid. In some embodiment, the universal donor cells are B2M null, with introduced expression of one or more of HLA-E, HLA-G, PD-L1, and increased or decreased expression of at least one safety switch protein. In another embodiment, the universal donor cells are HLA-A, HLA-B, and HLA-C null, with introduced expression of one or more of HLA-E, HLA-G, PD-L1, and at least one safety switch protein. In some embodiment, the universal donor cells are B2M null, with introduced expression of one or more of HLA-E, HLA-G PD-L1, and increased or decreased expression of at least one survival factor, e.g., MANF. Methods of generating any of the genetically modified cells described herein are contemplated to be performed using at least any of the gene editing methods described herein.

IV. Cell Types

Cells as described herein, e.g., universal donor cells (and corresponding unmodified cells) may belong to any possible class of cell type. In some embodiments, a cell, e.g., universal donor cell (and corresponding unmodified cell) may be a mammalian cell. In some embodiments, a cell, e.g., universal donor cell (and corresponding unmodified cell) may be a human cell. In some embodiments, a cell, e.g., universal donor cell (and corresponding unmodified cell) may be a stem cell. In some embodiments, a cell, e.g., universal donor cell (and corresponding unmodified cell) may be a pluripotent stem cell (PSC). In some embodiments, a cell, e.g., a universal donor cell (and corresponding unmodified cell) may be an embryonic stem cell (ESC), an adult stem cell (ASC), an induced pluripotent stem cell (iPSC), or a hematopoietic stem or progenitor cell (HSPC) (also called a hematopoietic stem cell (HSC)). In some embodiments, a cell, e.g., universal donor cell (and corresponding unmodified cell) may be a differentiated cell. In some embodiments, a cell, e.g., universal donor cell (and corresponding unmodified cell) may be a somatic cell, e.g., an immune system cell or a contractile cell, e.g., a skeletal muscle cell.

The cells, e.g., universal donor stem cells, described herein may be differentiated into relevant cell types to assess HLA expression, as well as the evaluation of immunogenicity of the universal stem cell lines. In general, differentiation comprises maintaining the cells of interest for a period time and under conditions sufficient for the cells to differentiate into the differentiated cells of interest. For example, the universal stem cells disclosed herein may be differentiated into mesenchymal progenitor cells (MPCs), hypoimmunogenic cardiomyocytes, muscle progenitor cells, blast cells, endothelial cells (ECs), macrophages, hepatocytes, beta cells (e.g., pancreatic beta cells), pancreatic endoderm progenitors, pancreatic endocrine progenitors, hematopoietic progenitor cells, or neural progenitor cells (NPCs). In some embodiments, the universal donor cell may be differentiated into definitive endoderm cells, primitive gut tube cells, posterior foregut cells, pancreatic endoderm cells (PEC), pancreatic endocrine cells, immature beta cells, or maturing beta cells.

Stem cells are capable of both proliferation and giving rise to more progenitor cells, these in turn having the ability to generate a large number of mother cells that can in turn give rise to differentiated or differentiable daughter cells. The daughter cells themselves can be induced to proliferate and produce progeny that subsequently differentiate into one or more mature cell types, while also retaining one or more cells with parental developmental potential. The term "stem cell" refers then, to a cell with the capacity or potential, under particular circumstances, to differentiate to a more specialized or differentiated phenotype, and which retains the capacity, under certain circumstances, to proliferate without substantially differentiating. In one aspect, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell that itself is derived from a multipotent cell, and so on. While each of these multipotent cells may be considered stem cells, the range of cell types that each can give rise to may vary considerably. Some differentiated cells also have the capacity to give rise to cells of greater developmental potential. Such capacity may be natural or may be induced artificially upon treatment with various factors. In many biological instances, stem cells can also be "multipotent" because they can produce progeny of more than one distinct cell type, but this is not required for "stem-ness."

A "differentiated cell" is a cell that has progressed further down the developmental pathway than the cell to which it is being compared. Thus, stem cells can differentiate into lineage-restricted precursor cells (such as a myocyte progenitor cell), which in turn can differentiate into other types of precursor cells further down the pathway (such as a myocyte precursor), and then to an end-stage differentiated cell, such as a myocyte, which plays a characteristic role in a certain tissue type, and may or may not retain the capacity to proliferate further. In some embodiments, the differentiated cell may be a pancreatic beta cell.

Embryonic Stem Cells

The cells described herein may be embryonic stem cells (ESCs). ESCs are derived from blastocytes of mammalian embryos and are able differentiate into any cell type and propagate rapidly. ESCs are also believed to have a normal karyotype, maintaining high telomerase activity, and exhibiting remarkable long-term proliferative potential, making these cells excellent candidates for use as universal donor cells.

Adult Stem Cells

The cells described herein may be adult stem cells (ASCs). ASCs are undifferentiated cells that may be found in mammals, e.g., humans. ASCs are defined by their ability to self-renew, e.g., be passaged through several rounds of cell replication while maintaining their undifferentiated state, and ability to differentiate into several distinct cell types, e.g., glial cells. Adult stem cells are a broad class of stem cells that may encompass hematopoietic stem cells, mammary stem cells, intestinal stem cells, mesenchymal stem cells, endothelial stem cells, neural stem cells, olfactory adult stem cells, neural crest stem cells, and testicular cells.

Induced Pluripotent Stem Cells

The cells described herein may be induced pluripotent stem cells (iPSCs). An iPSC may be generated directly from an adult human cell by introducing genes that encode critical transcription factors involved in pluripotency, e.g., OCT4, SOX2, cMYC, and KLF4. An iPSC may be derived from the same subject to which subsequent progenitor cells are to be administered. That is, a somatic cell can be obtained from a subject, reprogrammed to an induced pluripotent stem cell, and then re-differentiated into a progenitor cell to be administered to the subject (e.g., autologous cells). However, in the case of autologous cells, a risk of immune response and poor viability post-engraftment remain.

Human Hematopoietic Stem and Progenitor Cells

The cells described herein may be human hematopoietic stem and progenitor cells (hHSPCs). This stem cell lineage gives rise to all blood cell types, including erythroid (erythrocytes or red blood cells (RBCs)), myeloid (monocytes and macrophages, neutrophils, basophils, eosinophils, megakaryocytes/platelets, and dendritic cells), and lymphoid (T-cells, B-cells, NK-cells). Blood cells are produced by the proliferation and differentiation of a very small population of pluripotent hematopoietic stem cells (HSCs) that also have the ability to replenish themselves by self-renewal. During differentiation, the progeny of HSCs progress through various intermediate maturational stages, generating multi-potential and lineage-committed progenitor cells prior to reaching maturity. Bone marrow (BM) is the major site of hematopoiesis in humans and, under normal conditions, only small numbers of hematopoietic stem and progenitor cells (HSPCs) can be found in the peripheral blood (PB). Treatment with cytokines, some myelosuppressive drugs used in cancer treatment, and compounds that disrupt the interaction between hematopoietic and BM stromal cells can rapidly mobilize large numbers of stem and progenitors into the circulation.

Differentiation of Cells into Other Cell Types

Another step of the methods of the present disclosure may comprise differentiating cells into differentiated cells. The differentiating step may be performed according to any method known in the art. For example, human iPSCs are differentiated into definitive endoderm using various treatments, including activin and B27 supplement (Life Technologies). The definitive endoderm is further differentiated into hepatocyte, the treatment includes: FGF4, HGF, BMP2, BMP4, Oncostatin M, Dexamethasone, etc. (Duan et al, Stem Cells, 2010; 28:674-686; Ma et al, Stem Cells Translational Medicine, 2013; 2:409-419). In another embodiment, the differentiating step may be performed according to Sawitza et al, Sci Rep. 2015; 5:13320. A differentiated cell may be any somatic cell of a mammal, e.g., a human. In some embodiments, a somatic cell may be an exocrine secretory epithelial cells (e.g., salivary gland mucous cell, prostate gland cell), a hormone-secreting cell (e.g., anterior pituitary cell, gut tract cell, pancreatic islet), a keratinizing epithelial cell (e.g., epidermal keratinocyte), a wet stratified barrier epithelial cell, a sensory transducer cell (e.g., a photoreceptor), an autonomic neuron cells, a sense organ and peripheral neuron supporting cell (e.g., Schwann cell), a central nervous system neuron, a glial cell (e.g., astrocyte, oligodendrocyte), a lens cell, an adipocyte, a kidney cell, a barrier function cell (e.g., a duct cell), an extracellular matrix cell, a contractile cell (e.g., skeletal muscle cell, heart muscle cell, smooth muscle cell), a blood cell (e.g., erythrocyte), an immune system cell (e.g., megakaryocyte, microglial cell, neutrophil, Mast cell, a T cell, a B cell, a Natural Killer cell), a germ cell (e.g., spermatid), a nurse cell, or an interstitial cell.

In general, populations of the universal donor cells disclosed herein maintain expression of the inserted one or more nucleotide sequences over time. For example, at least about 50%, at least about 55%, at least about 60%, at least about 65%, at least about 70%, at least about 75%, at least about 80%, at least about 85%, at least about 90%, at least about 95%, or at least about 99% of the universal donor cells express the one or more tolerogenic factors. Moreover, populations of lineage-restricted or fully differentiated cells derived from the universal donor cells disclosed herein maintain expression of the inserted one or more nucleotide sequences over time. For example, at least about 50%, at least about 55%, at least about 60%, at least about 65%, at least about 70%, at least about 75%, at least about 80%, at least about 85%, at least about 90%, at least about 95%, or at least about 99% of the lineage-restricted or fully differentiated cells express the one or more tolerogenic factors.

V. Formulations and Administrations

Formulation and Delivery for Gene Editing

Guide RNAs, polynucleotides, e.g., polynucleotides that encode a tolerogenic factor or polynucleotides that encode an endonuclease, and endonucleases as described herein may be formulated and delivered to cells in any manner known in the art.

Guide RNAs and/or polynucleotides may be formulated with pharmaceutically acceptable excipients such as carriers, solvents, stabilizers, adjuvants, diluents, etc., depending upon the particular mode of administration and dosage form. Guide RNAs and/or polynucleotides compositions can be formulated to achieve a physiologically compatible pH, and range from a pH of about 3 to a pH of about 11, about pH 3 to about pH 7, depending on the formulation and route of administration. In some cases, the pH can be adjusted to a range from about pH 5.0 to about pH 8. In some cases, the compositions can comprise a therapeutically effective amount of at least one compound as described herein, together with one or more pharmaceutically acceptable excipients. Optionally, the compositions can comprise a combination of the compounds described herein, or can include a second active ingredient useful in the treatment or prevention of bacterial growth (for example and without limitation, anti-bacterial or anti-microbial agents), or can include a combination of reagents of the present disclosure.

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients can include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol), wetting or emulsifying agents, pH buffering substances, and the like.

Guide RNA polynucleotides (RNA or DNA) and/or endonuclease polynucleotide(s) (RNA or DNA) can be delivered by viral or non-viral delivery vehicles known in the art. Alternatively, endonuclease polypeptide(s) can be delivered by viral or non-viral delivery vehicles known in the art, such as electroporation or lipid nanoparticles. In further alternative aspects, the DNA endonuclease can be delivered as one or more polypeptides, either alone or pre-complexed with one or more guide RNAs, or one or more crRNA together with a tracrRNA.

Polynucleotides can be delivered by non-viral delivery vehicles including, but not limited to, nanoparticles, liposomes, ribonucleoproteins, positively charged peptides, small molecule RNA-conjugates, aptamer-RNA chimeras, and RNA-fusion protein complexes. Some exemplary non-viral delivery vehicles are described in Peer and Lieberman, Gene Therapy, 2011, 18: 1127-1133 (which focuses on non-viral delivery vehicles for siRNA that are also useful for delivery of other polynucleotides).

For polynucleotides of the disclosure, the formulation may be selected from any of those taught, for example, in International Application PCT/US2012/069610.

Polynucleotides, such as guide RNA, sgRNA, and mRNA encoding an endonuclease, may be delivered to a cell or a subject by a lipid nanoparticle (LNP).

A LNP refers to any particle having a diameter of less than 1000 nm, 500 nm, 250 nm, 200 nm, 150 nm, 100 nm, 75 nm, 50 nm, or 25 nm. Alternatively, a nanoparticle may range in size from 1-1000 nm, 1-500 nm, 1-250 nm, 25-200 nm, 25-100 nm, 35-75 nm, or 25-60 nm.

LNPs may be made from cationic, anionic, or neutral lipids. Neutral lipids, such as the fusogenic phospholipid DOPE or the membrane component cholesterol, may be included in LNPs as 'helper lipids' to enhance transfection activity and nanoparticle stability. Limitations of cationic lipids include low efficacy owing to poor stability and rapid clearance, as well as the generation of inflammatory or anti-inflammatory responses.

LNPs may also be comprised of hydrophobic lipids, hydrophilic lipids, or both hydrophobic and hydrophilic lipids.

Any lipid or combination of lipids that are known in the art can be used to produce a LNP. Examples of lipids used to produce LNPs are: DOTMA, DOSPA, DOTAP, DMRIE, DC-cholesterol, DOTAP-cholesterol, GAP-DMORIE-DPyPE, and GL67A-DOPE-DMPE-polyethylene glycol (PEG). Examples of cationic lipids are: 98N12-5, C12-200, DLin-KC2-DMA (KC2), DLin-MC3-DMA (MC3), XTC, MD1, and 7C1. Examples of neutral lipids are: DPSC, DPPC, POPC, DOPE, and SM. Examples of PEG-modified lipids are: PEG-DMG, PEG-CerC14, and PEG-CerC20.

The lipids can be combined in any number of molar ratios to produce a LNP. In addition, the polynucleotide(s) can be combined with lipid(s) in a wide range of molar ratios to produce a LNP.

A recombinant adeno-associated virus (AAV) vector can be used for delivery. Techniques to produce rAAV particles, in which an AAV genome to be packaged that includes the polynucleotide to be delivered, rep and cap genes, and helper virus functions are provided to a cell are standard in the art. Production of rAAV typically requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived, and may be from a different AAV serotype than the rAAV genome ITRs, including, but not limited to, AAV serotypes described herein. Production of pseudotyped rAAV is disclosed in, for example, international patent application publication number WO 01/83692.

Formulation and Administration of Cells, e.g., Universal Donor Cells

Genetically modified cells, e.g., universal donor cells, as described herein may be formulated and administered to a subject by any manner known in the art.

The terms "administering," "introducing", "implanting", "engrafting" and "transplanting" are used interchangeably in the context of the placement of cells, e.g., progenitor cells, into a subject, by a method or route that results in at least partial localization of the introduced cells at a desired site. The cells e.g., progenitor cells, or their differentiated progeny can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life time of the subject, i.e., long-term engraftment.

A genetically modified cell, e.g., universal donor cell, as described herein may be viable after administration to a subject for a period that is longer than that of an unmodified cell.

In some embodiments, a composition comprising cells as described herein may be administered by a suitable route, which may include intravenous administration, e.g., as a bolus or by continuous infusion over a period of time. In some embodiments, intravenous administration may be performed by intramuscular, intraperitoneal, intracerebrospinal, subcutaneous, intra-articular, intrasynovial, or intrathecal routes. In some embodiments, a composition may be in solid form, aqueous form, or a liquid form. In some embodiments, an aqueous or liquid form may be nebulized or lyophilized. In some embodiments, a nebulized or lyophilized form may be reconstituted with an aqueous or liquid solution.

A cell composition can also be emulsified or presented as a liposome composition, provided that the emulsification procedure does not adversely affect cell viability. The cells and any other active ingredient can be mixed with excipients that are pharmaceutically acceptable and compatible with the active ingredient, and in amounts suitable for use in the therapeutic methods described herein.

Additional agents included in a cell composition can include pharmaceutically acceptable salts of the components therein. Pharmaceutically acceptable salts include the acid addition salts (formed with the free amino groups of the polypeptide) that are formed with inorganic acids, such as, for example, hydrochloric or phosphoric acids, or such organic acids as acetic, tartaric, mandelic and the like. Salts formed with the free carboxyl groups can also be derived from inorganic bases, such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions that is effective in the treatment of a particular disorder or condition can depend on the nature of the disorder or condition, and can be determined by standard clinical techniques.

In some embodiments, a composition comprising cells may be administered to a subject, e.g., a human subject, who has, is suspected of having, or is at risk for a disease. In some embodiments, a composition may be administered to a subject who does not have, is not suspected of having or is not at risk for a disease. In some embodiments, a subject is a healthy human. In some embodiments, a subject e.g., a human subject, who has, is suspected of having, or is at risk for a genetically inheritable disease. In some embodiments, the subject is suffering or is at risk of developing symptoms indicative of a disease. In some embodiments, the disease is diabetes, e.g., type I diabetes or type II diabetes.

VI. Specific Compositions and Methods of the Disclosure

Accordingly, the present disclosure relates in particular to the following non-limiting compositions and methods.

In a first composition, Composition 1, the present disclosure provides a composition comprising a universal donor cell comprising a nucleotide sequence encoding a first tolerogenic factor inserted within or near a gene encoding a survival factor, wherein the universal donor cell expresses the tolerogenic factor and has disrupted expression of the survival factor, and the universal donor cell has increased immune evasion and/or cell survival compared to a control cell.

In another composition, Composition 2, the present disclosure provides a composition, as provided in Composition 1, wherein the control cell is a wild type cell or a cell that does not comprise the inserted nucleotide sequence.

In another composition, Composition 3, the present disclosure provides a composition, as provided in Compositions 1 or 2, wherein the disrupted expression of the survival factor comprises reduced or eliminated expression.

In another composition, Composition 4, the present disclosure provides a composition, as provided in any one of Compositions 1 to 3, wherein the first tolerogenic factor is PD-L1, HLA-E, HLA-G, CTLA-4, or CD47.

In another composition, Composition 5, the present disclosure provides a composition, as provided in any one of Compositions 1 to 4, wherein the survival factor is TXNIP, ZNF143, FOXO1, JNK, or MANF.

In another composition, Composition 6, the present disclosure provides a composition, as provided in any one of Compositions claims 1 to 5, wherein the first tolerogenic factor is HLA-E and the survival factor is TXNIP.

In another composition, Composition 7, the present disclosure provides a composition, as provided in Compositions 5 or 6, wherein the nucleotide sequence encoding HLA-E comprises sequence encoding a HLA-E trimer comprising a B2M signal peptide fused to an HLA-G presentation peptide fused to a B2M membrane protein fused to HLA-E without its signal peptide.

In another composition, Composition 8, the present disclosure provides a composition, as provided in Composition 7, wherein the sequence encoding the HLA-E trimer consists essentially of SEQ ID NO: 55.

In another composition, Composition 9, the present disclosure provides a composition, as provided in any one of Compositions 1 to 8, wherein the nucleotide sequence encoding the first tolerogenic factor is operably linked to an exogenous promoter, In another composition, Composition 10, the present disclosure provides a composition, as provided in Composition 9, wherein the exogenous promoter is a CMV, EF1α, PGK, CAG, or UBC promoter.

In another composition, Composition 11, the present disclosure provides a composition, as provided in any one of Compositions claims 1 to 10, further comprising a nucleotide sequence encoding a second tolerogenic factor inserted within or near a gene encoding a MHC-I or MHC-II human leukocyte antigen or a component or a transcriptional regulator of a MHC-I or MHC-II complex, wherein the universal donor cell expresses the tolerogenic factor and has disrupted expression of the MHC-I or MHC-II human leukocyte antigen or the component or the transcriptional regulator of the MHC-I or MHC-II complex.

In another composition, Composition 12, the present disclosure provides a composition, as provided in Composition 11, wherein the disrupted expression of the MHC-I or MHC-II human leukocyte antigen or the component or the transcriptional regulator of the MHC-I or MHC-II complex comprises reduced or eliminated expression.

In another composition, Composition 13, the present disclosure provides a composition, as provided in Compositions 11 or 12, wherein the second tolerogenic factor is PD-L1, HLA-E, HLA-G, CTLA-4, or CD47.

In another composition, Composition 14, the present disclosure provides a composition, as provided in any one of Compositions 11 to 13, wherein the MHC-I or MHC-II human leukocyte antigen or the component or the transcriptional regulator of the MHC-I or MHC-II complex is HLA-A, HLA-B, HLA-C, HLA-DP, HLA-DM, HLA-DOA, HLA-DOB, HLA-DQ, HLA-DR, B2M, NLRC5, CIITA, RFX5, RFXAP, or RFXANK In another composition, Composition 15, the present disclosure provides a composition, as provided in any one of Compositions 11 to 14, wherein the second tolerogenic factor is PD-L1 and the MHC-I or MHC-II human leukocyte antigen or the component or the transcriptional regulator of the MHC-I or MHC-II complex is B2M.

In another composition, Composition 16, the present disclosure provides a composition, as provided in Composition 15, wherein the nucleotide sequence encoding PD-L1 consists essentially of SEQ ID NO: 11.

In another composition, Composition 17, the present disclosure provides a composition, as provided in any one of Compositions 11 to 16, wherein the nucleotide sequence encoding the second tolerogenic factor is operably linked to an exogenous promoter, In another composition, Composition 18, the present disclosure provides a composition, as provided in Composition 17, wherein the exogenous promoter is a CMV, EF1α, PGK, CAG, or UBC promoter.

In another composition, Composition 19, the present disclosure provides a composition, as provided in any one of Compositions 11 to 18, wherein the first tolerogenic factor is HLA-E, the survival factor is TXNIP, the second tolerogenic factor is PD-L1, and the MHC-I or MHC-II human leukocyte antigen or the component or the transcriptional regulator of the MHC-I or MHC-II complex is B2M.

In another composition, Composition 20, the present disclosure provides a composition, as provided in any one of Compositions 1 to 19, wherein the cell is a stem cell.

In another composition, Composition 21, the present disclosure provides a composition, as provided in Composition 20, wherein the stem cell is an embryonic stem cell, an adult stem cell, an induced pluripotent stem cell, or a hematopoietic stem cell.

In another composition, Composition 22, the present disclosure provides a composition, as provided in any one of Compositions 1 to 19, wherein the cell is a differentiated cell or a somatic cell.

In another composition, Composition 23, the present disclosure provides a composition, as provided in any one of Compositions 1 to 19, wherein the cell is capable of being differentiated into lineage-restricted progenitor cells or fully differentiated somatic cells.

In another composition, Composition 24, the present disclosure provides a composition, as provided in Composition 23, wherein the lineage-restricted progenitor cells are pancreatic endoderm progenitors, pancreatic endocrine progenitors, mesenchymal progenitor cells, muscle progenitor cells, blast cells, hematopoietic progenitor cells, or neural progenitor cells.

In another composition, Composition 25, the present disclosure provides a composition, as provided in Composition 23, wherein the fully differentiated somatic cells are pancreatic beta cells, epithelial cells, endodermal cells, macrophages, hepatocytes, adipocytes, kidney cells, blood cells, cardiomyocytes, or immune system cells.

In another composition, Composition 26, the present disclosure provides a composition, as provided in any one of Compositions 1 to 25, wherein the composition comprises a plurality of universal donor cells.

In another composition, Composition 27, the present disclosure provides a composition, as provided in Composition 26, wherein the composition comprised a population of lineage-restricted progenitor cells or fully differentiated somatic cells derived from the plurality of universal donor cells.

In another composition, Composition 28, the present disclosure provides a composition, as provided in Composition 27, wherein the lineage-restricted progenitor cells are pancreatic endoderm progenitors, pancreatic endocrine progenitors, mesenchymal progenitor cells, muscle progenitor cells, blast cells, hematopoietic progenitor cells, or neural progenitor cells, and the fully differentiated somatic cells are pancreatic beta cells, epithelial cells, endodermal cells, macrophages, hepatocytes, adipocytes, kidney cells, blood cells, cardiomyocytes, or immune system cells.

In another composition, Composition 29, the present disclosure provides a composition, as provided in Compositions 6 or 19, wherein the composition comprises a plurality of universal donor cells.

In another composition, Composition 30, the present disclosure provides a composition, as provided in Composition 29, wherein the composition comprised a population of lineage-restricted progenitor cells or fully differentiated somatic cells derived from the plurality of universal donor cells.

In another composition, Composition 31, the present disclosure provides a composition, as provided in Composition 30, wherein the lineage-restricted progenitor cells are definitive endoderm cells, primitive gut tube cells, posterior foregut cells, pancreatic endoderm progenitors, pancreatic endocrine progenitors, immature beta cells, or maturing beta cells, and the fully differentiated somatic cells are pancreatic beta cells.

In another composition, Composition 32, the present disclosure provides a composition, as provided in Composition 26 or 29, wherein at least about 50%, at least about 70%, or at least about 90% of the cells express the first tolerogenic factor, the second tolerogenic factor, or the first and second tolerogenic factors.

In another composition, Composition 33, the present disclosure provides a composition, as provided in any one of Compositions 27, 28, 30, or 31, wherein at least about 50%, at least about 70%, or at least about 90% of the cells express the first tolerogenic factor, the second tolerogenic factor, or the first and second tolerogenic factors.

In another composition, Composition 34, the present disclosure provides a composition comprising the plurality of cells of Composition 26 or the population of cells of Compositions 27 or 28.

In another composition, Composition 35, the present disclosure provides a composition, as provided in Composition 34 for use in treating a subject in need thereof.

In another composition, Composition 36, the present disclosure provides a composition, as provided in Composition 35, wherein the subject has, is suspected of having, or is at risk for a disease.

In another composition, Composition 37, the present disclosure provides a composition, as provided in Composition 36, wherein the disease is a genetically inheritable disease.

In another composition, Composition 38, the present disclosure provides a composition comprising the plurality of cells of Composition 29 or the population of cells of Compositions 30 or 31.

In another composition, Composition 39, the present disclosure provides a composition, as provided in Composition 38 for treating diabetes in a subject in need thereof.

In another composition, Composition 40, the present disclosure provides a composition, as provided in Composition 39, wherein the subject has type I diabetes or type II diabetes.

In another composition, Composition 41, the present disclosure provides a composition, as provided in any one of Compositions 35 to 40, wherein the subject is human.

In a first method, Method 1, the present disclosure provides a method of obtaining cells for administration to a subject in need thereof, the method comprising: (a) obtaining or having obtained the plurality of universal donor cells of any one of Composition 26, 29, or 32, and (b) maintaining the plurality of universal donor cells for a time and under conditions sufficient for the cells to differentiate into lineage-restricted progenitor cells or fully differentiated somatic cells.

In another method, Method 2, the present disclosure provides a method for treating of a subject in need thereof, the method comprising: (a) obtaining or having obtained the plurality of universal donor cells of any one of Compositions 26, 29, or 32 following differentiation into lineage-restricted progenitor cells or fully differentiated somatic cells; and (b) administering the lineage-restricted progenitor cells or fully differentiated somatic cells to the subject.

In another method, Method 3, the present disclosure provides a method as provided in Method 2, wherein administering comprises implanting a device comprising the lineage-restricted progenitor cells or fully differentiated somatic cells into the subject.

In another method, Method 4, the present disclosure provides a method as provided in of any one of Methods 1 to 3, wherein the lineage-restricted progenitor cells are pancreatic endoderm progenitors, pancreatic endocrine progenitors, mesenchymal progenitor cells, muscle progenitor cells, blast cells, hematopoietic progenitor cells, or neural progenitor cells, and the fully differentiated somatic cells are pancreatic beta cells, epithelial cells, endodermal cells, macrophages, hepatocytes, adipocytes, kidney cells, blood cells, cardiomyocytes, or immune system cells.

In another method, Method 5, the present disclosure provides a method as provided in of any one of Methods 1 to 4, wherein the subject has, is suspected of having, or is at risk for a disease.

In another method, Method 6, the present disclosure provides a method as provided in Method 5, wherein the disease is a genetically inheritable disease.

In another method, Method 7, the present disclosure provides a method as provided in of any one of Methods 1 to 6, wherein the subject is human.

In another method, Method 8, the present disclosure provides a method for treating diabetes in a subject in need thereof, the method comprising: (a) obtaining or having obtained the plurality of universal donor cells of Composition 29 or 32 following differentiation into pancreatic endoderm cells, pancreatic endocrine cells, immature beta cells, maturing beta cells, or pancreatic beta cells; and (b) administering the pancreatic endoderm cells, pancreatic endocrine cells, immature beta cells, maturing beta cells, or pancreatic beta cells to the subject.

In another method, Method 9, the present disclosure provides a method as provided in Method 8, wherein administering comprises implanting a device comprising the pancreatic endoderm cells, pancreatic endocrine cells, immature beta cells, maturing beta cell, or pancreatic beta cells into the subject.

In another method, Method 10, the present disclosure provides a method as provided in Method 8 or 9, wherein the subject has type I diabetes or type II diabetes.

In another method, Method 11, the present disclosure provides a method as provided in any one of Methods 8 to 10, wherein the subject is human.

In another composition, Composition 41, the present disclosure provides a composition comprising a universal donor cell comprising a nucleotide sequence encoding HLA class I histocompatibility antigen, alpha chain E (HLA-E) inserted within or near a gene encoding thioredoxin interacting protein (TXNIP), wherein the universal donor cell expresses HLA-E and has disrupted expression of TXNIP, and the universal donor cell has increased immune evasion and/or cell survival compared to a control.

In another composition, Composition 42, the present disclosure provides a composition, as provided in Composition 41, wherein the control cell is a wild type cell or a cell that does not comprise the inserted nucleotide sequence.

In another composition, Composition 43, the present disclosure provides a composition, as provided in Composition 41, wherein the disrupted expression of TXNIP comprises reduced or eliminated expression.

In another composition, Composition 44, the present disclosure provides a composition, as provided in Composition 41, wherein the nucleotide sequence encoding HLA-E comprises a sequence encoding a HLA-E trimer comprising a B2M signal peptide fused to an HLA-G presentation peptide fused to a B2M membrane protein fused to HLA-E without its signal peptide.

In another composition, Composition 45, the present disclosure provides a composition, as provided in Composition 44, wherein the sequence encoding the HLA-E trimer consists essentially of SEQ ID NO: 55.

In another composition, Composition 46, the present disclosure provides a composition, as provided in Composition 41, wherein the nucleotide sequence encoding HLA-E is operably linked to an exogenous promoter, In another composition, Composition 47, the present disclosure provides a composition, as provided in Composition 41, wherein the exogenous promoter is a CAG promoter.

In another composition, Composition 48, the present disclosure provides a composition, as provided in Composition 41, wherein the cell is a stem cell.

In another composition, Composition 49, the present disclosure provides a composition, as provided in Composition 48, wherein the stem cell is an embryonic stem cell, an adult stem cell, an induced pluripotent stem cell, or a hematopoietic stem cell.

In another composition, Composition 50, the present disclosure provides a composition, as provided in Composition 41, wherein the cell is a differentiated cell or a somatic cell.

In another composition, Composition 51, the present disclosure provides a composition, as provided in Composition 41, wherein the cell is capable of being differentiated into lineage-restricted progenitor cells or fully differentiated somatic cells.

In another composition, Composition 52, the present disclosure provides a composition, as provided in Composition 51, wherein the lineage-restricted progenitor cells are definitive endoderm cells, primitive gut tube cells, posterior foregut cells, pancreatic endoderm progenitors, pancreatic endocrine progenitors, immature beta cells, or maturing beta cells, and the fully differentiated somatic cells are pancreatic beta cells.

In another composition, Composition 53, the present disclosure provides a composition comprising a plurality of universal donor cells as provided in Composition 41.

In another composition, Composition 54, the present disclosure provides a composition, as provided in Composition 53, wherein at least about 50% of the cells express HLA-E.

In another composition, Composition 55, the present disclosure provides a composition, as provided in Composition 53, wherein at least about 70% of the cells express HLA-E.

In another composition, Composition 56, the present disclosure provides a composition, as provided in Composition 53, wherein at least about 90% of the cells express HLA-E.

In another composition, Composition 57, the present disclosure provides a composition comprising a population of lineage-restricted progenitor cells or fully differentiated somatic cells derived from the plurality of universal donor cells of Composition 53.

In another composition, Composition 58, the present disclosure provides a composition, as provided in Composition 57, wherein the lineage-restricted progenitor cells are definitive endoderm cells, primitive gut tube cells, posterior foregut cells, pancreatic endoderm progenitors, pancreatic endocrine progenitors, immature beta cells, or maturing beta cells, and the fully differentiated somatic cells are pancreatic beta cells.

In another composition, Composition 59, the present disclosure provides a composition, as provided in Composition 58, wherein at least about 50% of the cells express HLA-E.

In another composition, Composition 60, the present disclosure provides a composition, as provided in Composition 59, wherein at least about 70% of the cells express HLA-E.

In another composition, Composition 61, the present disclosure provides a composition, as provided in Composition 59, wherein at least about 90% of the cells express HLA-E.

In another composition, Composition 62, the present disclosure provides a composition comprising a genetically modified cell having introduced or increased expression of HLA class I histocompatibility antigen, alpha chain E (HLA-E) and disrupted expression of thioredoxin interacting protein (TXNIP), wherein the genetically modified cell has increased immune evasion and/or cell survival compared to an unmodified cell.

In another composition, Composition 63, the present disclosure provides a composition, as provided in Composition 62, which comprises a nucleotide sequence encoding HLA-E inserted within or near a gene encoding TXNIP, thereby disrupting the TXNIP gene.

In another composition, Composition 64, the present disclosure provides a composition, as provided in Composition 62, wherein the disrupted expression of TXNIP comprises reduced or eliminated expression In another method, Method 12, the present disclosure provides a method for treating diabetes in a subject in need thereof, the method comprising: obtaining or having obtained the plurality of universal donor cells of Composition 53 following differentiation into pancreatic endoderm cells, pancreatic endocrine cells, immature beta cells, maturing beta cells, or pancreatic beta cells; and (b) administering the pancreatic endoderm cells, pancreatic endocrine cells, immature beta cells, maturing beta cell, or pancreatic beta cells to the subject.

In another method, Method 13, the present disclosure provides a method, as provided in Method 12, wherein administering comprises implanting a device comprising the pancreatic endoderm cells, pancreatic endocrine cells, immature beta cells, maturing beta cells, or pancreatic beta cells into the subject.

In another method, Method 14, the present disclosure provides a method, as provided in Method 12, wherein the subject has type I diabetes or type II diabetes.

In another method, Method 15, the present disclosure provides a method, as provided in Method 12, wherein the subject is human.

In another composition, Composition 65, the present disclosure provides a composition comprising a universal donor cell comprising (a) a nucleotide sequence encoding programmed death-ligand 1 (PD-L1) inserted within or near a gene encoding beta-2 microglobulin (B2M) and (b) a nucleotide sequence encoding HLA class I histocompatibility antigen, alpha chain E (HLA-E) inserted within or near a gene encoding thioredoxin interacting protein (TXNIP), wherein the universal donor cell expresses PD-L1 and HLA-E and has disrupted expression of B2M and TXNIP, and the universal donor cell has increased immune evasion and/or cell survival compared to a control cell.

In another composition, Composition 66, the present disclosure provides a composition, as provided in Composition 65, wherein the control cell is a wild type cell or a cell that does not comprise the inserted nucleotide sequence.

In another composition, Composition 67, the present disclosure provides a composition, as provided in Composition 65, wherein the disrupted expression of B2M comprises reduced or eliminated expression of B2M and the disrupted expression of TXNIP comprises reduced or eliminated expression of TXNIP.

In another composition, Composition 68, the present disclosure provides a composition, as provided in Composition 65, wherein the nucleotide sequence encoding PD-L1 consists essentially of SEQ ID NO: 11.

In another composition, Composition 69, the present disclosure provides a composition, as provided in Composition 65, wherein the nucleotide sequence encoding HLA-E comprises a sequence encoding a HLA-E trimer comprising a B2M signal peptide fused to an HLA-G presentation peptide fused to a B2M membrane protein fused to HLA-E without its signal peptide.

In another composition, Composition 70, the present disclosure provides a composition, as provided in Composition 69, wherein the sequence encoding the HLA-E trimer consists essentially of SEQ ID NO: 55.

In another composition, Composition 71, the present disclosure provides a composition, as provided in Composition 65, wherein the nucleotide sequence encoding PD-L1 is operably linked to an exogenous promoter, and the nucleotide sequence encoding HLA-E is operably linked to an exogenous promoter.

In another composition, Composition 72, the present disclosure provides a composition, as provided in Composition 71, wherein the exogenous promoter is a CAG promoter.

In another composition, Composition 73, the present disclosure provides a composition, as provided in Composition 65, wherein the cell is a stem cell.

In another composition, Composition 74, the present disclosure provides a composition, as provided in Composition 73, wherein the stem cell is an embryonic stem cell, an adult stem cell, an induced pluripotent stem cell, or a hematopoietic stem cell.

In another composition, Composition 75, the present disclosure provides a composition, as provided in Composition 65, wherein the cell is a differentiated cell or a somatic cell.

In another composition, Composition 76, the present disclosure provides a composition, as provided in Composition 65, wherein the cell is capable of being differentiated into lineage-restricted progenitor cells or fully differentiated somatic cells.

In another composition, Composition 77, the present disclosure provides a composition, as provided in Composition 76, wherein the lineage-restricted progenitor cells are definitive endoderm cells, primitive gut tube cells, posterior foregut cells, pancreatic endoderm progenitors, pancreatic endocrine progenitors, immature beta cells, or maturing beta cells, and the fully differentiated somatic cells are pancreatic beta cells.

In another composition, Composition 78, the present disclosure provides a composition comprising a plurality of universal donor cells as provided in Composition 65.

In another composition, Composition 79, the present disclosure provides a composition, as provided in Composition 78, wherein at least about 50% of the cells express PD-L1 and/or at least about 50% of the cells express HLA-E.

In another composition, Composition 80, the present disclosure provides a composition, as provided in Composition 78, wherein at least about 70% of the cells express PD-L1 and/or at least about 70% of the cells express HLA-E.

In another composition, Composition 81, the present disclosure provides a composition, as provided in Composition 78, wherein at least about 90% of the cells express PD-L1 and/or at least about 90% of the cells express HLA-E.

In another composition, Composition 82, the present disclosure provides a composition comprising a population of lineage-restricted progenitor cells or fully differentiated somatic cells derived from the plurality of universal donor cells, as provided in Composition 78.

In another composition, Composition 83, the present disclosure provides a composition, as provided in Composition 82, wherein the lineage-restricted progenitor cells are definitive endoderm cells, primitive gut tube cells, posterior foregut cells, pancreatic endoderm progenitors, pancreatic endocrine progenitors, immature beta cells, or maturing beta cells, and the fully differentiated somatic cells are pancreatic beta cells.

In another composition, Composition 84, the present disclosure provides a composition, as provided in Composition 83, wherein at least about 50% of the cells express PD-L1 and/or at least about 50% of the cells express HLA-E.

In another composition, Composition 85, the present disclosure provides a composition, as provided in Composition 83, wherein at least about 70% of the cells express PD-L1 and/or at least about 70% of the cells express HLA-E.

In another composition, Composition 86, the present disclosure provides a composition, as provided in Composition 83, wherein at least about 90% of the cells express PD-L1 and/or at least about 90% of the cells express HLA-E.

In another composition, Composition 87, the present disclosure provides a composition comprising a genetically modified cell having introduced or increased expression of PD-L1 and HLA-E and disrupted expression of B2M and TXNIP, wherein the genetically modified cell has increased immune evasion and/or cell survival compared to an unmodified cell.

In another composition, Composition 88, the present disclosure provides a composition, as provided in Composition 87, which comprises a nucleotide sequence encoding PD-L1 inserted within or near a gene encoding B2M, thereby disrupting the B2M gene, and a nucleotide sequence encoding HLA-E inserted within or near a gene encoding TXNIP, thereby disrupting the TXNIP gene.

In another composition, Composition 89, the present disclosure provides a composition, as provided in Composition 87, wherein disrupted expression of B2M and TXNIP comprises reduced or eliminated expression of B2M and TXNIP.

In another method, Method 16, the present disclosure provides a method for treating diabetes in a subject in need thereof, the method comprising: (a) obtaining or having obtained the plurality of universal donor cells of Composition 78 following differentiation into pancreatic endoderm cells, pancreatic endocrine cells, immature beta cells, maturing beta cell, or pancreatic beta cells; and (b) administering the pancreatic endoderm cells, pancreatic endocrine cells, immature beta cells, maturing beta cells, or pancreatic beta cells to the subject.

In another method, Method 17, the present disclosure provides a method, as provided in Method 16, wherein administering comprises implanting a device comprising the pancreatic endoderm cells, pancreatic endocrine cells, immature beta cells, maturing beta cells, or pancreatic beta cells into the subject.

In another method, Method 18, the present disclosure provides a method, as provided in Method 16, wherein the subject has type I diabetes or type II diabetes.

In another method, Method 19, the present disclosure provides a method, as provided in Method 16, wherein the subject is human.

In another method, Method 20, the present disclosure provides a method for generating a universal donor cell, the method comprising delivering to a cell: (a) a first site-directed nuclease targeting a site within or near a gene that encodes a survival factor; and (b) a first nucleic acid comprising a nucleotide sequence encoding a first tolerogenic factor that is flanked by (i) a nucleotide sequence homologous with a region located left of the target site of (a) and (ii) a nucleotide sequence homologous with a region located right of the target site of (a), wherein the first site-directed nuclease cleaves the target site of (a) and the first nucleic acid of (b) is inserted at a site that partially overlaps, completely overlaps, or is contained within, the site of (a), thereby generating a universal donor cell, wherein the universal donor cell has increased cell survival compared to a cell in which the nucleic acid of (b) has not been inserted.

In another method, Method 21, the present disclosure provides a method, as provided in Method 20, wherein the survival factor is TXNIP, ZNF143, FOXO1, JNK, or MANF.

In another method, Method 22, the present disclosure provides a method, as provided in Methods 20 or 21, wherein the first tolerogenic factor is PD-L1, HLA-E, HLA-G, CTLA-4, or CD47.

In another method, Method 23, the present disclosure provides a method, as provided in any one of Methods 20 to 22, wherein the survival factor is TXNIP.

In another method, Method 24, the present disclosure provides a method, as provided in Method 23, wherein the first tolerogenic factor is HLA-E.

In another method, Method 25, the present disclosure provides a method, as provided in any one of Methods 20 to 24, wherein the first site-directed nuclease is a CRISPR system comprising a CRISPR nuclease and a guide RNA (gRNA).

In another method, Method 26, the present disclosure provides a method, as provided in any one of Methods 20 to 25, wherein the CRISPR nuclease is a Type II Cas9 nuclease or a Type V Cfp1 nuclease, and the CRISPR nuclease is linked to at least one nuclear localization signal.

In another method, Method 27, the present disclosure provides a method, as provided in any one of Methods 20 to 26, wherein the gRNA comprises a spacer sequence corresponding to a target sequence consisting of SEQ ID NOS: 15-24.

In another method, Method 28, the present disclosure provides a method, as provided in any one of Methods 25 to 27, wherein the nucleotide sequence of (b)(i) consists essentially of SEQ ID NO: 25, and the nucleotide sequence of (b)(ii) consists essentially of SEQ ID NO: 32.

In another method, Method 29, the present disclosure provides a method, as provided in any one of Methods 20 to 28, wherein the method further comprises delivering to the cell: (c) a second site-directed nuclease targeting a site within or near a gene that encodes one or more of a MHC-I or MHC-II human leukocyte antigens or a component or a transcriptional regulator of a MHC-I or MHC-II complex; and (d) a second nucleic acid comprising a nucleotide sequence encoding a second tolerogenic factor that is flanked by (iii) a nucleotide sequence homologous with a region located left of the target site of (c) and a (iv) nucleotide sequence homologous with a region located right of the target site of (c), wherein the second tolerogenic factor of (d) differs from the first tolerogenic factor (b), wherein the second site-directed nuclease cleaves the target site of (c) and the second nucleic acid of (d) is inserted at a site that partially overlaps, completely overlaps, or is contained within, the site of (c), wherein the universal donor cell has increased immune evasion and/or cell survival compared to a cell in which the second nucleic acid of (d) has not been inserted.

In another method, Method 30, the present disclosure provides a method, as provided in Method 29, wherein the MHC-I or MHC-II human leukocyte antigen or the component or the transcriptional regulator of the MHC-I or MHC-II complex is HLA-A, HLA-B, HLA-C, HLA-DP, HLA-DM, HLA-DOA, HLA-DOB, HLA-DQ, HLA-DR, B2M, NLRC5, CIITA, RFX5, RFXAP, or RFXANK.

In another method, Method 31, the present disclosure provides a method, as provided in Methods 29 or 30, wherein the second tolerogenic factor is PD-L1, HLA-E, HLA-G, CTLA-4, or CD47.

In another method, Method 32, the present disclosure provides a method, as provided in any one of Methods 29 to 31, wherein the MHC-I or MHC-II human leukocyte antigen or the component or the transcriptional regulator of the MHC-I or MHC-II complex is B2M.

In another method, Method 33, the present disclosure provides a method, as provided in Method 32, wherein the second tolerogenic factor is PD-L1.

In another method, Method 34, the present disclosure provides a method, as provided in any one of Methods 29 to 33, wherein the second site-directed nuclease is CRISPR system comprising a CRISPR nuclease and a gRNA.

In another method, Method 35, the present disclosure provides a method, as provided in Method 34, wherein the CRISPR nuclease is a Type II Cas9 nuclease or a Type V Cfp1 nuclease, and the CRISPR nuclease is linked to at least one nuclear localization signal.

In another method, Method 36, the present disclosure provides a method, as provided in Methods 34 or 35, wherein the gRNA comprises a spacer sequence corresponding to a target sequence consisting of SEQ ID NOS: 1-3 or 35-44.

In another method, Method 37, the present disclosure provides a method, as provided in any one of Methods 34 to 36, wherein the nucleotide sequence of (d)(iii) consists essentially of SEQ ID NO: 7, and the nucleotide sequence of (d)(iv) consists essentially of SEQ ID NO: 13.

In another method, Method 38, the present disclosure provides a method, as provided in any one of Methods 25 to 28 or 34 to 37, wherein the CRISPR nuclease and the gRNA are present at a molar ratio of 1:3.

In another method, Method 39, the present disclosure provides a method, as provided in any one of Methods 20 to 38, wherein the nucleotide sequence encoding the first tolerogenic factor is operably linked to an exogenous promoter, and the nucleotide sequence encoding the second tolerogenic factor is operably linked to an exogenous promoter.

In another method, Method 40, the present disclosure provides a method, as provided in Method 39, wherein the exogenous promoter is a constitutive, inducible, temporal-, tissue-, or cell type-specific promoter, optionally wherein the exogenous promoter is a CMV, EF1α, PGK, CAG, or UBC promoter.

In another method, Method 41, the present disclosure provides a A method for generating a universal donor cell, the method comprising delivering to a cell: (a) a first site-directed nuclease targeting a site within or near a gene that encodes a survival factor; (b) a first nucleic acid comprising a nucleotide sequence encoding a first tolerogenic factor that is flanked by (i) a nucleotide sequence homologous with a region located left of the target site of (a) and (ii) a nucleotide sequence homologous with a region located right of the target site of (a), wherein the first site-directed nuclease cleaves the target site of (a) and, through a process of homologous recombination, the first nucleic acid of (b) is utilized as a template for inserting the nucleotide sequence encoding the first tolerogenic factor into a site that partially overlaps, completely overlaps, or is contained within, the site of (a), thereby disrupting the gene of (a); (c) a second site-directed nuclease targeting a site within or near a gene that encodes one or more of a MHC-I or MHC-II human leukocyte antigen or a component or a transcriptional regulator of a MHC-I or MHC-II complex; and (d) a second nucleic acid comprising a nucleotide sequence encoding a second tolerogenic factor that is flanked by (iii) a nucleotide sequence homologous with a region located left of the target site of (c) and a (iv) nucleotide sequence homologous with a region located right of the target site of (c), wherein the tolerogenic factor of (d) differs from the tolerogenic factor (b), wherein the second site-directed nuclease cleaves the target site of (c) and, through a process of homologous recombination, the second nucleic acid of (d) is utilized as a template for inserting the nucleotide sequence encoding the second tolerogenic factor into a site that partially overlaps, completely overlaps, or is contained within, the site of (c), thereby disrupting the gene of (c), thereby generating a universal donor cell, wherein the universal donor cell has increased cell survival compared to a cell in which the first nucleic acid of (b) and the second nucleic acid of (d) has not been inserted.

In another method, Method 42, the present disclosure provides a method, as provided in Method 41, wherein the survival factor is TXNIP, the first tolerogenic factor is HLA-E, the MHC-I or MHC-II human leukocyte antigen or a component or a transcriptional regulator of a MHC-I or MHC-II complex is B2M, and the second tolerogenic factor is PD-L1.

In another method, Method 43, the present disclosure provides a method, as provided in any one of Methods 20 to 42, wherein the cell is a mammalian cell, optionally wherein the cell is a human cell.

In another method, Method 44, the present disclosure provides a method, as provided in any one of Methods 20 to 43, wherein the cell is a stem cell.

In another method, Method 45, the present disclosure provides a method, as provided in any one of Methods 20 to 43, wherein the cell is a pluripotent stem cell, an embryonic stem cell, an adult stem cell, an induced pluripotent stem cell, or a hematopoietic stem cell.

In another method, Method 46, the present disclosure provides a method, as provided in any one of Methods 20 to 43, wherein the cell is a differentiated cell, or a somatic cell.

In another method, Method 47, the present disclosure provides a method, as provided in any one of Methods 20 to 43, wherein the universal donor cell is capable of being differentiated into lineage-restricted progenitor cells or fully differentiated somatic cells.

In another method, Method 48, the present disclosure provides a method, as provided in Method 47, wherein the lineage-restricted progenitor cells are pancreatic endoderm progenitors, pancreatic endocrine progenitors, mesenchymal progenitor cells, muscle progenitor cells, blast cells, hematopoietic progenitor cells, or neural progenitor cells.

In another method, Method 49, the present disclosure provides a method, as provided in Method 47, wherein the fully differentiated somatic cells are endocrine secretory cells such as pancreatic beta cells, epithelial cells, endodermal cells, macrophages, hepatocytes, adipocytes, kidney cells, blood cells, or immune system cells.

In another method, Method 49A, the present disclosure provides a method, as provided in Method 47, wherein the fully differentiated somatic cells are cardiomyocyte, or immune system cells.

In another composition, Composition 90, the present disclosure provides a composition comprising a plurality of universal donor cells generated by any one of Methods 20 to 49.

In another composition, Composition 91, the present disclosure provides a composition, as provided by Composition 90, maintained for a time and under conditions sufficient for the cells to undergo differentiation.

In another composition, Composition 92, the present disclosure provides a composition, as provided by Composition 90 or 91, for use in treating a subject in need thereof.

In another composition, Composition 93, the present disclosure provides a composition, as provided by Composition 92, wherein the subject is a human who has, is suspected of having, or is at risk for a disease.

In another method, Method 50, the present disclosure provides a method comprising administering to a subject the plurality of universal donor cells of Compositions 90 or 91.

In another method, Method 51, the present disclosure provides a method for treating of a subject in need thereof, the method comprising: (a) obtaining or having obtained the plurality of universal donor cells of Composition 90 following differentiation into lineage-restricted progenitor cells or fully differentiated somatic cells; and (b) administering the lineage-restricted progenitor cells or fully differentiated somatic cells to the subject.

In another method, Method 52, the present disclosure provides a method of obtaining cells for administration to a subject in need thereof, the method comprising: (a) obtaining or having obtained the universal donor cells of claim 31; and (b) maintaining the universal donor cells for a time and under conditions sufficient for the cells to differentiate into lineage-restricted progenitor cells or fully differentiated somatic cells.

In another method, Method 53, the present disclosure provides a method, as provided by Methods 51 or 52, wherein the lineage-restricted progenitor cells are pancreatic endoderm progenitors, pancreatic endocrine progenitors, mesenchymal progenitor cells, muscle progenitor cells, blast cells, hematopoietic progenitor cells, or neural progenitor cells.

In another method, Method 54, the present disclosure provides a method, as provided by Methods 51 or 52, wherein the fully differentiated somatic cells are endocrine secretory cells such as pancreatic beta cells, epithelial cells, endodermal cells, macrophages, hepatocytes, adipocytes, kidney cells, blood cells, or immune system cells.

In another method, Method 54A, the present disclosure provides a method, as provided in Method 51 or 52, wherein the fully differentiated somatic cells are cardiomyocytes.

In another method, Method 55, the present disclosure provides a method, as provided by Methods 50 to 54, wherein the subject is a human who has, is suspected of having, or is at risk for a disease.

In another method, Method 56, the present disclosure provides a method, as provided by Method 55, wherein the disease is a genetically inheritable disease.

In another composition, Composition 93, the present disclosure provides a guide RNA comprising a spacer sequence corresponding to a target sequence consisting of SEQ ID NO: 15-24.

In another method, Method 57, the present disclosure provides an in vitro method for generating a universal donor cell, the method comprising delivering to a stem cell: (a) an RNA-guided nuclease; (b) a guide RNA (gRNA) targeting a target site in a thioredoxin interacting protein (TXNIP) gene locus; and (c) a vector comprising a nucleic acid, the nucleic acid comprising: (i) a nucleotide sequence encoding a tolerogenic factor; (ii) a nucleotide sequence consisting essentially of SEQ ID NO: 25 and having sequence homology with a genomic region located left and within 50 nucleobases of the target site; and (iii) a nucleotide sequence consisting essentially of SEQ ID NO: 32 and having sequence homology with a genomic region located right and within 50 nucleobases of the target site, wherein (i) is flanked by (ii) and (iii); wherein the TXNIP gene locus is cleaved at the target site and the nucleic acid is inserted into the TXNIP gene locus, thereby disrupting the TXNIP gene and generating a universal donor cell, wherein the universal donor cell has increased immune evasion and/or cell survival compared to a control cell.

In another method, Method 57A, the present disclosure provides a method, as provided by Method 57, wherein the nucleic acid is inserted into the TXNIP gene locus within 50 base pairs of the target site.

In another method, Method 58, the present disclosure provides a method, as provided by Method 57, wherein the control cell is a wild type cell or a cell that does not comprise the inserted nucleic acid.

In another method, Method 59, the present disclosure provides a method, as provided by Method 57, wherein the disrupted TXNIP gene has reduced or eliminated expression of TXNIP.

In another method, Method 60, the present disclosure provides a method, as provided by Method 57, wherein the gRNA comprises a spacer sequence corresponding to a sequence consisting of SEQ ID NO: 15-24.

In another method, Method 61, the present disclosure provides a method, as provided by Method 57, wherein the gRNA comprises a spacer sequence corresponding to a sequence consisting of SEQ ID NO: 20.

In another method, Method 62, the present disclosure provides a method, as provided by Method 57, wherein the vector is a plasmid vector.

In another method, Method 63, the present disclosure provides a method, as provided by Method 57, wherein the tolerogenic factor is HLA class I histocompatibility antigen, alpha chain E (HLA-E).

In another method, Method 64, the present disclosure provides a method, as provided by Method 63, wherein the nucleotide sequence encoding HLA-E comprises a sequence encoding a HLA-E trimer comprising a B2M signal peptide fused to an HLA-G presentation peptide fused to a B2M membrane protein fused to HLA-E without its signal peptide.

In another method, Method 65, the present disclosure provides a method, as provided by Method 63, wherein the sequence encoding the HLA-E trimer consists essentially of SEQ ID NO: 55.

In another method, Method 66, the present disclosure provides a method, as provided by Method 65, wherein the sequence encoding the HLA-E trimer is operably linked to an exogenous promoter.

In another method, Method 67, the present disclosure provides a method, as provided by Method 66, wherein the exogenous promoter is a CMV, EF1α, PGK, CAG, or UBC promoter.

In another method, Method 68, the present disclosure provides a method, as provided by Method 57, wherein the RNA-guided nuclease is a Cas9 nuclease.

In another method, Method 69, the present disclosure provides a method, as provided by Method 68, wherein the Cas9 nuclease is linked to at least one nuclear localization signal.

In another method, Method 70, the present disclosure provides a method, as provided by Method 69, wherein the Cas9 nuclease and the gRNA are present in a molar ratio of 1:3.

In another method, Method 71, the present disclosure provides a method, as provided by Method 57, wherein the stem cell is an embryonic stem cell, an adult stem cell, an induced pluripotent stem cell, or a hematopoietic stem cell.

In another method, Method 72, the present disclosure provides a method, as provided by Method 57, wherein the stem cell is a human stem cell.

In another method, Method 73, the present disclosure provides an in vitro method for generating a universal donor cell, the method comprising delivering to a stem cell: (a) an RNA-guided nuclease; (b) a guide RNA (gRNA) targeting a target site in a thioredoxin interacting protein (TXNIP) gene locus, and (c) a vector comprising a nucleic acid, the nucleic acid comprising: (i) a nucleotide sequence encoding a tolerogenic factor; (ii) a nucleotide sequence having sequence homology with a genomic region located left and within 50 nucleobases of the target site; and (iii) a nucleotide sequence having sequence homology with a genomic region located right and within 50 nucleobases of the target site, wherein (i) is flanked by (ii) and (iii), and the vector comprises a nucleotide sequence consisting of SEQ ID NO: 34 or 56; wherein the TXNIP gene locus is cleaved at the target site and the nucleic acid is inserted into the TXNIP gene locus, thereby disrupting the TXNIP gene and generating a universal donor cell, wherein the universal donor cell has increased immune evasion and/or cell survival compared to a control cell.

In another method, Method 73A, the present disclosure provides a method, as provided by Method 73, wherein the nucleic acid is inserted into the TXNIP gene locus within 50 base pairs of the target site.

In another method, Method 74, the present disclosure provides a method, as provided by Method 73, wherein the control cell is a wild type cell or a cell that does not comprise the inserted nucleic acid.

In another method, Method 75, the present disclosure provides a method, as provided by Method 73, wherein the disrupted TXNIP gene has reduced or eliminated expression of TXNIP.

In another method, Method 76, the present disclosure provides a method, as provided by Method 73, wherein the gRNA comprises a spacer sequence corresponding to a sequence consisting of SEQ ID NO: 15-24.

In another method, Method 77, the present disclosure provides a method, as provided by Method 73, wherein the gRNA comprises a spacer sequence corresponding to a sequence consisting of SEQ ID NO: 20.

In another method, Method 78, the present disclosure provides a method, as provided by Method 73, wherein the vector is a plasmid vector.

In another method, Method 79, the present disclosure provides a method, as provided by Method 73, wherein the tolerogenic factor is HLA class I histocompatibility antigen, alpha chain E (HLA-E).

In another method, Method 80, the present disclosure provides a method, as provided by Method 73, wherein the RNA-guided nuclease is a Cas9 nuclease.

In another method, Method 81, the present disclosure provides a method, as provided by Method 80, wherein the Cas9 nuclease is linked to at least one nuclear localization signal.

In another method, Method 82, the present disclosure provides a method, as provided by Method 80, wherein the Cas9 nuclease and the gRNA are present in a molar ratio of 1:3.

In another method, Method 83, the present disclosure provides a method, as provided by Method 73, wherein the stem cell is an embryonic stem cell, an adult stem cell, an induced pluripotent stem cell, or a hematopoietic stem cell.

In another method, Method 84, the present disclosure provides a method, as provided by Method 73, wherein the stem cell is a human stem cell.

In another method, Method 85, the present disclosure provides an in vitro method for generating a universal donor cell, the method comprising delivering to a stem cell: (a) a first ribonucleoprotein (RNP) complex comprising an RNA-guided nuclease and a guide RNA (gRNA) targeting a target site in a beta-2 microglobulin (B2M) gene locus; (b) a first vector comprising a nucleic acid, the nucleic acid comprising: (i) a nucleotide sequence encoding a first tolerogenic factor; (ii) a nucleotide sequence consisting essentially of SEQ ID NO: 7 and having sequence homology with a genomic region located left and within 50 nucleobases of the target site in the B2M gene locus; and (iii) a nucleotide sequence consisting essentially of SEQ ID NO: 13 and having sequence homology with a genomic region located right and within 50 nucleobases of the target site in the B2M gene locus, wherein (i) is flanked by (ii) and (iii); wherein the B2M gene locus is cleaved at the target site and the nucleic acid comprising the nucleotide sequence encoding the first tolerogenic factor is inserted into the B2M gene locus, thereby disrupting the B2M gene; (c) a second RNP complex comprising an RNA-guided nuclease and a gRNA targeting a target site in a thioredoxin interacting protein (TXNIP) gene locus; and (d) a second vector comprising a nucleic acid, the nucleic acid comprising: (i) a nucleotide sequence encoding a second tolerogenic factor; (ii) a nucleotide sequence consisting essentially of SEQ ID NO: 25 and having sequence homology with a genomic region located left and within 50 nucleobases of the target site in the TXNIP gene locus; and (iii) a nucleotide sequence consisting essentially of SEQ ID NO: 32 and having sequence homology with a genomic region located right and within 50 nucleobases of the target site in the TXNIP gene locus, wherein (i) is flanked by (ii) and (iii); wherein the TXNIP gene locus is cleaved at the target site and the nucleic acid comprising the nucleotide sequence encoding the second tolerogenic factor is inserted into the TXNIP gene locus, thereby disrupting the TXNIP gene and generating a universal donor cell, wherein the universal donor cell has increased immune evasion and/or cell survival compared to a control cell.

In another method, Method 85A, the present disclosure provides a method, as provided by Method 85, wherein the nucleic acid in (b) is inserted into the B2M gene locus within 50 base pairs of the target site and/or wherein the nucleic acid in (d) is inserted into the TXNIP gene locus within 50 base pairs of the target site.

In another method, Method 86, the present disclosure provides a method, as provided by Method 85, wherein the control cell is a wild type cell or a cell that does not comprise the inserted nucleic acid.

In another method, Method 87, the present disclosure provides a method, as provided by Method 85, the disrupted B2M gene has reduced or eliminated expression of B2M, and the disrupted TXNIP gene has reduced or eliminated expression of TXNIP.

In another method, Method 88, the present disclosure provides a method, as provided by Method 85, wherein the gRNA of the first RNP complex comprises a spacer sequence corresponding to a sequence consisting of SEQ ID NO: 1-3 or 35-44, and the gRNA of the second RNP complex comprises a spacer sequence corresponding to a sequence consisting of SEQ ID NO: 15-24.

In another method, Method 89, the present disclosure provides a method, as provided by Method 85, wherein the gRNA of the first RNP complex comprises a spacer sequence corresponding to a sequence consisting of SEQ ID NO: 2, and the gRNA of the second RNP complex comprises a spacer sequence corresponding to a sequence consisting of SEQ ID NO: 20.

In another method, Method 90, the present disclosure provides a method, as provided by Method 85, wherein the first vector is a plasmid vector, and the second vector is a plasmid vector.

In another method, Method 91, the present disclosure provides a method, as provided by Method 85, wherein the first tolerogenic factor is programmed death-ligand 1 (PD-L1), and the second tolerogenic factor is HLA class I histocompatibility antigen, alpha chain E (HLA-E).

In another method, Method 92, the present disclosure provides a method, as provided by Method 91, wherein the nucleotide sequence encoding PD-L1 consists essentially of SEQ ID NO: 11.

In another method, Method 93, the present disclosure provides a method, as provided by Method 91, wherein the nucleotide sequence encoding HLA-E comprises a sequence encoding a HLA-E trimer comprising a B2M signal peptide fused to an HLA-G presentation peptide fused to a B2M membrane protein fused to HLA-E without its signal peptide, and the sequence encoding the HLA-E trimer consists essentially of SEQ ID NO: 55.

In another method, Method 94, the present disclosure provides a method, as provided by Method 85, wherein the nucleotide sequence encoding the first tolerogenic factor is operably linked to an exogenous promoter, and the nucleotide sequence encoding the second tolerogenic factor is operably linked to an exogenous promoter.

In another method, Method 95, the present disclosure provides a method, as provided by Method 94, wherein the exogenous promoter is a CMV, EF1α, PGK, CAG, or UBC promoter.

In another method, Method 96, the present disclosure provides a method, as provided by Method 85, wherein each of the first RNP complex and the second RNP complex comprises a molar ratio of RNA-guided nuclease to gRNA of 1:3.

In another method, Method 97, the present disclosure provides a method, as provided by Method 85, wherein the RNA-guided nuclease of each the first RNP complex and the second RNP complex is a Cas9 nuclease.

In another method, Method 98, the present disclosure provides a method, as provided by Method 97, wherein the Cas9 nuclease is linked to at least one nuclear localization signal.

In another method, Method 99, the present disclosure provides a method, as provided by Method 85, wherein the stem cell is an embryonic stem cell, an adult stem cell, an induced pluripotent stem cell, or a hematopoietic stem cell.

In another method, Method 100, the present disclosure provides a method, as provided by Method 85, wherein the stem cell is a human stem cell.

In another method, Method 101, the present disclosure provides an in vitro method for generating a universal donor cell, the method comprising delivering to a stem cell: (a) a first ribonucleoprotein (RNP) complex comprising an RNA-guided nuclease and a guide RNA (gRNA) targeting a target site in a beta-2 microglobulin (B2M) gene locus; (b) a first vector comprising a nucleic acid, the nucleic acid comprising: (i) a nucleotide sequence encoding a first tolerogenic factor; (ii) a nucleotide sequence having sequence homology with a genomic region located left and within 50 nucleobases of the target site in the B2M gene locus; and (iii) a nucleotide sequence having sequence homology with a genomic region located right and within 50 nucleobases of the target site in the B2M gene locus, wherein (i) is flanked by (ii) and (iii) and the first vector comprises a nucleotide sequence consisting of SEQ ID NO: 33; wherein the B2M gene locus is cleaved at the target site and the nucleic acid comprising the nucleotide sequence encoding the first tolerogenic factor is inserted into the B2M gene locus within, thereby disrupting the B2M gene; (c) a second RNP complex comprising an RNA-guided nuclease and a gRNA targeting a target site in a thioredoxin interacting protein (TXNIP) gene locus; and (d) a second vector comprising a nucleic acid, the nucleic acid comprising: (i) a nucleotide sequence encoding a second tolerogenic factor; (ii) a nucleotide sequence having sequence homology with a genomic region located left and within 50 nucleobases of the target site in the TXNIP gene locus; and (iii) a nucleotide sequence having sequence homology with a genomic region located right and within 50 nucleobases of the target site in the TXNIP gene locus, wherein (i) is flanked by (ii) and (iii) and the second vector that comprises a nucleotide sequence consisting of SEQ ID NO: 34 or 56 wherein the TXNIP gene locus is cleaved at the target site and the nucleic acid comprising the nucleotide sequence encoding the second tolerogenic factor is inserted into the TXNIP gene locus, thereby disrupting the TXNIP gene and generating a universal donor cell, wherein the universal donor cell has increased immune evasion and/or cell survival compared to a control cell.

In another method, Method 101A, the present disclosure provides a method, as provided by Method 101, wherein the nucleic acid in (b) is inserted into the B2M gene locus within 50 base pairs of the target site and/or wherein the nucleic acid in (d) is inserted into the TXNIP gene locus within 50 base pairs of the target site.

In another method, Method 102, the present disclosure provides a method, as provided by Method 101, wherein the control cell is a wild type cell or a cell that does not comprise the inserted nucleic acid.

In another method, Method 103, the present disclosure provides a method, as provided by Method 10, wherein the disrupted B2M gene has reduced or eliminated expression of B2M, and the disrupted TXNIP gene has reduced or eliminated expression of TXNIP.

In another method, Method 104, the present disclosure provides a method, as provided by Method 101, wherein the gRNA of the first RNP complex comprises a spacer sequence corresponding to a sequence consisting of SEQ ID NO: 1-3 or 35-44, and the gRNA of the second RNP complex comprises a spacer sequence corresponding to a sequence consisting of SEQ ID NO: 15-24.

In another method, Method 105, the present disclosure provides a method, as provided by Method 101, wherein the gRNA of the first RNP complex comprises a spacer sequence corresponding to a sequence consisting of SEQ ID NO: 2, and the gRNA of the second RNP complex comprises a spacer sequence corresponding to a sequence consisting of SEQ ID NO: 20.

In another method, Method 106, the present disclosure provides a method, as provided by Method 101, wherein the first vector is a plasmid vector, and the second vector is a plasmid vector.

In another method, Method 107, the present disclosure provides a method, as provided by Method 101, wherein the first tolerogenic factor is programmed death-ligand 1 (PD-L1), and the second tolerogenic factor is HLA class I histocompatibility antigen, alpha chain E (HLA-E).

In another method, Method 108, the present disclosure provides a method, as provided by Method 101, wherein each of the first RNP complex and the second RNP complex comprises a molar ratio of RNA-guided nuclease to gRNA of 1:3.

In another method, Method 109, the present disclosure provides a method, as provided by Method 101, wherein the RNA-guided nuclease of each the first RNP complex and the second RNP complex is a Cas9 nuclease.

In another method, Method 110, the present disclosure provides a method, as provided by Method 109, wherein the Cas9 nuclease is linked to at least one nuclear localization signal.

In another method, Method 111, the present disclosure provides a method, as provided by Method 101, wherein the stem cell is an embryonic stem cell, an adult stem cell, an induced pluripotent stem cell, or a hematopoietic stem cell.

In another method, Method 112, the present disclosure provides a method, as provided by Method 101, wherein the stem cell is a human stem cell.

In a first process, Process 1, the present disclosure provides a process for generating universal donor cells, the process comprising: (a) modifying stem cells by inserting a nucleotide sequence encoding programmed death-ligand 1 (PD-L1) within or near a gene encoding beta-2 microglobulin (B2M), thereby generating PD-L1 positive cells; (b) enriching for PD-L1 positive cells; (c) modifying the PD-L1 positive cells from (b) by inserting a nucleotide sequence encoding HLA class I histocompatibility antigen, alpha chain E (HLA-E) within or near a gene encoding thioredoxin interacting protein (TXNIP), thereby generating PD-L1, HLA-E double positive cells; (d) enriching for PD-L1, HLA-E double positive cells; (e) single cell sorting to select for PD-L1, HLA-E double positive cells; (f) characterizing cells from (e) as universal donor cells; and (g) freezing the universal donor cells for long term storage.

In another process, Process 2, the present disclosure provide a process, as provided in Process 1, wherein the modifying at (a) comprises delivering to the stem cells (1) a first ribonucleoprotein (RNP) complex comprising an RNA-guided nuclease and a guide RNA (gRNA) targeting a target site in the B2M gene locus and (2) a first vector comprising a nucleic acid, the nucleic acid comprising (i) a nucleotide sequence homologous with a region located left of the target site in the B2M gene locus, (ii) the nucleotide sequence encoding PD-L1, and (iii) a nucleotide sequence homologous with a region located right of the target site in the B2M gene locus, wherein the B2M gene locus is cleaved at the target site and the nucleic acid comprising the nucleotide sequence encoding PD-L1 is inserted into the B2M gene locus, thereby disrupting the B2M gene.

In another process, Process 2A, the present disclosure provides a method, as provided by Process 2, wherein the nucleic acid is inserted into the B2M gene locus within 50 base pairs of the target site.

In another process, Process 3, the present disclosure provide a process, as provided in Process 2, wherein the RNA-guided nuclease of the first RNP complex is a Cas9 nuclease and the gRNA of the first RNP complex comprises a spacer sequence corresponding to a target sequence consisting of SEQ ID NO: 2.

In another process, Process 4, the present disclosure provide a process, as provided in Process 3, wherein the Cas9 nuclease is linked to at least one nuclear localization signal.

In another process, Process 5, the present disclosure provide a process, as provided in Process 2, wherein the first RNP comprises a molar ratio of gRNA:RNA-guided nuclease of 3:1.

In another process, Process 6, the present disclosure provide a process, as provided in Process 2, wherein the nucleotide sequence of (a)(2)(i) consists essentially of SEQ ID NO: 7, and the nucleotide sequence of (a)(2)(iii) consists essentially of SEQ ID NO: 13.

In another process, Process 7, the present disclosure provide a process, as provided in Process 2, wherein the nucleotide sequence encoding PD-L1 consists essentially of SEQ ID NO: 11.

In another process, Process 8, the present disclosure provide a process, as provided in Process 2, wherein the nucleotide sequence encoding PD-L1 is operably linked to a CAG promoter.

In another process, Process 9, the present disclosure provide a process, as provided in Process 2, wherein the first vector is a plasmid vector and comprises a nucleotide sequence consisting of SEQ ID NO: 33.

In another process, Process 10, the present disclosure provide a process, as provided in Process 2, wherein the delivering of (a)(1) and (a)(2) comprises electroporation.

In another process, Process 11, the present disclosure provide a process, as provided in Process 1, wherein the enriching for PD-L1 positive cells at (b) comprises magnetic assisted cell sorting (MACS), single cell cloning, expanding said PD-L1 positive cells, or a combination thereof.

In another process, Process 12, the present disclosure provide a process, as provided in Process 1, wherein the modifying at (c) comprises delivering to the PD-L1 positive cells (1) a second RNP complex comprising an RNA-guided nuclease and a gRNA targeting a target site in the TXNIP gene locus and (2) a second vector comprising a nucleic acid, the nucleic acid comprising (i) a nucleotide sequence homologous with a region located left of the target site in the TXNIP gene locus, (ii) the nucleotide sequence encoding HLA-E, and (iii) a nucleotide sequence homologous with a region located right of the target site in the TXNIP gene locus, wherein the TXNIP gene locus is cleaved at the target site and the nucleic acid comprising the nucleotide sequence encoding HLA-E is inserted into the TXNIP gene locus, thereby disrupting the TXNIP gene.

In another process, Process 12A, the present disclosure provides a method, as provided by Process 12, wherein the nucleic acid is inserted into the TXNIP gene locus within 50 base pairs of the target site.

In another process, Process 13, the present disclosure provide a process, as provided in Process 12, wherein the RNA-guided nuclease of the second RNP complex is a Cas9 nuclease and the gRNA of the second RNP complex comprises a spacer sequence corresponding to a target sequence consisting of SEQ ID NO: 20.

In another process, Process 14, the present disclosure provide a process, as provided in Process 13, wherein the Cas9 nuclease is linked to at least one nuclear localization signal.

In another process, Process 15, the present disclosure provide a process, as provided in Process 12, wherein the second RNP comprises a molar ratio of gRNA:RNA-guided nuclease of 3:1.

In another process, Process 16, the present disclosure provide a process, as provided in Process 12, wherein the nucleotide sequence of (c)(2)(i) consists essentially of SEQ ID NO: 25, and the nucleotide sequence of (c)(2)(iii) consists essentially of SEQ ID NO: 32.

In another process, Process 17, the present disclosure provide a process, as provided in Process 12, wherein the nucleotide sequence encoding HLA-E comprises a sequence encoding a HLA-E trimer comprising a B2M signal peptide fused to an HLA-G presentation peptide fused to a B2M membrane protein fused to HLA-E without its signal peptide.

In another process, Process 18, the present disclosure provide a process, as provided in Process 17, wherein the sequence encoding the HLA-E trimer consists essentially of SEQ ID NO: 55.

In another process, Process 19, the present disclosure provide a process, as provided in Process 12, wherein the nucleotide sequence encoding HLA-E is operably linked to a CAG promoter.

In another process, Process 20, the present disclosure provide a process, as provided in Process 12, wherein the second vector is a plasmid vector and comprises a nucleotide sequence consisting of SEQ ID NO: 34 or 56.

In another process, Process 21, the present disclosure provide a process, as provided in Process 12, wherein the delivering of (c)(1) and (c)(2) comprises electroporation.

In another process, Process 22, the present disclosure provide a process, as provided in Process claim 1, wherein the enriching for PD-L1, HLA-E double positive cells at (d) comprises magnetic assisted cell sorting, single cell cloning, expanding said PD-L1, HLA-E double positive cells, or a combination thereof.

In another process, Process 23, the present disclosure provide a process, as provided in Process 1, wherein the single-cell sorting at (e) comprises fluorescence-activated cell sorting (FACS), single cell cloning, expanding said single cell sorted cells, or a combination thereof.

In another process, Process 24, the present disclosure provide a process, as provided in Process 1, wherein the characterizing at (f) comprises DNA analyses for zygosity and/or indel profile.

In another process, Process 25, the present disclosure provide a process, as provided in Process 1, wherein the characterizing at (f) comprises cell analyses for morphology, viability, karyotyping, endotoxin levels, mycoplasma levels, on/off target analysis, random vector insertion, residual Cas9, residual vector, pluripotency status, differentiation capacity, or a combination thereof.

In another process, Process 26, the present disclosure provide a process, as provided in Process 1, wherein the process further comprises freezing prior to the characterizing at (f).

In another process, Process 27, the present disclosure provide a process, as provided in Process 1, further comprising in (a) expanding the generated PD-L1 positive cells, in (c) expanding the generated PD-L1, HLA-E double positive cells, in (e) expanding the selected PD-L1, HLA-E double positive cells, or a combination thereof.

In another process, Process 28, the present disclosure provide a process for generating universal donor cells, the process comprising: (a) modifying stem cells by inserting a nucleotide sequence encoding a first tolerogenic factor within or near a gene encoding a MHC-I or MHC-II human leukocyte antigen or a component or a transcriptional regulator of a MHC-I or MHC-II complex, thereby generating first tolerogenic factor positive cells; (b) enriching for first tolerogenic factor positive cells; (c) modifying the first tolerogenic factor positive cells from (b) by inserting a nucleotide sequence encoding a second tolerogenic factor within or near a gene encoding a survival factor, thereby generating first tolerogenic factor positive/second tolerogenic factor positive cells; (d) enriching for first tolerogenic factor positive/second tolerogenic factor positive cells; (e) single cell sorting to select for first tolerogenic factor positive/second tolerogenic factor positive cells; (f) characterizing the cells from (e) as universal donor cells; and (g) freezing the universal donor cells for long term storage.

In another process, Process 29, the present disclosure provide a process, as provided in Process 28, wherein the enriching for first tolerogenic factor positive cells at (b) comprises magnetic assisted cell sorting (MACS), single cell cloning, expanding said first tolerogenic factor positive cells, or a combination thereof.

In another process, Process 30, the present disclosure provide a process, as provided in Process 28 or 29, wherein the enriching for first tolerogenic factor positive/second tolerogenic factor positive cells at (d) comprises magnetic assisted cell sorting, single cell cloning, expanding said first tolerogenic factor positive/second tolerogenic factor positive cells, or a combination thereof.

In another process, Process 31, the present disclosure provide a process, as provided in any one of Processes 28 to 30, further comprising in (a) expanding the generated first tolerogenic factor positive cells, in (c) expanding the generated first tolerogenic factor positive/second tolerogenic factor positive cells, in (e) expanding the selected first tolerogenic factor positive/second tolerogenic factor positive cells, or a combination thereof.

In another process, Process 32, the present disclosure provide a process, as provided in any one of Processes 28 to 31, wherein the modifying at (a) comprises delivering to the stem cells (1) a first RNA-guided nuclease and a first guide RNA (gRNA) targeting a target site in a MHC-I or MHC-II human leukocyte antigen or a component or a transcriptional regulator of a MHC-I or MHC-II complex gene locus and (2) a first vector comprising a first nucleic acid, the first nucleic acid comprising (i) a nucleotide sequence homologous with a region located left of the target site in the MHC-I or MHC-II human leukocyte antigens or a component or a transcriptional regulator of a MHC-I or MHC-II complex gene locus, (ii) the nucleotide sequence encoding the first tolerogenic factor, and (iii) a nucleotide sequence homologous with a region located right of the target site in the MHC-I or MHC-II human leukocyte antigens or a component or a transcriptional regulator of a MHC-I or MHC-II complex gene locus, wherein the MHC-I or MHC-II human leukocyte antigen or a component or a transcriptional regulator of a MHC-I or MHC-II complex gene locus is cleaved at the target site and the first nucleic acid comprising the nucleotide sequence encoding first tolerogenic factor is inserted into the MHC-I or MHC-II human leukocyte antigen or a component or a transcriptional regulator of a MHC-I or MHC-II complex gene locus, thereby disrupting the MHC-I or MHC-II human leukocyte antigen or a component or a transcriptional regulator of a MHC-I or MHC-II complex gene.

In another process, Process 32A, the present disclosure provides a method, as provided by Process 32, wherein the nucleic acid is inserted into the MHC-I or MHC-II human leukocyte antigen or a component or a transcriptional regulator of a MHC-I or MHC-II complex gene locus within 50 base pairs of the target site.

In another process, Process 33, the present disclosure provide a process, as provided in Process 32, wherein the first RNA-guided nuclease and the first gRNA form a first ribonucleoprotein (RNP) complex.

In another process, Process 34, the present disclosure provide a process, as provided in any one of Processes 28 to 33, wherein the modifying at (a) comprises delivering to the stem cells (1) a first ribonucleoprotein (RNP) complex comprising a first RNA-guided nuclease and a first guide RNA (gRNA) targeting a target site in a MHC-I or MHC-II human leukocyte antigen or a component or a transcriptional regulator of a MHC-I or MHC-II complex gene locus and (2) a first vector comprising a first nucleic acid, the first nucleic acid comprising (i) a nucleotide sequence homologous with a region located left of the target site in the MHC-I or MHC-II human leukocyte antigen or a component or a transcriptional regulator of a MHC-I or MHC-II complex gene locus, (ii) the nucleotide sequence encoding the first tolerogenic factor, and (iii) a nucleotide sequence homologous with a region located right of the target site in the MHC-I or MHC-II human leukocyte antigen or a component or a transcriptional regulator of a MHC-I or MHC-II complex gene locus, wherein the MHC-I or MHC-II human leukocyte antigen or a component or a transcriptional regulator of a MHC-I or MHC-II complex gene locus is cleaved at the target site and the first nucleic acid comprising the nucleotide sequence encoding first tolerogenic factor is inserted into the MHC-I or MHC-II human leukocyte antigen or a component or a transcriptional regulator of a MHC-I or MHC-II complex gene locus, thereby disrupting the MHC-I or MHC-II human leukocyte antigen or a component or a transcriptional regulator of a MHC-I or MHC-II complex gene.

In another process, Process 34A, the present disclosure provides a method, as provided by Process 34, wherein the nucleic acid is inserted into the MHC-I or MHC-II human leukocyte antigen or a component or a transcriptional regulator of a MHC-I or MHC-II complex gene locus within 50 base pairs of the target site.

In another process, Process 35, the present disclosure provide a process, as provided in any one of Processes 28 to 34, wherein the MHC-I or MHC-II human leukocyte antigen or a component or a transcriptional regulator of a MHC-I or MHC-II complex gene is HLA-A, HLA-B, HLA-C, HLA-DP, HLA-DM, HLA-DOA, HLA-DOB, HLA-DQ, HLA-DR, B2M, NLRC5, CIITA, RFX5, RFXAP, or RFXANK.

In another process, Process 36, the present disclosure provide a process, as provided in any one of Processes 28 to 35, wherein the MHC-I or MHC-II human leukocyte antigen or a component or a transcriptional regulator of a MHC-I or MHC-II complex gene is B2M.

In another process, Process 37, the present disclosure provide a process, as provided in Process 36, wherein the nucleotide sequence of (a)(2)(i) consists essentially of SEQ ID NO: 7, and the nucleotide sequence of (a)(2)(iii) consists essentially of SEQ ID NO: 13.

In another process, Process 38, the present disclosure provide a process, as provided in Processes 36 or 37, wherein the first gRNA comprises a spacer sequence corresponding to a target sequence consisting of SEQ ID NO: 2.

In another process, Process 39, the present disclosure provide a process, as provided in any one of Processes 32 to 38, wherein the first RNA-guided nuclease is a Cas9 nuclease.

In another process, Process 40 the present disclosure provide a process, as provided in Process 39, wherein the Cas9 nuclease is linked to at least one nuclear localization signal.

In another process, Process 41, the present disclosure provide a process, as provided in any one of Processes 32 to 40, wherein the first RNP comprises a molar ratio of first gRNA:first RNA-guided nuclease of 3:1.

In another process, Process 42, the present disclosure provide a process, as provided in any one of Processes 28 to 41, wherein the first tolerogenic factor is PD-L1, HLA-E, HLA-G, CTLA-4, or CD47.

In another process, Process 43, the present disclosure provide a process, as provided in any one of Processes 28 to 42, wherein the nucleotide sequence encoding the first tolerogenic factor is operably linked to an exogenous promoter.

In another process, Process 44, the present disclosure provide a process, as provided in Processe 43, wherein the exogenous promoter is a CMV, EF1α, PGK, CAG, or UBC promoter.

In another process, Process 45, the present disclosure provide a process, as provided in any one of Processes 28 to 44, wherein the first tolerogenic factor is PD-L1.

In another process, Process 46, the present disclosure provide a process, as provided in Process 45, wherein the nucleotide sequence encoding PD-L1 consists essentially of SEQ ID NO: 11.

In another process, Process 47, the present disclosure provide a process, as provided in Process 46, wherein the nucleotide sequence encoding PD-L1 is operably linked to a CAG promoter.

In another process, Process 48, the present disclosure provide a process, as provided in any one of Processes 45 to 47, wherein the first vector comprises a nucleotide sequence consisting of SEQ ID NO: 33.

In another process, Process 49, the present disclosure provide a process, as provided in any one of Processes 28 to 48, wherein the modifying at (c) comprises delivering to the stem cells (1) a second RNA-guided nuclease and a second guide RNA (gRNA) targeting a target site in a survival factor gene locus and (2) a second vector comprising a second nucleic acid, the second nucleic acid comprising (i) a nucleotide sequence homologous with a region located left of the target site in the survival factor gene locus, (ii) the nucleotide sequence encoding the second tolerogenic factor, and (iii) a nucleotide sequence homologous with a region located right of the target site in the survival factor gene locus, wherein the survival factor gene locus is cleaved at the target site and the second nucleic acid comprising the nucleotide sequence encoding the second tolerogenic factor is inserted into the survival factor gene locus, thereby disrupting the survival factor gene.

In another process, Process 49A, the present disclosure provides a method, as provided by Process 49, wherein the nucleic acid is inserted into the survival factor gene locus within 50 base pairs of the target site.

In another process, Process 50, the present disclosure provide a process, as provided in Process 49, wherein the second RNA-guided nuclease and the second gRNA form a second ribonucleoprotein (RNP) complex.

In another process, Process 51, the present disclosure provide a process, as provided in any one of Processes 28 to 48, wherein the modifying at (c) comprises delivering to the first tolerogenic factor positive cells (1) a second ribonucleoprotein (RNP) complex comprising a second RNA-guided nuclease and a second guide RNA (gRNA) targeting a target site in a survival factor gene locus and (2) a second vector comprising a second nucleic acid, the second nucleic acid comprising (i) a nucleotide sequence homologous with a region located left of the target site in the survival factor gene locus, (ii) the nucleotide sequence encoding the second tolerogenic factor, and (iii) a nucleotide sequence homologous with a region located right of the target site in the second survival factor gene locus, wherein the survival factor gene locus is cleaved at the target site and the second nucleic acid comprising the nucleotide sequence encoding the second tolerogenic factor is inserted into the survival factor gene locus, thereby disrupting the survival factor gene.

In another process, Process 51A, the present disclosure provides a method, as provided by Process 51, wherein the nucleic acid is inserted into the survival factor gene locus within 50 base pairs of the target site.

In another process, Process 52, the present disclosure provide a process, as provided in any one of Processes 28 to 51, wherein the survival gene is TXNIP, ZNF143, FOXO1, JNK, or MANF.

In another process, Process 53, the present disclosure provide a process, as provided in Process 52, wherein the survival gene is TXNIP.

In another process, Process 54, the present disclosure provide a process, as provided in Process 53, wherein the second gRNA comprises a spacer sequence corresponding to a target sequence consisting of SEQ ID NO: 20.

In another process, Process 55, the present disclosure provide a process, as provided in Process 52 or 53, wherein the nucleotide sequence of (c)(2)(i) consists essentially of SEQ ID NO: 25, and the nucleotide sequence of (c)(2)(iii) consists essentially of SEQ ID NO: 32.

In another process, Process 56, the present disclosure provide a process, as provided in any one of Processes 49 to 55, wherein the second RNA-guided nuclease is a Cas9 nuclease.

In another process, Process 57, the present disclosure provide a process, as provided in Process 56, wherein the Cas9 nuclease is linked to at least one nuclear localization signal.

In another process, Process 58, the present disclosure provide a process, as provided in any one of Processes 49 to 57, wherein the second RNP comprises a molar ratio of second gRNA:second RNA-guided nuclease of 3:1.

In another process, Process 59, the present disclosure provide a process, as provided in any one of Processes 49 to 58, wherein the second tolerogenic factor is PD-L1, HLA-E, HLA-G, CTLA-4, or CD47.

In another process, Process 60, the present disclosure provide a process, as provided in any one of Processes 28 to 59, wherein the nucleotide sequence encoding the second tolerogenic factor is operably linked to an exogenous promoter.

In another process, Process 61, the present disclosure provide a process, as provided in Process 60, wherein the exogenous promoter is a CMV, EF1α, PGK, CAG, or UBC promoter.

In another process, Process 62, the present disclosure provide a process, as provided in any one of Processes 28 to 61, wherein the second tolerogenic factor is HLA-E.

In another process, Process 63, the present disclosure provide a process, as provided in Process 62, wherein the nucleotide sequence encoding HLA-E comprises a sequence encoding a HLA-E trimer comprising a B2M signal peptide fused to an HLA-G presentation peptide fused to a B2M membrane protein fused to HLA-E without its signal peptide.

In another process, Process 64, the present disclosure provide a process, as provided in Process 63, wherein the sequence encoding the HLA-E trimer consists essentially of SEQ ID NO: 55.

In another process, Process 65, the present disclosure provide a process, as provided in Process 63 or 64, wherein the nucleotide sequence encoding HLA-E is operably linked to a CAG promoter.

In another process, Process 66, the present disclosure provide a process, as provided in any one of Processes 62 to 65, wherein the second vector comprises a nucleotide sequence consisting of SEQ ID NO: 34 or 56.

In another process, Process 67, the present disclosure provide a process, as provided in any one of Processes 28 to 66, wherein the single-cell sorting at (e) comprises fluorescence-activated cell sorting (FACS), single cell cloning, expanding said single cell sorted cells, or a combination thereof.

In another process, Process 68, the present disclosure provide a process, as provided in any one of Processes 28 to 67, wherein the characterizing at (f) comprises DNA analyses for zygosity and/or indel profile.

In another process, Process 69, the present disclosure provide a process, as provided in any one of Processes 28 to 68, wherein the characterizing at (f) comprises cell analyses for morphology, viability, karyotyping, endotoxin levels, mycoplasma levels, on/off target analysis, random vector insertion, residual Cas9, residual vector, pluripotency status, differentiation capacity, or a combination thereof.

In another process, Process 70, the present disclosure provide a process, as provided in any one of Processes 28 to 69, wherein the process further comprises freezing prior to the characterizing at (f).

VII. Examples

The examples below describe generation and characterization of specific universal donor cells according to the present disclosure.

Example 1

Cell Maintenance and Expansion

Maintenance of hESC/hiPSCs. Cells of human embryonic stem cell line CyT49 (proprietary hES cell line, ViaCyte, Inc., San Diego, Calif.) were maintained, cultured, passaged, proliferated, and plated as described in Schulz et al. (2012) PLoS ONE 7(5): e37004. CyT49 cells were disassociated using ACCUTASE® (Stemcell Technologies 07920 or equivalent).

Human induced pluripotent stem cells (hiPSCs), such as the TC1133 cell line (Lonza), were maintained in StemFlex Complete (Life Technologies, A3349401) on BIOLAMININ 521 CTG (BioLamina Cat #CT521) coated tissue culture plates. The plates were pre-coated with a 1:10 or a 1:20 dilution of BIOLAMININ in DPBS, calcium, magnesium (Life Technologies, 14040133) for 2 hours at 37° C. The cells were fed daily with StemFlex media. For passaging of the cells, same densities of cells as for CyT49 were used. For plating of the cells as single cells, the cells were plated with 1% RevitaCell™ Supplement (100×) (Thermofisher Cat #A2644501) in StemFlex on BIOLAMININ coated plates.

Single cell cloning of hPSCs. For single cell cloning, hPSCs (hESCs or hiPSCs) were fed with StemFlex Complete with Revitacell (for final concentration of 1× Revitacell) 3-4 hours prior to dissociation with ACCUTASE®. Following dissociation, the cells were sorted as a single cell per well of a BIOLAMININ coated 96 well tissue culture plate. The WOLF FACS-sorter (Nanocellect) was used to sort single cells into the wells. The plates were pre-filled with 100-200 µL of StemFlex Complete with Revitacell. Three days post cell seeding, the cells were fed with fresh StemFlex and continued to be fed every other day with 100-200 µL of media. After 10 days of growth, the cells were fed daily with StemFlex until day 12-14. At this time, the plates were dissociated with ACCUTASE® and the collected cell suspensions were split 1:2 with half going into a new 96 well plate for maintenance and half going into a DNA extraction solution QuickExtract™ DNA Extraction Solution (Lucigen). Following DNA extraction, PCR was performed to assess presence or absence of desired gene edits at the targeted DNA locus. Sanger sequencing was used to verify desired edits.

Expansion of single cell derived hPSCs clones. For CyT49 (ViaCyte), successfully targeted clones were passaged onto 24-well plates with pure 10% XF KSR A10H10 media but on BIOLAMININ-coated plates. Following the 24-well stage, CyT49 clones were passaged as described in Schulz et al. (2012) PLoS ONE 7(5): e37004.

For hiPSCs (TC1133), cells were maintained in StemFlex Complete throughout the cloning and regular maintenance processes on BIOLAMININ-coated plates with Revitacell at the passaging stages.

Example 2

Generation of B2M Knock-Out (KO) Human Pluripotent Stem Cells (hPSCs)

Guide RNA (gRNA) selection for B2M in hPSCs. Three B2M targeting gRNAs were designed for targeting exon 1 of the B2M coding sequence. These gRNAs had predicted low off-target scores based on sequence homology prediction using gRNA design software. The target sequences of the gRNAs are presented in Table 1. A gRNA comprises RNA sequence corresponding to the target DNA sequence.

TABLE 1

B2M gRNA Target Sequences

| Name | Target Sequence (5'-3') | SEQ ID NO: | PAM |
| --- | --- | --- | --- |
| B2M-1 gRNA (Exon 1_T12) | GCTACTCTCTCTTTCTGGCC | 1 | TGG |
| B2M-2 gRNA (Exon 1_T2) | GGCCGAGATGTCTCGCTCCG | 2 | TGG |
| B2M-3 gRNA (Exon 1_T8) | CGCGAGCACAGCTAAGGCCA | 3 | CGG |
| Exon 1_T1 | TATAAGTGGAGGCGTCGCGC | 35 | TGG |
| Exon 1_T3 | GAGTAGCGCGAGCACAGCTA | 36 | AGG |
| Exon 1_T4 | ACTGGACGCGTCGCGCTGGC | 37 | GGG |
| Exon 1_T5 | AAGTGGAGGCGTCGCGCTGG | 38 | CGG |
| Exon 1_T6 | GGCCACGGAGCGAGACATCT | 39 | CGG |
| Exon 1_T7 | GCCCGAATGCTGTCAGCTTC | 40 | AGG |
| Exon 1_T9 | CTCGCGCTACTCTCTCTTTC | 41 | TGG |
| Exon 1_T10 | TCCTGAAGCTGACAGCATTC | 42 | GGG |
| Exon 1_T11 | TTCCTGAAGCTGACAGCATT | 43 | CGG |
| Exon 1_T13 | ACTCTCTCTTTCTGGCCTGG | 44 | AGG |

To assess their cutting efficiency in hPSCs, CyT49 cells (ViaCyte proprietary hES cell line) were electroporated using the Neon Electroporator (Neon Transfection System ThermoFisher Cat #MPK5000) with a ribonucleoprotein (RNP) mixture of Cas9 protein (Biomay) and guide RNA (Synthego) (See Table 3 for gRNA sequences) at a molar ratio of 3:1 (gRNA:Cas9) with absolute values of 125 pmol Cas9 and 375 pmol gRNA. To form the RNP complex, gRNA and Cas9 were combined in one vessel with R-buffer (Neon Transfection System 100 µL Kit ThermoFisher Cat #MPK10096) to a total volume of 25 µL and incubated for 15 min at RT. Cells were dissociated using ACCUTASE®, then resuspended in DMEM/F12 media (Gibco, cat #11320033), counted using an NC-200 (Chemometec) and centrifuged. A total of 1×10$^6$ cells were resuspended with the RNP complex and R-buffer was added to a total volume of 125 µL. This mixture was then electroporated with 2 pulses for 30 ms at 1100 V. Following electroporation, the cells were pipetted out into an Eppendorf tube filled with StemFlex media with RevitaCell. This cell suspension was then plated into tissue culture dishes pre-coated with BIOLAMININ 521 CTG at 1:20 dilution. Cells were cultured in a normoxia incubator (37° C., 8% CO$_2$) for 48 hours. After 48 hours, genomic DNA was harvested from the cells using QuickExtract (Lucigen, Middleton, Wis.; Cat #QE09050).

PCR for the target B2M sequence was performed and the resulting amplified DNA was assessed for cutting efficiency by TIDE analysis. PCR for relevant regions was performed using Platinum Taq Supermix (Invitrogen, cat #125320176 and Cat #11495017). The sequence of the PCR primers are presented in Table 2; and the cycling conditions provided in Table 3.

TABLE 2

B2M TIDE Primers

| Name | Type | Sequence (5'-3') | SEQ ID NO: |
|---|---|---|---|
| B2MF2 | forward | CAGACAGCAAACTCACCCAG | 4 |
| B2MR2 | reverse | AAACTTTGTCCCGACCCTCC | 5 |

TABLE 3

B2M PCR Cycling Parameters

| Step | Temperature | Time | Cycles |
|---|---|---|---|
| Denaturation | 94° C. | 2 min | 1 |
| Denaturation | 94° C. | 15 sec | 38 |
| Annealing | 55° C. ° C. | 30 sec | |
| Extension | 68° C. | 45 sec | |
| Elongation | 68° C. | 5 min | 1 |
| Hold | 4 | hold | |

The resulting amplicons were submitted for PCR cleanup and Sanger sequencing. Sanger sequencing results were input into Tsunami software along with the guide sequence. Indel percentages and identities were calculated by the software. Particular gRNAs were then selected based on their indel frequency in hPSCs. FIG. 1 shows the cutting efficiency of B2M-1, B2M-2, and B2M-3 gRNAs.

Off-targets of the selected gRNAs were assessed in the stem cell-derived DNA using hybrid capture analysis of the sequence similarity predicted sites. B2M-2 and B2M-3 guides did not show detectable off-target effects. B2M-2 gRNA was chosen for further clone generation due to its high on-target activity and undetectable off-target activity.

B2M KO hPSC clone generation and characterization. Using B2M-2 gRNA, CyT49 hESCs (ViaCyte) were electroporated and single-cell sorted 3 days post electroporation using the WOLF FACS-sorter (Nanocellect) into BIO-LAMININ 521 CTG coated 96-well plates with StemFlex and Revitacell. Plated single cells were grown in a normoxia incubator (37° C., 8% CO$_2$) with every other day media changes until colonies were large enough to be re-seeded as single cells. When confluent, samples were split for maintenance and genomic DNA extraction.

Figure 2A:
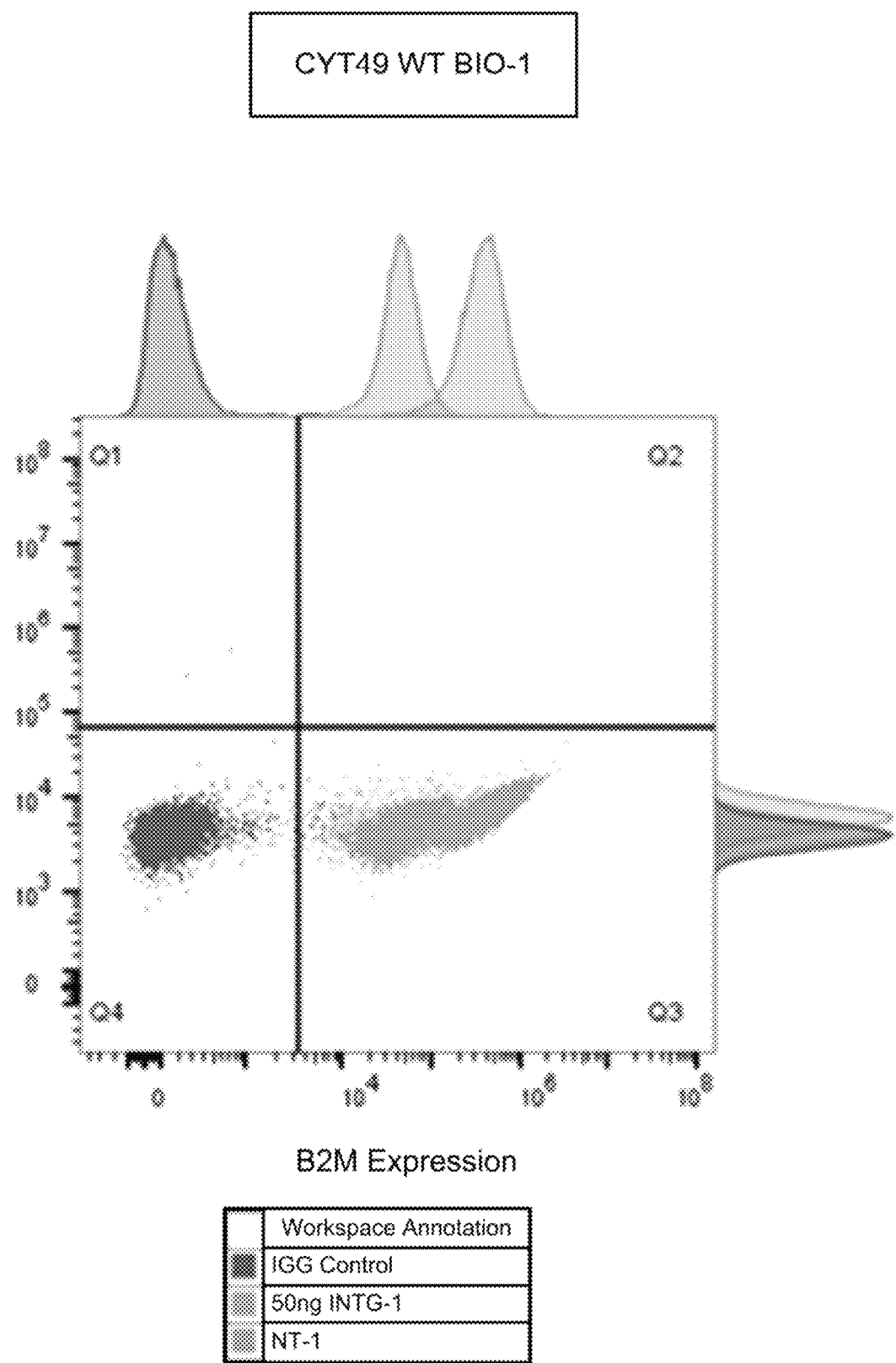
FIGS. 2A-2B show flow cytometry assessment of B2M expression with and without IFN-γ in WT CyT49 cells (FIG. 2A) and B2M KO CyT49 cells (FIG. 2B).
Figure 2B:
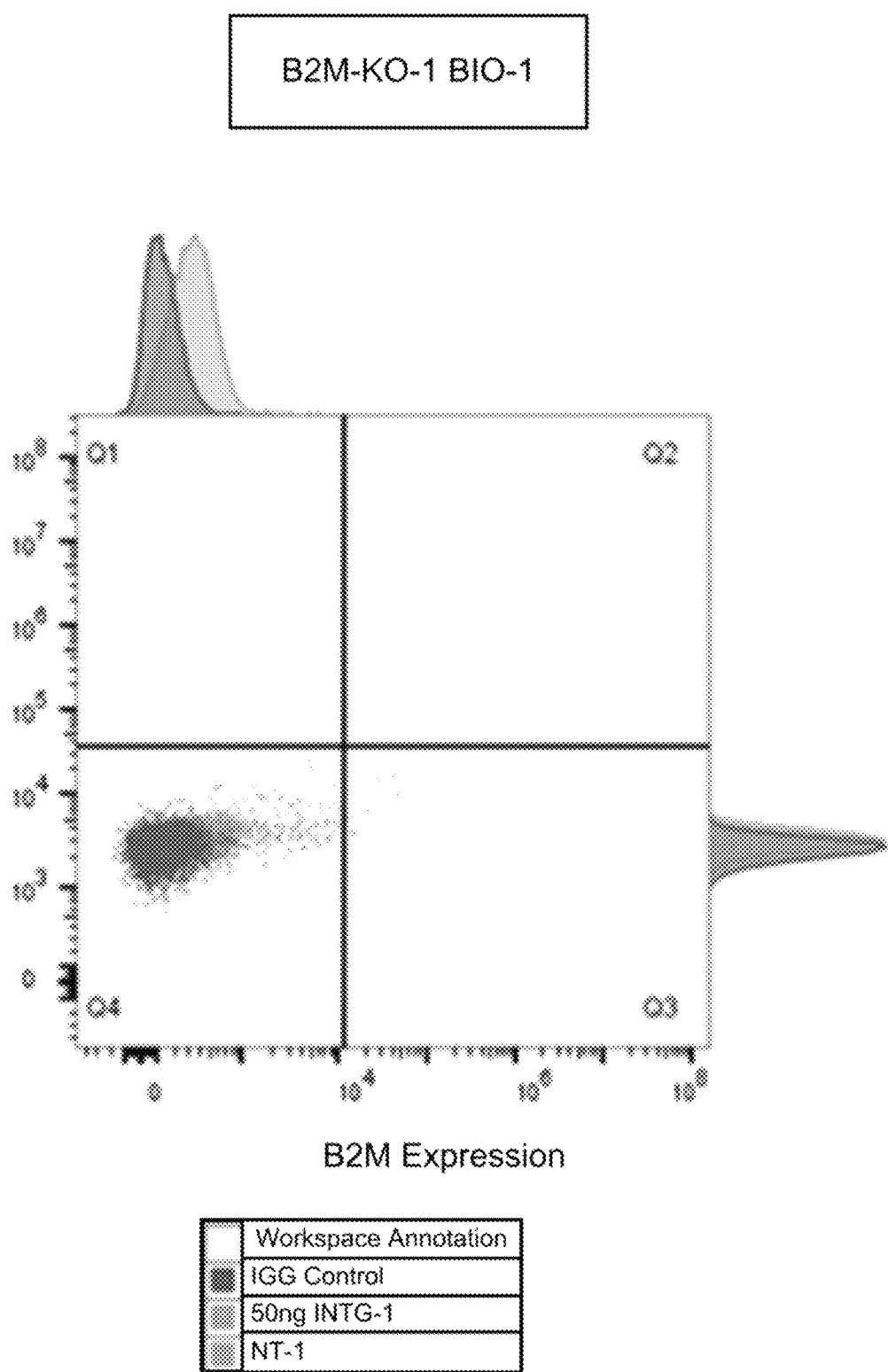

The B2M KO state of clones was confirmed via PCR and Sanger sequencing. The resulting DNA sequences of the target B2M region were aligned in Snapgene software to determine indel identity and zygosity. Clones with desired edits were expanded and further verified through flow cytometry assessment for B2M expression (See Table 4 for list of antibodies utilized). Clones were assessed with or without Interferon-gamma treatment (25 ng/mL, R & D Systems, 285-IF). FIG. 2A shows B2M expression in wild type cells and FIG. 2B presents B2M expression in B2M KO cells. Karyotypic status of clones was evaluated through Cell Line Genetics service (Madison, Wis.) and normal karyotype was reported.

TABLE 4

Antibodies for Pluripotency Flow Cytometry

| Antigen | Clone | Fluorophore | Manufacturer | Catalog # |
|---|---|---|---|---|
| Oct3/4 | 40/3 | Alexa 647 | BD Bioscience | 560329 |
| SOX2 | 030-678 | PE | BD Bioscience | 562195 |
| B2M | 2M2 | PE | Biolegend | 316305 |
| HLA-ABC | W6/32 | Alexa 488 | Biolegend | 311415 |
| mIgG1 kappa | N/A | PE | BD Bioscience | 555749 |
| PD-L1 | B7-H1 | Alexa-488 | ThermoFisher | 53-5983-42 |
| HLA-E | 3D12 | PE | ThermoFisher | 12-9953-42 |

Clones were confirmed to retain pluripotency through intracellular flow cytometry for pluripotency markers OCT4 and SOX2. Confirmed pluripotent clones were differentiated to pancreatic endocrine progenitors using previously established methods (Schulz et al. (2012) PLoS ONE 7(5): e37004).

Example 3

Generation of B2M KO/PD-L1 Knock-In (KI) Human Pluripotent Stem Cells (hPSCs)

Figure 3:
FIG. 3 shows the plasmid map of B2M-CAGGS-PD-L1 donor vector for HDR.

Design of B2M KO/PD-L1 KI strategy. Plasmid design to insert PD-L1 (CD274) into the B2M locus was made such that the starting codon of B2M was removed after undergoing homology directed repair (HDR) to insert PD-L1, nullifying any chance of partial B2M expression. FIG. 3 presents a schematic of the plasmid and Table 5 identifies the elements and locations therein. The donor plasmid contained a CAGGS promoter driven cDNA of PD-L1 flanked by 800 base pair homology arms with identical sequence to the B2M locus around exon 1. The complete sequence of the plasmid comprises SEQ ID NO: 33.

TABLE 5

Elements of B2M-CAGGS-PD-L1 Donor Plasmid

| Element | Location (size in bp) | SEQ ID NO: |
|---|---|---|
| Left ITR | 1-130 (130) | 6 |
| LHA-B2M | 145-944 (800) | 7 |
| CMV enhancer | 973-1352 (380) | 8 |
| chicken β-actin promoter | 1355-1630 (276) | 9 |
| chimeric intron | 1631-2639 (1009) | 10 |
| PD-L1 | 2684-3556 (873) | 11 |
| bGH poly(A) signal | 3574-3798 (225) | 12 |

TABLE 5-continued

Elements of B2M-CAGGS-PD-L1 Donor Plasmid

| Element | Location (size in bp) | SEQ ID NO: |
|---|---|---|
| RHA-B2M | 3805-4604 (800) | 13 |
| Right ITR | 4646-4786 (141) | 14 |
| Entire plasmid | 7133 bp | 33 |

The B2M-2 gRNA was used to facilitate insertion of the PD-L1 transgene at the targeted B2M locus. The PD-L1 donor plasmid was introduced along with the RNP complex made up of the B2M targeting gRNA and Cas9 protein. Per 1 million of CyT49 cells (ViaCyte), 4 μg of plasmid DNA was delivered along with the RNP. Electroporation was carried out as described in Example 2. Seven days post electroporation, the cells were sorted for PD-L1 surface expression using the WOLF FACS-sorter (Nanocellect) into BIOLAMININ 521 CTG coated 96-well plates with Stem-Flex with Revitacell. For FACS-sorting, unedited cells served as a negative control. PD-L1 positive cells were selected for sorting and single cell cloning.

To detect the PD-L1 surface expression, anti-PD-L1 fluorescent antibodies were used (see Table 4). Plated single cells were grown in a normoxia incubator (37° C., 8% $CO_2$) with every other day media changes until colonies were large enough to be re-seeded as single cells. When confluent, samples were split for maintenance and genomic DNA extraction.

Figure 4:
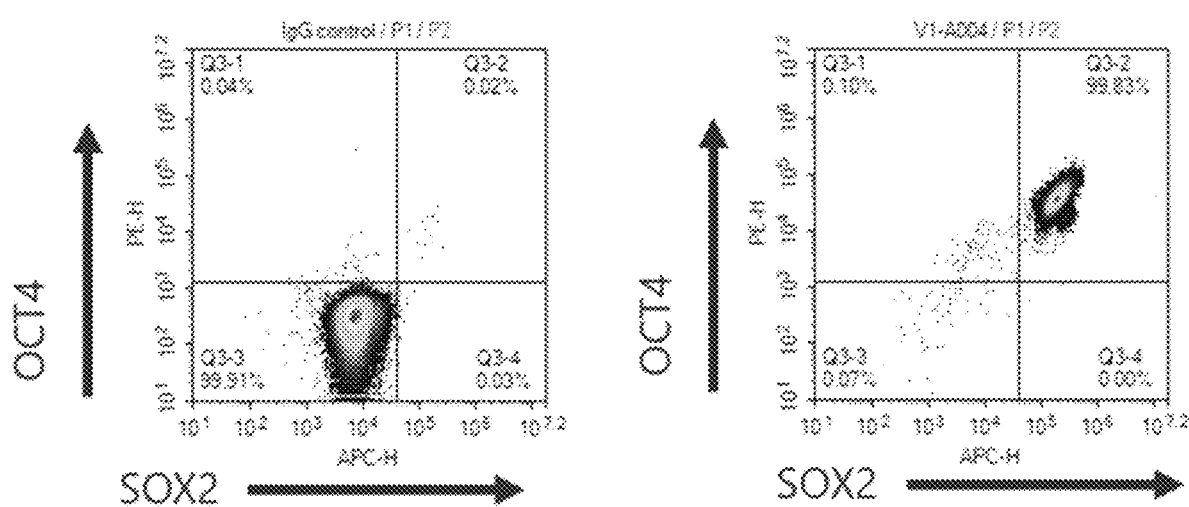
FIG. 4 shows flow cytometry analysis for pluripotency of B2M KO/PD-L1 KI CyT49 stem cells. The derived clones were >99% double positive for OCT4 and SOX2, two transcription factors vital for pluripotency. IgG was used as a negative control.
Figure 5A:
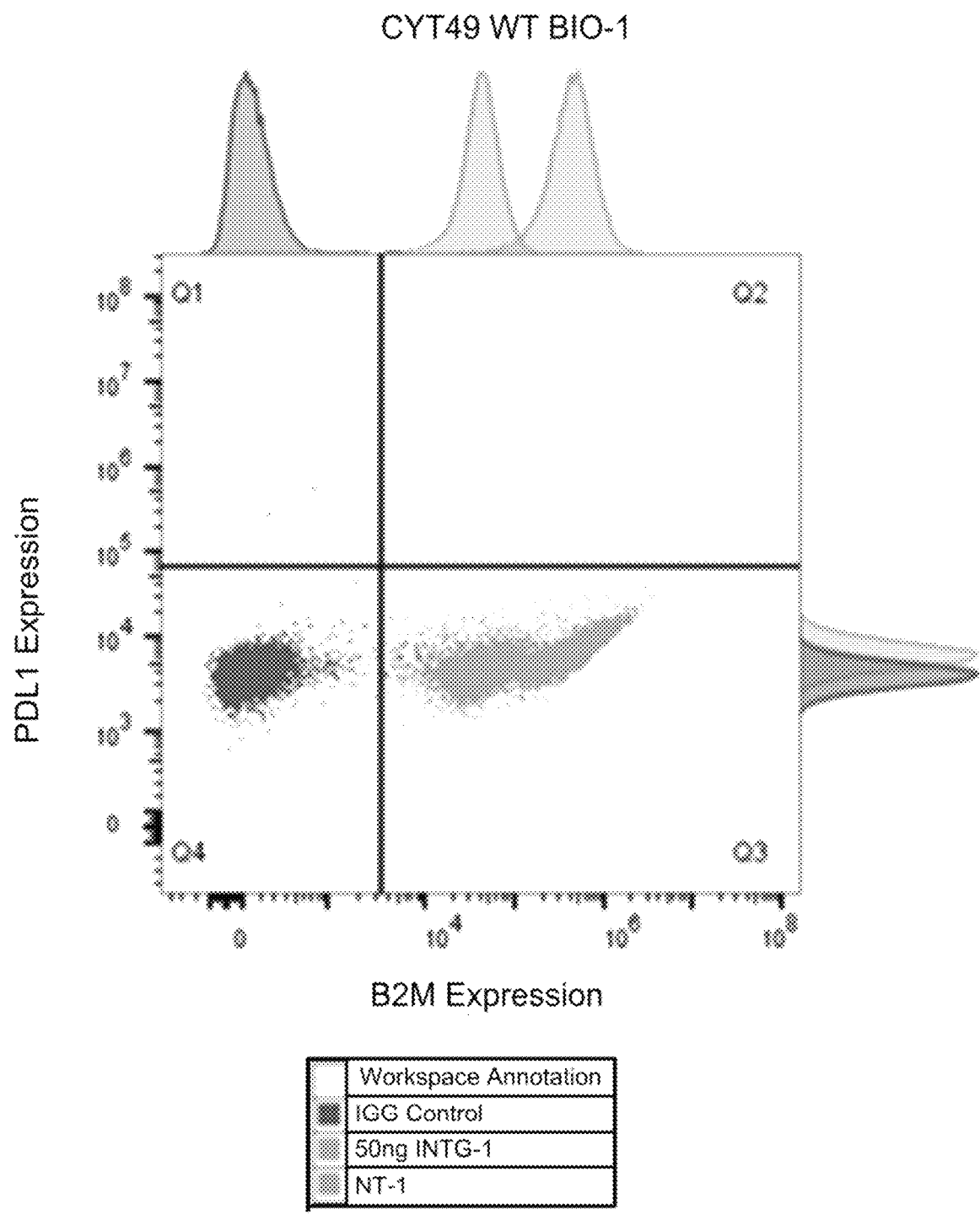
FIGS. 5A-5B show the flow cytometry analysis of WT CyT49 (FIG. 5A) and a B2M KO/PD-L1 KI (FIG. 5B) derived stem cell clones. WT cells upregulate B2M expression in response to IFNγ. B2M KO/PD-L1 KI clones fully express PD-L1 and do not express B2M with or without IFNγ treatment. NT-1=no treatment. INTG-1=50 ng/mL IFNγ 48 hour treated cells.
Figure 5B:
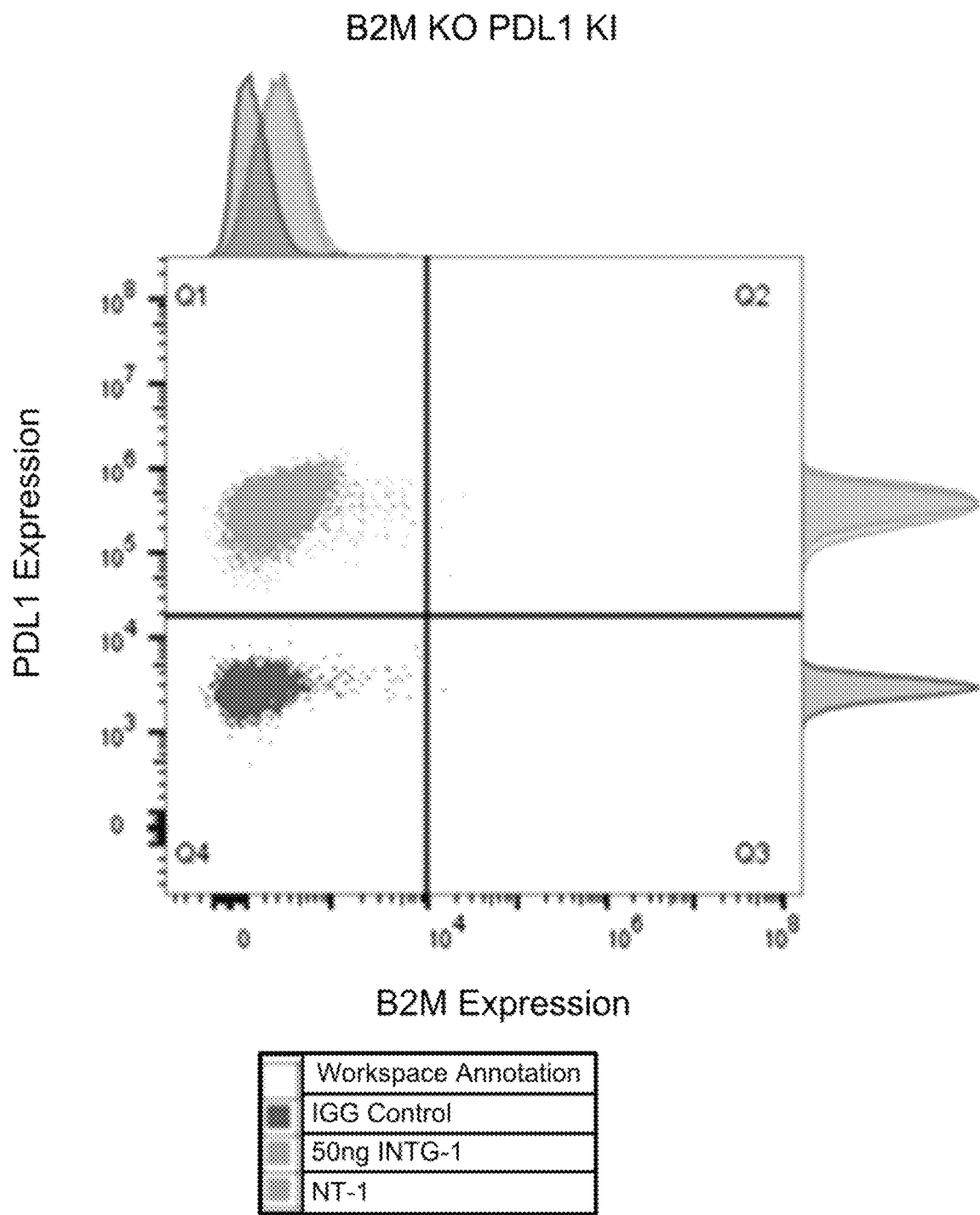

Correctly targeted clones were identified via PCR for the PD-L1 knock-in (KI) insertion using primers that amplify a region from outside the plasmid homology arms to the PD-L1 cDNA insertion enabling amplification of the KI integrated DNA only. On-target insertion was tested for zygosity by PCR to assess if KI occurred in a heterozygous or homozygous manner. If a heterozygous clone was identified, the KI negative allele was sent for Sanger sequencing to verify that it contained a B2M-disrupting indel in the non-KI allele. The correct KI clones with full B2M disruption (either via KI insertion or indel formation) were expanded in increasing tissue culture formats until a population size of 30 million cells was reached. Approximately 10 clones were expanded in this manner and confirmed to be pluripotent by testing for OCT4 and SOX2 via intracellular flow cytometry (FIG. 4). Clones that passed the above tests, were then tested further for karyotypic analysis (Cell Line Genetics), as described below. Additionally, the clones were then tested for their competence to differentiate to pancreatic endoderm precursors (PEC) via the established protocol (Schulz et al. (2012) PLoS ONE 7(5): e37004), as described below. The loss of B2M was further confirmed by lack of expression of B2M with or without interferon-gamma treatment (25 ng/mL, R & D Systems, 285-IF) through flow cytometry. FIGS. 5A and 5B show PD-L1 expression in wildtype and B2M KO/PD-L1 KI cells, respectively.

Example 4

Karyotype Analysis of Edited Clones

C-Band Karyotyping Analysis of Edited Embryonic Stem (ES) Cells. 1 million of edited ES cells were passaged into a T-25 culture flask with culture media (DMEM/F12+10% Xeno-free KSR with 10 ng/mL Activin and 10 ng/mL Heregulin). After culturing overnight, three T25 culture flasks were shipped to Cytogenetics Laboratory (Cell Line Genetics, Inc.) for Karyotyping analysis; FISH analysis for Chromosome 1, 12, 17, 20; and array comparative genomic hybridization (aCGH) analysis with standard 8×60K array. The G-banding results of selected cells electroporated with non-cutting guides ("NCG"), B2M KO clones, and B2M KO/PD-L1 KI clones ("V1-A") are shown in Table 6.

TABLE 6

G-band Karyotyping Results

| Cell Line | Type | Passage | Karyotyping analysis | FISH analysis | aCGH array analysis |
|---|---|---|---|---|---|
| NCG #1 | non-cutting guide | P36 | Normal | Normal | PASS |
| NCG #2 | non-cutting guide | P36 | Normal | Normal | PASS |
| B2M KO #1 | B2M KO | P38 | Normal | Normal | PASS |
| B2M KO #2 | B2M KO | P36 | Normal | Normal | PASS |
| B2M KO #3 | B2M KO | P36 | Normal | Normal | PASS |
| V1-A003 | B2M KO/ PD-L1 KI | P37 | Normal | Normal | PASS |
| V1-A004 | B2M KO/ PD-L1 KI | P38 | Normal | Normal | PASS |
| V1-A007 | B2M KO/ PD-L1 KI | P37 | Normal | Normal | PASS |
| V1-A008 | B2M KO/ PD-L1 KI | P38 | Normal | Normal | PASS |

Example 5

Differentiation of Edited Human Embryonic Stem Cells to Pancreatic Endoderm Cells (PECs)

Maintenance of edited human embryonic stem cells (ES). The edited human embryonic stem cells at various passages (P38-42) were seeded at 33,000 cells/cm$^2$ for a 4-day passage or 50,000 cells/cm$^2$ for a 3-day passage with hESM medium (DMEM/F12+10% KSR+10 ng/mL Activin A and 10 ng/mL Heregulin) and final 10% human AB serum.

Aggregation of edited human embryonic stem cells for PECs differentiation. The edited ES were dissociated into single cells with ACCUTASE® and then centrifuged and resuspended in 2% StemPro (Cat #A1000701, Invitrogen, CA) in DMEM/F12 medium at 1 million cells per ml, and total 350-400 million of cells were seeded in one 850 cm$^2$ roller bottle (Cat #431198, Corning, N.Y.) with rotation speed at 8 RPM±0.5 RPM for 18-20 hours before differentiation. The ES aggregates from edited human embryonic stem cells were differentiated into pancreatic lineages using in roller bottles as described in Schulz et al. (2012) PLoS ONE 7(5): e37004.

Example 6

Characterization of Differentiated Pancreatic Endoderm Cells (PECs)

Flow cytometry for FOXA2 and SOX17 at Stage 1 (DE) and CHGA, PDX1 and NKX6.1 at PEC stage. hESC-derived stage 1 aggregates, or hESC-derived pancreatic aggregates, were washed with PBS and then enzymatically dissociated to single cells suspension at 37° C. using ACCUMAX™ (Catalog #A7089, Sigma, MO). MACS Separation Buffer (Cat #130-091-221, Miltenyi Biotec, North Rhine-Westphalia, Germany) was added and the suspension was passed through a 40 μm filter and pelleted. For intracellular marker staining, cells were fixed for 30 mins in 4% (wt/v) paraformaldehyde, washed in FACS Buffer (PBS, 0.1% (wt/v) BSA, 0.1% (wt/v) NaN$_3$) and then cells were permeabilized with Perm Buffer (PBS, 0.2% (v/v) Triton X-100 (Cat #A16046, Alfa Aesar, MA), 5% (v/v) normal donkey serum, 0.1% (wt/v) NaN$_3$) for 30 mins on ice and then washed with washing buffer (PBS, 1% (wt/v) BSA, 0.1% (wt/v) NaN$_3$). Cells were incubated with primary antibodies (Table 7) diluted with Block Buffer (PBS, 0.1% (v/v) Triton X-100, 5% (v/v) normal donkey serum, 0.1% (wt/v) NaN$_3$) overnight at 4° C. Cells were washed in IC buffer and then incubated with appropriate secondary antibodies for 60 mins at 4° C. Cells were washed in IC buffer and then in FACS Buffer. Flow cytometry data were acquired with NovoCyte Flow Cytometer (ACEA Biosciences, Brussels). Data were analyzed using FlowJo software (Tree Star, Inc.). Intact cells were identified based on forward (low angle) and side (orthogonal, 90°) light scatter. Background was estimated using antibody controls and undifferentiated cells. In the figures, a representative flow cytometry plot is shown for one of the sub-populations. Numbers reported in the figures represent the percentage of total cells from the intact cells gate.

TABLE 7

Antibodies for flow cytometry for characterization of differentiated PECs

| Antigen | Fluorophore | Source | Dilution |
|---|---|---|---|
| SOX17 | AF647 | BD Bioscience (Cat #562594) | 1:50 |
| FOXA2 | PE | Miltenyi Biotechnology (Cat #130-107-773) | 1:10 |
| PDX1 | PE | BD Bioscience (Cat #562161) | 1:2.5 |
| NKX6.1 | AF647 | BD Bioscience (Cat #563338) | 1:2.5 |
| CHGA | AF405 | Novus (Cat #NBP2-33198AF405) | 1:1000 |

Figure 6:
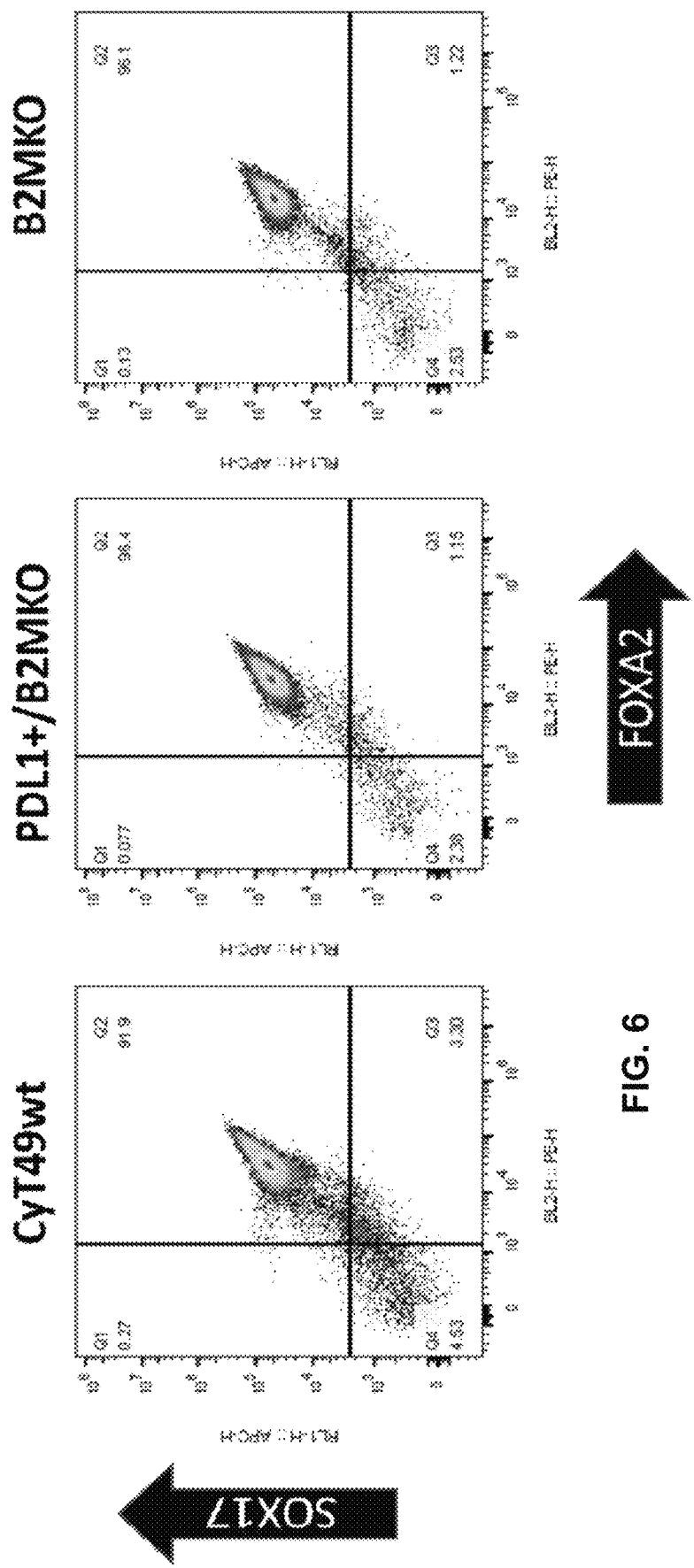
FIG. 6 shows flow cytometry for FOXA2 and SOX17 at Stage 1 (Definitive Endoderm) cells differentiated from wild type CyT49, PD-L1 KI/B2M KO, or B2M KO CyT49 cells.
Figure 7:
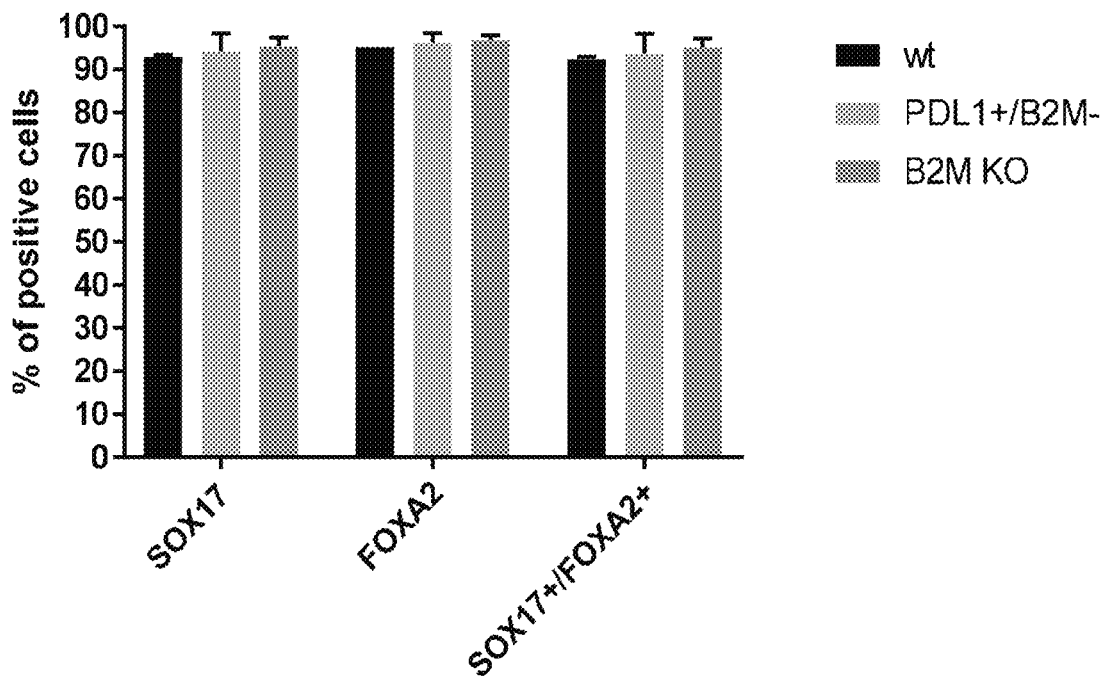
FIG. 7 shows quantitative percentage of FOXA2 and SOX17 expression in Stage 1 (Definitive Endoderm) cells differentiated from wild type, PD-L1 KI/B2M KO, or B2M KO cells.

At DE stage, the population of FOXA2 and SOX17 double positive cells were more than 90% of total cells from CyT49 wild types differentiated cells. The PD-L1 KI/B2M KO and B2M KO cells showed comparable percentage of DE compared to wild type cells (FIG. 6 and FIG. 7).

Figure 8:
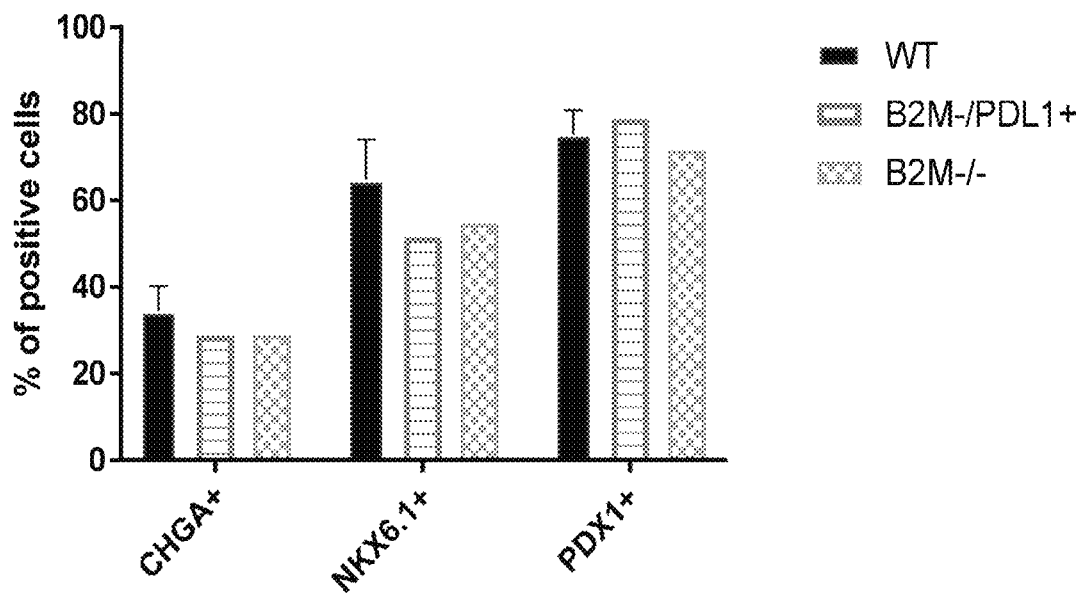
FIG. 8 shows quantitative percentage of CHGA, PDX1 and NKX6.1 expression in Stage 4 (PEC) cells differentiated from wild type, PD-L1 KI/B2M KO, or B2M KO cells.
Figure 9:
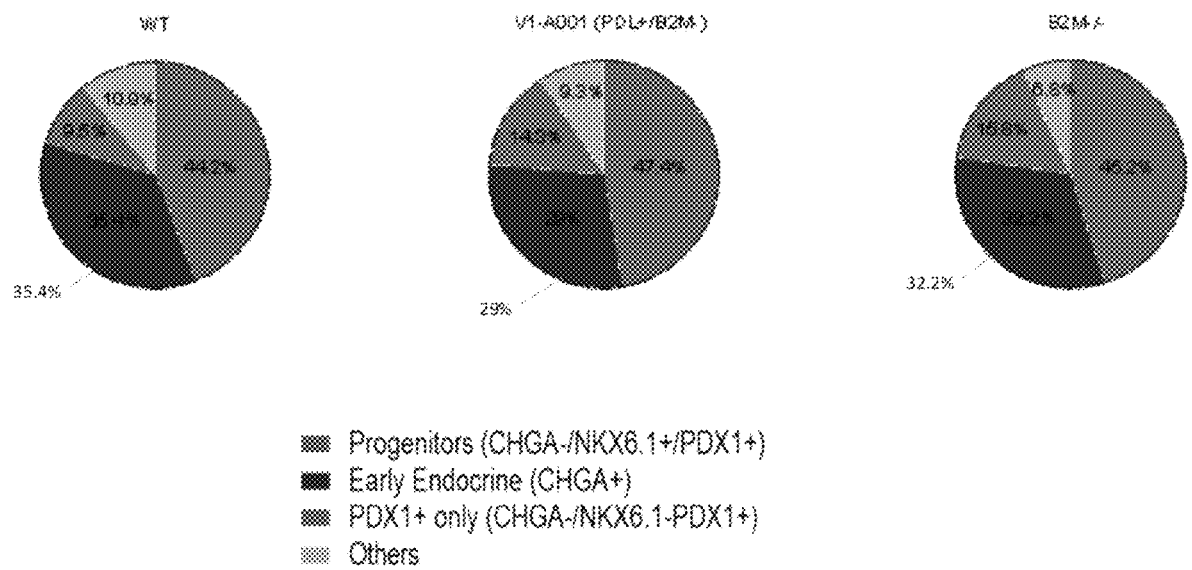
FIG. 9 shows heterogeneous populations of cells at Stage 4 (PEC).

At PECs stage, flow cytometry for chromogranin (CHGA), PDX1 and NKX6.1 was performed. The heterogeneous population at PEC stage include pancreatic progenitors and early endocrine cells (FIG. 8). From the pie chart of the heterogeneous population (FIG. 9), the distribution of cell populations from differentiated edited cells (PD-L1 KI/B2M KO or B2M KO) were very similar to wild type cells.

Targeted RNAseq. Targeted RNAseq for gene expression analysis was performed using Illumina TruSeq and a custom panel of oligos targeting 111 genes. The panel primarily contained genes that are markers of the developmental stages during pancreatic differentiation. At end of each differentiation stage, 10 µL APV (aggregated pellet volume) was collected and extracted using the Qiagen RNeasy or RNeasy 96 spin column protocol, including on-column DNase treatment. Quantification and quality control were performed using either the TapeStation combined with Qubit, or by using the Qiagen QIAxcel. 50-200 ng of RNA was processed according to the Illumina TruSeq library preparation protocol, which consists of cDNA synthesis, hybridization of the custom oligo pool, washing, extension, ligation of the bound oligos, PCR amplification of the libraries, and clean-up of the libraries, prior to quantification and quality control of the resulting dsDNA libraries using either the TapeStation combined with Qubit, or by using the Qiagen QIAxcel. The libraries were subsequently diluted to a concentration of 4 nM and pooled, followed by denaturing, spike in of PhiX control, and further dilution to 10-12 pM prior to loading on the Illumina MiSeq sequencer. Following the sequencing run, initial data analysis was performed automatically through BaseSpace, generating raw read counts for each of the custom probes. For each gene, these read counts were then summed for all probes corresponding to that gene, with the addition of 1 read count (to prevent downstream divisions by 0). Normalization was performed to the gene SF3B2, and the reads were typically visualized as fold change vs. Stage 0. When the data was processed for principal component analysis, normalization was performed using the DEseq method.

Figure 10:
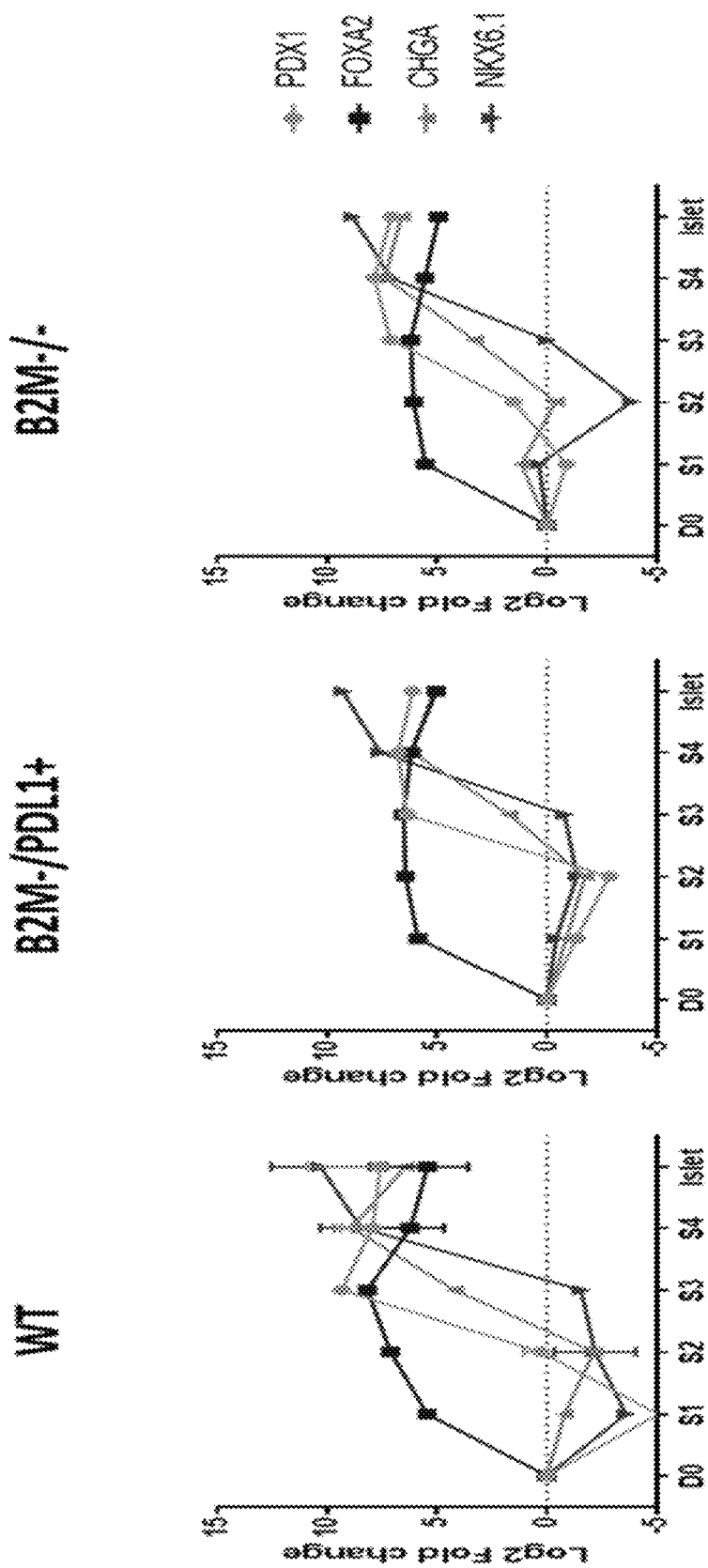
FIG. 10 show selected gene expression over differentiation time course in cells differentiated from wild type, PD-L1 KI/B2M KO, or B2M KO cells.

Selected gene expression was shown in FIG. 10. The kinetic expression pattern of FOXA2, CHGA, PDX1 and NKX6.1 from PD-L1 KI/B2M KO, or B2M KO cells was similar to wild type cells.

Figure 11A:
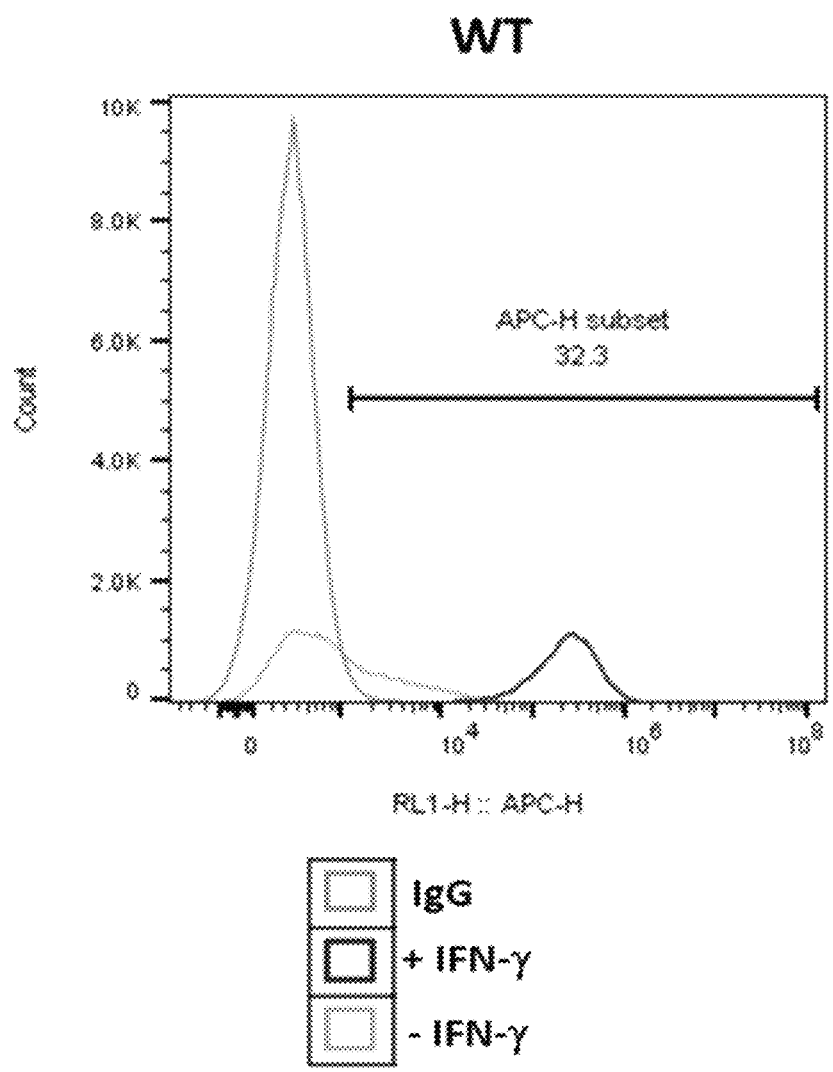
FIGS. 11A-11F show selected gene expression over differentiation time course in cells differentiated from wild type, PD-L1 KI/B2M KO, or B2M KO cells.
Figure 11B:
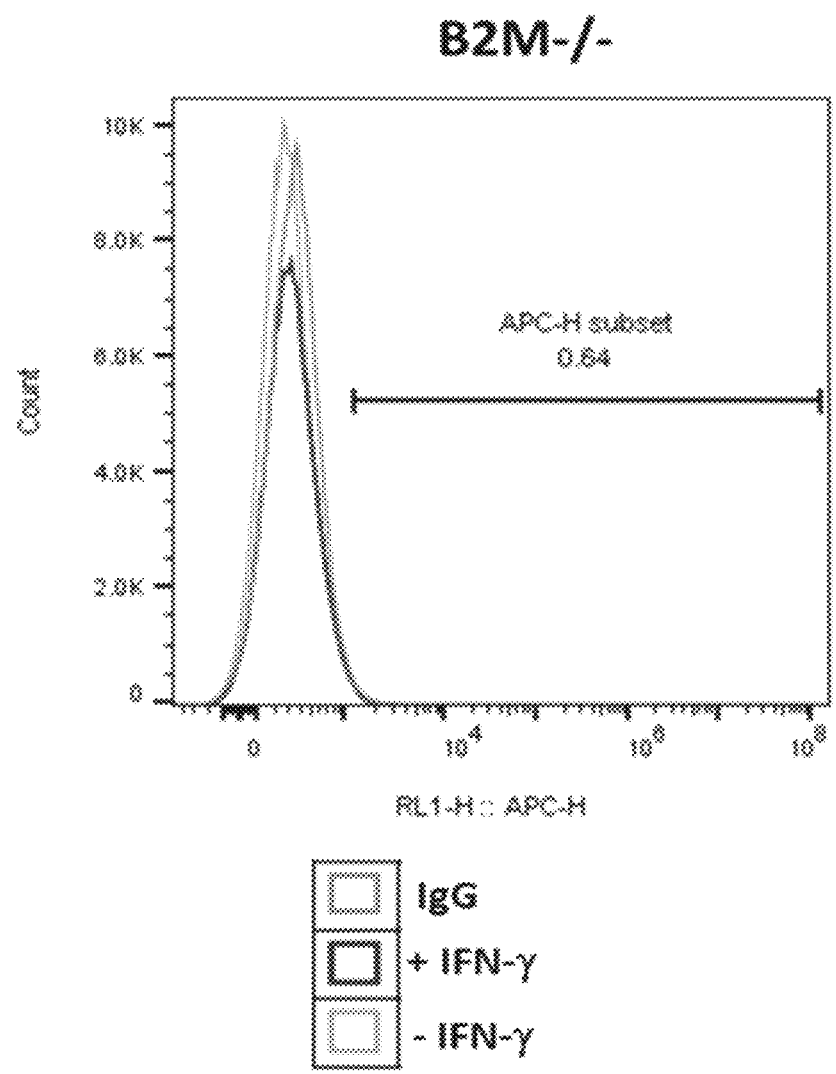
Figure 11C:
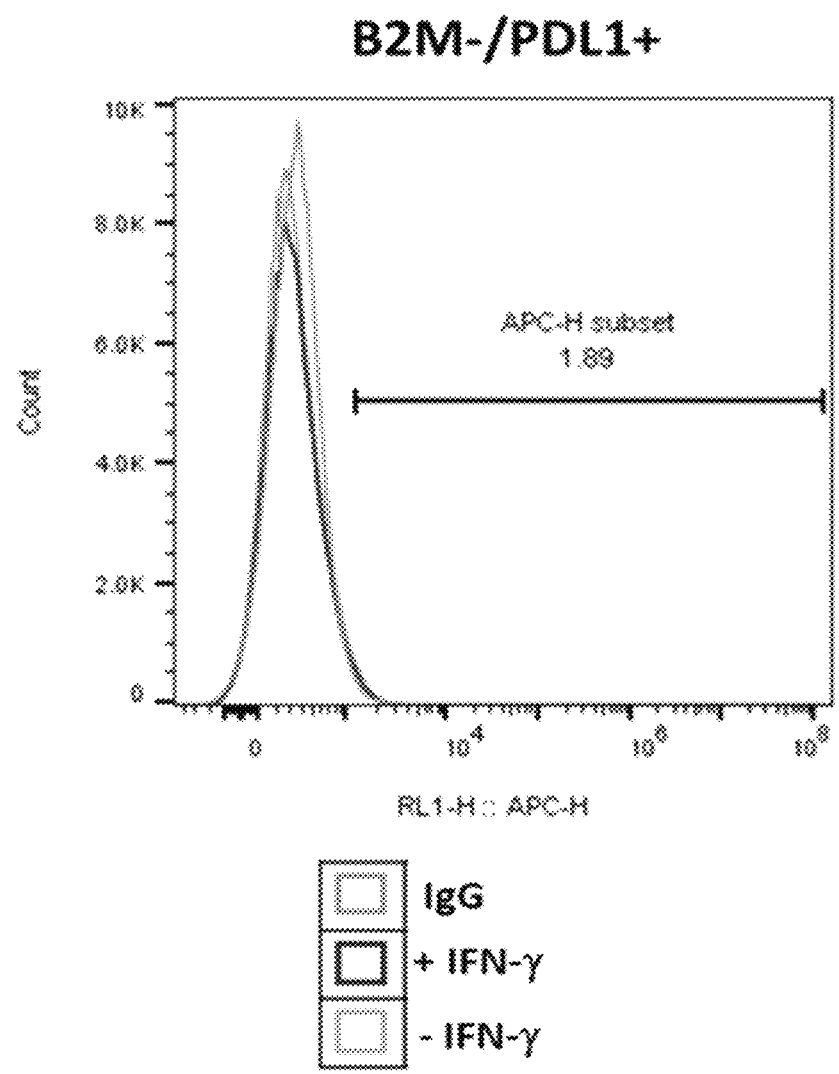
Figure 11D:
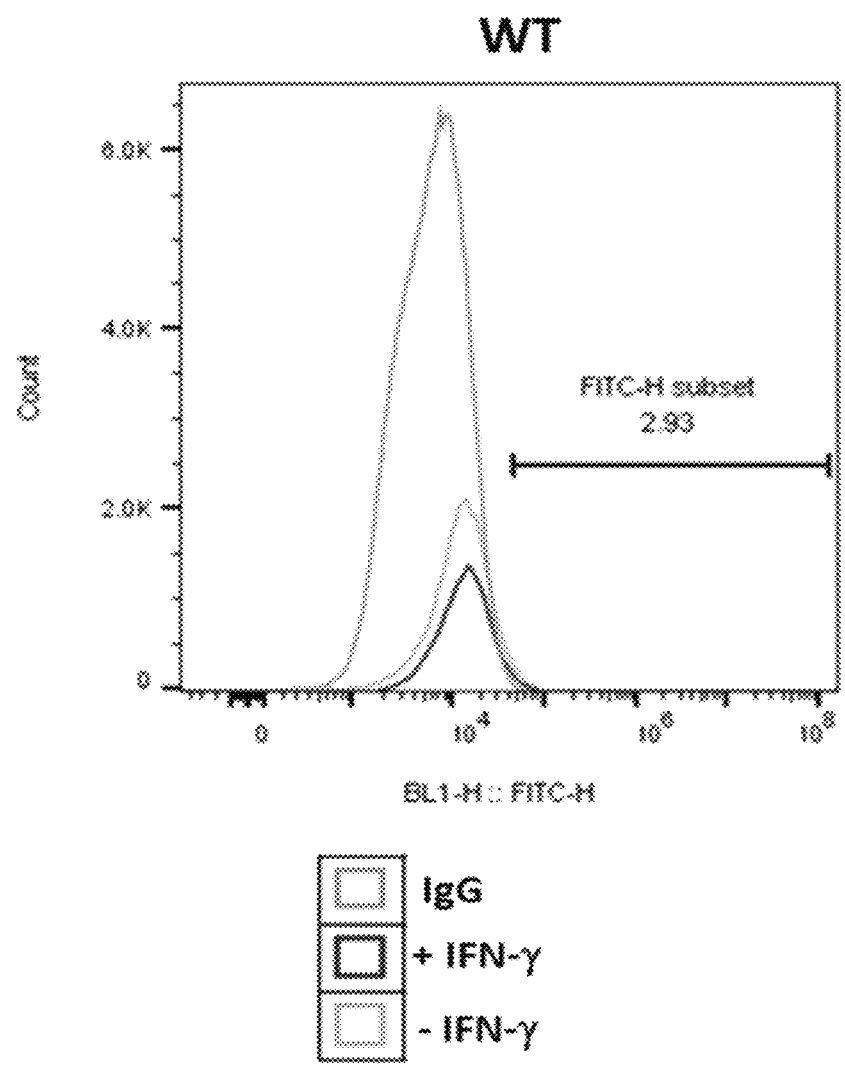
Figure 11E:
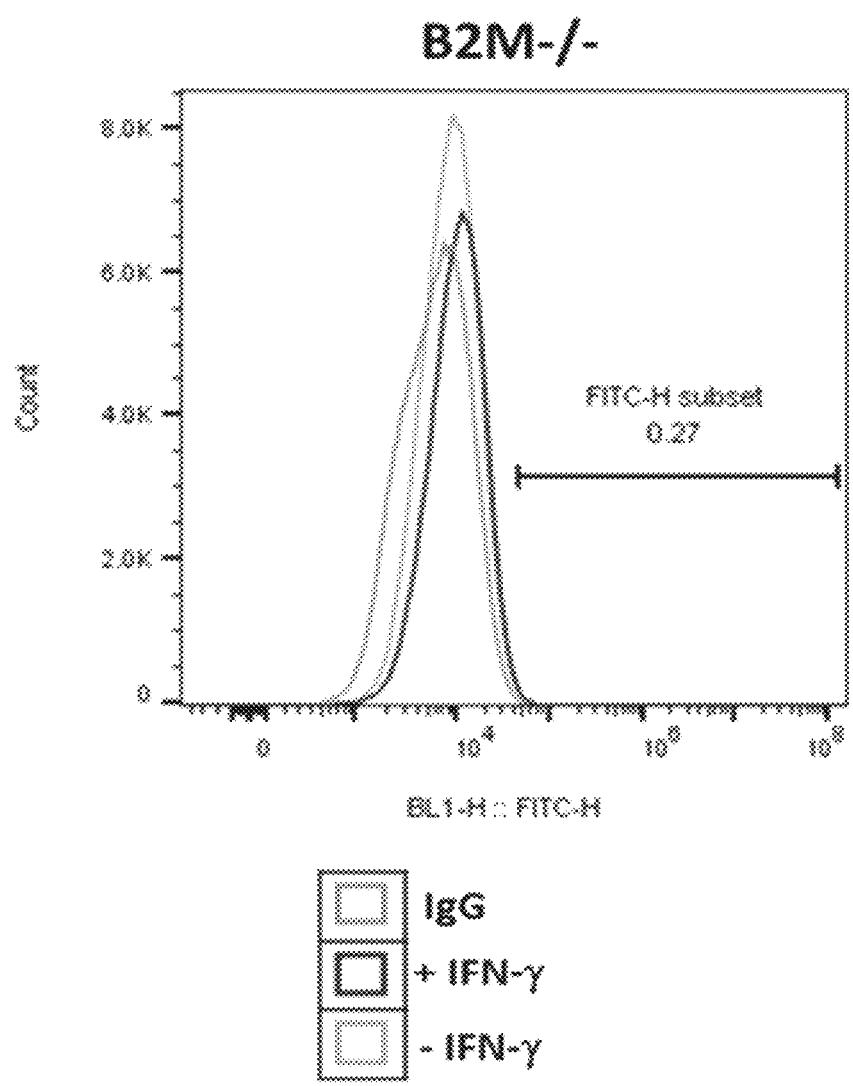
Figure 11F:
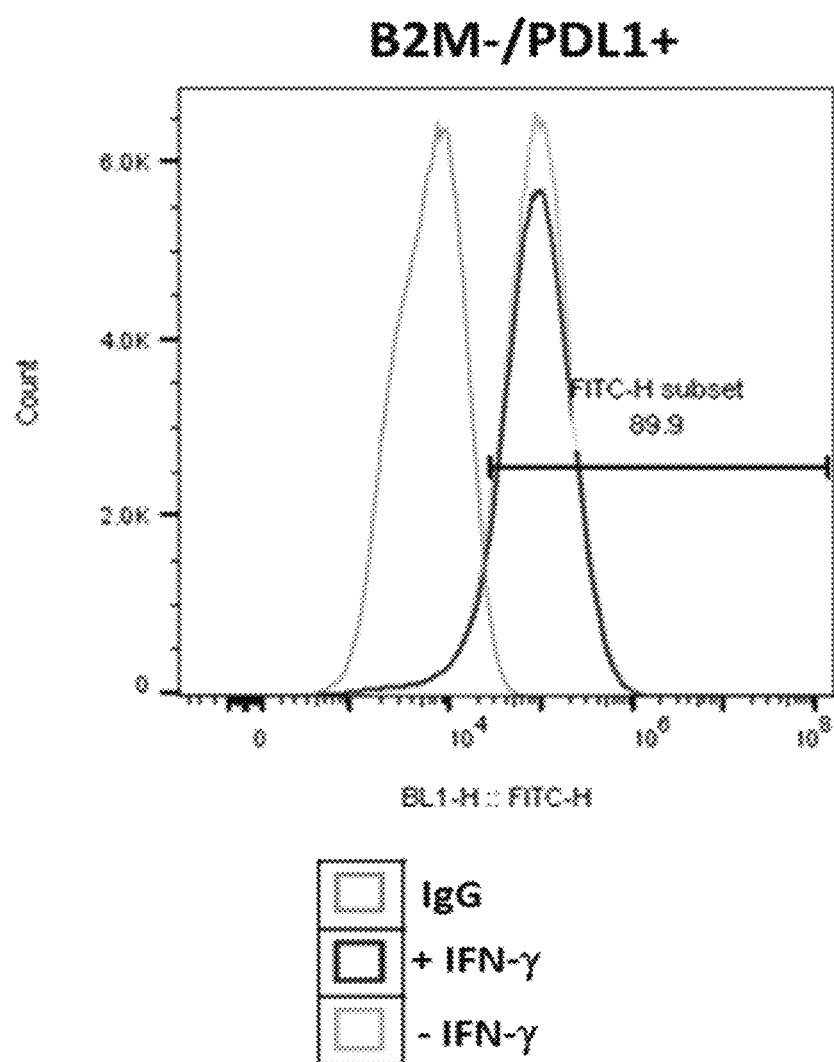

Confirmation of B2M and PD-L1 expression at PEC stage. At PEC stage, differentiated aggregates were treated with or without interferon-gamma (50 ng/ml) for 48 hours. The aggregates washed with PBS and then enzymatically dissociated into single cells suspension at 37° C. using ACCUMAX™ (Catalog #A7089, Sigma, MO). MACS Separation Buffer (Cat #130-091-221, Miltenyi Biotec, North Rhine-Westphalia, Germany) was added and the suspension was passed through a 40 µm filter and pelleted. For surface marker staining, dissociated cells were incubated with fluorescent-conjugated antibody diluted in MACS Separation Buffer for 20 mins and then washed in MACS Separation Buffer. Cells were resuspended in FACS buffer for flow acquisition. Flow cytometry data were acquired with NovoCyte Flow Cytometer. As shown the FIGS. 11A-11F, B2M expression was below the detection limit in differentiated PECs from B2M KO (FIG. 11B) or PD-L1 KI/B2M KO (FIG. 11C), and PD-L1 was expressed in the differentiated PECs from PD-L1 KI/B2M KO (FIG. 11F). In general, more than about 90% of the PECs expressed PD-L1 indicating a homogenous population of cells. Frequently, there is a loss of transgene expression over time following differentiation of gene-edited stem cells (Hong et al., Mol. Ther., 2017, 25(1):44-53).

Figure 12A:
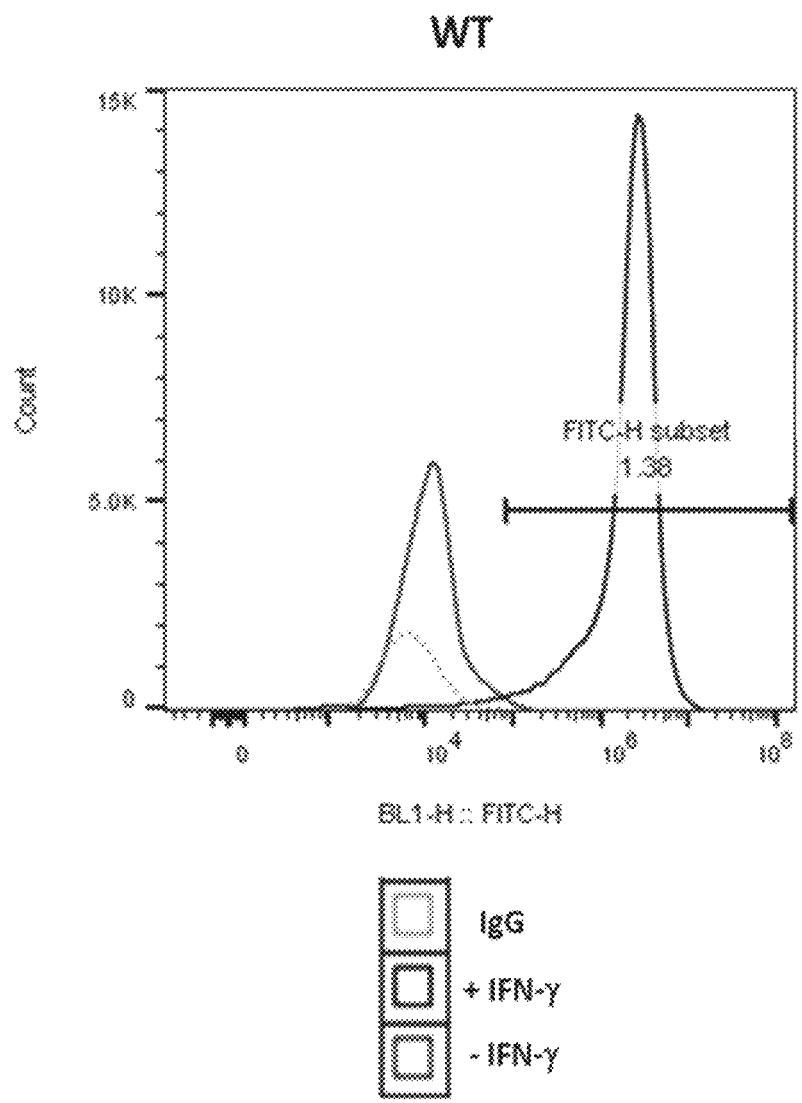
FIGS. 12A-12F show MHC class I and class II expression at PEC stage in cells differentiated from wild type, PD-L1 KI/B2M KO, or B2M KO cells.
Figure 12B:
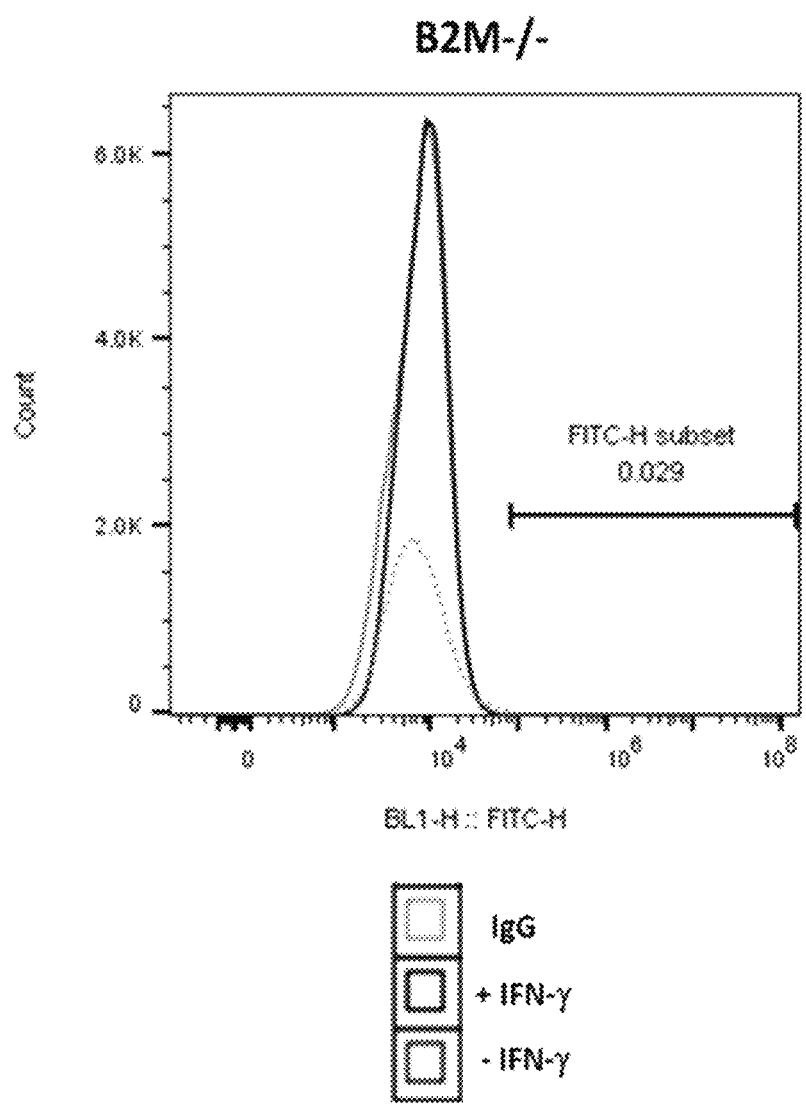
Figure 12C:
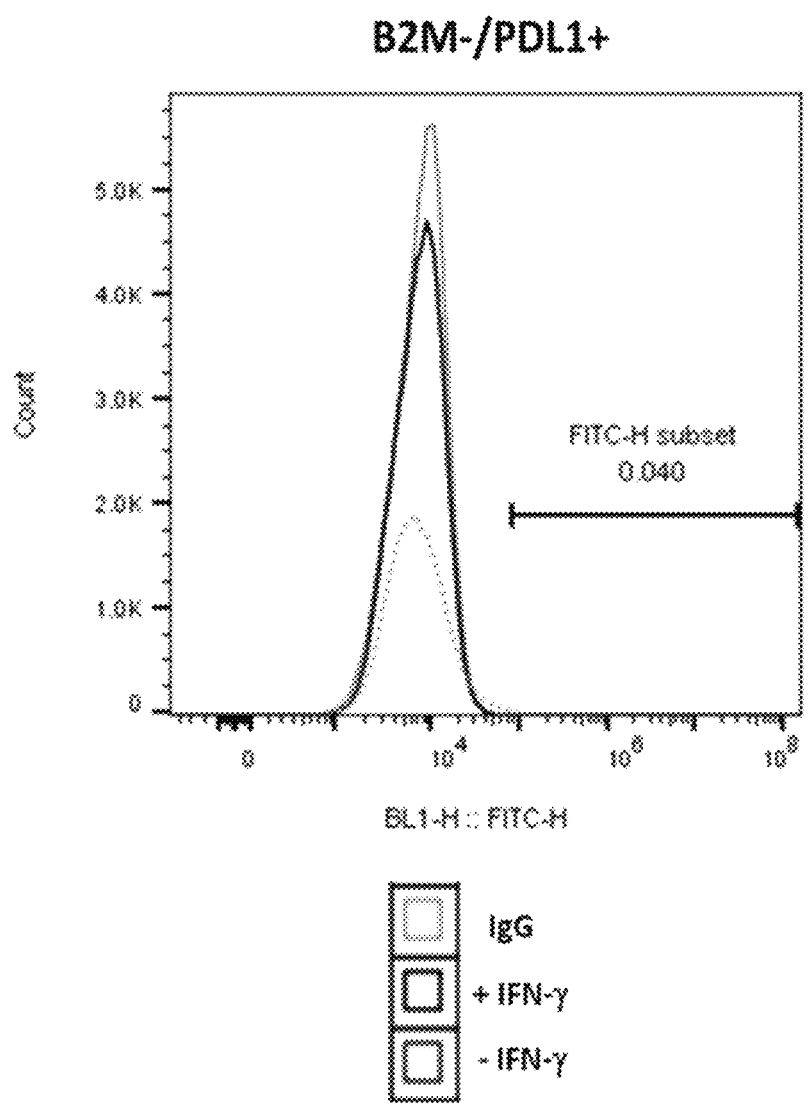
Figure 12D:
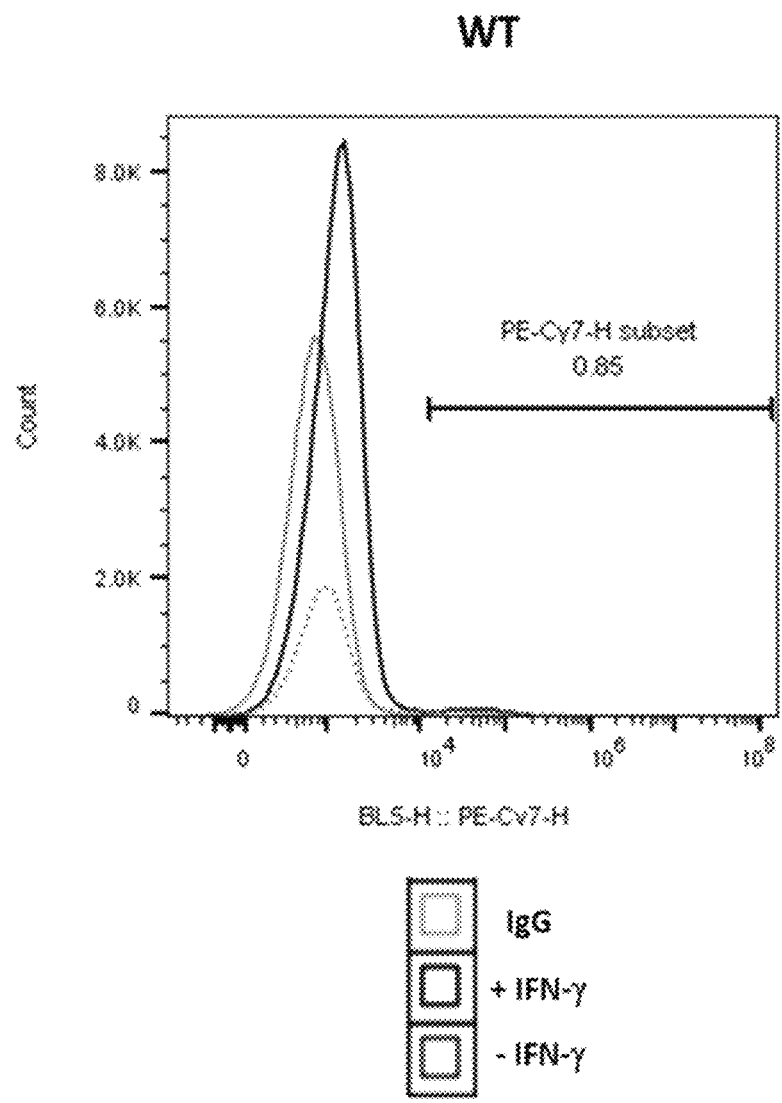
Figure 12E:
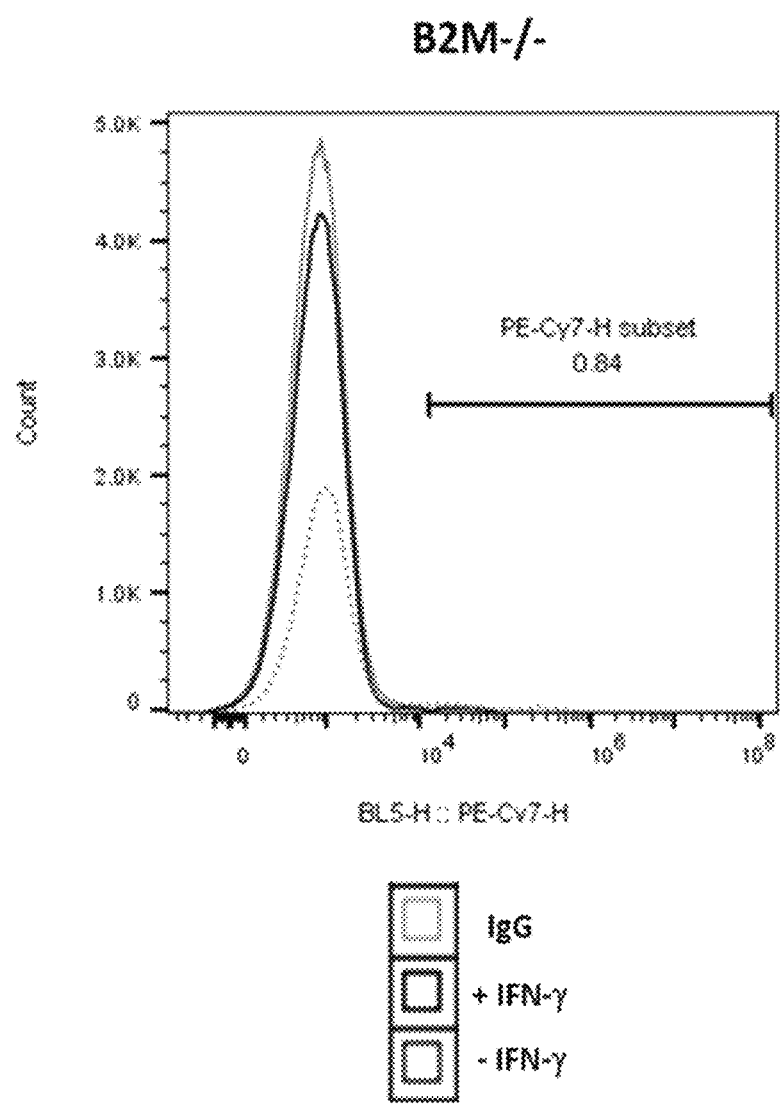
Figure 12F:
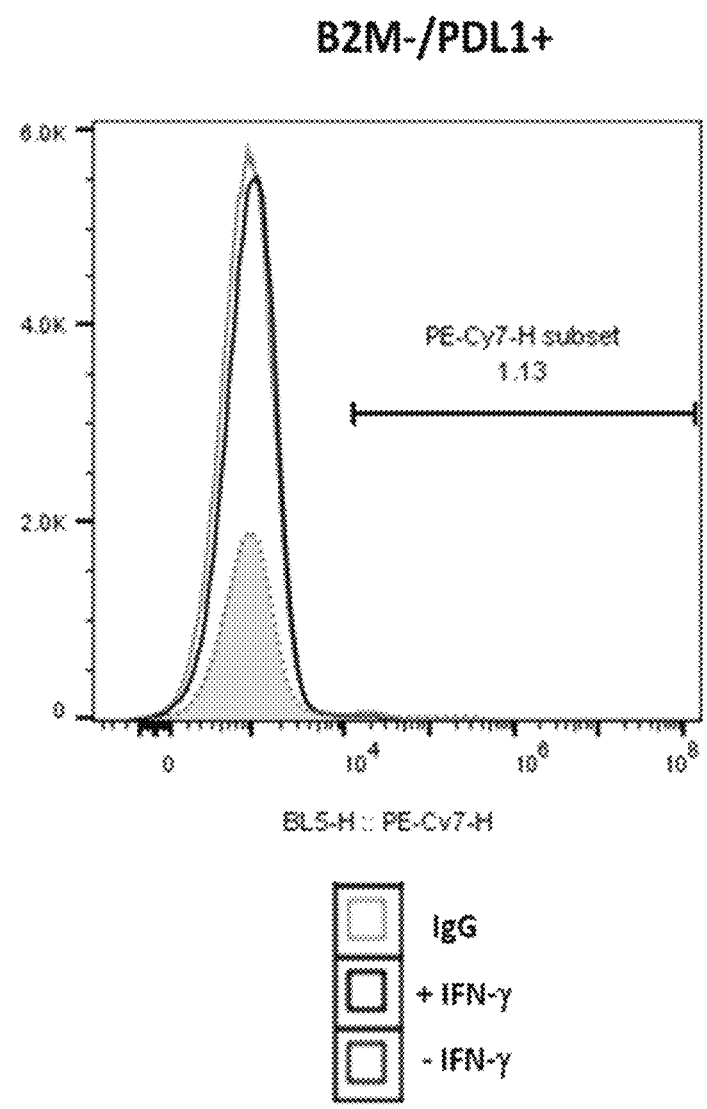

Immune phenotype of PEC cells. At PEC stage, differentiated aggregates were treated with or without interferon-gamma (50 ng/ml) for 48 hours. The aggregates were harvested for MHC class I and II staining. No MHC class II expression at PEC stage from wild type or edited cells (PD-L1 KI/B2M KO and B2M KO) (FIGS. 12D-12F). The expression of HLA-ABC (MHC class I) was low (1.3% from wild type cells) and it was highly regulated upon IFN-γ stimulation. However, HLA-ABC was not expressed even under IFN-γ stimulation in the edited cells (PD-L1 KI/B2M KO and B2M KO) (FIG. 12A-12C).

Example 7

Generation of TXNIP KO Human Pluripotent Stem Cells (hPSCs)

Guide RNA (gRNA) selection for TXNIP. Ten TXNIP targeting gRNAs were designed for targeting exon 1 and exon 2 of the TXNIP coding sequence (Table 8). The PAM sequences are presented in bold font in the target sequences presented in Table 8, and the DNA sequences corresponding to the guide sequences are presented in Table 8. These gRNAs had predicted low off-target scores based on sequence homology prediction using gRNA design software.

TABLE 8

Selected TXNIP Target Sequences and gRNA Sequences

| Name | Target Sequence (5'-3') (PAM sequence in bold) | SEQ ID NO: | DNA Version of Guide Sequence (5'-3') | SEQ ID NO: |
|---|---|---|---|---|
| TXNIP_Exon 1_T1 | GAAGCGTGTCTTCATA GCGCAGG | 45 | GAAGCGTGTCTTCATA GCGC | 15 |
| TXNIP_Exon 1_T21 | TTACTCGTGTCAAAGC CGTTAGG | 46 | TTACTCGTGTCAAAGC CGTT | 16 |
| TXNIP_Exon 1_T22 | TGTCAAAGCCGTTAGG ATCCTGG | 47 | TGTCAAAGCCGTTAGG ATCC | 17 |
| TXNIP_Exon 1_T23 | GCCGTTAGGATCCTGG CTTGCGG | 48 | GCCGTTAGGATCCTGG CTTG | 18 |
| TXNIP_Exon 1_T25 | GCGGAGTGGCTAAAGT GCTTTGG | 49 | GCGGAGTGGCTAAAGT GCTT | 19 |
| TXNIP_Exon 1_T5 | TCCGCAAGCCAGGATC CTAACGG | 50 | TCCGCAAGCCAGGATC CTAA | 20 |
| TXNIP_Exon 2_T4 | GTTCGGCTTTGAGCTT CCTCAGG | 51 | GTTCGGCTTTGAGCTT CCTC | 21 |
| TXNIP_Exon 2_T2 | GAGATGGTGATCATGA GACCTGG | 52 | GAGATGGTGATCATGA GACC | 22 |
| TXNIP_Exon 2_T1 | TTGTACTCATATTTGT TTCCAGG | 53 | TTGTACTCATATTTGT TTCC | 23 |
| TXNIP_Exon 2_T3 | AACAAATATGAGTACA AGTTCGG | 54 | AACAAATATGAGTACA AGTT | 24 |

TXNIP KO hiPSC clone generation and characterization. To assess the cutting efficiency of these gRNAs in hiPSCs, TC1133 hiPSC cells were electroporated using the Neon Electroporator (Neon Transfection System ThermoFisher Cat #MPK5000) with an RNP mixture of Cas9 protein (Biomay) and guide RNA (Synthego) at a molar ratio of 3:1 (gRNA:Cas9) with absolute values of 125 pmol of Cas9 and 375 pmol of gRNA. To form the RNP complex, gRNA and Cas9 were combined in one vessel with R-buffer to a total volume of 25 μL and incubated for 15 min at RT. Cells were dissociated using ACCUTASE®, then resuspended in DMEM/F12 media (Gibco, cat #11320033), counted using an NC-200 (Chemometec) and centrifuged. A total of $1 \times 10^6$ cells were resuspended with the RNP complex and R-buffer was added to a total volume of 125 μL. This mixture was then electroporated using the parameters: 2 pulses, 30 ms, 1100 V. Following electroporation, the cells were pipetted out into an Eppendorf tube filled with StemFlex media with RevitaCell. This cell suspension was then plated into tissue culture dishes pre-coated with BIOLAMININ 521 CTG. Cells were cultured in a normoxia incubator (37° C., 8% $CO_2$) for 48 hours. After 48 hours, genomic DNA was harvested from the cells using QuickExtract.

Figure 13:
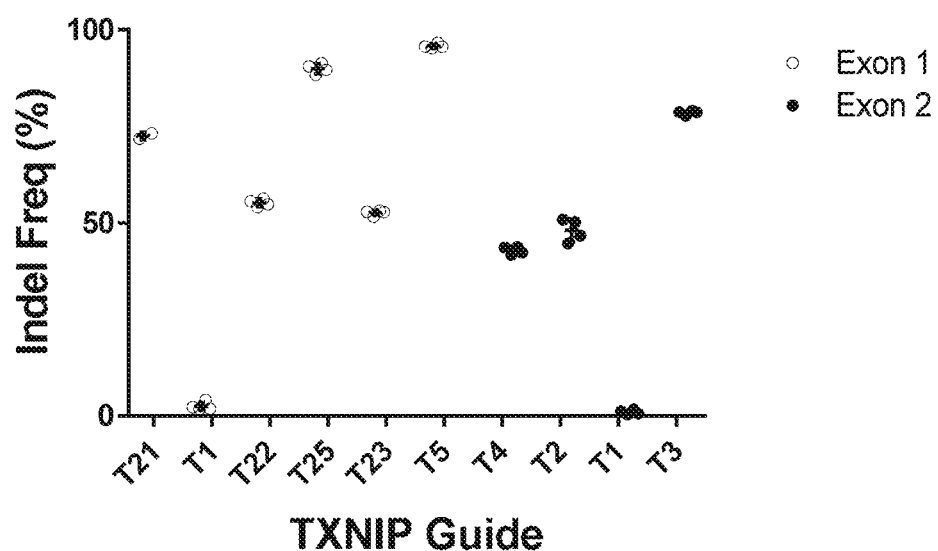
FIG. 13 shows TIDE analysis of TXNIP gRNA cutting in TC1133 hiPSCs. Guide T5 appeared to be best at cutting at exon 1.

PCR for the target TXNIP sequence was performed and the resulting amplified DNA was Sanger sequenced. TIDE analysis was used to analyze the output sequencing data for indel percentages using Tsunami software. FIG. 13 shows the cutting efficiency for the TXNIP gRNAs. gRNAs were then selected based on their indel frequency in hPSCs.

Off-targets of the most cutting efficient gRNAs were assessed in the stem cell-derived DNA using hybrid capture analysis of the sequence similarity predicted sites. Further experiments with TXNIP gRNA T5 were performed as it did not show detectable off-target effects and demonstrated high on-target activity.

TXNIP KO hPSC clone generation and characterization. Using TXNIP gRNA T5, CyT49 hESCs (Viacyte) were electroporated and single-cell sorted at 3 days post electroporation using the WOLF FACS-sorter (Nanocellect) into BIOLAMININ 521 CTG 96-well plates with StemFlex and Revitacell. Plated single cells were grown in a normoxia incubator (37° C., 8% $CO_2$) with every other day media changes until colonies were large enough to be re-seeded as single cells. When confluent, samples were split for maintenance and genomic DNA extraction.

The TXNIP KO state of clones was confirmed via PCR and Sanger sequencing. The resulting DNA sequences of the target TXNIP region were aligned in Snapgene software to determine indel identity and zygosity. Clones with desired edits were expanded and further verified through flow cytometry assessment for TXNIP expression. Karyotypic status of clones was evaluated through Cell Line Genetics service and normal karyotype was reported (Table 9).

TABLE 9

| Karyotype Analysis | | | | |
|---|---|---|---|---|
| Cell Line | Passage | Karyotyping analysis | FISH analysis | aCGH array analysis |
| TXNIPKO #2 | P31 | Normal | Normal | PASS |
| TXNIPKO #13 | P31 | Normal | Normal | PASS |

Clones were confirmed to retain pluripotency through intracellular flow cytometry for pluripotency markers OCT4 and SOX2. Confirmed pluripotent clones were differentiated to pancreatic endocrine progenitors using previously established methods (Schulz et al. (2012) PLoS ONE 7(5): e37004).

Figure 20:
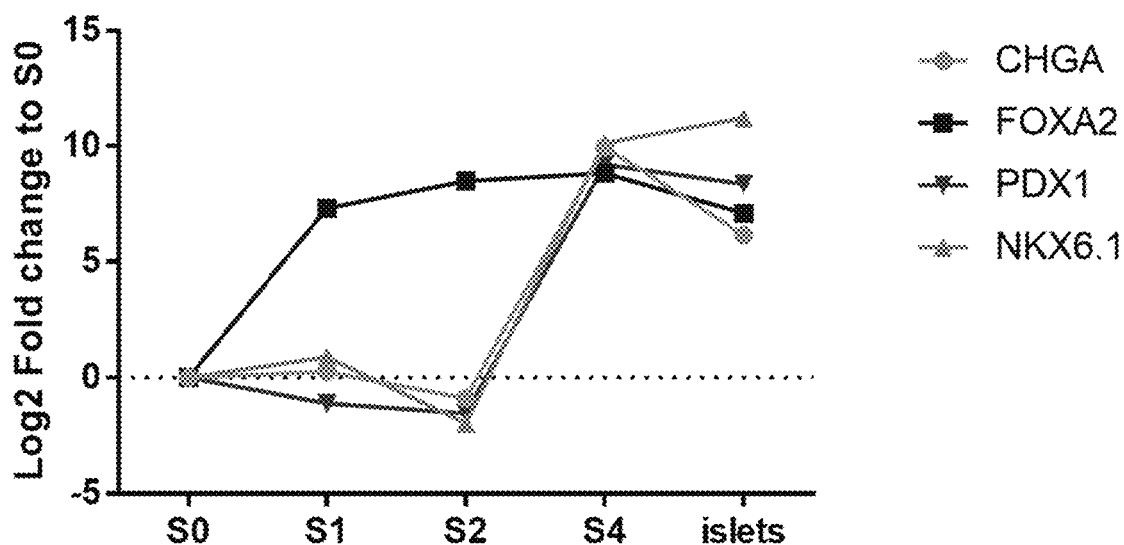
FIG. 20 shows selected gene expression over a differentiation time course of cells differentiated from TXNIP KO cells.
Figure 21:
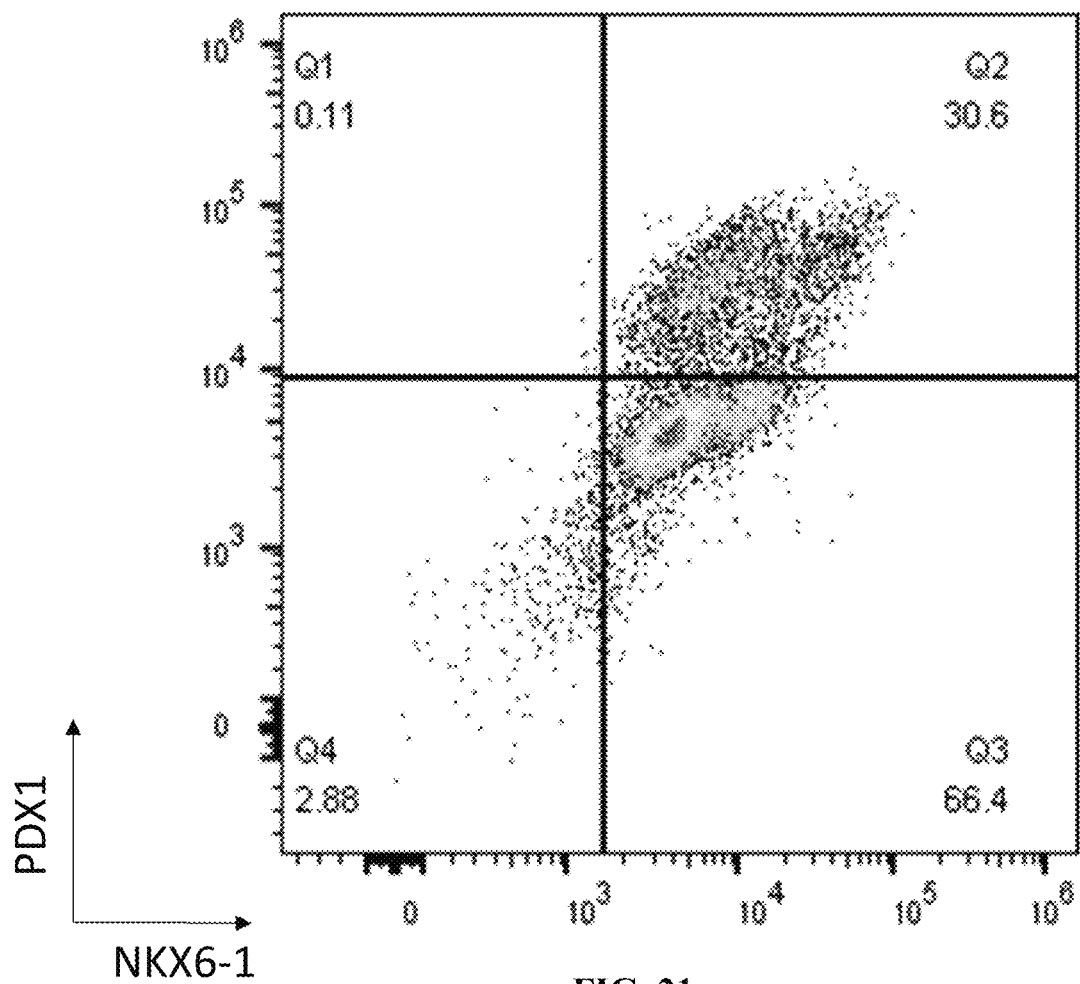
FIG. 21 shows flow cytometry assessment of PDX1 and NKX6.1 expression in PEC cells differentiated from TXNIP KO cells.

Targeted RNAseq for gene expression analysis was performed using Illumina TruSeq and a custom panel of oligos, as described above. Selected gene expression was shown in FIG. 20. The kinetic expression pattern of FOXA2, CHGA, PDX1 and NKX6.1 from TXNIP KO cells was similar to wild type cells. At PECs stage, flow cytometry for chromogranin (CHGA), PDX1 and NKX6.1 was also performed. The heterogeneous population at PEC stage included 30.6% pancreatic progenitor cells (i.e., CHGA$^-$/NKX6.1$^+$/PDX1$^+$) (FIG. 21).

Example 8

Generation of B2M KO/PD-L1 KI and TXNIP KO/HLA-E KI Human Pluripotent Stem Cells (hPSCs)

Design of B2M KO/PD-L1 KI and TXNIP KO/HLA-E KI strategy. Cells were generated in which PD-L1 coding sequence was inserted in the B2M locus (thereby knocking out the B2M gene) and HLA-E coding sequence was inserted in the TXNIP locus (thereby knocking out the TXNIP gene).

Plasmid design to insert PD-L1 (CD274) into the B2M locus was depicted in Example 3. The donor plasmid contains a CAGGS promoter driven cDNA of PD-L1 flanked by 800 base pair homology arms with identical sequence to the B2M locus around exon 1. The B2M-2 gRNA was used to facilitate insertion of the PD-L1 transgene at the targeted B2M locus. The PD-L1 donor plasmid was introduced along with the RNP complex made up of the B2M targeting gRNA and Cas9 protein. Per 1 million of CyT49 cells (ViaCyte), 4 μg of plasmid DNA was delivered along with the RNP.

Electroporation was carried out as described in Example 2. Seven days post electroporation, the cells were enriched for PD-L1 positive cells via magnetic assisted cell sorting (MACS) using Miltenyi reagents (Anti-Mouse IgG Micro-Beads Cat #130-048-401, LS Columns Cat #130-042-401, and MidiMACS Separator Cat #130-042-302) or Thermofisher reagents (DynaMag™-15 Magnet Cat #12301D, CELLection™ Pan Mouse IgG Kit Cat #11531D, Dynabeads™ Pan Mouse IgG Cat #11042).

Figure 14:
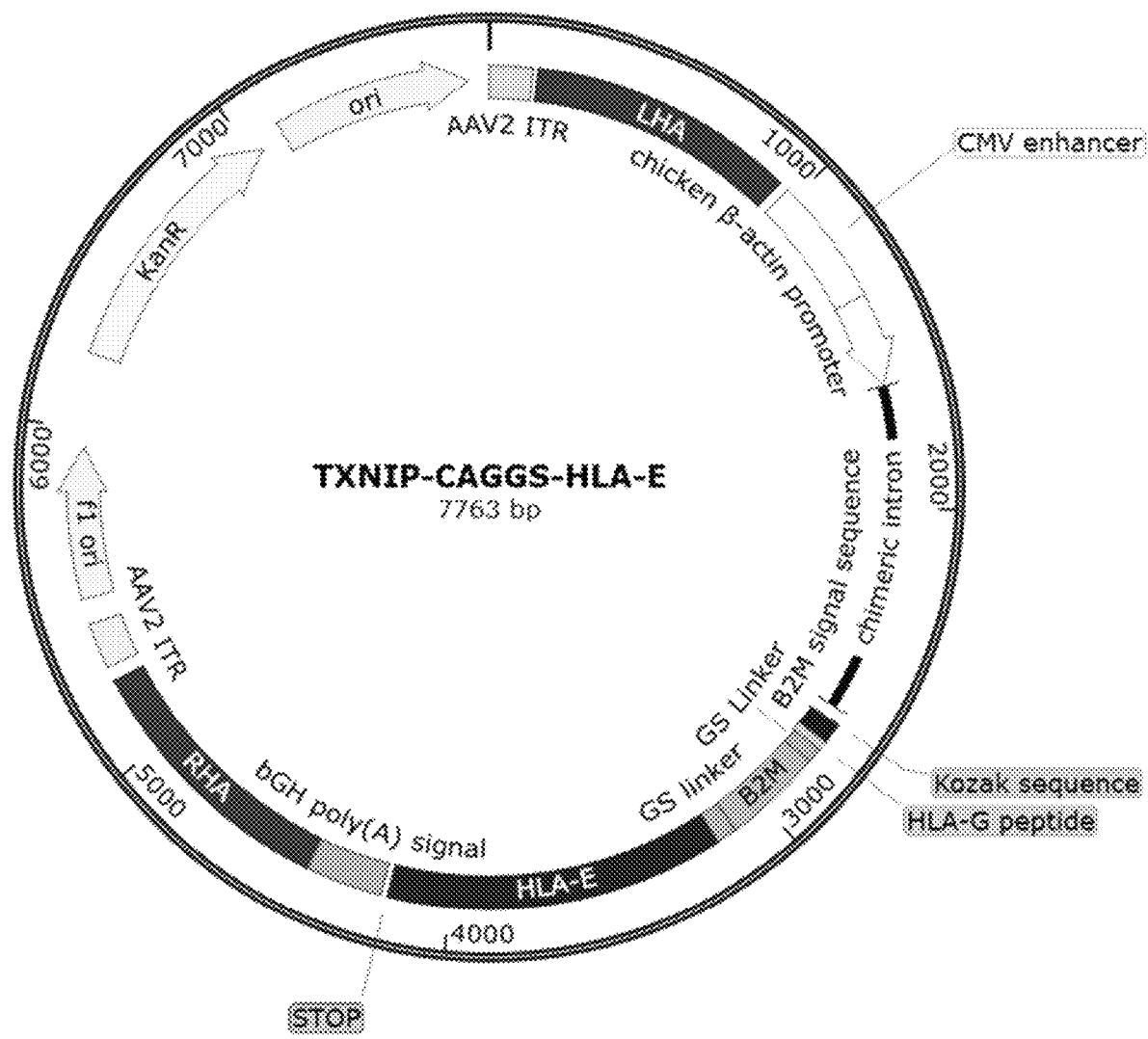
FIG. 14 shows the plasmid map of TXNIP-CAGGS-HLA-E donor vector for HDR.

After the enriched PD-L1 positive population was expanded, an HLA-E trimer cDNA transgene was inserted into the TXNIP genomic locus via CRISPR induced HDR using a donor plasmid comprising the HLA-E sequence. The HLA-E trimer cDNA was composed of a B2M signal peptide fused to an HLA-G presentation peptide fused to the B2M membrane protein fused to the HLA-E protein without its signal peptide. This trimer design has been previously published (Gornalusse et al. (2017) Nat. Biotechnol. 35(8): 765-772). The HLA-E trimer coding sequence (including linkers) is SEQ ID NO: 55 (i.e., SEQ ID NOs: 26-31). The donor plasmid for HLA-E delivery contains a CAGGS promoter driving expression of the HLA-E trimer flanked by 800 base pair homology arms with identical sequence to the TXNIP locus around exon 1 (FIG. 14, Table 10 and Table 11). In some embodiments, the donor plasmid comprises SEQ ID NO: 34 or 56.

TABLE 10

Elements of TXNIP-CAGGS-HLA-E Donor Plasmid 1

| Element | Location (size in bp) | SEQ ID NO: |
|---|---|---|
| Left ITR | 1-130 (130) | 6 |
| LHA-TXNIP | 145-944 (800) | 25 |
| CMV enhancer | 973-1352 (380) | 8 |
| chicken β-actin promoter | 1355-1630 (276) | 9 |
| chimeric intron | 1631-2639 (1009) | 10 |
| B2M signal sequence | 2684-2743 (60) | 26 |
| HLA-G peptide | 2744-2770 (27) | 27 |
| GS Linker | 2771-2815 (45) | 28 |
| B2M membrane protein | 2816-3112 (297) | 29 |
| GS Linker | 3113-3172 (60) | 30 |
| HLA-E | 3173-4183 (1011) | 31 |
| bGH poly(A) signal | 4204-4428 (225) | 12 |
| RHA-TXNIP | 4435-5234 (800) | 32 |
| Right ITR | 5276-5416 (141) | 14 |
| Entire Plasmid | 7763 bp | 34 |

TABLE 11

Elements of TXNIP-CAGGS-HLA-E Donor Plasmid 2

| Element | Location (size in bp) | SEQ ID NO: |
|---|---|---|
| Left ITR | 1-130 (130) | 6 |
| LHA-TXNIP | 145-944 (800) | 25 |
| CMV enhancer | 973-1352 (380) | 8 |
| chicken β-actin promoter | 1355-1630 (276) | 9 |
| chimeric intron (truncated) | 1631-2336 (706) | 57 |
| B2M signal sequence | 2381-2440 (60) | 26 |
| HLA-G peptide | 2441-2467 (27) | 27 |
| GS Linker | 2468-2512 (45) | 28 |
| B2M membrane protein | 2513-2809 (297) | 29 |
| GS Linker | 2810-2869 (60) | 30 |
| HLA-E | 2870-3880 (1011) | 31 |
| bGH poly(A) signal | 3901-4125 (225) | 12 |
| RHA-TXNIP | 4132-4931 (800) | 32 |
| Right ITR | 4973-5113 (141) | 14 |
| Entire Plasmid | 7460 bp | 56 |

The TXNIP-T5 gRNA was used to facilitate insertion of the HLA-E transgene at the targeted TXNIP locus. The HLA-E donor plasmid was introduced along with the RNP complex made up of the TXNIP-T5 gRNA and Cas9 protein. Per 1 million of PD-L1+ cells, 4 µg of HLA-E donor plasmid DNA (SEQ ID NO: 56) was delivered along with the RNP. Alternatively, HLA-E donor plasmid DNA (SEQ ID NO: 34) can be used. Electroporation was carried out as described in Example 2. Seven days post electroporation, the cells were enriched for HLA-E positive cells via MACS using Miltenyi reagents or Thermofisher reagents. Post HLA-E enrichment, the cells were single-cell sorted using the WOLF FACS-sorter (Nanocellect) into BIOLAMININ 521 CTG coated 96-well plates with StemFlex and Revitacell. Plated single cells were grown in a normoxia incubator (37° C., 8% $CO_2$) with every other day media changes until colonies were large enough to be re-seeded as single cells. When confluent, samples were split for maintenance and genomic DNA extraction. The anti-PD-L1 and anti-HLA-E antibodies (Table 4) were used for MACS enrichment and FACS-sorting into 96-well plates with gating set for HLA-E and PD-L1 double positive cells. For FACS-sorting, unedited cells served as a negative control.

Figure 15:
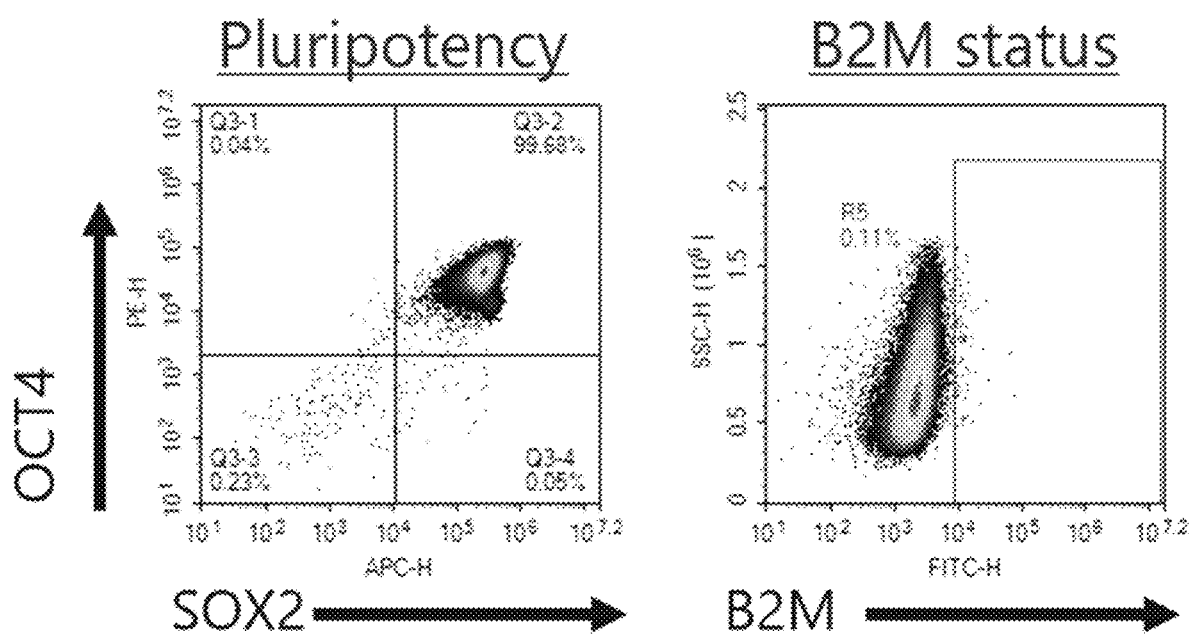
FIG. 15 shows flow cytometry analysis for pluripotency of B2M KO/PD-L1 KI and TXNIP KO/HLA-E KI CyT49 stem cells. The derived clones were >99% double positive for OCT4 and SOX2, two transcription factors vital for pluripotency. The clones also do not express B2M. The clones do not express MHC-I.

Correctly targeted clones were identified via PCR for the PD-L1 KI insertion and the HLA-E KI insertion using primers that amplify a region from outside the plasmid homology arms to the PD-L1 cDNA insertion or the HLA-E cDNA insertion, respectively, enabling amplification of the KI integrated DNA only. On-target insertion was tested for zygosity by PCR to assess if KI occurred in a heterozygous or homozygous manner. If a heterozygous clone was identified, the KI negative allele was sent for Sanger sequencing to verify that it contained a B2M-disrupting indel or a TXNIP-disrupting indel, respectively. The correct KI clones with full B2M and TXNIP disruptions (either via KI insertion or indel formation) were expanded in increasing tissue culture formats until a population size of 30 million cells was reached. Approximately 10 clones were expanded in this manner and confirmed to be pluripotent by testing for OCT4 and SOX2 via intracellular flow cytometry (FIG. 15).

Clones that passed the above tests, were then tested further for karyotypic analysis (Cell Line Genetics), as described above. The G-banding results of selected B2M KO/PD-L1 KI+TXNIP KO/HLA-E KI ("V1-B") clones are shown in Table 12. Additionally, the V1-B clones were then tested for their competence to differentiate to pancreatic endoderm precursors (PEC).

TABLE 12

| G-banding results | | | | |
|---|---|---|---|---|
| Cell Line | Passage | Karyotyping analysis | FISH analysis | aCGH array analysis |
| V1-B003 | P37 | Normal | Normal | PASS |
| V1-B007 | P37 | Normal | Normal | PASS |
| V1-B008 | P36 | Normal | Normal | PASS |

Figure 16:
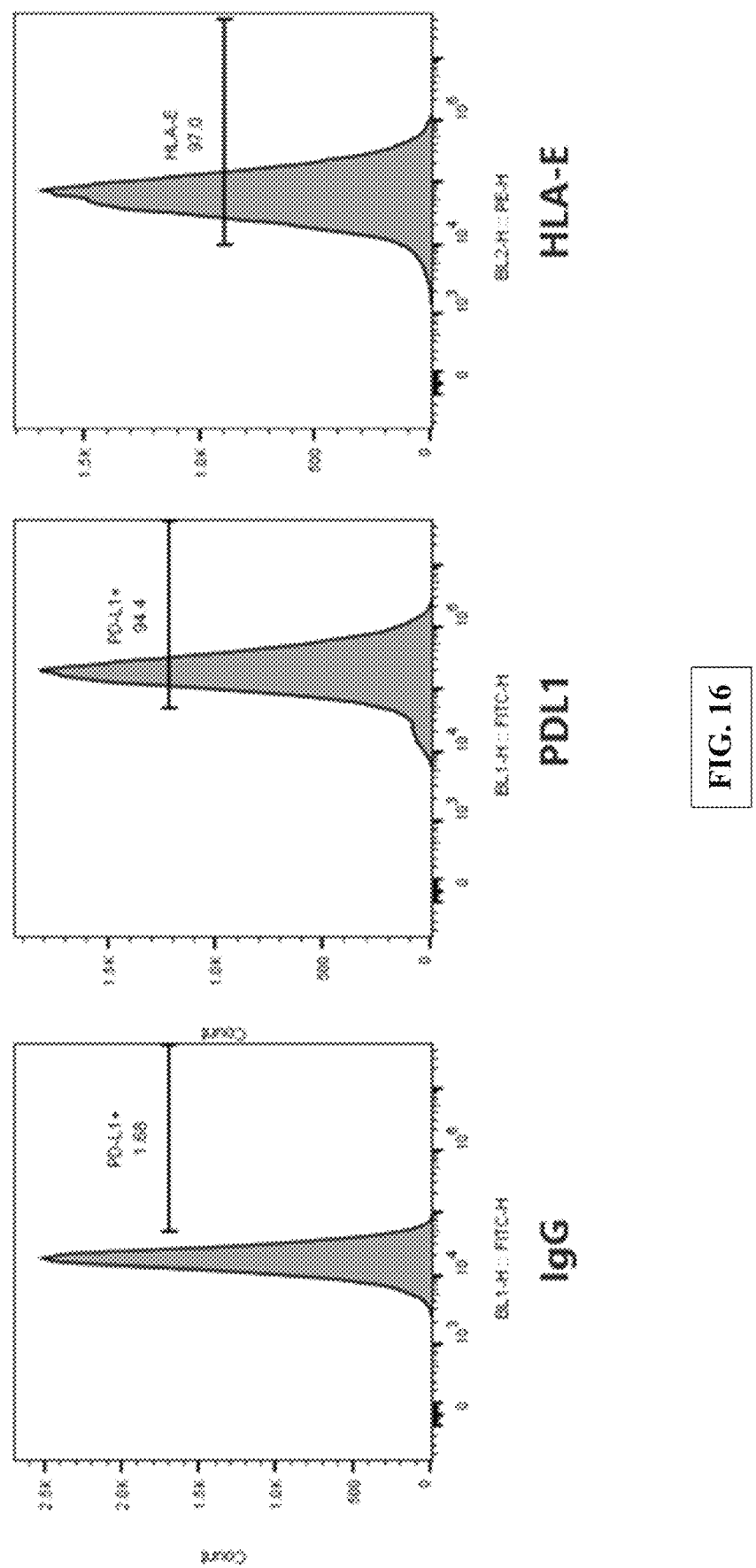
FIG. 16 shows flow cytometry analysis for pluripotency of B2M KO/PD-L1 KI and TXNIP KO/HLA-E KI CyT49 stem cells. The derived clones express PD-L1 and HLA-E after undergoing differentiation to Stage 6 (immature beta cells). IgG was used as a negative control.
Figure 22:
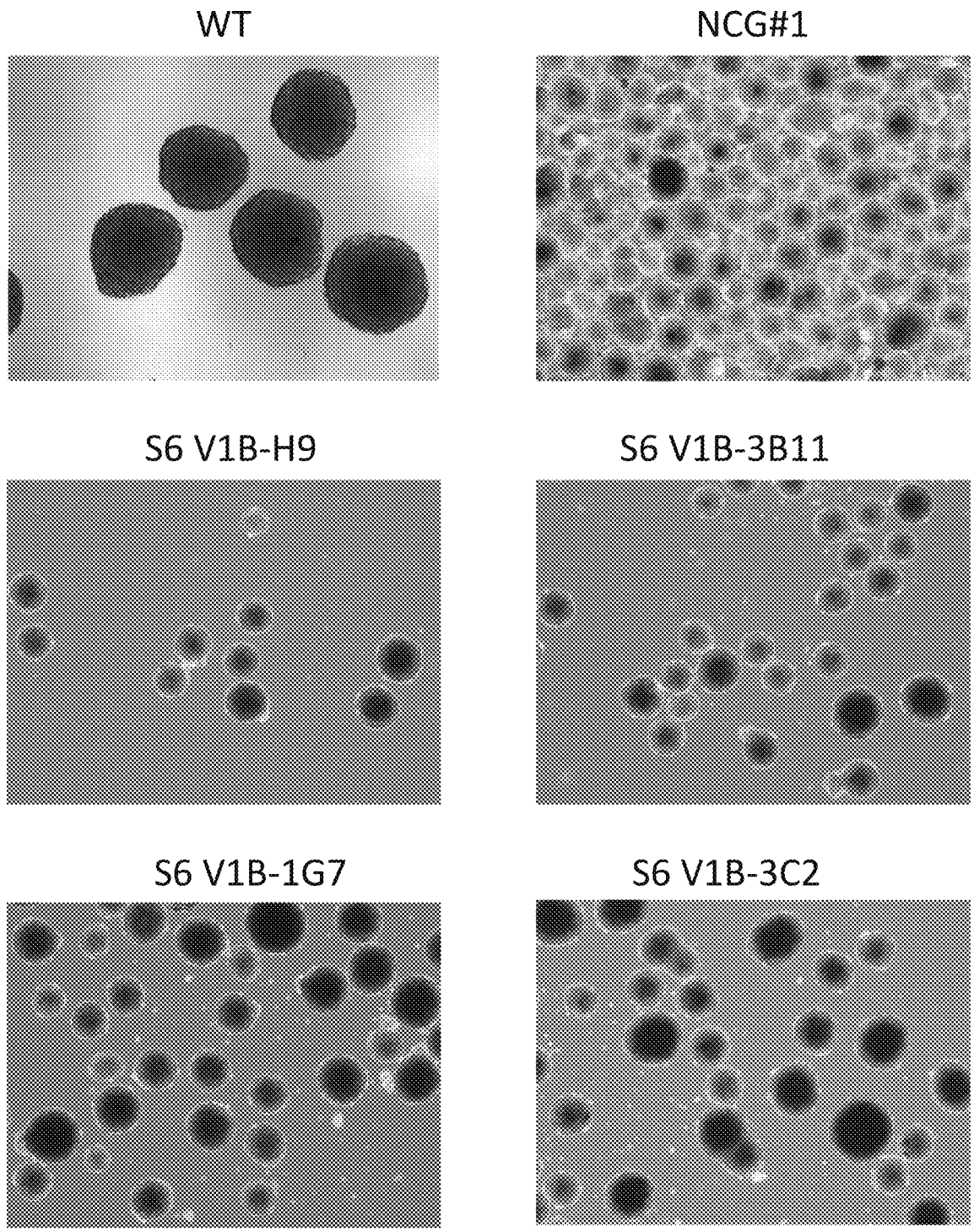
FIG. 22 shows the morphology of the various B2M KO/PD-L1 KI and TXNIP KO/HLA-E KI clones ("S6-V1B-H9," "S6-V1B-3B11," "S6-V1B-1G7," and "S6-V1B-3C2") compared to wild-type ("WT") and non-cutting guide control ("NCG #1") cells after differentiation to Stage 6.
Figure 23A:
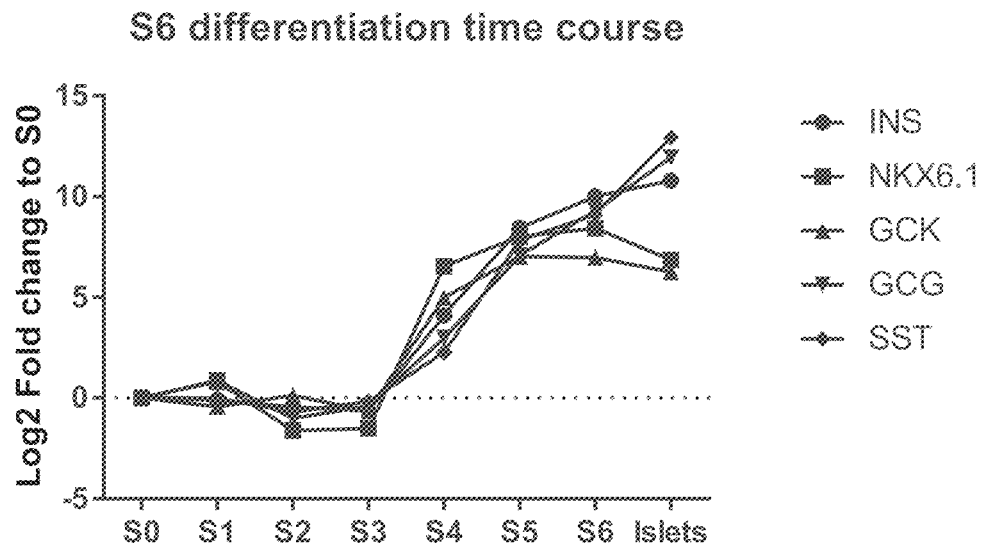
FIGS. 23A-23F show selected gene expression of the clones after differentiation to Stage 6.
Figure 23B:
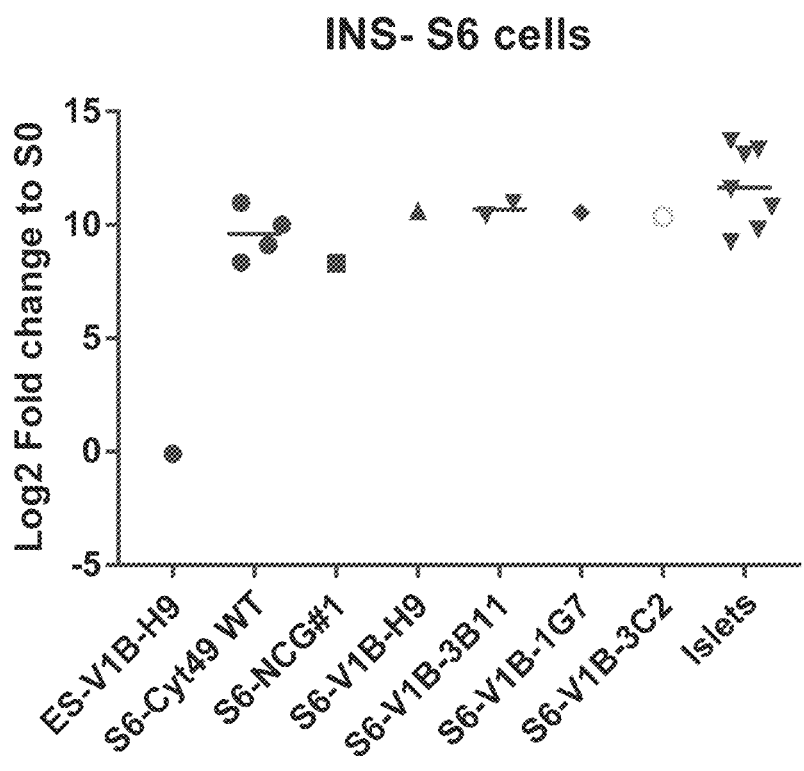
Figure 23C:
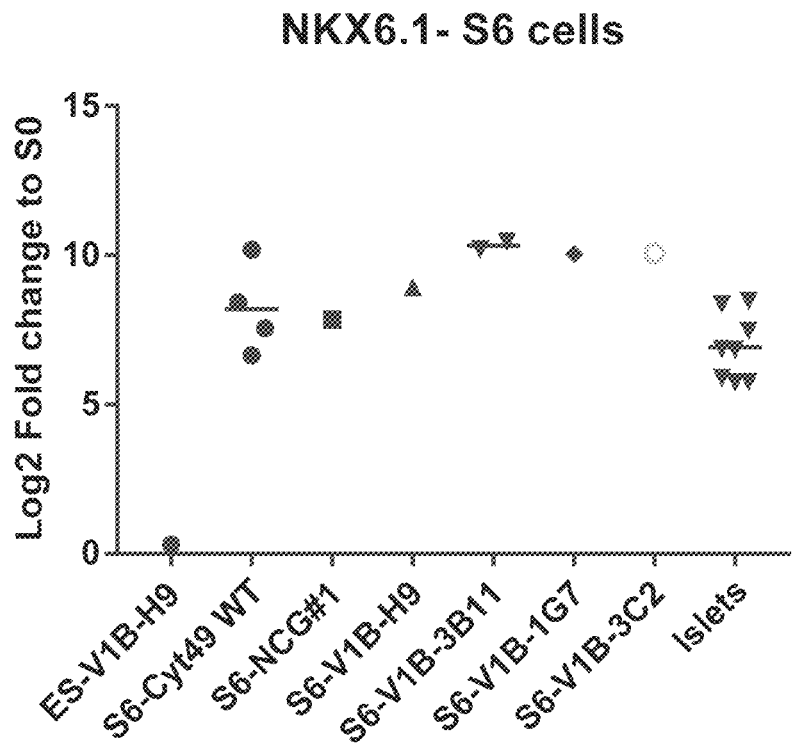
Figure 23D:
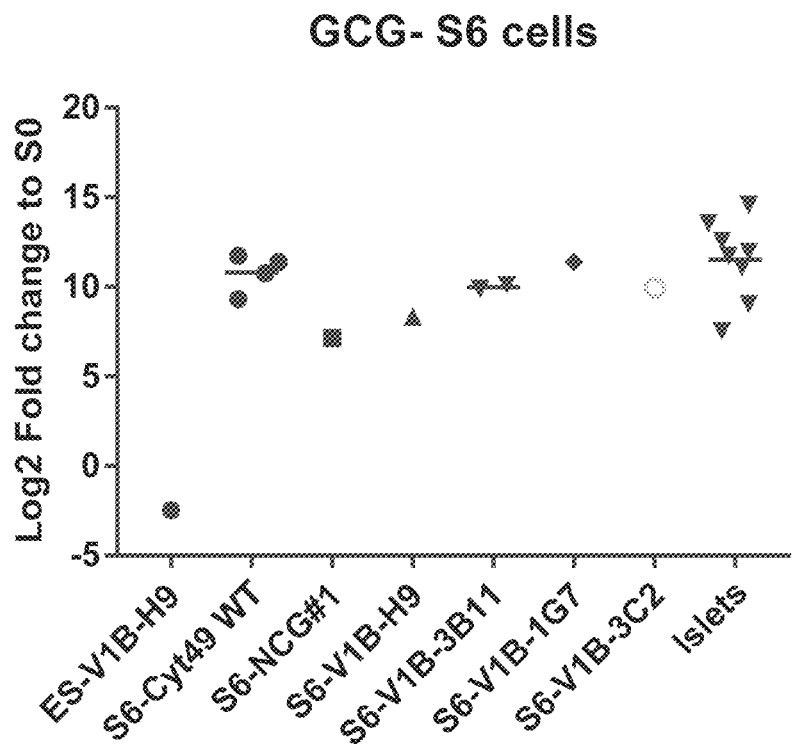
Figures 23E, 23F:
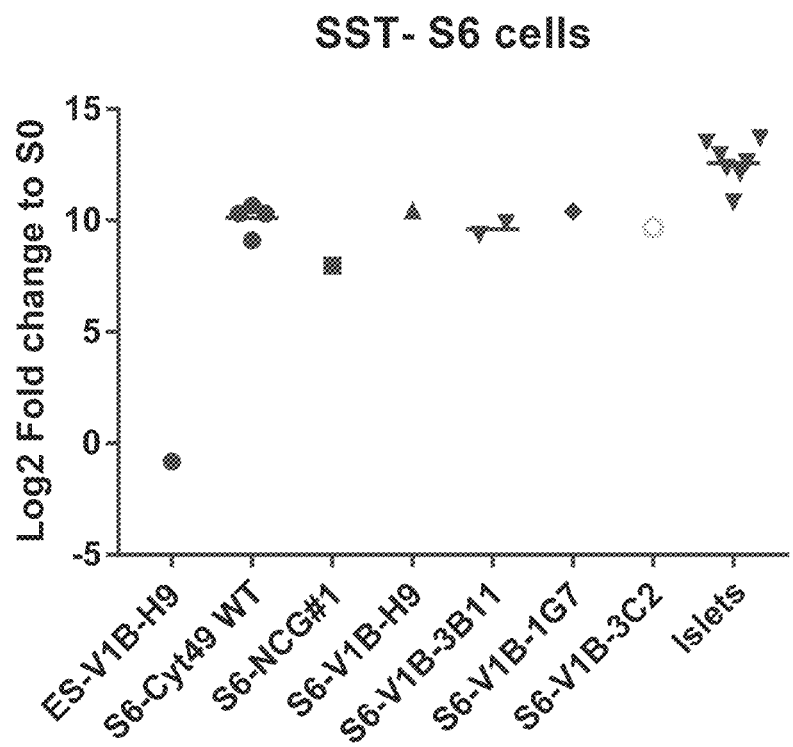

PD-L1 and HLA-E continued to be expressed after differentiation to Stage 6 cells per the previously reported pancreatic endocrine protocol (Rezania et al. (2014) Nat. Biotechnol. 32(11): 1121-1133) (FIG. 16). The population of differentiated cells is homogeneous in terms of expression of the transgene, e.g., 94.4% of the cells express PD-L1 and 97.0% of the cells expression HLA-E. FIG. 22A shows similar morphology of the various clone cells ("56-V1B-H9," "S6-V1B-3B11," "S6-V1B-1G7," and "S6-V1B-3C2") differentiated to Stage 6 compared to wild-type and non-cutting guide control cells. Selected gene expression of B2M KO/PD-L1KI and TXNIP KO/HLA-E KI clones are shown in FIG. 23A-FIG. 23F. The kinetic expression pattern of INS, NKX6.1, GCK, GCG, and SST from B2M KO/PD-L1 KI and TXNIP KO/HLA-E KI clone cells was similar to wild type cells (FIG. 23A). The expression levels of Stage 6 markers INS (FIG. 23B), NKX6.1 (FIG. 23C), GCG (FIG. 23D), SST (FIG. 23E), and GCK (FIG. 23F) from various differentiated B2M KO/PD-L1 KI and TXNIP KO/HLA-E KI clones ("S6-V1B-H9," "S6-V1B-3B11," "S6-V1B-1G7," and "S6-V1B-3C2") were similar to levels in Stage 6 wild-type cells and wild-type islets. An undifferentiated B2M KO/PD-L1 KI and TXNIP KO/HLA-E KI clone ("ES-V1B-H9") was used as a negative control.

Figure 24A:
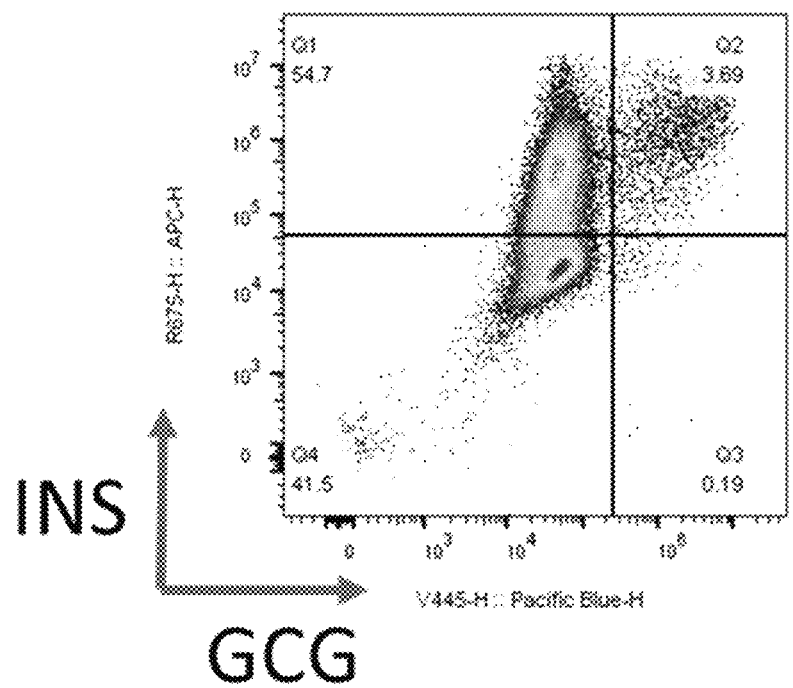
FIGS. 24A-24B show flow cytometry assessment of INS and GCG expression (FIG. 24A) and INS and NKX6.1 expression (FIG. 24B) in Stage 6 cells differentiated from a B2M KO/PD-L1 KI and TXNIP KO/HLA-E KI clone.
Figure 24B:
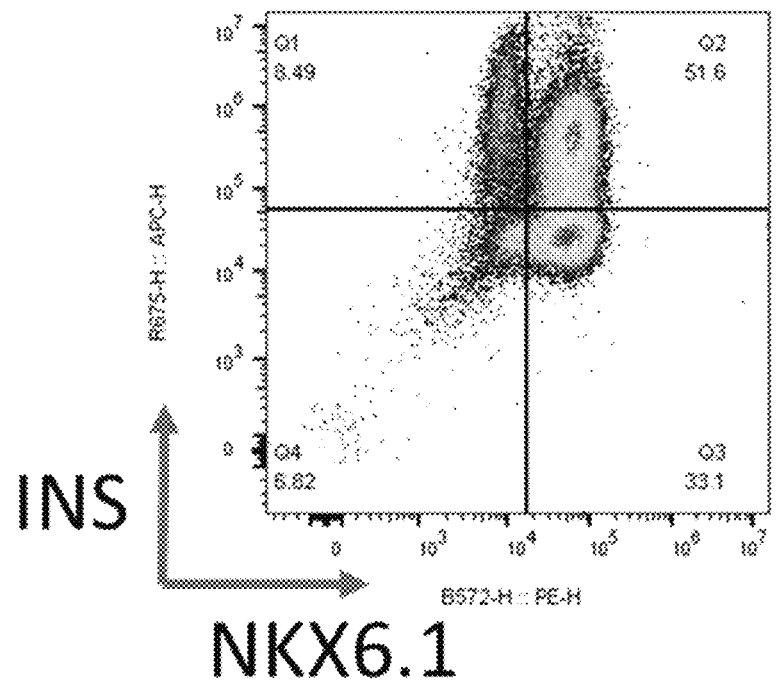
Figure 25A:
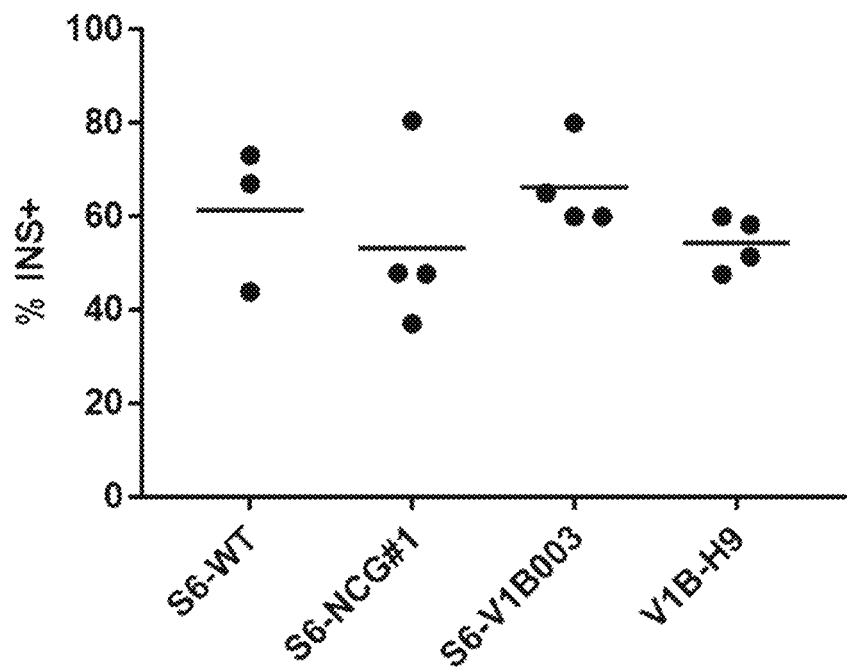
FIGS. 25A-25B show the percentage of INS expression (FIG. 25A) and NKX6.1 expression (FIG. 25B) in Stage 6 cells differentiated from wild-type cells ("S6-WT"), non-cutting guide control cells ("S6-NCG #1"), and two B2M KO/PD-L1 KI and TXNIP KO/HLA-E KI clones ("S6-V1B003" and "V1B-H9").
Figure 25B:
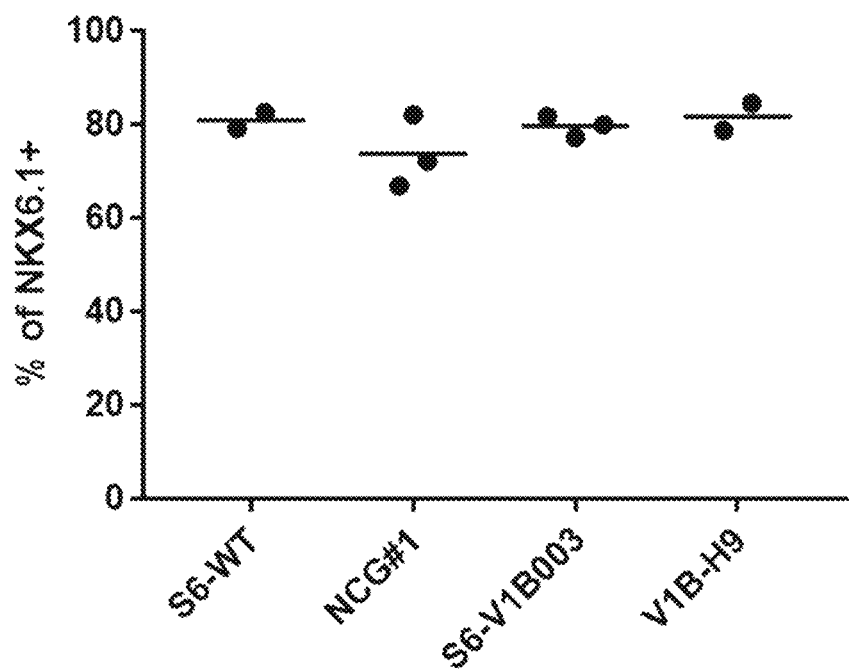

FIGS. 24A-24B show the flow cytometry assessment of INS and GCG expression (FIG. 24A) and INS and NKX6.1 expression (FIG. 24B) in Stage 6 cells differentiated from a B2M KO/PD-L1 KI and TXNIP KO/HLA-E KI clone. FIGS. 25A-25B show the percentage of INS expression (FIG. 25A) and NKX6.1 expression (FIG. 25B) in Stage 6 cells differentiated from two B2M KO/PD-L1 KI and TXNIP KO/HLA-E KI clones ("S6-V1B003" and "V1B-H9"). Expression in both was similar to that of wild-type and non-cutting guide control cells.

Figure 17:
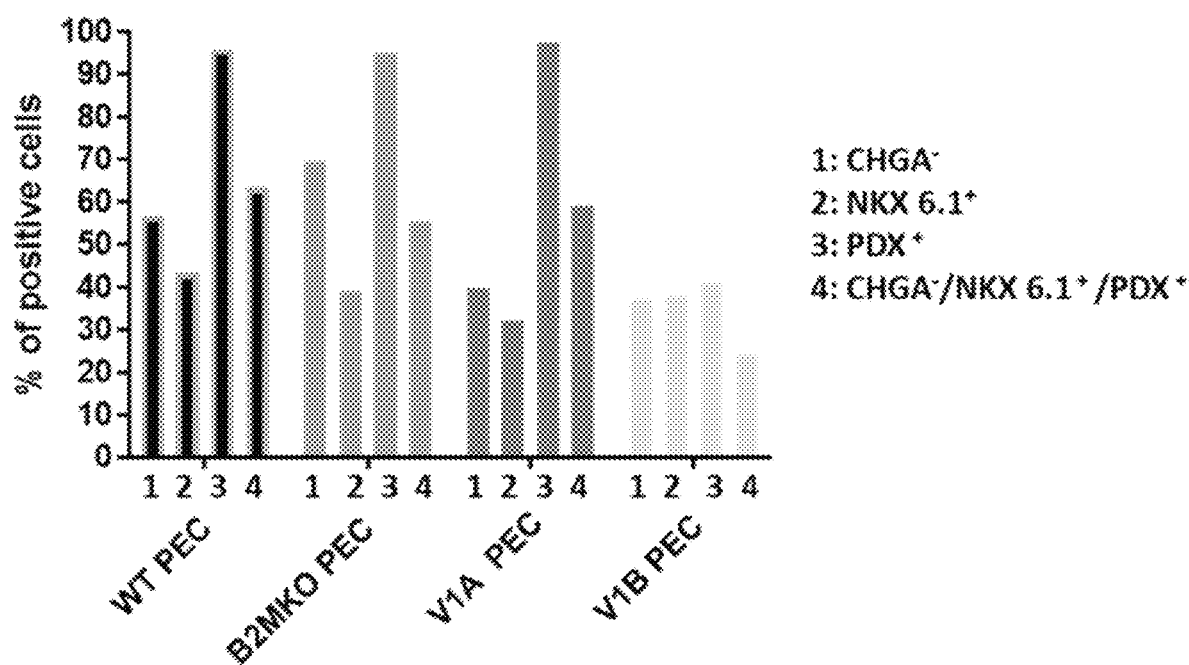
FIG. 17 shows quantitative percentage of CHGA, PDX1 and NKX6.1 expression in Stage 4 (PEC) cells differentiated from wild type, B2M KO, PD-L1 KI/B2M KO (V1A), or TXNIP KO/HLA-E KI (V1B) hESCs.
Figure 18A:
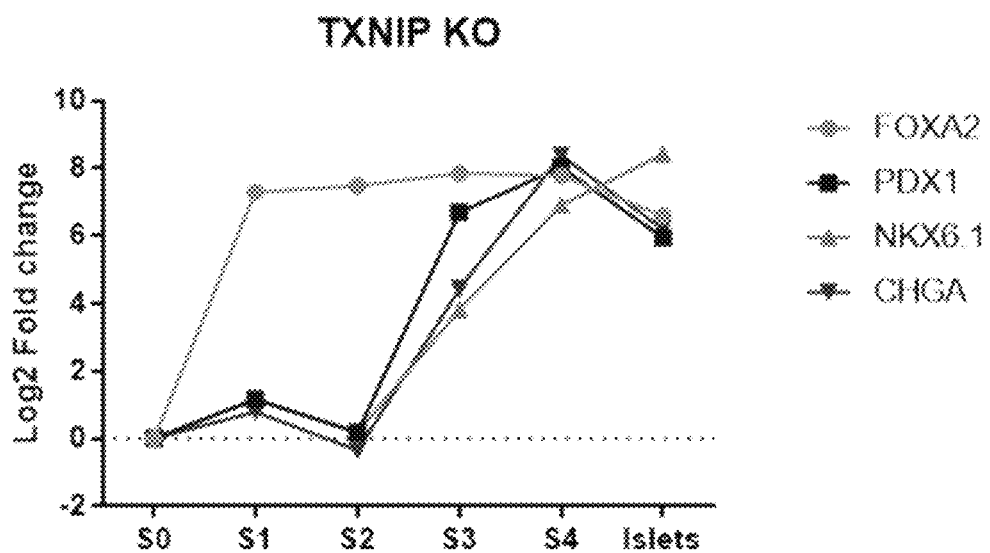
FIGS. 18A-18B show selected gene expression over differentiation time course in TXNIP KO cells (FIG. 18A) or TXNIP KO/HLA-E KI (V1B) (FIG. 18B) cells.
Figure 18B:
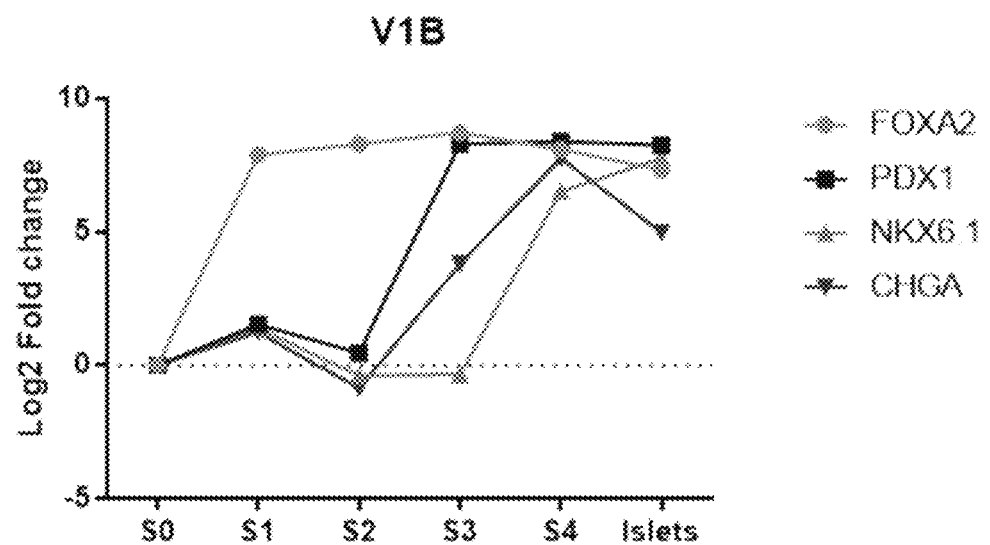

At PECs stage, flow cytometry for chromogranin (CHGA), PDX1 and NKX6.1 were performed. The heterogeneous population at PEC stage include pancreatic progenitors, early endocrine (FIG. 17). Targeted RNAseq for gene expression analysis was performed, as described above. Selected gene expression for the TXNIP KO clone is shown in FIG. 18A and selected gene expression for the V1-B clone is shown in FIG. 18B. The kinetic expression pattern of FOXA2, CHGA, PDX1 and NKX6.1 from V1-B or TXNIP KO clone cells was similar to wild type cells.

Figure 28:
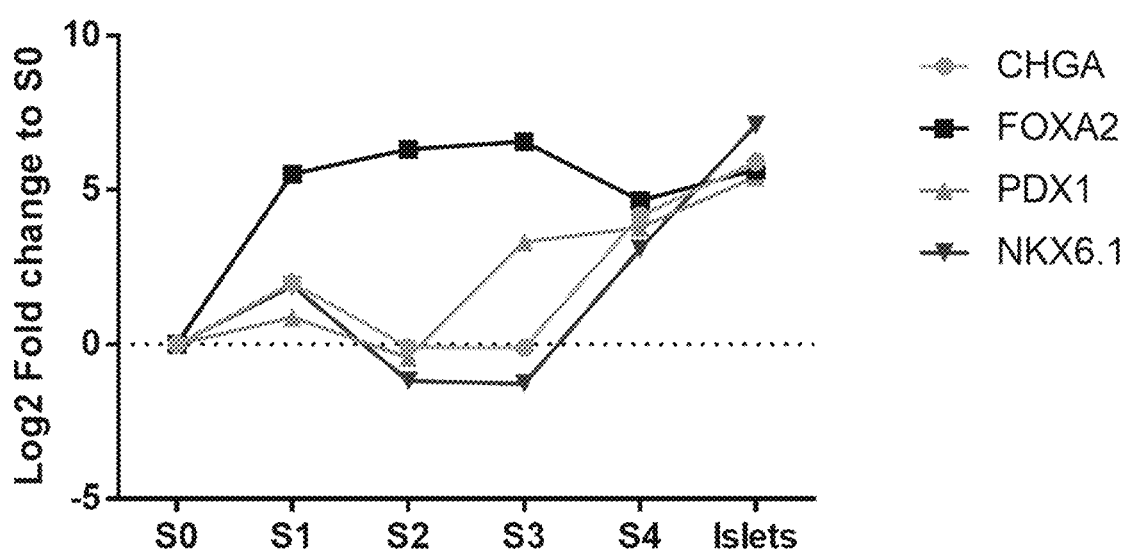
FIG. 28 shows selected gene expression over a differentiation time course of cells differentiated from TXNIP KO/HLA-E KI clones.

Cells were generated in which the HLA-E coding sequence was inserted in the TXNIP locus (thereby knocking out the TXNIP gene) using the HLA-E donor vector comprising the nucleotide sequence of SEQ ID NO: 56. Targeted RNAseq for gene expression analysis was performed, as described above. Selected gene expression for the TXNIP KO/HLA-E KI clone is shown in FIG. 28. The kinetic expression pattern of FOXA2, CHGA, PDX1 and NKX6.1 from TXNIP KO/HLA-E KI cells was similar to wild type cells.

Alternatively, cells were generated in which the HLA-E coding sequence was inserted in the TXNIP locus using the HLA-E donor vector comprising the nucleotide sequence of SEQ ID NO: 34. Bulk edited cells were differentiated to PEC stage and expressed HLA-E in at least 75% of the population of cells (data not shown). Flow cytometry assessment of PDX1 and NKX6.1 expression in PEC cells differentiated from TXNIP KO cells was similar to PEC cells differentiated from wild-type cells (data not shown).

Example 9

T-Cell Activation/Proliferation Assay

Figure 19A:
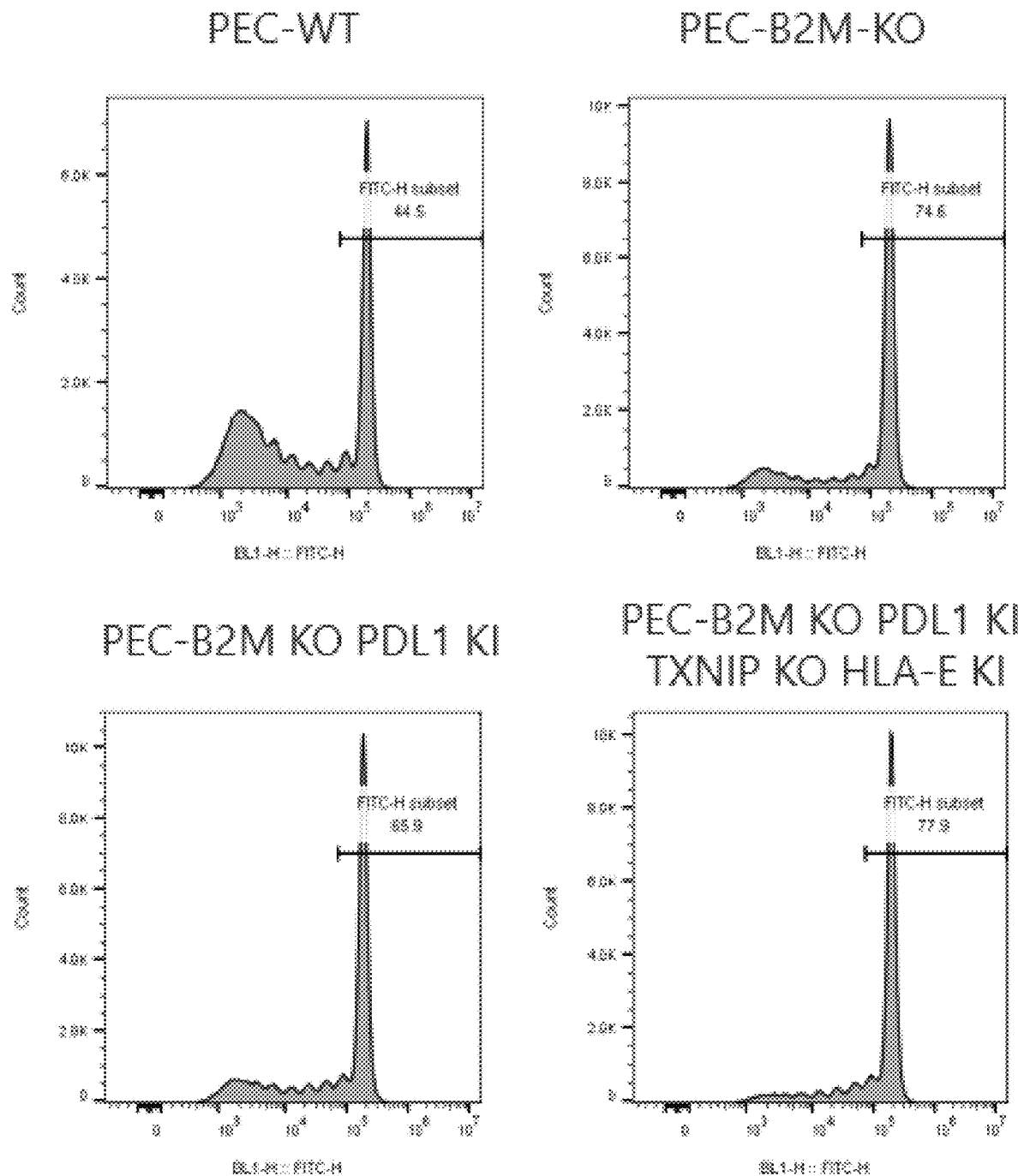
FIGS. 19A-19B show flow cytometry analysis for T-cell activation using the CFSE proliferation assay. Human primary CD3+ T cells were co-incubated with PEC derived from WT, B2M KO, B2M KO/PD-L1 KI, or B2M KO/PD-L1 KI+TXNIP KO/HLA-E KI CyT49 clones (FIG. 19A).
Figure 19B:
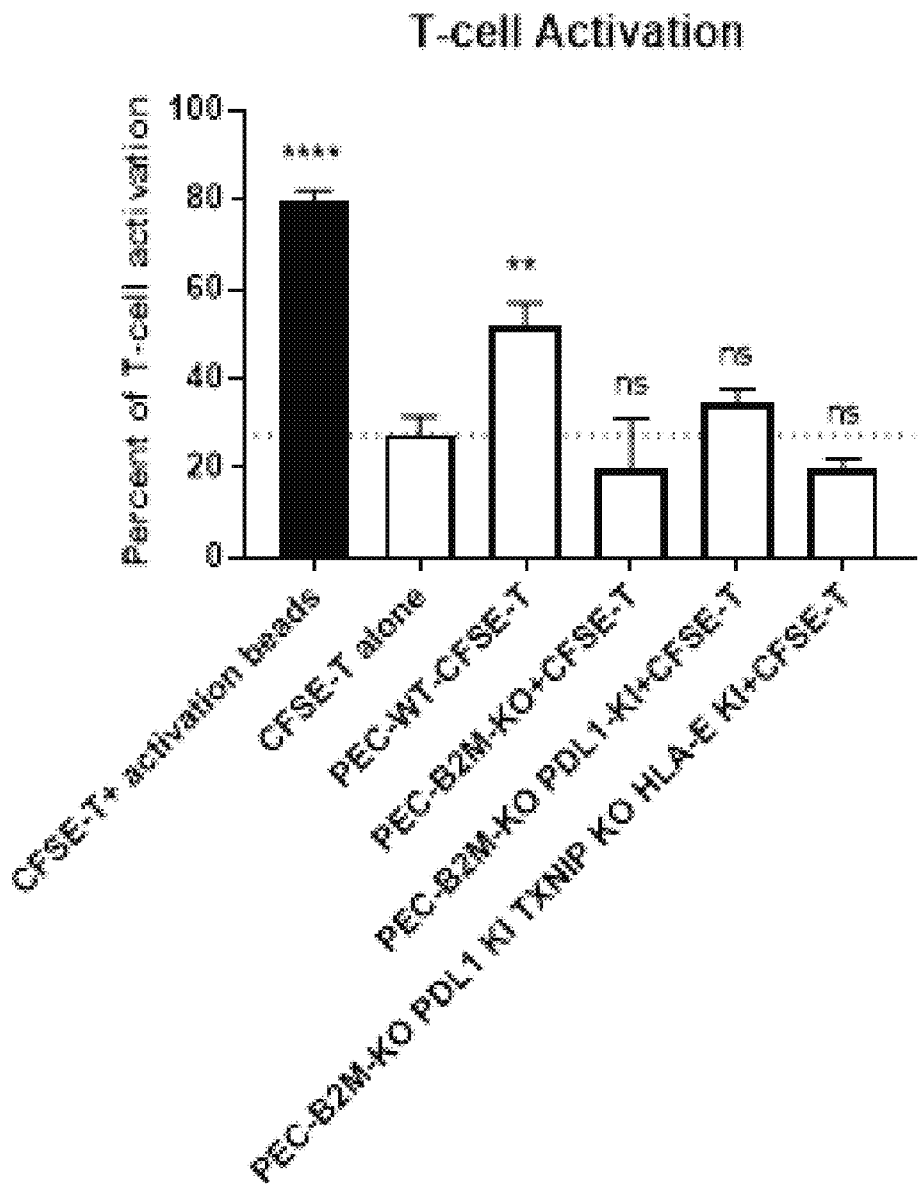

PEC-differentiated cells were tested for their ability to trigger an immune response via in vitro human T-cell activation/proliferation assays. Fresh donor PBMCs were purchased from Hemacare and CD3+ T-cells were purified using the Pan T-Cell Isolation Kit, human (Miltenyi Cat #130-096-535). The isolated T-cells were labeled with CellTrace™ CFSE Cell Proliferation Kit Protocol (Thermofisher Cat #C34554) per manufacturer instructions and co-incubated with differentiated PEC for 5 days. Dynabeads™ Human T-Activator CD3/CD28 for T-Cell Expansion and Activation (Thermofisher Cat #11161D) were used as a positive control to activate T-cells. T-cells alone were labeled with CFSE and used as a negative control. Percent of CD3+ CFSE+ cells was measured to assess percent of T-cell proliferation (FIGS. 19A-19B). WT PEC triggered T-cell proliferation above T-cell alone control. B2M KO, B2M KO/PD-L1 KI, and B2M KO/PD-L1 KI+TXNIP KO/HLA-E KI CyT49-derived PEC did not trigger T-cell proliferation above T-cell only control showing the hypo immunogenic nature of edited cells.

Example 10

In Vivo Efficacy Study of Gene Targeted Clonal Lines

Pancreatic endoderm cells were produced from CyT49-derived clonal hES cell lines with the following genetic modifications: 1) the targeted deletion of B2M expression and forced expression of PD-L1, 2) the targeted deletion of B2M expression and forced expression of HLA-E, or 3) the targeted deletion TXNIP. In addition, a clonal un-modified cell line was obtained from transfection with a non-cutting guide-RNA (NCG).

Following standard procedures, pancreatic endoderm aggregates derived from the indicated clonal lines were loaded into perforated devices (PD) to produce test or control articles. The PDs permit direct vascularization upon subcutaneous transplantation, and the encapsulated pancreatic progenitor cells mature in vivo into functional pancreatic endocrine cells including glucose-responsive, insulin-producing cells.

As summarized in Table 13, five groups of athymic nude rats were implanted subcutaneously with two articles, each containing approximately $7 \times 10^6$ pancreatic endoderm cells obtained from differentiations of the four clonal lines described above, or wild-type CyT49 hES (ViaCyte) cells.

TABLE 13

| | | | Study Design | | | |
|---|---|---|---|---|---|---|
| | | | | Genetic Modification | | |
| Group Number | Group ID | hESC Origin | Knock-out (Loss of Function) | Knock-in (Gain of Function) | Number of Animals | End Point |
| 1 | Control | Un-modified CyT49 | None | None | 6 per Group | 20 Weeks |
| 2 | NCG | CyT49 sub-clone | None | None | | |
| 3 | TXNIP KO | CyT49 sub-clone | TXNIP | None | | |
| 4 | B2M KO/ PD-L1 | CyT49 sub-clone | B2M | PD-L1 | | |
| 5 | B2M KO/ HLA-E | CyT49 sub-clone | B2M | HLA-E | | |

Starting at 12 weeks all surviving animals were subjected to efficacy evaluation through glucose stimulated insulin secretion (GSIS) testing. Blood samples were obtained from non-fasted animals prior to and after intraperitoneal administration of 3 g/kg glucose. Serum concentrations of human C-peptide were determined through standard enzyme linked immunosorbent assays.

GSIS testing was performed at 12, 16, and 20 weeks. Results indicated there were no substantial differences between experimental groups, especially beyond the 12-week time point. Compared to the C-peptide levels detected in the control group (Group 1, <40 pM to 2.0 nM, mean 1.1 nM) C-peptide levels were elevated in 2 of 6 animals from Group 3 (TXNIP KO, mean 1.5 nM). The other groups, Group 2 (NCG, mean 0.5 nM), Group 4 (B2M KO/PD-L1 KI, mean 0.5 nM), and Group 5 (B2M KO/HLA-E KI, mean 0.4 nM), presented a similar range of C-peptide levels compared to the control group, but with more animals near the lower end of the range. However, these differences were not statistically significant. These results indicated that neither the genetic modifications that were introduced nor the manipulations required to generate clonal lines affected the ability for the cell lines in question to differentiate into pancreatic endoderm cells in vitro and subsequently generate functional beta cells in vivo.

At 20 weeks, after GSIS testing, animals were euthanized and explanted test articles were fixed in neutral buffered formalin, processed to slides, and stained with H&E and by immunohistochemistry for insulin and glucagon.

In vivo efficacy evaluations through GSIS testing showed no substantial differences between unedited control articles and edited test articles formulated with pancreatic endoderm cells derived from clonal cell lines each carrying a subset of genetic modifications. The results suggest the individual genetic modifications and the process by which they are introduced may be tolerated in vivo.

Example 11

In Vivo Efficacy Study of B2M KO/PD-L1 KI, TXNIP KO/HLA-E KI Cell Lines

Four clonal lines were generated essentially as described above in Example 8 and loaded into perforated devices to form test articles. Control articles contained un-modified CyT49 cells (ViaCyte). Articles comprising about $7 \times 10^6$ pancreatic endoderm cells were subcutaneously implanted into athymic nude rats (2 articles/rat, 8 rats/group).

At 12, 16, 20, and 24 weeks, all surviving animals were subjected to glucose stimulated insulin secretion (GSIS) testing. Blood samples were obtained from fasted animals prior to and after intraperitoneal administration of 3 g/kg glucose. Serum concentrations of human C-peptide were determined through standard enzyme linked immunosorbent assays. Serum C-peptide was detected in most animals at 12 weeks after implant. The serum C-peptide levels at 16, 20, and 24 weeks post implant are presented in Table 14. No statistically significant differences were observed between the groups of animals implanted with gene-edited versus control cells.

TABLE 14

In vivo Serum C-peptide Levels.

| Groups | Serum C-peptide (pmol) | | |
|---|---|---|---|
| | Mean | Lower 95% | Upper (95% |
| Gene-edited cells - 16 weeks | 729 | 40 | 1418 |
| Gene-edited cells - 20 weeks | 1080 | 391 | 1769 |
| Gene-edited cells - 24 weeks | 1676 | 987 | 2365 |
| Control cells - 16 weeks | 1075 | 386 | 1764 |
| Control cells - 20 weeks | 1883 | 1193 | 2572 |
| Control cells -24 weeks | 2466 | 1777 | 3155 |

At 25 weeks, surviving animals will be subjected to an insulin challenge (insulin tolerance test, ITT) to assess serum human C-peptide changes in response to diminishing blood glucose in the absence of access to food. Blood samples will be obtained from fasted animals prior to and at multiple time points (15, 30, 60 minutes) after intraperitoneal administration of 1 unit of insulin per kg body weight. Serum concentrations of human C-peptide will be determined through standard enzyme linked immunosorbent assays.

At 26 weeks, surviving animals will be euthanized and explanted test articles will be processed to slides and stained with H&E and by immunohistochemistry (IHC) for insulin and glucagon to identify human pancreatic endocrine cells. Additional IHC for human-specific nuclear marker NuMA1 will be performed to identify the potential location of graft-derived cells outside of the lumen of the test article explant.

Example 12

In Vivo Efficacy Study of B2M KO/PD-L1 KI, TXNIP KO/HLA-E KI Cell Line

Aggregates of B2M KO/PD-L1 KI, TXNIP KO/HLA-E KI pancreatic endoderm cells (comprising approximately $7 \times 10^6$ cells) will be formulated into test articles. Forty-six athymic nude rats will be implanted subcutaneously with two test articles each. Animals on study will be evaluated for GSIS, ITT, and non-fasting blood glucose (NFBG). Ten animals per group will be euthanized at scheduled termination time points of 13, 17, 26, and 39 weeks, while 6 additional animals will be on study to account for possible early unscheduled terminations. From each animal the two explanted test articles will be randomly assigned to either histological evaluation or total C-peptide content assessment. Table 15 presents the study design.

TABLE 15

Study Design

| Group Number | Number of Test Articles | Number of Animals | GSIS Time Points (Weeks) | ITT Time Points (Weeks) | End Point (Weeks) | Explant Analyses |
|---|---|---|---|---|---|---|
| 1 | 20 | 10 male | 12 | NA | 13 | For each Group: |
| 2 | 20 | 10 male | 12, 16 | NA | 17 | |
| 3 | 20 | 10 male | 12, 16, 20, 24 | 25 | 26 | Histology 5 animals |
| 4 | Up to 32 | Up to 16 male | 12, 16, 20, 24, 30, 36 | 25, 33 | 39 | C-peptide content 5 animals |
| Total | 92 | 46 male | | | | |

At 12, 16, 20, 24, 30, and 36 weeks, all surviving animals will be subjected to efficacy evaluations through glucose stimulated insulin secretion (GSIS) testing. Blood samples will be obtained from fasted animals prior to and after intraperitoneal administration of 3 g/kg glucose. Serum concentrations of human C-peptide will be determined through standard enzyme linked immunosorbent assays.

At 25 and 33 weeks, surviving animals will be subjected to an insulin challenge (insulin tolerance test, ITT) to assess serum human C-peptide changes in response to diminishing blood glucose in the absence of access to food. Blood samples will be obtained from fasted animals prior to and multiple time points (15, 30, 60 minutes) after intraperitoneal administration of 1 unit of insulin per kg body weight. Serum concentrations of human C-peptide will be determined through standard enzyme linked immunosorbent assays.

Non-fasting blood glucose (NFBG) will be measured prior to initiation of fasting for GSIS and ITT testing, at approximately 12, 16, 20, 24, 25, 30, 33, and 36 weeks.

At the scheduled end points identified in Table 13, animals will be euthanized. Euthanasia will be performed by $CO_2$ inhalation followed by bilateral thoracotomy. Gross necropsy will be performed on all scheduled and unscheduled terminations and macroscopic abnormalities will be recorded.

Designated explants will be frozen followed by homogenization of lumen content. Total C-peptide content of the homogenate will be determined through standard enzyme linked immunosorbent assays. Total explant C-peptide content will be used to project clinical dosing.

Designated explanted test articles will be fixed in neutral buffered formalin, processed to slides, and stained with H&E and by immunohistochemistry (IHC) for insulin and glucagon to identify human pancreatic endocrine cells. Additional IHC for human-specific nuclear marker NuMA1 will be performed to identify the potential location of graft-derived cells outside of the lumen of the test article explant.

Example 13

Generation of B2M KO/PD-L1 KI, TXNIP KO/HLA-E KI in Human iPSCs

Human iPSCs (iPSC 0025) were generated in which the PD-L1 coding sequence was inserted in the B2M locus. An RNP complex was formed by combining B2M-2 gRNA (SEQ ID NO: 2) and Cas9 protein in molar ratio of 3:1 (gRNA:Cas9). To form the RNP complex, gRNA and Cas9 were combined in one vessel with R-buffer to a total volume of 25 µL and incubated for 15 min at RT. Cells were dissociated using ACCUTASE®, then resuspended in DMEM/F12 media (Gibco, cat #11320033), counted using an NC-200 (Chemometec) and centrifuged. A total of $1 \times 10^6$ cells were resuspended with the RNP complex. Four µg of the B2M-CAGGS-PD-L1 donor plasmid (SEQ ID NO: 33) and R-buffer were added for a total volume of 125 µL. This mixture was then electroporated using the parameters: 2 pulses, 30 ms, 1100 V. Seven days post electroporation, the cells were enriched for PD-L1 positive cells via MACS using Miltenyi reagents or Thermofisher reagents essentially as described above in Example 8.

After the enriched PD-L1 positive population was expanded, the cells were electroporated with an RNP complex comprising TXNIP-T5 gRNA (SEQ ID NO: 20) and Cas9 protein in molar ratio of 3:1 (gRNA:Cas9) and 4 µg of the TXNIP-CAGGS-HLA-E donor plasmid 2 (SEQ ID NO: 56) essentially as described above. Seven days post electroporation, the cells were enriched for HLA-E positive cells via MACS using Miltenyi reagents or Thermofisher reagents. Post HLA-E enrichment, the cells were single-cell sorted using the WOLF FACS-sorter (Nanocellect) into BIOLAMININ 521 CTG coated 96-well plates with StemFlex and Revitacell. Plated single cells were grown in a normoxia incubator (37° C., 8% $CO_2$) with every other day media changes until colonies were large enough to be re-seeded as single cells. When confluent, samples were split for maintenance and genomic DNA extraction. The anti-PD-L1 and anti-HLA-E antibodies (Table 4) were used for MACS enrichment and FACS-sorting into 96-well plates with gating set for HLA-E and PD-L1 double positive cells. For FACS-sorting, unedited cells served as a negative control.

Correctly targeted clones were identified via PCR for the PD-L1 KI insertion and the HLA-E KI insertion using primers that amplify a region from outside the plasmid homology arms to the PD-L1 cDNA insertion or the HLA-E cDNA insertion, respectively, enabling amplification of the KI integrated DNA only. On-target insertion was tested for zygosity by PCR to assess if KI occurred in a heterozygous or homozygous manner. If a heterozygous clone was identified, the KI negative allele was sent for Sanger sequencing to verify that it contained a B2M-disrupting indel or a TXNIP-disrupting indel, respectively. The correct KI clones with full B2M and TXNIP disruptions (either via KI insertion or indel formation) were expanded in increasing tissue culture formats until a population size of 30 million cells was reached. Selected clones were expanded in this manner and confirmed to be pluripotent by testing for OCT4 and SOX2 via intracellular flow cytometry.

Figure 26A:
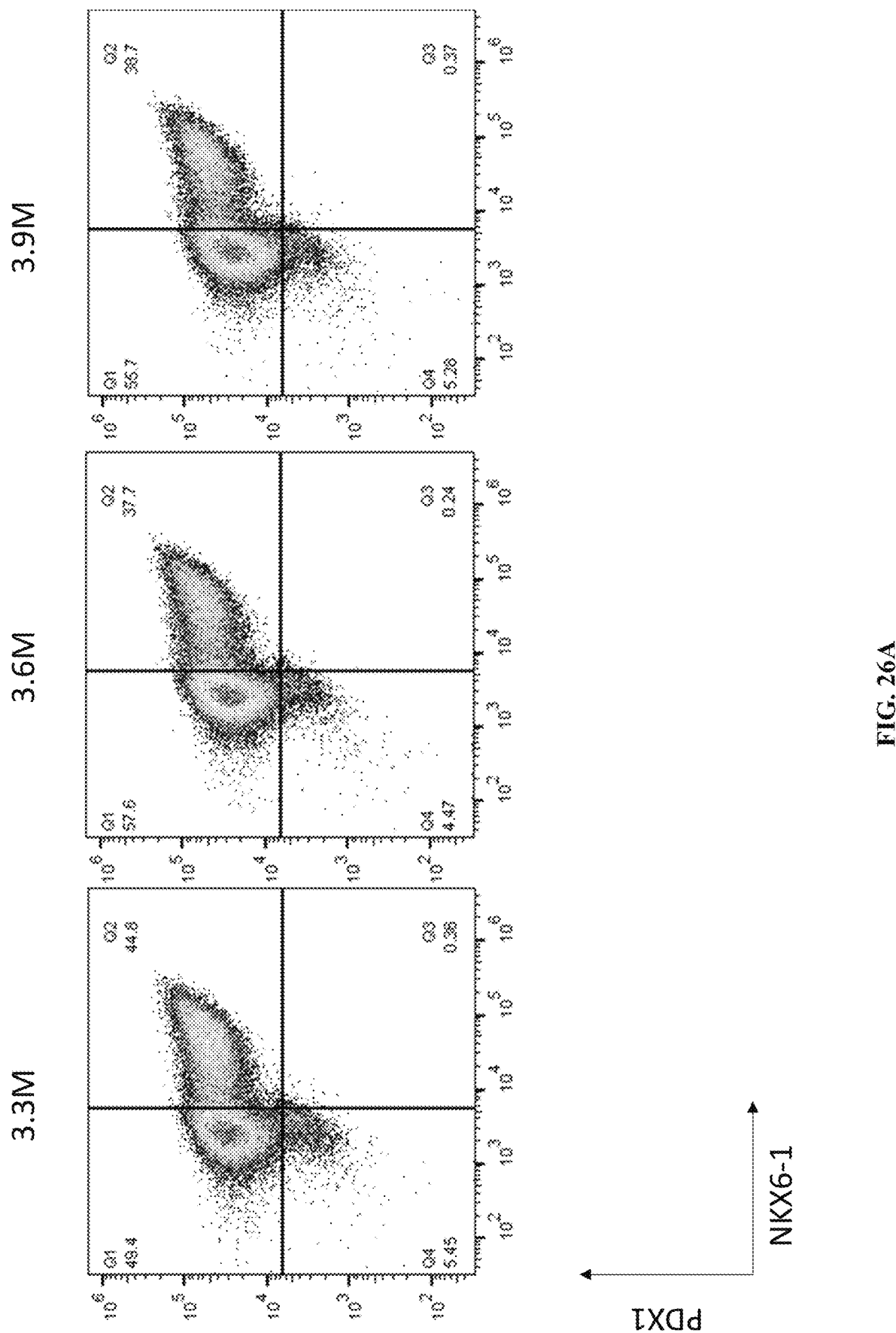
FIG. 26A shows flow cytometry assessment of PDX1 and NKX6.1 expression in Stage 4 cells differentiated from clone 1 (B2M KO/PD-L1 KI and TXNIP KO/HLA-E KI) cells with different seeding densities.
Figure 26B:
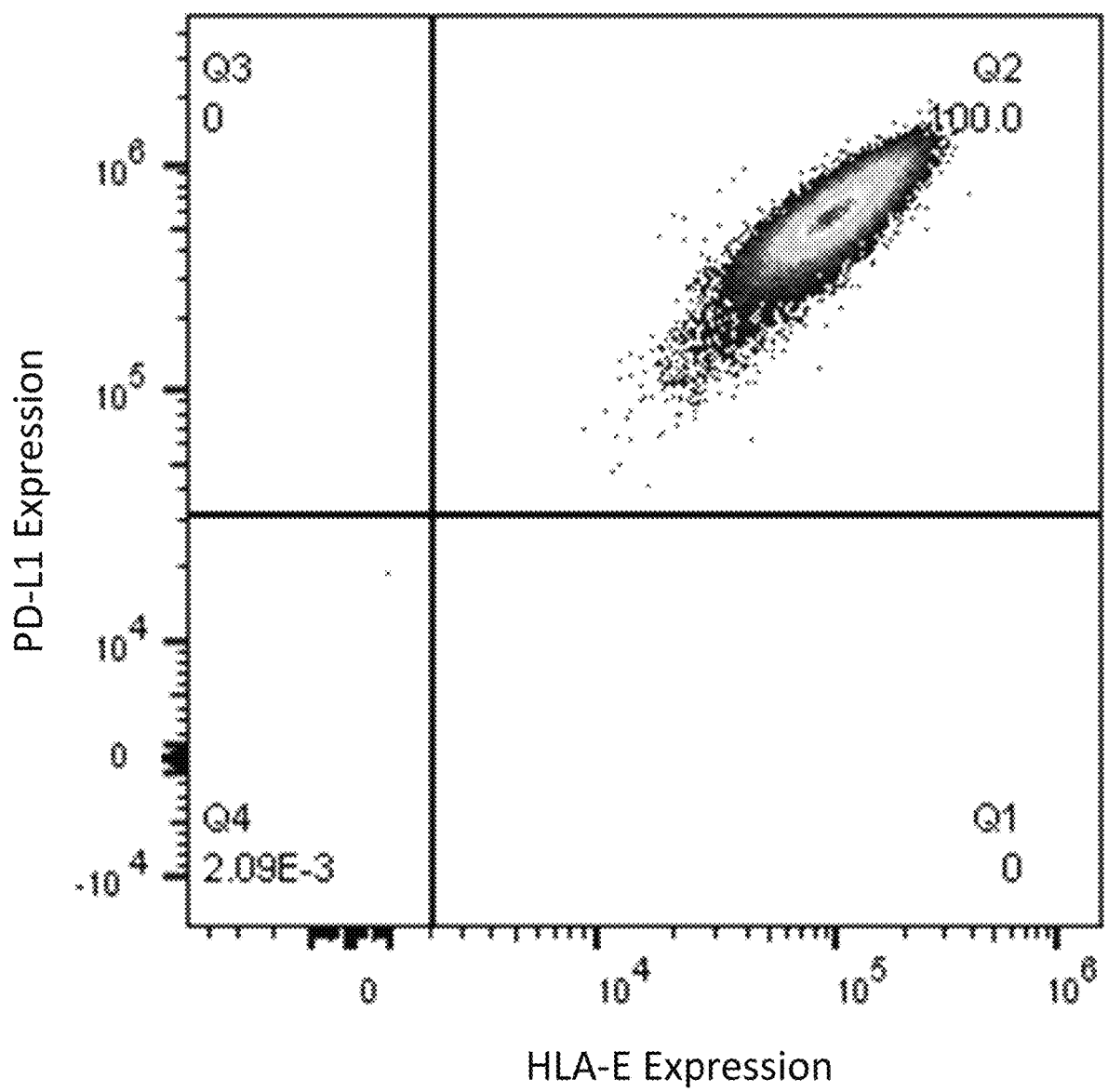
FIG. 26B shows flow cytometry assessment for PD-L1 and HLA-E expression in Stage 4 cells differentiated from clone 1 (B2M KO/PD-L1 KI and TXNIP KO/HLA-E KI) cells.

Four edited hiPSCs clones (VI-B) were differentiated using the pancreatic endocrine protocol of Rezania et al. (Nat Biotechnol. 2014 November; 32(11):1121-33). At Stage 4, flow cytometry for chromogranin (CHGA), PDX1 and NKX6.1 was performed. The results for PDX1 and NKX6.1 of a clone (clone 1) seeded at different representative densities is shown in FIG. 26A. CHGA was negative for all four clones. Flow cytometry for PD-L1 and HLA-E was also performed. The results for PD-L1 and HLA-E of a clone (clone 1) is shown in FIG. 26B.

Example 14

Process for Manufacturing B2M KO/PD-L1 KI, TXNIP KO/HLA-E KI Human Pluripotent Stem Cells (hPSCs) Cryo Cell Banks CyT49 hESCs (ViaCyte) were electroporated with an RNP complex comprising B2M-2 gRNA (SEQ ID NO: 2) and Cas9 protein in molar ratio of 3:1 (gRNA:Cas9) and 4 µg of the B2M-CAGGS-PD-L1 donor plasmid (SEQ ID NO: 33) for 2 pulses of 30 ms at 1100 V. Following electroporation, the cells were pipetted out into an Eppendorf tube filled with StemFlex media with RevitaCell. This cell suspension was then plated into tissue culture dishes pre-coated with BIOLAMININ 521 CTG at 1:20 dilution. Cells were cultured in a normoxia incubator (37° C., 8% $CO_2$).

Seven days post electroporation, the cells were enriched for PD-L1 positive cells via MACS using Alexa-488 labeled anti-PD-L1 antibodies and magnetic beads (DYNABEADS® Pan Mouse IgG; Thermo Fisher). The PD-L1 positive cells were expanded by culturing in XF-KSR expansion media (Gibco) for 7 days.

The PD-L1 positive cells were then electroporated with an RNP complex comprising TXNIP-T5 gRNA (SEQ ID NO: 20) and Cas9 protein in molar ratio of 3:1 (gRNA:Cas9) and 4 of the TXNIP-CAGGS-HLA-E donor plasmid 2 (SEQ ID NO: 56) for 2 pulses of 30 ms at 1100 V. Following electroporation, the cells were pipetted out into an Eppendorf tube filled with StemFlex media with RevitaCell. This cell suspension was then plated into tissue culture dishes pre-coated with BIOLAMININ 521 CTG at 1:20 dilution. Cells were cultured in a normoxia incubator (37° C., 8% $CO_2$).

Seven days post electroporation, the cells were enriched for HLA-E positive cells via MACS using PE-labeled anti-HLA-E antibodies and magnetic beads (DYNABEADS® Pan Mouse IgG; Thermo Fisher). The PD-L1 and HLA-E double positive cells were expanded by culturing in XF-KSR expansion media (Gibco) for about 5 days.

The PD-L1 and HLA-E double positive cells were single cell sorted. For this, the cells were fed with StemFlex Complete with Revitacell (for final concentration of 1× Revitacell) 3-4 hours prior to dissociation with ACCUTASE®. Following dissociation, single cells were sorted into single wells of BIOLAMININ coated 96 well tissue culture plate. The WOLF FACS-sorter (Nanocellect) was used to sort single cells into the wells using the anti-PD-L1 and anti-HLA-E antibodies described above. The plates were pre-filled with 100-200 µL of StemFlex Complete with Revitacell. Three days post cell seeding, the cells were fed with fresh StemFlex and continued to be fed every other day with 100-200 µL of media. After 10 days of growth, the cells were fed daily with StemFlex until day 12-14. At this time, the plates were dissociated with ACCUTASE® and the collected cell suspensions were split 1:2 into two 96 well plates, which were cultured for about 4 days.

A portion of the cells were harvested for visual analysis (morphology) and DNA analysis (PCR and DNA sequencing for zygosity analysis and indel profile), and the remainder of the cells were cultured and expanded for culturing in T175 flasks. After about two weeks of culturing, clones were selected for freezing. The cells were characterized before and after freezing for morphology, viability, endotoxins, mycoplasma, karyotype, pluripotency, differentiation capacity, on/off target analysis, random plasmid integration, residual Cas9/plasmid using standard procedures. The cells were frozen in cryo media and stored in cryo vials at −80° C. or liquid nitrogen.

Figure 27A:
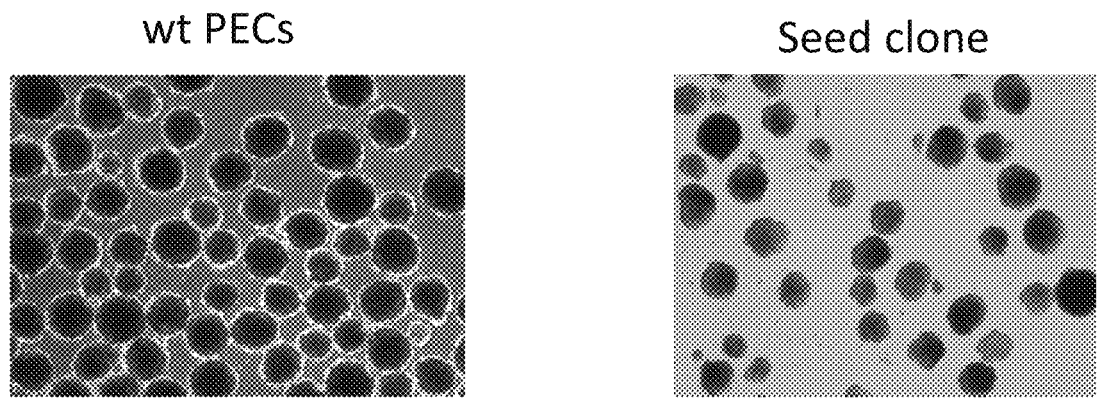
FIGS. 27A-27C show the characterization analysis of a seed clone differentiated to PEC stage.
Figure 27B:
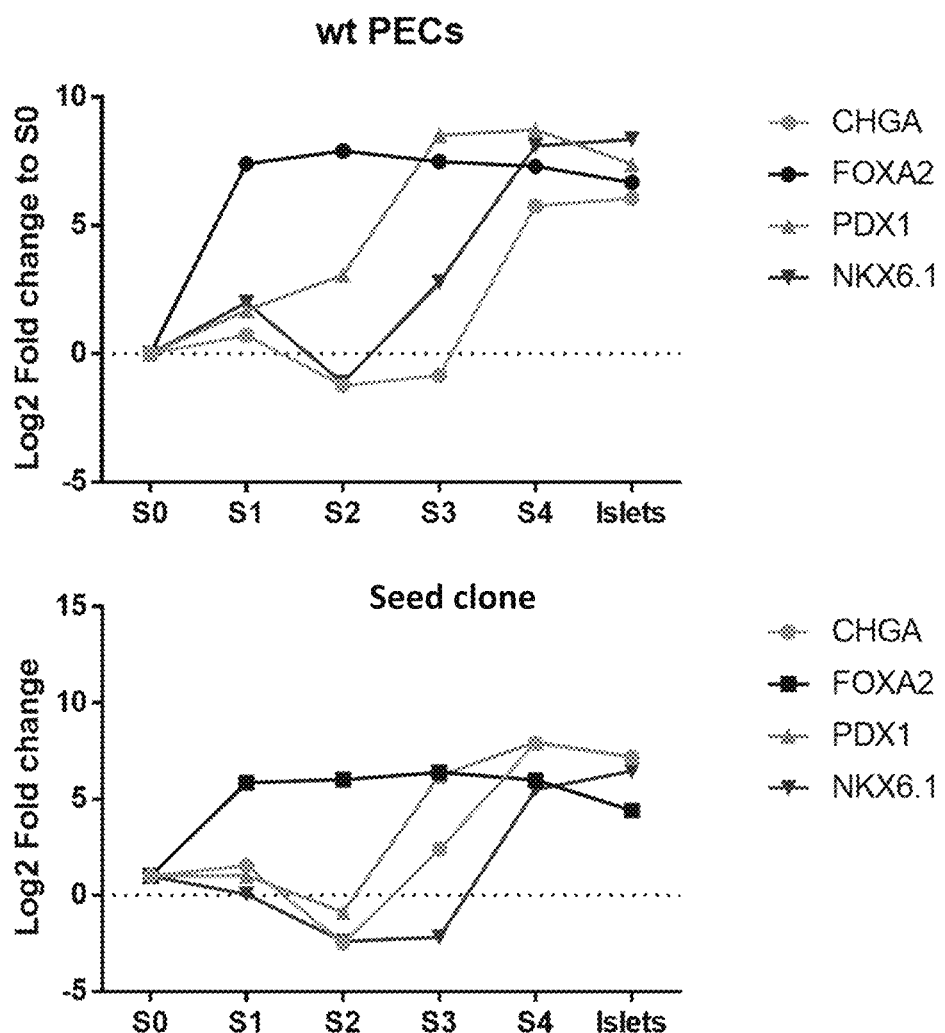
Figure 27C:
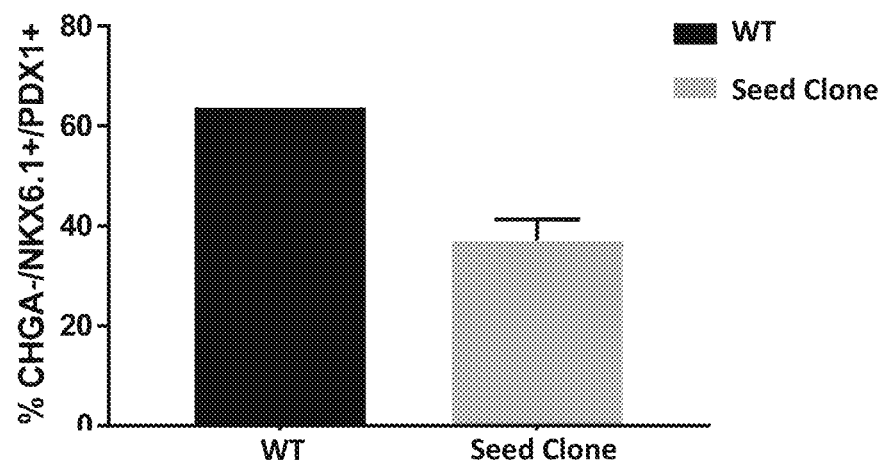

A particular B2M KO/PD-L1 KI+TXNIP KO/HLA-E KI clone ("seed clone") was manufactured and isolated by said process. The seed clone was differentiated to PEC stage and characterized. FIG. 27A shows the morphology of the seed clone at the PEC stage was similar to wild type cells. FIG. 27B shows the kinetic expression pattern of FOXA2, CHGA, PDX1 and NKX6.1 over a differentiation time course in cells differentiated from the seed clone was similar to wild type cells. FIG. 27C shows the percentage of $CHGA^-/NKX6.1^+/PDX1^+$ cells in the differentiated population.

The invention claimed is:

1. A process for generating a population of genetically modified cells, the process comprising:
   (a) modifying stem cells by cleaving a beta-2 microglobulin (B2M) gene locus at a target site and inserting a nucleotide sequence encoding programmed death-ligand 1 (PD-L1) into the B2M gene locus, thereby disrupting the B2M gene locus and generating PD-L1 positive cells;
   (b) enriching for PD-L1 positive cells;
   (c) delivering to the PD-L1 positive cells from (b): (1) a ribonucleoprotein (RNP) complex comprising an RNA-guided nuclease and a gRNA targeting a target site in a thioredoxin interacting protein (TXNIP) gene locus, wherein the gRNA comprises a spacer sequence corresponding to a target sequence consisting of SEQ ID NO: 16-20, and (2) a vector comprising a nucleic acid, the nucleic acid comprising (i) a nucleotide sequence homologous with a region located left of the target site in the TXNIP gene locus; (ii) a nucleotide sequence encoding HLA class I histocompatibility antigen, alpha chain E (HLA-E), and (iii) a nucleotide sequence homologous with a region located right of the target site in the TXNIP gene locus, wherein the TXNIP gene locus is cleaved at the target site and the nucleic acid comprising the nucleotide sequence encoding HLA-E is inserted into the TXNIP gene locus, thereby disrupting the TXNIP gene locus and generating PD-L1, HLA-E double positive cells;
   (d) enriching for PD-L1, HLA-E double positive cells; and
   (e) single cell sorting to select for PD-L1, HLA-E double positive cells, thereby generating the population of genetically modified cells that are B2M⁻/PD-L1⁺ and TXNIP⁻/HLA-E⁺.

2. The process of claim 1, wherein the modifying at (a) comprises delivering to the stem cells: (1) a second RNP complex comprising an RNA-guided nuclease and a gRNA targeting the target site in the B2M gene locus, wherein the gRNA comprises a spacer sequence corresponding to a target sequence consisting of SEQ ID NO: 1-3, and (2) a second vector comprising a nucleic acid, the nucleic acid comprising (i) a nucleotide sequence homologous with a region located left of the target site in the B2M gene locus, (ii) the nucleotide sequence encoding PD-L1, and (iii) a nucleotide sequence homologous with a region located right of the target site in the B2M gene locus.

3. The process of claim 2, wherein the RNA-guided nuclease of the second RNP complex is a Cas9 nuclease and the gRNA of the second RNP complex comprises a spacer sequence corresponding to a target sequence consisting of SEQ ID NO: 2.

4. The process of claim 3, wherein the Cas9 nuclease is linked to at least one nuclear localization signal.

5. The process of claim 2, wherein the second RNP comprises a molar ratio of gRNA:RNA-guided nuclease of 3:1.

6. The process of claim 2, wherein the nucleotide sequence of (a)(2)(i) consists essentially of SEQ ID NO: 7, and the nucleotide sequence of (a)(2)(iii) consists essentially of SEQ ID NO: 13.

7. The process of claim 2, wherein the nucleotide sequence encoding PD-L1 consists essentially of SEQ ID NO: 11.

8. The process of claim 2, wherein the nucleotide sequence encoding PD-L1 is operably linked to a CAG promoter.

9. The process of claim 2, wherein the second vector is a plasmid vector and comprises a nucleotide sequence consisting of SEQ ID NO: 33.

10. The process of claim 2, wherein the delivering of (a)(1) and (a)(2) comprises electroporation.

11. The process of claim 1, wherein the enriching for PD-L1 positive cells at (b) comprises magnetic assisted cell sorting (MACS), single cell cloning, expanding said PD-L1 positive cells, or a combination thereof.

12. The process of claim 1, wherein the RNA-guided nuclease of the RNP complex delivered at (c) is a Cas9 nuclease and the gRNA of the RNP complex delivered at (c) comprises a spacer sequence corresponding to a target sequence consisting of SEQ ID NO: 20.

13. The process of claim 12, wherein the Cas9 nuclease is linked to at least one nuclear localization signal.

14. The process of claim 1, wherein the RNP delivered at comprises a molar ratio of gRNA:RNA-guided nuclease of 3:1.

15. The process of claim 1, wherein the nucleotide sequence of (c)(2)(i) consists essentially of SEQ ID NO: 25, and the nucleotide sequence of (c)(2)(iii) consists essentially of SEQ ID NO: 32.

16. The process of claim 1, wherein the nucleotide sequence encoding HLA-E comprises a sequence encoding a HLA-E trimer comprising a B2M signal peptide fused to an HLA-G presentation peptide fused to a B2M membrane protein fused to HLA-E without its signal peptide.

17. The process of claim 16, wherein the nucleotide sequence encoding the HLA-E trimer consists essentially of SEQ ID NO: 55.

18. The process of claim 1, wherein the nucleotide sequence encoding HLA-E is operably linked to a CAG promoter.

19. The process of claim 1, wherein the vector delivered at is a plasmid vector and comprises a nucleotide sequence consisting of SEQ ID NO: 34 or 56.

20. The process of claim 1, wherein the delivering of the RNP and the vector at (c) comprises electroporation.

21. The process of claim 1, wherein the enriching for PD-L1, HLA-E double positive cells at (d) comprises magnetic assisted cell sorting, single cell cloning, expanding said PD-L1, HLA-E double positive cells, or a combination thereof.

22. The process of claim 1, wherein the single-cell sorting at (e) comprises fluorescence-activated cell sorting (FACS), single cell cloning, expanding said single cell sorted cells, or a combination thereof.

23. The process of claim 1, further comprising characterizing the population of genetically modified cells for zygosity, indel profile, morphology, viability, karyotyping, endotoxin levels, mycoplasma levels, on/off target analysis, random vector insertion, residual RNA-guided nuclease, residual vector, pluripotency status, differentiation capacity, or a combination thereof.

24. The process of claim 1, further comprising freezing the population of genetically modified cells.

25. The process of claim 1, further comprising in (a) expanding the generated PD-L1 positive cells, in (c) expanding the generated PD-L1, HLA-E double positive cells, in (e) expanding the selected PD-L1, HLA-E double positive cells, or a combination thereof.

* * * * *